(12) United States Patent
Laing

(10) Patent No.: US 11,028,133 B2
(45) Date of Patent: Jun. 8, 2021

(54) MODIFIED FLAVIVIRUS ENVELOPE SEQUENCES COMPRISING UNIQUE GLYCOSYLATION SITES

(71) Applicant: Excivion Ltd., Cambridgeshire (GB)

(72) Inventor: Peter Laing, Cambridge (GB)

(73) Assignee: Excivion LTD, Willingham (GB)

( * ) Notice: Subject to any disclaimer, the term of this patent is extended or adjusted under 35 U.S.C. 154(b) by 0 days.

(21) Appl. No.: 16/303,588

(22) PCT Filed: May 22, 2017

(86) PCT No.: PCT/US2017/033882
§ 371 (c)(1),
(2) Date: Nov. 20, 2018

(87) PCT Pub. No.: WO2017/201543
PCT Pub. Date: Nov. 23, 2017

(65) Prior Publication Data
US 2019/0300580 A1    Oct. 3, 2019

(30) Foreign Application Priority Data

May 20, 2016  (GB) ..................................... 1608896

(51) Int. Cl.
| | | |
|---|---|---|
| *C07K 14/18* | (2006.01) | |
| *A61P 31/14* | (2006.01) | |
| *A61K 39/12* | (2006.01) | |
| *G01N 33/569* | (2006.01) | |
| *C07K 14/005* | (2006.01) | |
| *A61K 39/00* | (2006.01) | |

(52) U.S. Cl.
CPC .......... *C07K 14/1825* (2013.01); *A61K 39/12* (2013.01); *A61P 31/14* (2018.01); *C07K 14/005* (2013.01); *G01N 33/56983* (2013.01); *A61K 2039/5254* (2013.01); *A61K 2039/5258* (2013.01); *A61K 2039/53* (2013.01); *C12N 2770/24122* (2013.01); *C12N 2770/24134* (2013.01); *G01N 2333/185* (2013.01)

(58) Field of Classification Search
CPC ...... C07K 14/1825; C12N 2770/24122; C12N 2770/24134
See application file for complete search history.

(56) References Cited

U.S. PATENT DOCUMENTS 7,943,148 B1    5/2011   Sagripanti et al.

FOREIGN PATENT DOCUMENTS

| EP | 0640619 B2 | 3/2005 |
|---|---|---|
| WO | 2007015783 A2 | 2/2007 |
| WO | 2016012800 A1 | 1/2016 |

OTHER PUBLICATIONS

Dubayle, J., et al., 2015, Site-specific characterization of envelope protein N-glycosylation on Sanofi Pasteur's tetravalent CYD dengue vaccine, Vaccine 33:1360-1368.*
Alving, C. R., et al., Liposomal adjuvants for human vaccines, Expert Opinion on Drug Delivery, Jun. 2016;13(6):807-816.
Bournazos, S., et al, Signaling by Antibodies: Recent Progress, Annual Review of Immunology, 2017;35:285-311.
Dalziel, M., el al. Emerging Principles for the Therapeutic Exploitation of Glycosylation, Science, Jan. 2014;343(6166):1235681.
Davis C. W., et al., The Location of Asparagine-linked Glycans on West Nile Virions Controls Their Interactions with CD209 (Dendritic Cell-specific ICAM-3 Grabbing Nonintegrin), J Biol Chem, Dec. 2006;281(48):37183-37194.
Dejnirattisai, W., et al., A new class of highly potent, broadly neutralizing antibodies isolated from 10 viremic patients infected with dengue virus, Nature Immunology, 2014;16(2):170-177.
Dejnirattisai, W., et al., Dengue virus sero-cross-reactivity drives antibody-dependent enhancement of infectionwith Zika virus, Nature Immunology, 2016;17(9):1102-1108.
Elliott, S., et al., Enhancement of therapeutic protein in vivo activities through glycoengineering, Nature Biotechnology, 2003;21(4):414-421.
Frietze, K. M., et al, Engineering virus-like particles as vaccine platforms, Current Opinion in Virology, 2016;18:44-49.
Hadinegoro, S. R., et al., Efficacy and Long-Term Safety of a Dengue Vaccine in Regions of Endemic Disease, The New England Journal of Medicine, Sep. 2015;373(13):1195-1206.
Halstead, S. B., et al, Original antigenic sin in dengue, The American Journal of Tropical Medicine and Hygiene, Jan. 1983;32(1):154-156.
Hanley, K. A., The Double-Edged Sword: How Evolution Can Make or Break a Live-Attenuated Virus Vaccine, Evolution: Education and Outreach, 2011;4(4):635-643.
Hatzifoti, C., et al, Liposomal Co-Entrapment of CD40mAb Induces Enhanced IgG Responses against Bacterial Polysaccharide and Protein. PLoS One, 2008;3(6):e2368.
Kostyuchenko, V. A., et al., Structure of the thermally stable Zika virus, Nature, 2016;553:425-428.
Laing, P., et al., The "co-delivery" approach to liposomal vaccines: application to the development of influenza-A and hepatitis-B vaccine candidates, Journal of Liposome Research, 2006;16(3):229-235.

(Continued)

*Primary Examiner* — Jeffrey S Parkin
(74) *Attorney, Agent, or Firm* — Koren Anderson

(57) ABSTRACT

The invention relates to isolated recombinant analogues of flavivirus E-protein fusion loops comprising at least one glycosylation site for an N-linked glycan that is not present in the natural flavivirus E-protein fusion loop sequence, wherein the at least one glycosylation site is an N-linked glycosylation sequon (Asn-X-Ser/Thr) and the Asn (N) residue of the sequon occupies any of positions 98-110 (SEQ ID NO: 1) (DRGWGNGCGLFGK) of the natural flavivirus E-protein fusion loop amino acid sequence, wherein X is any amino acid residue except proline and Ser/Thr denotes a serine or threonine residue.

18 Claims, 20 Drawing Sheets

Specification includes a Sequence Listing.

(56) References Cited

OTHER PUBLICATIONS

Larocca, R., et al., Vaccine protection against Zika virus from Brazil, Aug. 25, 2016, Nature;536(7617):474-478.

Paul, L.M., et al., Dengue virus antibodies enhance Zika virus infection, Clinical & Translational Immunology, 2016;5:e117.

Ramsauer, K., et al, Immunogenicity, safety, and tolerability of a recombinant measles-virus-based chikungunya vaccine: a randomised, double-blind, placebo-controlled, active-comparator, first-in-man trial, The Lancet, Infectious Diseases, 2015;15(5):519-527.

Roby J. A., et al., West Nile Virus Genome with Glycosylated Envelope Protein and Deletion of Alpha Helices 1,2, and 4 in the Capsid Protein Is Noninfectious and Efficiently Secretes Subviral Particles, J Virol, Dec. 2013;87(23):13063-13069.

Roby, J. A., et al., Increased expression of capsid protein in trans enhances production 10 of single-round infectious particles by West Nile virus DNA vaccine candidate, J Gen Virol, Oct. 2014;95:2176-2191.

Russell, P. K., The Zika Pandemic—A Perfect Storm?, PLoS Neglected Tropical Diseases, 2016;10(3).

Sirohi, D., et al, The 3.8 A resolution cryo-EM structure of Zika virus, Science, 2016;352(6284):467-470.

Stiasny K et al., Cryptic Properties of a Cluster of Dominant Flavivirus Cross-Reactive Antigenic Sites, J Virol, 2006;80(19):9557-68.

Tregoning J. S., et al, Using Plasmids as DNA Vaccines for Infectious Diseases. Microbiology Spectrum, 2014;2(6):1-16.

Tretyakova, I., et al, Plasmid DNA initiates replication of yellow fever vaccine in vitro and elicits virus-specificimmune response in mice, Virology, 2014;468-470:28-35.

Zhao, H., et al., Structural Basis of Zika Virus-Specific Antibody Protection, Cell, 2016;166(4):1016-1027.

* cited by examiner

Fig. 1

Western blot of wild type (left of each pair) and hyperglycosylated forms of dengue and Zika E-protein exodomains, +2 = plus two additional glycans, +1 = plus one additional glycan Purified hyperglycosylated E-protein exodomains from the four dengue virus strains and Zika MR$_2$|CIGISNR$_9$|DFVEGVSGGSWVDIVLEHGSCVTTMAK$_{36}$|NK$_{38}$|PTLDFELIK$_{47}$|TEAK$_{51}$|
T1   T2         T3                              T4    T5              T6

Site 1 ↓

QPATLR$_{57}$|K$_{58}$|YCIEAK$_{64}$|LTN$_{67}$TTTESR$_{73}$|CPTQGEPSLNEEQDK$_{88}$|R$_{89}$|FVCK$_{93}$|HSMVDR$_{99}$|
T7          T8      T9          T10            T11                  T12    T13       T14

Site 2 ↓   Site 3 ↓

GN$_{101}$GSGCGLN$_{108}$GSGGIVTCAMFTCK$_{122}$|K$_{123}$|NMEGK$_{128}$|VVQPENLEYTIVITPHSGEEH
                    T15                          T16    T17        T18

Site 4 ↓

AVGN$_{153}$DTGK$_{157}$|HGK$_{160}$|EIK$_{163}$|ITPQSSITEAELTGYGTVTMECSPR$_{188}$|TGLDFNEMVLLQM
T18               T19       T20     T21                       T22

ENK$_{204}$|AWLVHR$_{210}$|QWFLDLPLPWLPGADTQGSNWIQK$_{234}$|ETLVTFK$_{241}$|NPHAK$_{246}$|K$_{247}$|
T22       T23            T24                          T25          T26          T27

QDVVVLGSQEGAMHTALTGATEIQMSSGNLLFTGHLK$_{284}$|CR$_{286}$|LR$_{288}$|MDK$_{291}$|LQLK$_{295}$|
                  T28                         T29      T30       T31       T32

GMSYSMCTGK$_{305}$|FK$_{307}$|VVK$_{310}$|EIAETQHGTIVIR$_{323}$|VQYEGDGSPCK$_{334}$|PFEIMDLEK$_{344}$|
      T33           T34      T35         T36                T37               T38

R$_{345}$|HVLGR$_{350}$|LITVNPIVTEK$_{361}$|DSPVNIEAEPPFGDSYIIIGVEPGQLK$_{388}$|LNWFK$_{393}$|K$_{394}$|
T39    T40          T41                 T42                              T43          T44

GSSGGGSHHHHHH$_{407}$
       T45

Fig. 3c

IR$_2$|CIGVSNR$_9$|DFVEGMSGGTWVDVVLEHGGCVTVMAQDK$_{36}$|PTVDIELVTTTVSNMAEVR$_{57}$|
T1   T2           T3                              T4

Site 1 ↓

SYCYEASISDMASDSR$_{73}$|CPTQGEAYLDK$_{84}$|QSDTQYVCK$_{93}$|R$_{94}$|TLVDR$_{99}$|N$_{100}$HTNGCGLFG
        T5              T6            T7       T8    T9    T10

Site 2 ↓

K$_{110}$|GSLVTCAK$_{118}$|FACSK$_{123}$|K$_{124}$|MTGK$_{128}$|SIQPENLEYR$_{138}$|IMLSVHGSQHSGMIVN$_{154}$DTGH
T10   T11         T12      T13    T14     T15              T16

ETDENR$_{164}$|AK$_{166}$|VEITPNSPR$_{175}$|AEATLGGFGSLGLDCEPR$_{193}$|TGLDFSDLYYLTMNNK$_{209}$|
T16       T17     T18          T19                     T20

HWLVHK$_{215}$|EWFHDIPLPWHAGADTGTPHWNNK$_{239}$|EALVEFK$_{246}$|DAHAK$_{251}$|R$_{252}$|QTVVVLGS
T21         T22                       T23         T24     T25    T26

QEGAVHTALAGALEAEMDGAK$_{281}$|GR$_{283}$|LSSGHLK$_{290}$|CR$_{292}$|LK$_{294}$|MDK$_{297}$|LR$_{299}$|LK$_{301}$|
T26                    T27     T28        T29    T30    T31    T32    T33

GVSYSLCTAAFTFTK$_{316}$|IPAETLHGTVTVEVQYAGTDGPCK$_{340}$|VPAQMAVDMQTLTPVGR$_{357}$|
T34                 T35                         T36

LITANPVITESTENSK$_{373}$|MMLELDPPFGDSYIVIGVGEK$_{394}$|K$_{395}$|THHWHR$_{402}$|SGSTGGSGGS
T37                  T38                    T39     T40      T41

GGSHHHHHH$_{421}$
T41

Fig. 3d

IR₂CIGVSNR₉DFVEGMSGGTWVDVVLEHGGCVTVMAQDK₃₈PTVDIELVTTTVSNMAEVR₅₇
　　　　　　　　L1　　　　　　　　　　　　　　　　　　　L2
　　　　　　　　　　　　　　　　　　　　　　　Site 1 ↓

SYCYEASISDMASDSR₇₃CPTQGEAYLDK₈₄QSDTQYVCK₉₃R₉₄TLVDR₉₉N₁₀₀HTNGCGLFG
　　　L2　　　　　　　　L3　　　　　　　　　　　　L4
　　　　　　　　　　　　　　　　　　　　　　　Site 2 ↓

K₁₁₀GSLVTCAK₁₁₈FACSK₁₂₃K₁₂₄MTGK₁₂₈SIQPENLEYR₁₃₈MLSVHGSQHSGMIVN₁₅₄DTGH
L4　　L5　　　L6　　L7　　L8　　　　　　　L9

ETDENR₁₆₄AK₁₆₆VEITPNSPR₁₇₅AEATLGGFGSLGLDCEPR₁₉₃TGLDFSDLYYLTMNNK₂₀₉
L9　　　　　　　　　　　　　L10

HWLVHK₂₁₅EWFHDIPLPWHAGADTGTPHWNNK₂₃₉EALVEFK₂₄₆DAHAK₂₅₁R₂₅₂QTVVVLGS
　L10　　　　　L11　　　　　　　　L12　　　L13　　L14

QEGAVHTALAGALEAEMDGAK₂₈₁GR₂₈₃LSSGHLK₂₉₀CR₂₉₂LK₂₉₄MDK₂₉₇LR₂₉₉LK₃₀₁
L14　　　　　　　　　　　　　　L15　　　L16　　L17　　L18

GVSYSLCTAAFTFTK₃₁₆IPAETLHGTVTVEVQYAGTDGPCK₃₄₀VPAQMAVDMQTLTPVGR₃₅₇
　　L19　　　　　　　　　L20　　　　　　　　　　L21

LITANPVITESTENSK₃₇₃MMLELDPPFGDSYIVIGVGEK₃₉₄K₃₉₅ITHHWHR₄₀₂SGSTGGSGGS
L21　　　　　　　L22　　　　　　L23　　　L24

GGSHHHHHH₄₂₁
L24

Fig. 3e

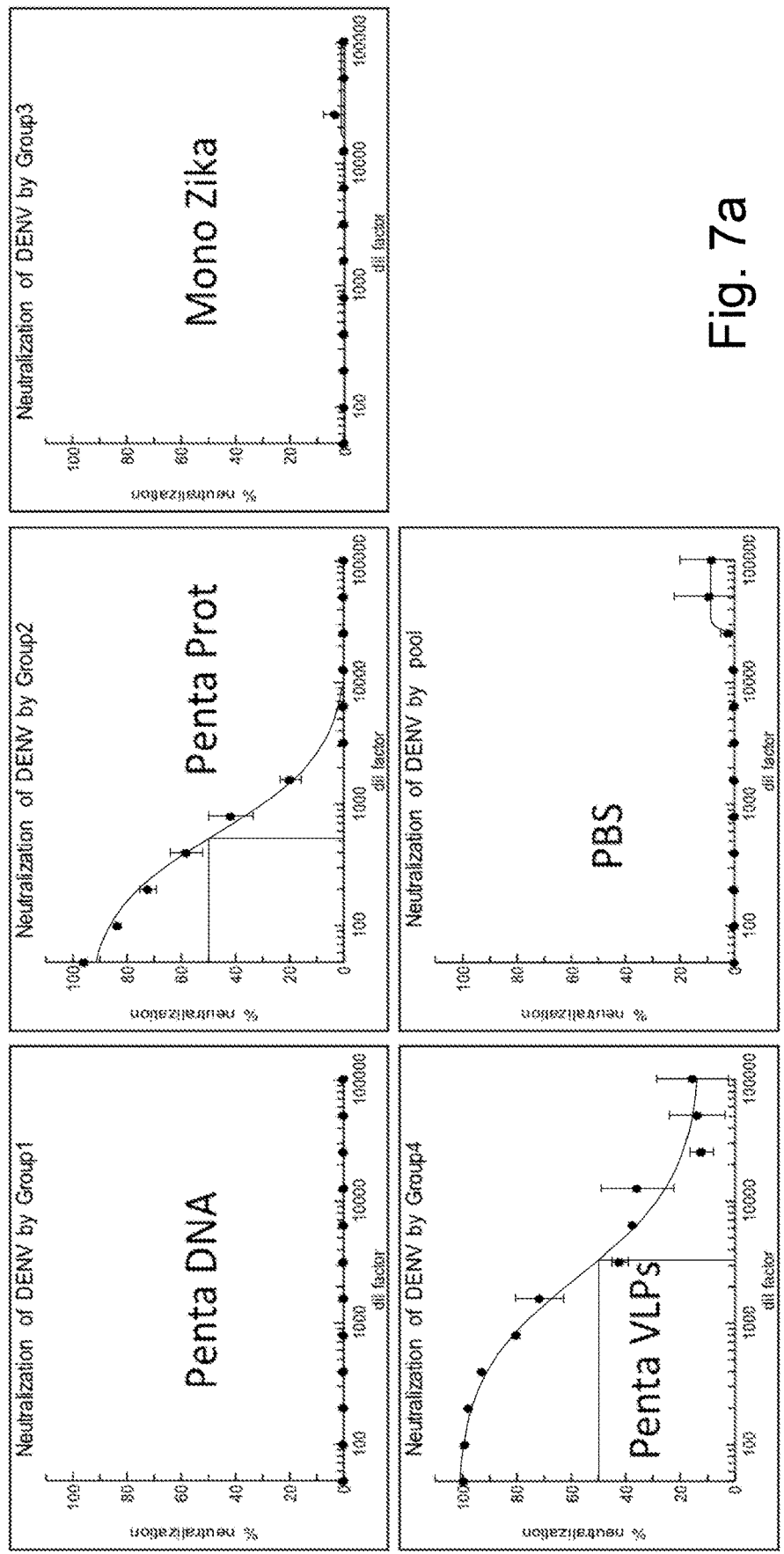

Sample Group 1-5: Dose-response curves against ZIKV

Fig. 7b

MODIFIED FLAVIVIRUS ENVELOPE SEQUENCES COMPRISING UNIQUE GLYCOSYLATION SITES

TECHNICAL FIELD

The invention relates to nucleic acid and protein variants of the wild-type E proteins of Flaviviruses (e.g., a dengue or Zika virus) and binding molecules, such as complementary nucleic acids or antigen-binding molecules, e.g., antibodies, specific thereto, as well as to compositions, such as therapeutic, prophylactic or diagnostic compositions, kits, kit-of-parts, methods and uses relating thereto, in particular for diagnosis of Flavivirus infection and for vaccines to immunise against Flavivirus infection.

SEQUENCE LISTING

This application hereby incorporates by reference the material of the electronic Sequencing Listing filed concurrently herewith. The material in the electronic Sequence Listing is submitted as a text (.txt) file entitled "EXCI001WO1US1_Sequence Listing-Oct2020.txt" created on 23 Oct. 2020, which has a file size of 157,503 bytes, and is herein incorporated by reference in its entirety.

BACKGROUND ART

The Flaviviridae are a family of positive, single-stranded, enveloped RNA viruses. They are found in arthropods, (primarily ticks and mosquitoes), and can infect humans. Members of this family belong to a single genus, Flavivirus, and cause widespread morbidity and mortality throughout the world. Some of the mosquito-transmitted viruses include: Dengue Fever, Zika virus, Yellow Fever, Japanese encephalitis and West Nile viruses. Other Flaviviruses are transmitted by ticks and are responsible of encephalitis and hemorrhagic diseases: Tick-borne Encephalitis (TBE), Kyasanur Forest Disease (KFD) and Alkhurma disease, and Omsk hemorrhagic fever.

Flaviviruses are small spherical virions encoding ten viral proteins: three structural (capsid, precursor membrane/membrane, and envelope (E)) and seven nonstructural proteins. The E protein has important roles in viral attachment to cells, fusion with endosomal compartments, and modulating host immune responses. The ectodomain of the virus E protein folds into three structurally distinct domains (DI, DII, and DIII) forming head-to-tail homodimers on the surface of the virion. DI is the central domain that organizes the entire E protein structure. DII is formed from two extended loops projecting from DI and lies in a pocket at the DI and DIII interface of the adjacent E protein in the dimer. At the distal end of DII is a glycine-rich, hydrophobic sequence called the fusion loop, which encompasses residues 98-110, and is highly conserved among flaviviruses. This region has been implicated in the pH-dependent type II fusion event; during this process it becomes exposed and reoriented outward, making it available for membrane contact. DIII forms a seven-stranded Ig-like fold, is the most membrane distal domain in the mature virion, and has been suggested to be involved in receptor binding. A stem region links the ectodomain to a two-helix C-terminal transmembrane anchor that is important for virion assembly and fusion.

Dengue disease is a mosquito-borne viral infection caused by dengue virus (DENV), one of the most important human pathogens worldwide. The infection produces a systemic disease with a broad spectrum of outcomes, ranging from non-symptomatic/mild febrile illness (Dengue Fever, DF) to severe plasma leakage and haemorrhagic manifestations (Dengue Haemorrhagic Fever, DHF) that can further evolve into potentially fatal conditions (Dengue Shock Syndrome, DSS). DENV, is spread by *Aedes* spp. mosquitoes and is widely distributed throughout the tropical and subtropical regions of the world. About 3 billion people, in over 100 countries, are estimated to be at risk of infection, with over 300 million infections, 500,000 episodes of DHF manifestations and 20,000 deaths reported each year. The spread and impact of Dengue disease has led the World Health Organization to classify it as the "most important mosquito-borne viral disease in the world".

Four different serotypes of dengue viruses (DENV1, DENV2, DENV3 and DENV4) have been identified to date; each serotype is pathogenic in humans. Infection with any one serotype induces lifelong immunity against that specific serotype, with only transient cross-protection against the three other serotypes. Severe manifestations of dengue infection are associated with secondary infections involving different viral serotypes; this happens through a mechanism known as antibody-dependent enhancement of infection (ADE). In ADE, recognition of viral particles by cross-reacting, but weakly or non-neutralising antibodies, leads to an increased Fc receptor-mediated uptake of immature or incompletely neutralised viruses by monocytes, macrophages and dendritic cells (the primary targets of dengue virus infections in humans) resulting in increased infectivity and deterioration of the patient's clinical condition. ADE is a critical consideration in dengue vaccine development, because an immunogen that does not elicit fully-neutralising antibodies to all four serotypes may contribute to disease, rather than prevent infection. Given the lack of efficient treatment against the infection and the risk to human health, there is a need to develop an efficient vaccine that provides a protective response without the potential to cause antibody-dependent enhancement.

One dengue vaccine has been licensed, Dengvaxia® (CYD-TDV), developed by Sanofi Pasteur. Approximately five additional dengue vaccine candidates are in clinical development, with two candidates (developed by Butantan and Takeda) expected to begin Phase III trials in early 2016.

In clinical trials, the Dengvaxia® vaccine was found to increase risk of hospitalization due to dengue haemorrhagic fever (the very disease it is meant to prevent) in young children (<5 years). As a result, Dengvaxia® vaccine has a limited license, i.e., only for persons of 9 years of age and above. Given the antigenic cross-reactivity of Zika and dengue, there is concern that vaccination with Dengvaxia® vaccine and other dengue vaccines under development may promote ADE of Zika virus, increasing the incidence of Guillain-Barre' syndrome in adults and microcephaly in infants, and that vaccines in development against Zika may likewise increase risk of dengue haemorrhagic fever, as does Dengvaxia in some subjects.

Zika virus is a mosquito-borne flavivirus that was first identified in Uganda in 1947 in monkeys, it was later identified in humans in 1952 in Uganda and the United Republic of Tanzania. Outbreaks of Zika virus disease have been recorded in Africa, the Americas, Asia and the Pacific. From the 1960s to 1980s, human infections were found across Africa and Asia, typically accompanied by mild illness. The symptoms are similar to infections such as dengue, and include fever, skin rashes, conjunctivitis, muscle and joint pain, malaise, and headache. These symptoms are usually mild and last for 2-7 days. However, Zika virus infection may cause complications in some subjects. Zika virus infection during pregnancy has been recognised as a cause of congenital brain abnormalities, including microcephaly. Zika virus is a trigger of Guillain-Barré syndrome. Links between Zika virus and a range of neurological disorders are being investigated.

Sanofi reported in 2016 its collaboration with the Walter Reed Army Institute of Research (WRAIR) in the United States and Fiocruz public health center in Brazil to develop a Zika vaccine and reported in 2016 that immunization with a plasmid DNA vaccine or a purified inactivated virus vaccine provided complete protection in susceptible mice against challenge with a strain of Zika virus involved in an outbreak in northeast Brazil (Larocca et al., 2016 Nature 536, 474-478 (25 Aug. 2016)

However, plasmid DNA vaccination in man requires 'gene gun' or similar technology (e.g., electroporation) for delivery and this approach is not considered to provide a global solution to the problems of dengue and Zika. Also, both the DNA vaccine and inactivated virus vaccine approaches in development contain dengue-Zika cross-reactive epitopes implicated in the causation of ADE.

After infection, or vaccination, the body's immune system produces neutralizing antibodies that bind to the surface proteins of a virus to block infection. Antibody-dependent enhancement (ADE) occurs when antibodies elicited by one virus can bind to, but do not block (neutralise) the infection of a similar virus.

ADE is most commonly observed for dengue virus. The 4 known serotypes of dengue virus have distinct, but related surface proteins. Infection with a first dengue virus serotype typically results in mild, or no, symptoms in the infected subject. If the subject is infected subsequently with a second dengue serotype, the immune system will produce antibodies to the first serotype that bind to the second serotype of virus, but will not always block infection and which have the potential to cause ADE. As a result there is antibody-mediated uptake of virus into cells that dengue virus does not normally infect (i.e., cells having receptors for the 'tail' or Fc region of the antibody). This can result in a more severe form of disease such as dengue hemorrhagic fever or dengue shock syndrome. Only young infants develop dengue haemorrhagic fever upon a first exposure to dengue, as a result of transplacentally transmitted maternal anti-dengue antibodies. As such, antibodies are equal partners with virus in (severe) disease causation in adults and infants alike.

Dengue virus antibodies not only promote ADE of other dengue virus serotypes, but also enhance Zika virus infection. Dejnirattisai et al., (2016) Nature Immunology 17, 1102-1108. "Dengue virus sero-cross-reactivity drives antibody-dependent enhancement of infection with Zika virus". Dejnirattisai et al. tested the effect of dengue neutralizing antibodies or serum from dengue virus patients on Zika virus in cell culture. In the absence of antibody, Zika virus poorly infected the cells, but when Zika virus was incubated with dengue serum or neutralizing antibodies, Zika virus robustly infected these cells, indicating the operation of ADE. The physiological relevance of this finding requires confirmation in epidemiological studies, but these findings pose an obvious risk for current vaccine approaches. To date no satisfactory solution to this problem has been conceived or advocated.

While vaccines in this field may transpire to have net benefit on a population basis, on an individual basis the picture is different. In some subjects, tragically, preventing one disease may increase the severity or risk of mortality from another. Paul L M et al. Clinical & Translational Immunology (2016) 5, e117 "Dengue virus antibodies enhance Zika virus infection" have reported that:

"For decades, human infections with Zika virus (ZIKV), a mosquito-transmitted Flavivirus, were sporadic, associated with mild disease, and went underreported since symptoms were similar to other acute febrile diseases. Recent reports of severe disease associated with ZIKV have greatly heightened awareness. It is anticipated that ZIKV will continue to spread in the Americas and globally where competent *Aedes* mosquito vectors are found. Dengue virus (DENV), the most common mosquito-transmitted human flavivirus, is both well-established and the source of outbreaks in areas of recent ZIKV introduction. DENV and ZIKV are closely related, resulting in substantial antigenic overlap. Through antibody-dependent enhancement (ADE), anti-DENV antibodies can enhance the infectivity of DENV for certain classes of immune cells, causing increased viral production that correlates with severe disease outcomes. Similarly, ZIKV has been shown to undergo ADE in response to antibodies generated by other flaviviruses. We tested the neutralizing and enhancing potential of well-characterized broadly neutralizing human anti-DENV monoclonal antibodies (HMAbs) and human DENV immune sera against ZIKV using neutralization and ADE assays. We show that anti-DENV HMAbs, cross-react, do not neutralize, and greatly enhance ZIKV infection in vitro. DENV immune sera had varying degrees of neutralization against ZIKV and similarly enhanced ZIKV infection. Our results suggest that pre-existing DENV immunity may enhance ZIKV infection in vivo and may lead to increased disease severity. Understanding the interplay between ZIKV and DENV will be critical in informing public health responses and will be particularly valuable for ZIKV and DENV vaccine design and implementation strategies."

Dengue virus antibodies can promote ADE of Zika virus. Zika virus antibodies can promote ADE of dengue virus. Thus, immunization against Zika virus could increase the incidence of dengue hemorrhagic fever or dengue shock syndrome, or foster the development of these conditions in individuals that would not otherwise have developed them, but for immunisation. Given the interval between infections, which can be several years, it will be years before post-marketing surveillance studies are able to inform if, and to what extent, new vaccines predispose to severe dengue disease (haemorrhagic fever, shock syndrome) or severe Zika sequelae, such as Guillain Barre' syndrome or microcephaly.

Accordingly, there is a clear need for vaccine approaches that are designed purposefully to avoid the problem of antibody-dependent enhancement.

Specific diagnosis of Flavivirus infections using current serological testing is complicated by the cross-reactivity between antibodies against other clinically-relevant flaviviruses. Cross-reactivity is particularly problematic in areas where different flaviviruses co-circulate or in populations that have been immunized with vaccines to Flaviviruses. The majority of cross-reactive antibodies are raised against the immunodominant flavivirus envelope (E) protein target a conserved epitope in the fusion loop at the distal end of domain II.

There is a need for a diagnostic approach that can differentiate between closely-related Flaviviruses, to assess if an individual is seronegative and thus has not been exposed to dengue or Zika, or if an individual is seropositive and has been exposed to Zika and/or dengue and for those who are seropositive, to distinguish to which of Zika and/or the four dengue serotypes the individual has been exposed. There is a need for a diagnostic approach that can be used to select subjects for immunization, or assess seroconversion to determine if immunization has raised a protective immune response against dengue or Zika. There is thus a need for diagnostic approaches that enable interrogation of the immune response to distinguish antibodies against the dengue virus serotypes and against Zika virus.

WO2016012800 discloses identification and characterisation of cross-reactive neutralising antibodies obtained from patients infected with dengue virus. The acute human antibody response was found to be focused on two major epitopes; a known epitope on the fusion loop (FL FLE), and a second epitope, said to be novel, which was found on intact virions or dimers of envelope protein and which encompassed areas of domains I, II and III. Antibodies reactive with the second epitope, the Envelope Dimer Epitope, or EDE, were reported to fully neutralise virus made in both insect and primary human cells in the low picomolar range. A subunit vaccine comprising a stabilized soluble protein E dimer was therefore proposed as a dengue vaccine. WO2016012800 discloses that a dengue virus envelope glycoprotein E ectodomain (sE; soluble envelope polypeptide/glycoprotein) refers to the 1-395 amino acid fragment of the envelope glycoprotein E of the dengue virus serotypes 1, 2 and 4, and to the 1-393 amino acid fragment of the envelope glycoprotein E of the dengue virus serotype 3. WO2016012800 described the EDE as a stabilised dimer of sE, selected from DENY-1 sE, DENV-2 sE, DENV-3 sE, DENV-4 sE and mutant sE thereof having at least one mutation (substitution) selected among H27F, H27W, L107C, F108C, H244F, H244W, S255C, A259C, T/S262C, T/A265C, L278F, L292F, L294N, A313C (S313C in DEN3) and T315C, which mutations are considered to contribute to increased stability in the dimer configuration. It is disclosed that mutant sE thereof may further comprise at least one mutation (substitution) selected from Q227N, E174N and D329N; preferably all three mutations Q227N, E174N and D329N, which mutations are said to mask non-appropriate immunogenic regions and allow the stabilized recombinant sE dimer of the invention to preferentially elicit neutralizing antibodies directed to all four dengue virus serotypes.

The sE dimer mutations described are said not to interfere with immunogenicity but to provide a higher dimer affinity, by including cysteine mutations at the dimer contacts to provide stabilization by cross-links, and/or by introduction of new glycosylation sites to allow chemical cross-linking between adjacent sugars on the dimer by click chemistry, and/or by substitution of at least one amino acid residue in the amino acid sequence of at least one sE monomer with at least one bulky side chain amino acid to allow forming cavities at the dimer interface or in domain 1 (D1)/domain 3 (D3) linker of each monomer.

WO2016012800 discloses that the envelope protein may be engineered such that an improved EDE is generated, an EDE which is incapable of being recognised or raising anti-fusion loop (anti-FL) antibodies was considered to be an improved EDE. It is disclosed that such improvement may be accomplished by one or more mutations, deletions or insertions in the envelope protein, by generating a hybrid protein wherein the specific epitope (without any antigens which would raise anti-FL antibodies) is fused to a scaffold protein, or by engineering the envelope protein by modifying the internal surface of the dimer (projecting to the inside of the virus) with sugars to make it less immunogenic by adding N or O linked glycan sequences.

Roby et al., (2013, 2014) describe an approach to development of a vaccine candidates for West Nile virus by introduction of large internal deletions within the capsid (C) gene of flavivirus genomes to generate replication-competent RNAs that are unable to be packaged into virions, yet maintain secretion of highly immunogenic subviral particles (SVPs) without generating infectious virus. Such pseudoinfectious C-deleted vaccines are able to replicate and secrete large amounts of non-infectious immunogenic subviral particles (SVPs) from transfected cells and thus are said to offer the combined benefit of the safety of noninfectious inactivated or subunit vaccines with the robust immune response generated by the replication of live vaccines.

Roby et al., (2013) generated a construct, pKUNdC/C (KUNdC18-100/CMV-C), with C-deleted CMV-promoter driven cDNA of West Nile virus Kunjin (KUNV) in which alpha helices 1, 2, and 4 were removed in two separate segments and the hydrophilic alpha helix 3 was maintained. In pKUNdC/C C-deleted WNV cDNA was placed under the control of one copy of the cytomegalovirus (CMV) promoter and the C gene was placed under the control of a second copy of the CMV promoter in the same plasmid DNA. The conservation of the larger cytosolic moiety (alpha helix 3) led to a significant improvement in SVP secretion compared to that of constructs with deletions of all alpha helices of C and dC44-59. Additional improvements to SVP secretion were also observed upon the incorporation of an Asn-linked glycosylation motif at N154 of the E protein, a feature of many circulating strains of WNV and recent isolates of KUNV, corresponding to an NYS motif at amino acids 154 to 156 of the E protein. pKUNdC/C was shown to generate single-round infectious particles (SRIPs) capable of delivering self-replicating C-deleted RNA producing SVPs to surrounding cells. However, the amounts of both SRIPs and SVPs produced from pKUNdC/C DNA were relatively low.

Roby et al., (2014) reported production of a second generation constructs with C-deleted cDNA of West Nile virus Kunjin (KUNV) in which the CMV promoter was replaced by a more powerful elongation factor EF1a promoter and different forms of C were used to attempt to increase SRIP production by optimizing trans-C expression. A construct containing an elongation factor EF1a promoter encoding an extended form of C was demonstrated to produce the highest titres of SRIPs and was immunogenic in mice. SRIP and SVP titres were further improved via incorporation of the N154 glycosylation motif in the envelope protein (corresponding to an NYS motif at amino acids 154 to 156 of the E protein) which enhanced secretion of SVPs.

Davis et al., (2014) investigated the ability of West Nile virus (WNV) to infect CD209-expressing cells. Mammalian cell-derived West Nile virus preferentially infects cells expressing the C-type lectin CD209L but not cells expressing CD209; by contrast, Dengue virus (DENV) infection is enhanced in cells expressing either attachment factor. DENV and WNV virions have very similar structures. Their surfaces consist of a regular array of 180 envelope (E) protein subunits arranged in an icosahedral lattice (36). The small membrane (M) protein, generated following furin-mediated processing of pre-membrane protein (prM), is also present on the virion surface but is mostly buried in the viral membrane. The major structural differences between DENV and WNV virions stem from the number and location of N-linked glycosylation sites in the DENV viral E proteins. Most DENV isolates contain glycosylation sites at residues 67 and 153, although the site at 153 may not always be utilized; WNV E proteins only contain an N-linked glycan at asparagine 154, although this is absent in many virus strains. The presence of N-glycosylation on the WNV E protein has been linked in some studies to increased neuro-invasiveness in mice and to altered cellular tropism in vitro. Davis et al. introduced a glycosylation site at position 67 into West Nile virus E. Reporter virus particles pseudotyped with this E protein infected cells using either CD209 or CD209L. Glycosylation sites were introduced at several other positions. The WNV strain NY99 prM-E expression plasmid pCBWN and a derivative of this plasmid lacking the N-linked glycosylation site at E protein residue 154 (NY99-N154Q) were used as templates for the introduction of novel N-linked glycosylation sites into the WNV E protein by site-directed mutagenesis. The following amino acid changes were introduced into NY99-N154Q: (i) Ala-54 to Thr (A54T) adds an N-linked glycosylation site at Asn-52; (ii) D67N adds a site at Asn-67; (iii) K84T adds a site at Asn-82; (iv) A173N and P174G (AP173NG) add a site at Asn-173; (v) Glu-182 to NGS (E182NGS) adds a site at Asn-182 by mutating Glu-182 to Asn and inserting two amino acids (Gly-Ser) to complete the sequon; (vi) S230N and V232T (STV230NTT) add a site at Asn-230; (vii) V279T adds a site at Asn-277; (viii) T301N and G303S (TYG301NYS) add a site at Asn-301; (ix) T330N adds a site at Asn-330; (x) K370T adds a site at Asn-368; (xi) G389N and Q391T (GEQ389NET) add a site at Asn-389. All sites allowed CD209L mediated infection, but only a subset promoted CD209 use. As seen for other viruses, mannose-rich glycans on West Nile virus were required for its interactions with CD209, however, mannose-rich glycans were not required for CD209L mediated infection. Complex glycans, particularly N-acetylglucosamine-terminated structures, were able to mediate reporter virus particle interactions with CD209L. Davis et al. proposed that that CD209L recognizes glycosylated flaviviruses with broad specificity, whereas CD209 is selective for flaviviruses bearing mannose-rich glycans and thus that the location of the N-linked glycosylation sites on a virion determines the types of glycans incorporated, thus controlling viral tropism for CD209-expressing cells.

STATEMENT OF INVENTION

The invention provides an isolated recombinant analogue of a flavivirus E-protein fusion loop comprising at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon may occupy any of positions 98-110 (SEQ ID NO: 1 DRGWGNGCGLFGK) of the natural flavivirus E-protein fusion loop amino acid sequence, wherein X is any amino acid residue except proline and Ser/Thr denotes a serine or threonine residue.

An isolated recombinant analogue of a flavivirus E-protein fusion loop according to the invention may comprise two glycosylation sites that are not present in a natural flavivirus E-protein fusion loop sequence.

The invention provides an isolated recombinant analogue of a flavivirus E-protein comprising an analogue of a flavivirus E-protein fusion loop of the invention. In some embodiments the only modifications to the sequence of the isolated recombinant analogue of a flavivirus E-protein are the modifications of the invention in the fusion loop to introduce N-linked glycosylation sequon(s) (Asn-X-Ser/Thr), in other embodiments one or more further modifications may be introduced in flavivirus E-protein at residues outside the fusion loop.

An analogue of the invention having at least one additional glycan attached thereto is provided. Preferably the at least one additional glycan is an N-linked glycan. Preferably an analogue of the invention is the product of expression of a recombinant DNA or RNA sequence. The at least one additional glycan may be present at one or more native glycosylation sites in the flavivirus E-protein outside the flavivirus E-protein fusion loop.

An analogue of the invention, may comprise an N-linked glycosylation sequon (Asn-X-Ser/Thr) such that an Asn (N) residue of the sequon occupies any of positions 98-101 and/or 106-110.

Preferably, in an analogue of the invention, X is any of the following 13 amino acid residues Gly, His, Asn, Gln, Tyr, Val, Ala, Met, Ile, Lys, Arg, Thr or Ser.

In preferred analogues of the invention, the flavivirus E-protein is a dengue virus E-protein and the Asn (N) residue of a sequon occupies position 101, 108 or both 101 and 108 of the amino-acid sequence of the analogue flavivirus E-protein fusion loop or the flavivirus E-protein is a Zika E-protein and the Asn (N) residue of a sequon occupies position 100 of the amino acid sequence of the analogue flavivirus E-protein fusion loop.

In a preferred analogue of the invention, the flavivirus is a dengue virus and the amino acid sequence of the analogue flavivirus E-protein fusion loop 98-110 is selected from: SEQ ID NO: 2 DRGNGSGCGLNGS, SEQ ID NO: 3 DRGNGSGCGLFGK and SEQ ID NO: 4 DRGWGNGCGLNGS.

In another preferred analogue of the invention, the flavivirus is a Zika virus and the amino acid sequence of the analogue flavivirus E-protein fusion loop 98-110 is SEQ ID NO: 5 DRNHTNGCGLFGK.

The invention further provides an isolated recombinant DNA or RNA sequence comprising a sequence encoding an analogue of a flavivirus E-protein fusion loop according to the invention.

An isolated recombinant DNA sequence may be a plasmid or a linear DNA-based vaccine. An isolated recombinant DNA sequence of the invention may encode an analogue of a flavivirus E-protein according to the invention under control of a mammalian promoter.

The invention yet further provides a host cell comprising a DNA or RNA sequence according to the invention. The host cell may be an eukaryotic host cell comprising a DNA sequence according to the invention or a plasmid or linear DNA-based vaccine immunogen according to the invention.

Preferably, a host cell of the invention is capable of expressing an analogue of the invention. Further preferably, a host cell of the invention is capable of expressing and glycosylating an analogue of the invention.

The invention provides a method of making an analogue of the invention comprising culturing a host cell according to the invention in conditions suitable for expression of the analogue and isolating the analogue.

Further provided is a composition comprising an analogue of the invention and a diluent.

A composition of the invention may be an immunogenic (vaccine) composition capable of inducing an immunological response in a subject inoculated with said composition, the composition comprising an analogue according to the invention together with a pharmaceutically acceptable diluent, adjuvant and/or carrier.

A composition of the invention may comprise one or more flavivirus analogues of the invention selected from an analogue of DEN-1, an analogue of DEN-2, an analogue of DEN-3, an analogue of DEN-4 and an analogue of Zika.

A composition of the invention may comprise four dengue analogues of the invention representing each of the four dengue virus serotypes DEN-1 DEN-2 DEN-3 and DEN-4.

A composition of the invention may comprise a zika virus analogue of the invention.

A composition of the invention may comprise four dengue analogues of the invention representing each of the four dengue serotypes DEN-1 DEN-2 DEN-3 and DEN-4 and a zika virus analogue of the invention.

The invention also provides a binding molecule capable of binding specifically to an analogue of the invention. The binding molecule may be an antibody or a fragment thereof, a domain antibody, a protein scaffold, or an aptamer, provided that it is capable of binding specifically to an analogue of the invention.

The invention provides an analogue, composition or binding molecule of the invention for use as a medicament.

Further, the invention provides an analogue, composition or binding molecule of the invention for use as a vaccine.

Also provided is an analogue, composition or binding molecule of the invention for use as a medicament for the prophylactic or therapeutic treatment of a flavivirus infection or for use in the manufacture of a medicament for the prophylactic or therapeutic treatment of a flavivirus infection.

The invention provides a method for the protection of a subject against infection by a Flavivirus, comprising administering an analogue, composition of or binding molecule of the invention to said subject.

In preferred embodiments the flavivirus infections is a dengue virus infection or a Zika virus infection.

The invention provides an analogue, composition or binding molecule of the invention for use as a diagnostic.

The invention provides a diagnostic kit comprising an analogue, composition or binding molecule of the invention and a reagent capable of detecting an immunological (antigen-antibody) complex which contains said isolated analogue or binding molecule.

A diagnostic test kit in accordance with the invention may further comprise one or more control standards and/or a specimen diluent and/or washing buffer.

In a diagnostic test kit of the invention, the analogue and/or binding molecule specific thereto of the invention may be immobilized on a solid support. The solid support may be a microplate well. In a diagnostic test kit according to the invention, an immunological complex which contains said isolated analogue or binding molecule may be detected by ELISA or by lateral flow.

The invention provides vaccine approaches that are designed purposefully to avoid the problem of antibody-dependent enhancement.

The invention provides diagnostic approaches that can differentiate between closely-related Flaviviruses, to assess if an individual is seronegative and thus has not been exposed to dengue or Zika, or if an individual is seropositive and has been exposed to Zika and/or dengue and for those who are seropositive, to distinguish to which of Zika and/or the four dengue serotypes the individual has been exposed. The invention provides diagnostic approaches that can be used to select subjects for immunization, or assess seroconversion to determine if immunization has raised a protective immune response against dengue or Zika. The invention provides diagnostic approaches that enable interrogation of the immune response to distinguish antibodies against the dengue virus serotypes and against Zika virus.

DETAILED DESCRIPTION OF THE INVENTION

The invention is be described with reference to various embodiments of different aspects of the invention. It is appreciated that certain features of the invention, which are, for clarity, described in the context of separate embodiments, may also be provided in combination in one or more embodiments or in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The invention provides modified Flavivirus nucleic acid and protein sequences in which the natural (native, wild-type) E-protein fusion loop epitope, known to be associated with generation of flavivirus cross-reactive, infection-enhancing antibodies has been modified to comprise one or more (e.g., 2) glycosylation sites for glycosylation of the protein with an N-linked glycan that is not normally present on the native fusion loop epitope. Such modification alters the fusion loop amino acid sequence and the presence of a glycan further disguises the epitope. Thus the modified Flavivirus nucleic acid and protein sequences of the invention are designed to generate a protective response without concomitant generation of flavivirus cross-reactive infection-enhancing antibodies, thereby intending to avoid the problems of antibody-dependent enhancement observed with existing vaccine approaches. The modified Flavivirus nucleic acid and protein sequences of the invention are also designed for diagnostic use, either as antigens for detection of a specific Flavivirus or to generate binding molecules such as antibodies for detection of a specific Flavivirus.

By antibody we include the meaning of a substantially intact antibody molecule, as well as a chimeric antibody, humanised antibody (wherein at least one amino acid is mutated relative to a non-human antibody, for example a naturally occurring non-human antibody or antibody assembled from non-human antibody sequences), single chain antibody, bi-specific antibody, antibody heavy chain, antibody light chain, homo-dimer or heterodimer of antibody heavy and/or light chains, and antigen binding portions and derivatives of the same. When the compound is a protein, for example an antibody or fragment thereof is administered to a human subject and if the antibody is not a human antibody or fragment thereof, then it can be humanized in order to reduce immunogenicity in human. Methods for producing humanized antibodies or fragments thereof are known in the art.

A binding molecule of the invention is preferably an antibody or antigen binding portion thereof. The antigen binding portion may be a Fv fragment; a Fab-like fragment (e.g. a Fab fragment, a Fab' fragment, a F(ab)2 fragment, Fv or scFv fragments); or a domain antibody. The antibody binding portion may be derived from the linear amino acid sequence present in an intact antibody, or may comprise a set of non-consecutive amino acids, optionally interspersed with other amino acids, for example may comprise particular amino acids that are required for contact with an epitope, but may for example not comprise the amino acids required for the framework of a native antibody, which, in some cases, may be replaced by a heterologous scaffold protein, for example. An antibody according to the present invention is obtainable by a method comprising a step of immunizing a mammal, such as a human, a monkey, a rabbit or a mouse; and/or by an in vitro method, for example comprising a phage display selection step, as will be well known to those skilled in the art.

The term antibody also includes all classes of antibodies, including IgG, IgA, IgM, IdD and IgE. The term antibody also includes variants, fusions and derivatives of any defined antibodies and antigen binding portions thereof.

By neutralise we mean reduce the ability of the virus to infect previously uninfected cells. The person skilled in the art will be well aware of suitable techniques to monitor viral neutralising ability.

Methods for manipulation of nucleic acid sequences to introduce sequence changes as described herein are well known in the art.

E-proteins, 4 residues were changed to make two glycosylation sites (pCRO21-24). In the case of Zika E-protein, 3 residues were changed to make one glycosylation site (pCRO28).

The constructs pCRO25, 29, 30 and 31 did not express well in the expression system chosen, thus in some contexts the recombinant analogue sequences of the invention do not comprise the following sequences:

```
pCRO25
                                         (SEQ ID NO: 7)
CKRTLVDRGNGSGCGLNGSGSLVICAKFA pCRO29
                                         (SEQ ID NO: 8)
CKRTLVDRGWGNGCGNHTKGSLVTCAKFA pCRO30
                                         (SEQ ID NO: 9)
CKRTLVDRGNGSGCGLFGKGSLVTCAKFA
```

TABLE 1

Alignment of amino acids 98-110 of a group of wild-type sequences of flaviviruses and recombinant analogue sequences of the invention.

| | | |
|---|---|---|
| 1 | ZIKV_H/PF/2013 | DRGWGNGCGLFGK (SEQ ID NO: 1) |
| 2 | ZIKV_MR766 | DRGWGNGCGLFGK (SEQ ID NO: 1) |
| 3 | DENV_1_SG/07K3640DK1/2008 | DRGWGNGCGLFGK (SEQ ID NO: 1) |
| 4 | DENV_2_16681 | DRGWGNGCGLFGK (SEQ ID NO: 1) |
| 5 | DENV_3_SG/05K863DK1/2005 | DRGWGNGCGLFGK (SEQ ID NO: 1) |
| 6 | DENV_4_SG/06K2270DK1/2005 | DRGWGNGCGLFGK (SEQ ID NO: 1) |
| 7 | WNV_NY99 | DRGWGNGCGLFGK (SEQ ID NO: 1) |
| 8 | JEV_SA14 | DRGWGNGCGLFGK (SEQ ID NO: 1) |
| 9 | YFV_Asibi | DRGWGNGCGLFGK (SEQ ID NO: 1) |
| 10 | pCRO21 (dengue-1 HX) | DRGNGSGCGLNGS (SEQ ID NO: 2) |
| 11 | pCRO22 (dengue-2 HX) | DRGNGSGCGLNGS (SEQ ID NO: 2) |
| 12 | pCRO23 (dengue-3 HX) | DRGNGSGCGLNGS (SEQ ID NO: 2) |
| 13 | pCRO24 (dengue-4 HX) | DRGNGSGCGLNGS (SEQ ID NO: 2) |
| 14 | pCRO28 (Zika HX) | DRNHTNGCGLFGK (SEQ ID NO: 5) |
| 15 | pCRO26 (dengue-1 HX) | DRGNGSGCGLFGK (SEQ ID NO: 3) |
| 16 | pCRO27 (dengue-1 HX) | DRGWGNGCGLNGS (SEQ ID NO: 2) |
| 17 | pCRO25 (Zika) | DRGNGSGCGLNGS (SEQ ID NO: 2) |
| 18 | pCRO29 (Zika) | DRGWGNGCGNHTK (SEQ ID NO: 6) |
| 19 | pCRO30 (Zika) | DRGNGSGCGLFGK (SEQ ID NO: 3) |
| 20 | pCRO31 (Zika) | DRGWGNGCGLNGS (SEQ ID NO: 2) |

The fusion loop DRGWGNGCGLFGK (defined as residues 98-110, SEQ ID NO: 1) in the wild type sequences (rows 1 to 9) is shown in bold. The residues changed to make the N-linked glycosylation sequons in the modified analogue HX sequences are shown in bold in rows 10-20 The constructs pCRO21-24, 26, and 28 expressed well and were selected for further investigation. In the case of dengue

```
-continued
pCRO31
                                        (SEQ ID NO: 10)
CKRTLVDRGWGNGCGLNGSGSLVTCAKFA.
```

In an analogue of the invention, the N-linked glycosylation sequon (Asn-X-Ser/Thr) may be present such that an Asn (N) residue of the sequon occupies any of positions 98-101 and/or 106-110. That is, the N residue may occupy position a position selected from 98, 99, 100, and 101 and/or a position selected from 106, 107, 108, 109 and 110.

Preferably, in an analogue of the invention, X is any of the following 13 amino acid residues Gly, His, Asn, Gln, Tyr, Val, Ala, Met, Ile, Lys, Arg, Thr or Ser, with Gly or His being particularly preferred. In specific embodiments of the invention described herein for dengue viruses it is preferred that X is Gly and for Zika is preferred that X is His.

In preferred analogues of the invention, the flavivirus E-protein is a dengue virus E-protein and the Asn (N) residue of a sequon occupies position 101, 108 or both 101 and 108 of the amino-acid sequence of the analogue flavivirus E-protein fusion loop or the flavivirus E-protein is a Zika E-protein and the Asn (N) residue of a sequon occupies position 100 of the amino acid sequence of the analogue flavivirus E-protein fusion loop.

In a preferred analogue of the invention, the flavivirus is a dengue virus and the amino acid sequence of the analogue flavivirus E-protein fusion loop 98-110 is selected from:

DRGNGSGCGLNGS, (SEQ ID NO: 2)

DRGNGSGCGLFGK (SEQ ID NO: 3)
and

DRGWGNGCGLNGS. (SEQ ID NO: 4)

In another preferred analogue of the invention, the flavivirus is a Zika virus and the amino acid sequence of the analogue flavivirus E-protein fusion loop 98-110 is DRNHTNGCGLFGK (SEQ ID NO: 5).

The nucleic acid sequence encoding recombinant analogue E-protein fusion loop protein or encoding recombinant analogue E-protein comprising such fusion loop protein can be generally be expressed following the functional and operable insertion of the DNA sequence into an expression vector containing control sequences and secretory signal sequences.

A suitable promoter for expression of nucleic acid sequences of the invention is CMV.

Host cells that may be employed in accordance with the invention include HEK and CHO cell lines. The host may be genetically engineered to produce therapeutic glycoproteins with human-like N-linked glycans.

The immunogenic composition of the invention may be administered with or without adjuvant. Adjuvants can be added directly to the immunogenic composition or can be administered separately, either concurrently with or shortly after, administration of the vaccine. Such adjuvants include but are not limited to aluminium salts (aluminium hydroxide), oil-in-water emulsion formulations with or without specific stimulating agents such as muramyl peptides, saponin adjuvants, cytokines, detoxified mutants of bacteria toxins such as the cholera toxin, the pertussis toxin, or the *E. coli* heat-labile toxin.

The immunogenic composition of the invention may be administered with other immunogens or immunoregulatory agents, for example, immunoglobulins, cytokines, lymphokines and chemokines.

In specific embodiments described herein the adjuvant used was Alhydrogel®, which is an acceptable adjuvant for human and veterinary use. However it should be apparent to a person skilled in the art that other suitable adjuvants and adjuvantation and formulation strategies are available for either (or both) nucleic acid and protein forms of the antigens. Alhydrogel requires proteins to be negatively charged at neutral or near-neutral pH values (eg. pH 7.4) in order to be maximally effective. This is because Alhydrogel has a net positive charge under such conditions of pH. Aluminium phosphate, conversely has a net negative charge and is generally better for proteins that are positively charged under physiological conditions of pH used for vaccine formulation. If proteins have a near neutral isoelectric point they may not bind well to Alhydrogel or aluminium phosphate adjuvants, limiting the adjuvant effect, and would benefit from other adjuvantation strategies.

For example vaccine adjuvants based on oil-in-water emulsions or liposome suspensions have made considerable progress in licensed vaccine products and in clinical trials recently (Alving, Beck, Matyas, & Rao, 2016). These adjuvant materials exploit either natural or synthetic versions of monophosphoryl lipid-A, with and without other adjuvant materials such as QS21 saponin and CpG adjuvant. Such strategies have allowed the development of a highly efficacious vaccine against shingles and a promising malaria vaccine candidate (after 30 years of research) which is expected to be licensed soon.

Other promising delivery and adjuvantation strategies have been developed, e.g. Virosomes, which may be suitable for use with the glycosylated exodomain proteins of the present disclosure. Likewise there are promising adjuvant materials and strategies in earlier stages of development such as CD40 agonistic antibodies as stand-alone, conjugate or liposomal vaccine components (Hatzifoti C, Bacon A, Marriott H, Laing P, Heath A W (2008) Liposomal Co-Entrapment of CD40mAb Induces Enhanced IgG Responses against Bacterial Polysaccharide and Protein. PLOS ONE 3(6): e2368). Compositions of the invention may be used in co-delivery strategies for administration of protein and DNA vaccines, such as by liposomal formulation (Laing et al., 2006).

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, Molecular Cloning: A Laboratory Manual, Second Edition (1989), Oligonucleotide Synthesis (M. J. Gait Ed., 1984), Animal Cell Culture (R. I. Freshhey, Ed., 1987), the series Methods in Enzymology (Academic Press, Inc.); Gene Transfer Vectors for Mammalian Cells (J. M. Miller and M. P. Calos eds. 1987), Handbook of Experimental Immunology, (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

Standard three and one-letter terminology is used for amino acid residues.

As used herein, the term "recombinant" refers to the use of genetic engineering methods (cloning, amplification) to produce an analogue, or a binding molecule such as an antibody or an antibody fragment of the present invention.

The principal problem of dengue vaccine development, wherein the use of vaccines runs the risk (in a finite number of cases) of giving rise to 'antibody dependent enhancement' of dengue infection, making the illness worse rather than preventing it. The application relates quite generally to flavivirus vaccines, because it applies to highly conserved sequences of the envelope protein 'E' of this family of viruses. Enhancement is a feature of natural infection (where antibodies sent to neutralize the virus are subverted to gain access to human myeloid cells), usually upon encounter with a second 'serotype' of virus, resulting in more severe symptoms (Halstead, Rojanasuphot, & Sangkawibha, 1983). Vaccination, while for the most part conferring protection, is also liable on some occasions to predispose a recipient to severe dengue, including dengue haemorrhagic fever (DHF), upon first exposure to a wild dengue virus: i.e., 'iatrogenic' cases of severe dengue or DHF, which would not have occurred but for the vaccine. Furthermore, existing vaccine approaches also have the potential to create a population of vaccinated individuals who develop severe iatrogenic dengue, at some interval after the vaccine (or vaccine course) has been administered (e.g. a decade). This is because, as immunity to dengue wanes, protective antibodies reach a concentration where they 'enhance' rather than prevent infection. Also, the rate of decay of 'immunological memory' (where the immune system recalls encounter with a wild virus or vaccine dose) is not synchronous for the four serotypes of the vaccine, such that immunity to each serotype (at the antibody and memory level) of dengue is lost at different times, successively increasing the risk of severe disease. This gradual failure of immune memory likewise creates a new population of individuals who are now predisposed to severe dengue (when bitten by an infected mosquito), instead of protected, as a result of previous vaccination. The solution is to make a vaccine that has zero or minimal propensity to give rise to 'antibody dependent enhancement', while preserving efficacy, in a manner amenable to incorporation into several of the various vaccine formats now in existence (live vector, DNA vaccine, oral vaccine, subunit vaccine, virus-like particles etc.). The invention of the present application avoids cases of vaccine-induced enhancement of disease by dengue and/or Zika vaccines by creating novel immunogens that fail to produce antibodies that facilitate infection. This is achieved by introducing one or more additional glycosylation sites (e.g. N-linked glycosylation sites) into particular site(s) of recombinantly expressed E-proteins of dengue and Zika viruses that are particularly associated with the generation of infection-enhancing antibodies, thereby cloaking such sites, and preventing them from generating antibodies following vaccination.

While current vaccines against dengue (licensed and in development) may meanwhile prove to be of substantial 'net' benefit to public health, improved safety is still desirable in order to avoid cases of vaccine-induced dengue (i.e., iatrogenically-caused severe dengue). The likely role of natural dengue infection in paving the way for pandemic Zika infection has been elaborated recently by Philip K Russell of the Sabin Vaccine Institute (Russell, 2016). While no systematic investigation has been conducted that would determine the risk of dengue vaccination predisposing to Zika virus infection or of dengue vaccination giving rise to Zika infections of enhanced severity, it is a logical extension of Russell's observations to expect such cases. Likewise although dengue-vaccine-induced predisposition to severe dengue has not yet been reported or investigated 'as such', in a recent three-year follow-up study of the Sanofi-Pasteur vaccine there was an increased rate of hospitalisation in children less than nine years of age (Hadinegoro et al., 2015) which could be explained by vaccine-induced enhancement of susceptibility to severe dengue. These new epidemiological developments, and laboratory data (below) indicate that there is a significant risk that vaccines (unless designed to avoid enhancement) will cause, in some instances, enhancement of disease: i.e. dengue vaccination will result in cases of severe dengue that would not otherwise have happened. It is also possible that dengue vaccines could facilitate the spread of Zika virus infection if used on a population-wide basis. The legitimacy of this concern is supported additionally by in vitro experimental data which demonstrates that dengue virus antibodies enhance the infection of human myeloid cells by Zika virus (Paul et al., 2016). Furthermore, it follows that a stand-alone Zika vaccine could give rise to similar antibodies that would (conversely) enhance dengue infection giving rise to cases of severe iatrogenic dengue, by generating anti-Zika antibodies that cross-react with dengue virus, and that facilitate dengue infection. For the purposes of this application, while not wishing to be bound by any particular hypothesis, Zika virus is accorded the status of a 'fifth dengue serotype'. This is because dengue infection (and dengue vaccines) have the potential to facilitate the spread of Zika by generating infection-enhancing antibodies which also react with Zika virus facilitating its infection of bodily cells. In addition to novel immunogens, the present disclosure has an additional safety feature which minimises any tendency for vaccine to enhance dengue or Zika infection (upon being bitten by an infected mosquito), by combining these vaccines in a single dose or course of vaccination, in the form of a pentavalent vaccine representing the four serotypes of dengue, plus Zika virus.

The invention relates to vaccines to prevent flavivirus infections, in particular to vaccines to prevent dengue and Zika infections. Since the advent of Zika as a pandemic phenomenon, its rapid global spread apparently facilitated by dengue-infection (Russell, 2016), the problem of vaccination (i.e. how to make a vaccine that does not, in some cases, worsen disease) has become more complicated. A new vaccine design is required in order to avoid homologous enhancement (whereby a dengue vaccine would facilitate, in some cases, dengue infection) and cross-enhancement (whereby a dengue vaccine would facilitate, in some cases, Zika infection); and moreover, whereby a Zika vaccine would facilitate, in some cases, dengue infection. Conventional approaches to the antibody enhancement problem, which involve such stratagems as combining all four serotypes of dengue in a single vaccine (Sanofi-Pasteur) or, for example, a subunit approach using N-terminal regions of the E-proteins of dengue (Merck) have recognized the antibody enhancement problem but have not provided a comprehensive solution appropriate to the Zika-pandemic situation. The most advanced dengue vaccine (the licensed Sanofi-Pasteur live attenuated tetravalent dengue vaccine), fails to deal with Zika, and from the epidemiological and in vitro observations above may be capable of promoting cases of Zika virus infection by cross-enhancement (even while having a net benefit community-wide by dint of herd immunity).

It is important to recognize that the distinction between enhancing epitopes and protective epitopes of flaviviruses is not 'binary' in character. Generally speaking, almost all anti-dengue-E antibodies (for example) have the potential to be both neutralising and infection-enhancing, the latter property emerging at lower antibody concentrations (Dejnirattisai et al., 2014), e.g. as immunity to a vaccine or an exposure wanes. Moreover, Dejnirattisai et. al. also found that antibodies against the fusion loop of the dengue E-protein (which comprise about half of all antibodies generated convalescently) are markedly worse than antibodies against other sites on the E-protein in terms of their propensity for antibody-dependent enhancement of infection.

The present disclosure provides a vaccine that deals with the issues of antibody-dependent enhancement and cross-enhancement, by providing immunogens that have reduced capacity to elicit or stimulate infection-enhancing antibodies. In order to ensure that infection-enhancing antibodies are not generated, the present disclosure uses E-proteins with an additional glycan planted in the fusion loop, by virtue of engineering an additional, novel, glycosylation site into the nucleotide and amino acid sequence of recombinantly expressed E-proteins. The 'cloaking' effect of the glycan prevents antibodies being generated against the fusion loop site, while preserving other sites better situated to generate neutralising antibodies. In this way, glycans, which are usually considered an impediment to the generation of neutralising antibodies (e.g. in the case of HIV where they mask much of the protein surface with glycan structures that are substantially identical to those of host glycoproteins) are used to advantageous effect, i.e. in the present disclosure to mask a site on a vaccine immunogen that would otherwise give rise to problematic antibody responses (in this case, infection-enhancing antibodies).

In the case of dengue, four vaccine antigens are needed, namely the E-proteins of the four serotypes, suitably modified by glycoengineering to mask epitopes involved in antibody dependent enhancement. However, because of the risk of mutual cross-enhancement of dengue and Zika virus infections as a result of infection or vaccination, it is apparent that a Zika component is also desirable, i.e. a 'pentavalent' vaccine covering the four serotypes of dengue 'and' Zika.

Fortunately, from the point of view of the present vaccine design, the E-protein of Zika virus is highly homologous in terms of its amino acid sequence and three-dimensional structure, to that of the dengue virus E-proteins. The recent cryo-EM 3.8 Angstrom structure of the Zika virion E-protein clearly identifies (by analogy) the Zika E-protein fusion loop location (Kostyuchenko et al., 2016; Sirohi et al., 2016). Indeed Sirohi et. al. catalogue the remarkable degree of homology among diverse flaviviruses with respect to the fusion loop sequence "DRGWGNGCGLFGK" SEQ ID NO: 1 (residues 98-110), which is perfectly preserved among diverse virus isolates of Zika, the four dengue serotypes, West-Nile, Japanese encephalitis and yellow fever viruses (see supplementary figure S2 of Sirohi).

There are notable differences between dengue and Zika E-proteins, such as a five amino acid insert in the Zika E-protein, and the fact that Zika has a single N-linked glycan rather than two per monomer, but these differences are highly permissive of the present vaccine design. In the present disclosure it is anticipated that the E-protein fusion loop of Zika virus will be a site recognized particularly by infection-enhancing antibodies capable of homologous and heterologous enhancement of infection, i.e. a site against which antibody production during infection or vaccination is not desirable.

Methods for introducing additional glycosylation sites into proteins by site directed mutagenesis are well known in the art. In particular the creation of Aranesp (darbepoetin alfa), a modified form of the natural hormone erythropoietin, is a good example (Elliott ("EP0640619A1," 2010), (Elliott et al., 2003). It is important in making suitable genetic constructs to ensure that the leader sequence of the protein is incorporated into recombinant plasmid or other vector DNA sequences, in order to direct the nascent polypeptide chain into the endoplasmic reticulum of the host cell, allowing glycosylation and to facilitate protein folding. Various eukaryotic cell systems are suitable for recombinant production—such as Chinese hamster ovary cells (CHO), as well as yeast (e.g., *Pichia pastoris*) and other vector systems such as baculovirus (which has the added advantage of equipping the viral protein immunogen with an insect glycan, as per the inoculum form of the flavivirus). However, prokaryotic systems such as those based on *E. coli* are not suitable, because they do not have the cellular apparatus required to effect glycosylation of proteins.

In the case of Aranesp, the molecule has two additional N-linked glycosylation sites, strategically placed to avoid hindrance of interaction of the glycoengineered molecule with the erythropoietin receptor. The purpose of glycoengineering the earlier erythropoietin-based product in this way was to improve the longevity of the molecule in circulation by increasing its size giving rise to a product that can be administered once instead of thrice weekly (Elliott et al., 2003). Glycoengineering is 're-purposed' in the present disclosure, to cloak a site on a vaccine immunogen that would otherwise have adverse consequences of antibody dependent enhancement of infection.

Viruses have been demonstrated to exploit the immune-evasion properties of glycans thwarting the generation of neutralising antibodies. In the field of vaccine development (e.g. against HIV glycoprotein gp160/120), glycans have generally been regarded as a problem (rather than an aid to vaccine development), limiting the access of antibodies to the protein surface of a glycoprotein antigen by forming a dense glycocalyx comprised of host glycans, to which the immune system of the host is programmed to be immunologically tolerant. There are notable exceptions that prove the generality of this rule: e.g. where the glycan itself or a minor variant is a target or part thereof, which is the case for rare anti-HIV neutralising antibodies; and in the case of insect-specific glycan epitopes on arboviruses, which are themselves targets in some vaccine designs)(Dalziel, Crispin, Scanlan, Zitzmann, & Dwek, 2014). The present disclosure is different from the prior art in exploiting the stealth qualities of glycans to advantageous effect in a vaccine immunogen. In this novel application a glycan is used to cloak a troublesome site on a vaccine immunogen, preventing antibodies from being generated that would recognise the equivalent uncloaked site on the natural virion. Glycoengineering (unlike deletion or truncation of amino acid sequence elements) allows this cloaking to be achieved while causing minimal interference with the underlying structure of the protein part of the antigen. Preservation of protein structure by employing glycoengineering rather than deletion or truncation protects remote neutralising epitopes that might otherwise be altered to detrimental effect.

The glycoengineered flavivirus E-proteins of the present disclosure are amenable to incorporation into various forms for the purpose of vaccination. These forms may be protein (i.e. glycoprotein) or nucleic acid in character. They may be represented in a vaccine formulation as a mixture of purified proteins (as a subunit vaccine, e.g. with aluminium hydroxide or aluminium phosphate as adjuvant), as virus-like particles (Frietze, Peabody, & Chackerian, 2016), or as mammalian-expressible DNA constructs (e.g. plasmid DNA with cytomegalovirus promoter) for administration as DNA vaccines using subunit (Tregoning & Kinnear, 2014) or infectious-attenuated clone approaches as exemplified for the YFD strain of yellow fever virus (Tretyakova et al., 2014). They are also amenable to incorporation into live attenuated virus vectors such as measles vector vaccines as per the Chikungunya vaccine candidate by Themis Bioscience GmbH (Ramsauer et al., 2015). Likewise the glycoengineered flavivirus E-proteins of the present disclosure would be suitable candidates for advanced adjuvant strategies such as 'Co-Delivery' where mammalian-expressible DNA and protein representations of the same immunogen are co-formulated in the selfsame particles (e.g. liposomes) giving dramatic improvements in antibody responses compared to protein or DNA immunogens used in isolation (Laing et al., 2006).

Since the present glycoengineering approach involves defined changes at multiple base positions in the nucleic acid sequence of the E-protein, then live attenuated vaccines of the present disclosure will have a high level of resistance to reversion by mutation to wild type, which is a known problem in live attenuated approaches (e.g. the Sabin polio vaccine which was replaced by the non-viable Salk version in the USA for this reason): i.e. they will be safer and less likely to give rise to cases of disease by reversion to wild-type or de novo mutation to increased virulence (Hanley, 2011). From the reasoning of Hanley, and given the present disclosure, it is now evident that introduction of further glycosylation sites into viral proteins (i.e., more than is needed to achieve cloaking of infection-enhancing epitopes) is a viable strategy to guard against adverse mutation in live attenuated viral vaccines, and to guard against 'mosquito competence' whereby a live attenuated flavivirus vaccine might be spread, allowing evolution to increased virulence enabled via vector transmission in mosquitoes. Such additional glycosylation sites are best placed at non-neutralising sites of the flaviviral E-protein.

In the case of flavivirus subunit vaccines of the present disclosure (as distinct from live vector approaches) favoured sites for a second additional glycan would include sequence elements comprising contact surfaces of E with the underlying M-protein of the virion. These highly soluble hyperglycosylated E-proteins allow for monovalent engagement of antigen-specific B-cells, favouring higher affinity neutralising antibodies by creating greater competition for antigen during clonal selection and somatic mutation of antigen-specific B-cells.

The invention is further described by the following clauses:

1 An analogue of a flavivirus E-protein comprising an amino-acid sequence that includes a site for glycosylation that is not present in the natural sequence 2 The analogue of clause 1 wherein the glycosylation site is for an N-linked glycan 3 The analogue of clause 1 wherein the glycosylation site is for an O-linked glycan 4 The analogue of clause 1 having at least one additional glycan attached thereto 5 The analogue of clause 4 wherein the glycan is an N-linked glycan 6 The analogue of clause 4 wherein the glycan is an O-linked glycan 7 The analogue of clauses 1-6 which is the product of expression of a recombinant DNA sequence 8 The analogue of clause 2 wherein an N-linked glycosylation sequon (Asn-X-Ser/Thr) is substituted such that the Asn (N) residue of the sequon occupies any of positions 98-110 being any of the following residues DRGWGNGCGLFGK (SEQ ID NO: 1) of the amino-acid sequence of a flavivirus E-protein where X is any amino acid residue except proline and Ser/Thr denotes a serine or threonine residue 9. The analogue of clause 2 wherein an N-linked glycosylation sequon (Asn-X-Ser/Thr) is substituted such that the Asn (N) residue of the sequon occupies any of positions 98-101 or 106-110

10 The analogues of clause 8 wherein X is any of the following 13 amino-acid residues Asn, Gln, Tyr, Val, Ala, Met, Ile, Lys, Gly, Arg, Thr, His or Ser 11 The analogues of clause 8 wherein the substituted sequon is NTT where T (Thr) is substituted explicitly in the 'X' position of the sequon and the optional Ser/Thr element of the sequon is T 12 An analogue of clause 8 wherein the substituted sequence reads DRGWGNNCTLFGK (SEQ ID NO: 11) exploiting the natural cysteine residue (C) as part (X) of the N-linked glycosylation sequon 13 An analogue of clause 8 wherein the substituted sequence reads DRGWGNNCSLFGK (SEQ ID NO: 12) exploiting the natural cysteine residue (C) as part of the N-linked glycosylation sequon and a having a serine residue in place of the threonine sequon residue of clause 11

14 A DNA sequence encoding an analogue of a flavivirus E protein according to any one of clauses 1 to 13

15 A plasmid or linear DNA-based vaccine immunogen encoding an analogue of a flavivirus E-protein according to any one of clauses 1 to 13 having a mammalian expressible promoter 16 A eukaryotic host cell transfected with a DNA sequence according to clause 1 in a manner allowing the host cell to express said analogue of a flavivirus E-protein 17 A vaccine composition comprising a therapeutically effective amount of a flavivirus-E protein analogue according to any one of clause 1-16 together with a pharmaceutically acceptable diluent, adjuvant or carrier 18 A vaccine composition of clause 17 containing a therapeutically effective amount of four dengue E-proteins representing the four dengue serotypes DEN-1 DEN-2 DEN-3 and DEN-4

19 A vaccine composition of clause 17 comprising a therapeutically effective amount of a zika virus E-protein 20 A vaccine composition of cause 18 containing additionally a therapeutically effective amount of a zika virus E-protein

BRIEF DESCRIPTION OF DRAWINGS

The invention will now be described with reference to the accompanying drawing in which:

FIG. 1. Design of vaccine immunogens of the invention, to avoid generation of cross-reactive fusion loop antibodies and the elicitation or stimulation of infection-enhancing antibodies.

FIG. 1 'A' shows the effect of vaccination with a flavivirus vaccine, such as a live attenuated vaccine known in the art comprising the four dengue serotypes DEN-1, DEN-2, DEN-3 and DEN-4. Attenuated vaccine virions are shown as round structures with the E-protein moiety stem projecting therefrom, the fusion loop is depicted as a small spur on the stem of the virion E-protein moiety; antibodies are depicted as Y-shaped molecules, infection-enhancing antibodies are shown in solid black whereas neutralising antibodies are shown in white outlined in black, 'B' illustrates a vaccine immunogen design of the invention. The novel immunogen contains an E-protein wherein the fusion loop sequence has been substituted to include a glycosylation site for attachment of a glycan (depicted as a crescent attached to the fusion loop spur, to generate neutralising antibodies against the E-proteins of the vaccine without generating infection-enhancing antibodies. 'C' shows how infection-enhancing antibodies against the fusion loop of the E-proteins, when bound to the E-protein of a wild-type flavivirus virion, are able to engage with high affinity the Fc-gamma-receptor-IIa (depicted as a white rectangle outlined in black), facilitating infection of myeloid cells that carry the Fc-gamma receptor IIa. 'D' represents occasional failure of a vaccine to elicit a protective level of antibody response in some subjects (e.g., the immunosuppressed). While not protected against dengue, such immunocompromised subjects (immunized with the vaccine of the present disclosure) are at least not predisposed to dengue by the novel vaccine because they have not mounted an antibody response against the fusion loop. This may be contrasted to a vaccine of conventional design containing an uncloaked fusion loop, where a subject might then be predisposed to severe dengue infection by the conventional vaccine having elicited sub-neutralising concentrations of fusion-loop antibody.

1: pSF236 transfected cells WT, 2: pCRO21 transfected cells, 3: pSF237 transfected cells WT, 4: pCRO22 transfected cells, 5: pSF238 transfected cells WT, 6: pCRO23 transfected cells, 7: pSF239 transfected cells WT, 8: pCRO24 transfected cells, 9: pSF233 transfected cells WT, 10: pCRO25 transfected cells. 11: pSF236 transfected cells WT, 12: pCRO21 transfected cells, 13: pSF237 transfected cells WT, 14: pCRO22 transfected cells, 15: pSF238 transfected cells WT, 16: pCRO23 transfected cells, 17: pSF239 transfected cells WT, 18: pCRO24 transfected cells, 19: pSF233 transfected cells WT, 20: pCRO25 transfected cells. For lanes 1 to 10, the supernatant concentrate was 1 ul/1.1 ml, for lanes 11 to 20 the supernatant concentrate Talon eluate concentration was 26 ul/400 ul.

Figure 2A:
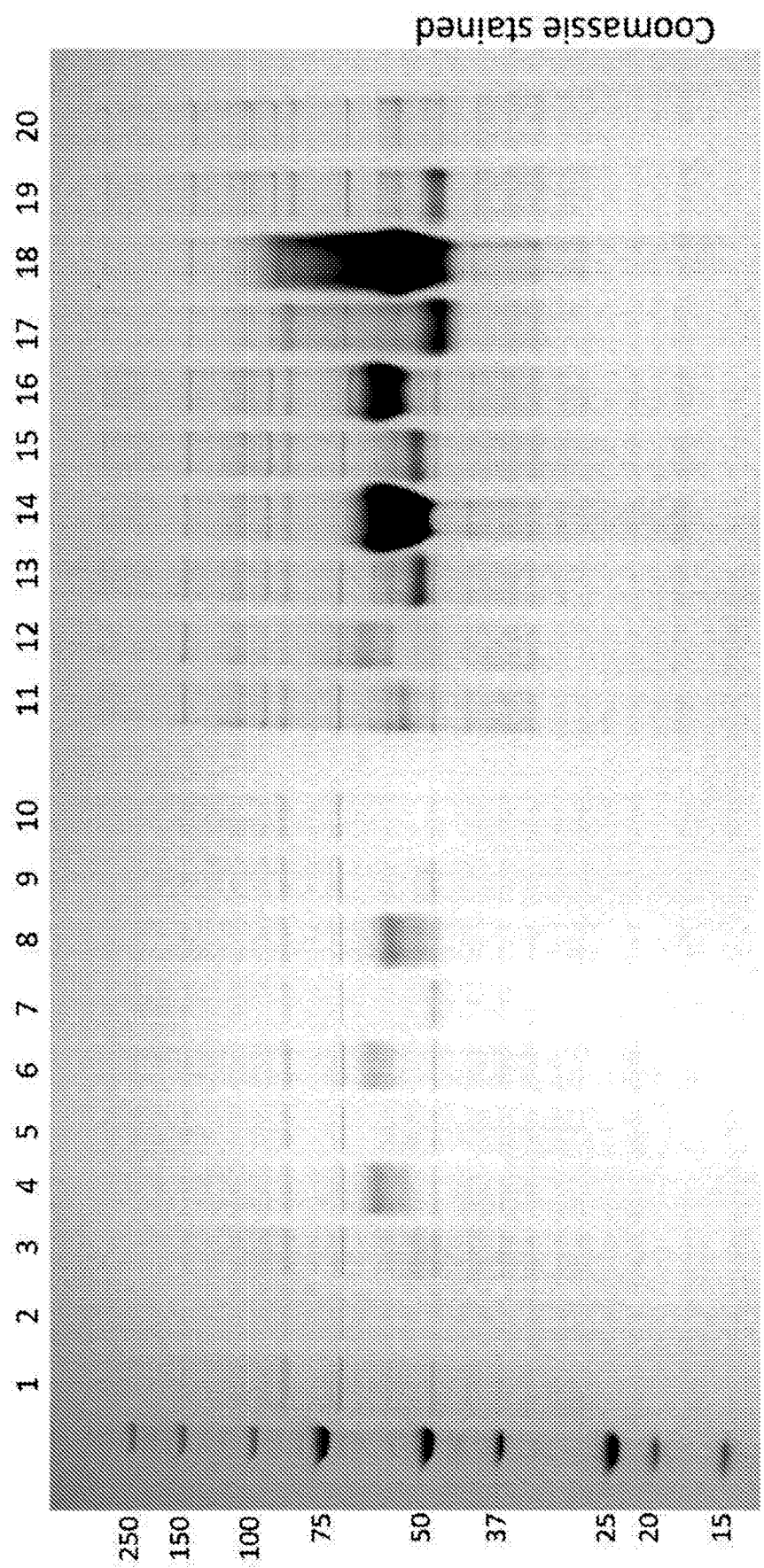
FIG. 2a: Coomassie stained gel showing evaluation of expression of dengue and Zika constructs in HEK293 cells, lanes shown as follows.
Figure 2B:
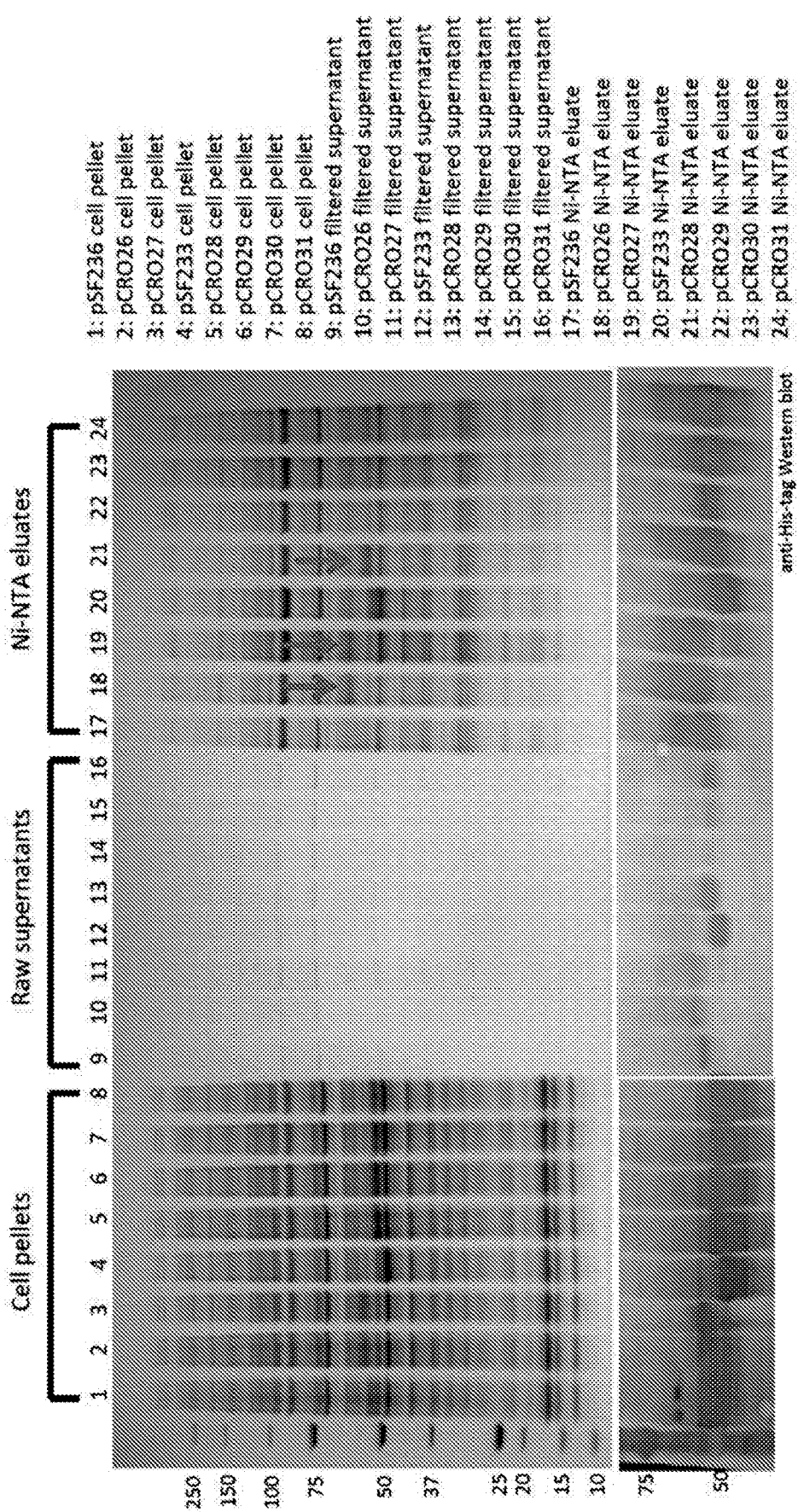
FIG. 2. Recombinant expression of glycoengineered forms of dengue and Zika exodomain proteins.

FIG. 2b: Anti-his-tag Western blot showing further expression evaluation of dengue-1 and Zika constructs. Lanes 1-8 show cell pellets, lanes 9-16 show raw (filtered) supernatants, lanes 17-24 show Ni-NTA eluates, as follows: 1: pSF236 cell pellet, 2: pCRO26 cell pellet, 3: pCRO27 cell pellet, 4: pSF233 cell pellet 5: pCRO28 cell pellet, 6: pCRO29 cell pellet, 7: pCRO30 cell pellet, 8: pCRO31 cell pellet, 9: pSF236 filtered supernatant, 10: pCRO26 filtered supernatant, 11: pCRO27 filtered supernatant, 12: pSF233 filtered supernatant, 13: pCRO28 filtered supernatant, 14: pCRO29 filtered supernatant, 15: pCRO30 filtered supernatant, 16: pCRO31 filtered supernatant, 17: pSF236 Ni-NTA eluate, 18: pCRO26 Ni-NTA eluate, 19: pCRO27 Ni-NTA eluate, 20: pSF233 NI-NTA eluate, 21: pCRO28 Ni-NTA eluate, 22: pCRO29 Ni-NTA eluate, 23: pCRO30 Ni-NTA eluate, 24: pCRO31 Ni-NTA eluate. Three arrows indicate detected hyperglycosylated exodomain forms.

Figure 2C:
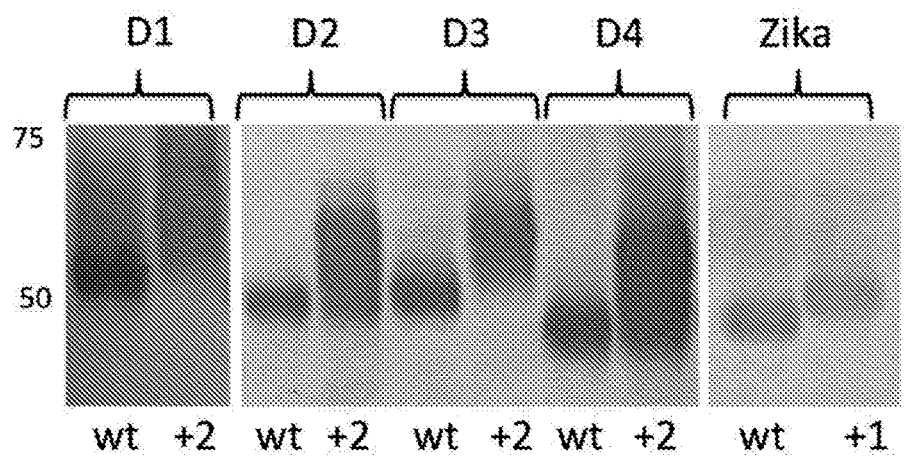

FIG. 2c shows a Western blot of the hyperglycosylated forms pCRO21, pCRO22, pCRO23, pCRO24 for dengue serotypes 1-4 (D1, D2, D3 and D4) respectively and pCRO28 for Zika. The left lane of each pair shows the wild type (wt), whereas the right lane of each pair shows the hyperglycosylated form of the dengue or Zika E-protein exodomain. +2 indicates two additional glycosylation sites/glycans, +1 indicates one additional glycosylation site/glycan.

Figure 2D:
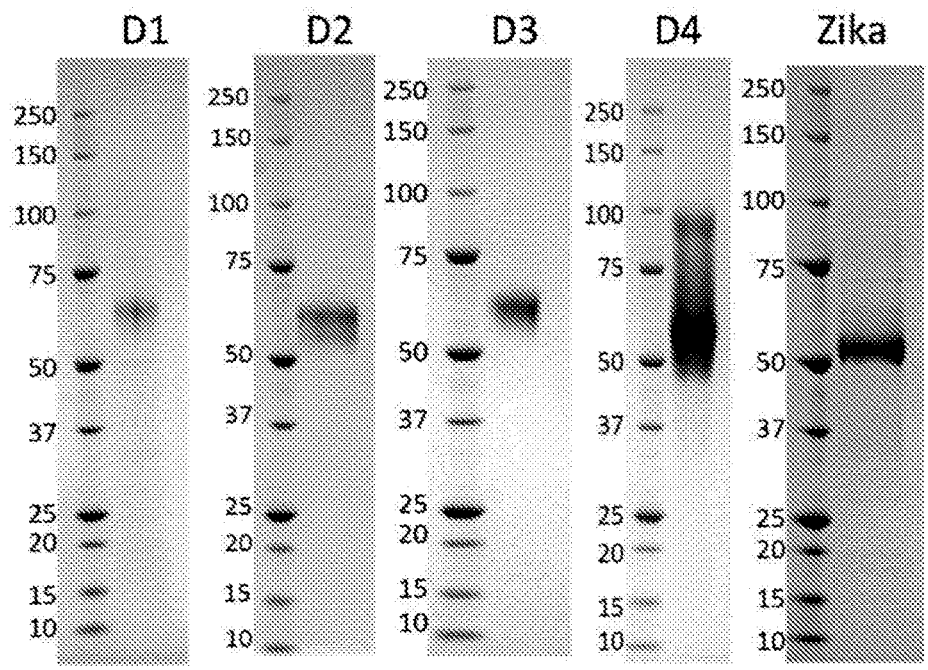

FIG. 2d shows Coomassie blue stained gels of the purified hyperglycosylated E exodomain proteins D1, D2, D3, D4 and Zika, which correspond to plasmids pCRO21, pCRO22, pCRO23, pCRO24 and pCRO28, respectively, in the sequence listings. The scale to the left is the migration position of molecular weight markers in '000s.

FIG. 3. Characterisation of glycans present on the glycoengineered dengue 2 and Zika exodomain proteins and degree of occupancy of sequence-programmed N-linked-glycosylation-sites FIG. 3a shows an SDS-PAGE analysis of dengue and Zika samples prior to and after PNGase digestion.

Figure 3A:
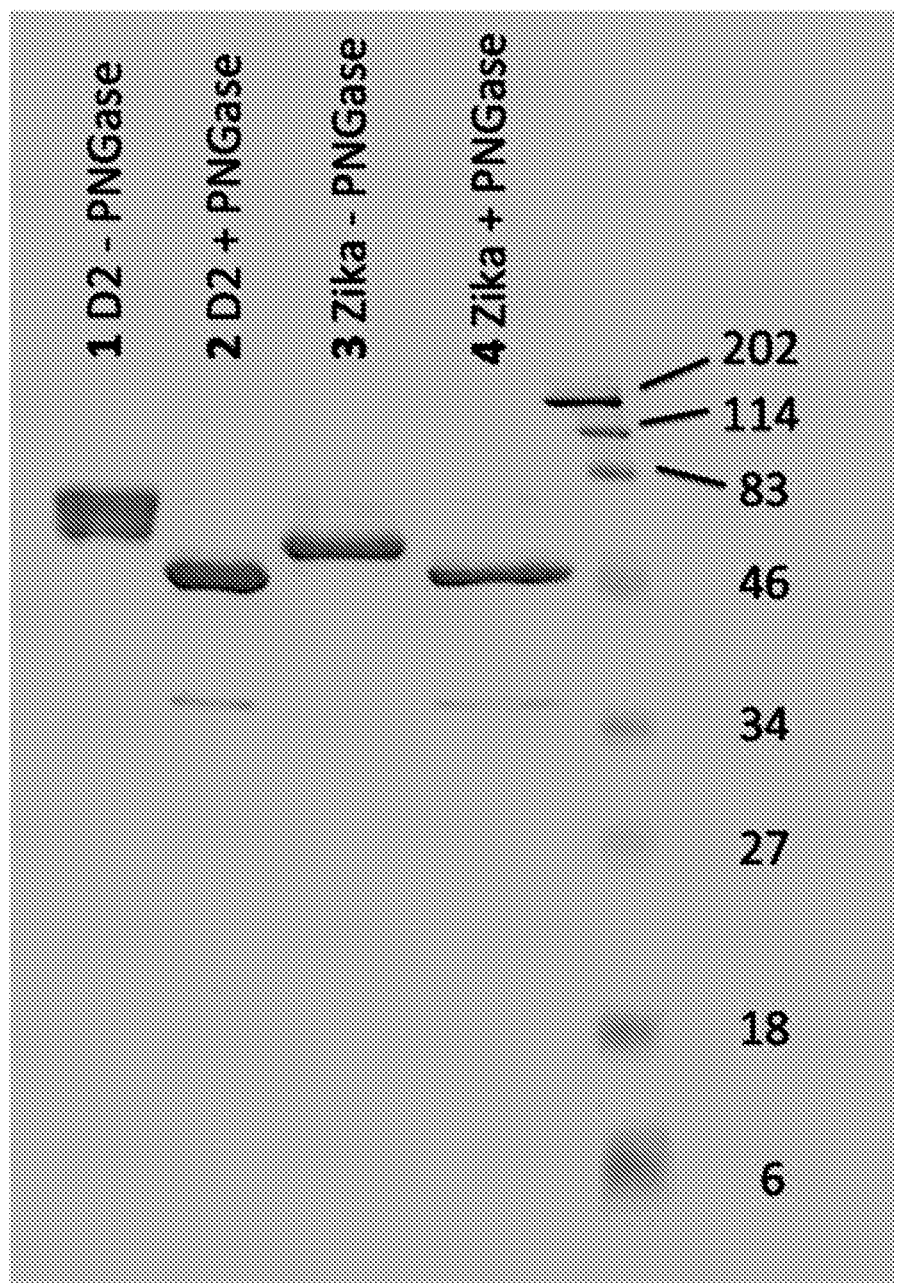
Figure 3B:
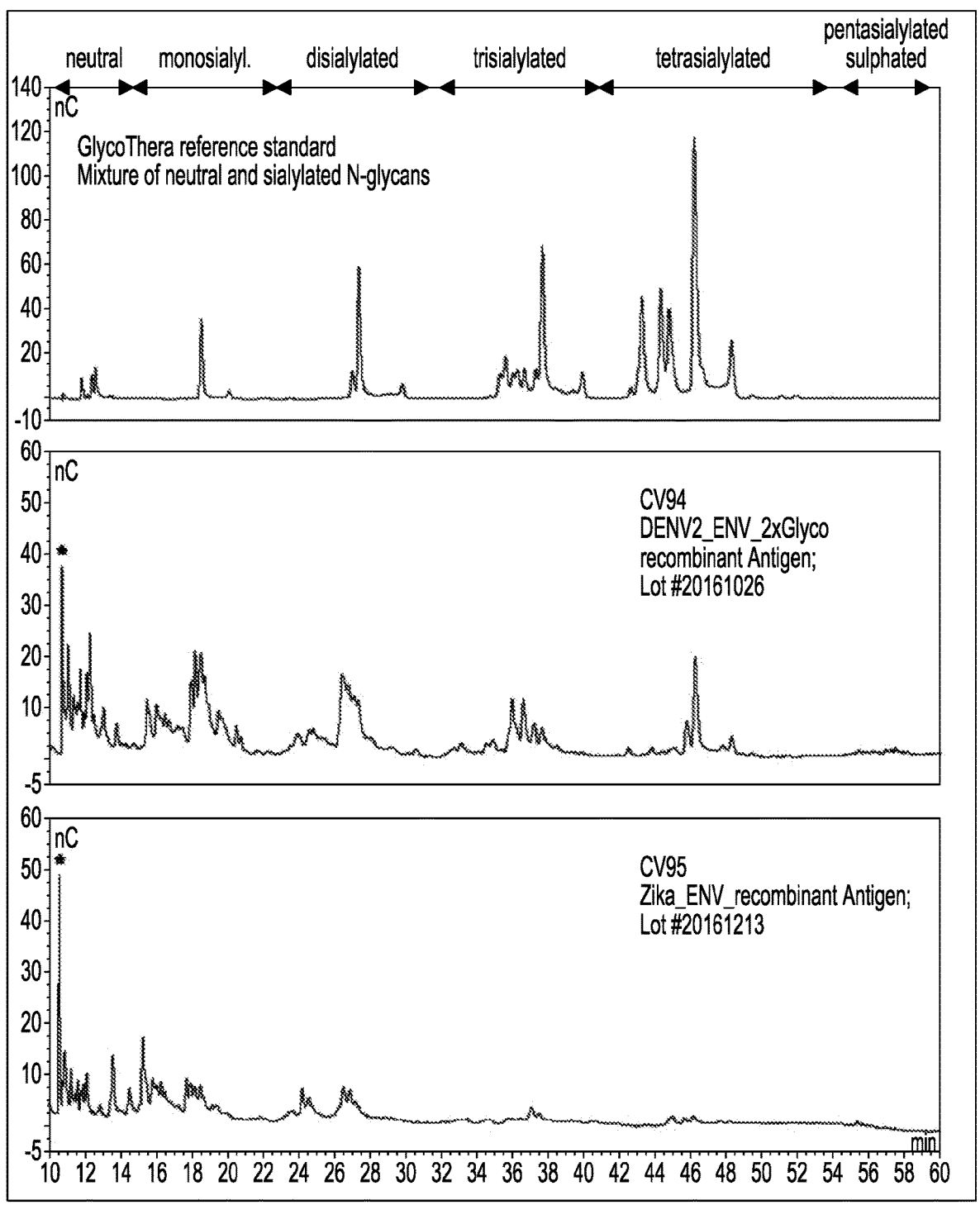

FIG. 3b shows analysis of glycans released from dengue-2 and Zika compared to reference standards by HPAEC-PAD.

FIG. 3c shows dengue-2 (SEQ ID NO: 49) tryptic cleavage sites and peptide fragments: T1, T2 (SEQ ID NO: 50), T3 (SEQ ID NO: 51), T4, T5 (SEQ ID NO: 52), T6 (SEQ ID NO: 53), T7 (SEQ ID NO: 54), T8, T9 (SEQ ID NO: 55), T10 (SEQ ID NO: 56), T11 (SEQ ID NO: 57), T12, T13 (SEQ ID NO: 58), 114 (SEQ ID NO: 59), T15 (SEQ ID NO: 60), T16, T17 (SEQ ID NO: 61), T18 (SEQ ID NO: 62), T19, T20, T21 (SEQ ID NO: 63), T22 (SEQ ID NO: 64), T23 (SEQ ID NO: 65), T24 (SEQ ID NO: 66), T25 (SEQ ID NO: 67), T26 (SEQ ID NO: 68), T27, T28 (SEQ ID NO: 69), T29, 130, T31, T32 (SEQ ID NO: 70), T33 (SEQ ID NO: 71), T34, T35, T36 (SEQ ID NO: 72), T37 (SEQ ID NO: 73), T38 (SEQ ID NO: 74), T39, 140 (SEQ ID NO: 75), 141 (SEQ ID NO: 76), T42 (SEQ ID NO: 77), T43 (SEQ ID NO: 78), T44 and T45 (SEQ ID NO: 79).

FIG. 3d shows Zika (SEQ ID NO: 80) tryptic cleavage sites and peptide fragments: T1, T2 (SEQ ID NO: 81), T3 (SEQ ID NO: 82), T4 (SEQ ID NO: 83), T5 (SEQ ID NO: 84), T6 (SEQ ID NO: 85), T7 (SEQ ID NO: 86), T8, T9 (SEQ ID NO: 87), T10 (SEQ ID NO: 88), T11 (SEQ ID NO: 89), T12 (SEQ ID NO: 90), T13, T14 (SEQ ID NO: 91), T15 (SEQ ID NO: 92), T16 (SEQ ID NO: 93), T17, T18 (SEQ ID NO: 94), T19 (SEQ ID NO: 95), T20 (SEQ ID NO: 96), T21 (SEQ ID NO: 97), T22 (SEQ ID NO: 98), T23 (SEQ ID NO: 99), T24 (SEQ ID NO: 100), T25, T26 (SEQ ID NO: 101), T27, T28 (SEQ ID NO: 102), T29, T30, T31, T32, T33, T34 (SEQ ID NO: 103), T35 (SEQ ID NO: 104), T36 (SEQ ID NO: 105), T37 (SEQ ID NO: 106), T38 (SEQ ID NO: 107), T39, 140 (SEQ ID NO: 108) and 141 (SEQ ID NO: 109).

FIG. 3e shows Zika (SEQ ID NO: 80) Endo-Lys-C cleavage sites and peptide fragments: L1 (SEQ ID NO: 110), L2 (SEQ ID NO: 111), L3 (SEQ ID NO: 112), L4 (SEQ ID NO:113), L5 (SEQ ID NO: 114), L6 (SEQ ID NO: 115), L7, L8 (SEQ ID NO: 116), L9 (SEQ ID NO:117), L10 (SEQ ID NO: 118), L11 (SEQ ID NO: 119), L12 (SEQ ID NO: 120), L13 (SEQ ID NO: 121), L14 (SEQ ID NO: 122), L15 (SEQ ID NO: 123), L16 (SEQ ID NO: 124), L17, L18 (SEQ ID NO: 125), L19 (SEQ ID NO: 126), L20 (SEQ ID NO: 127), L21 (SEQ ID NO: 128), L22 (SEQ ID NO: 129), L23 and L24 (SEQ ID NO: 130).

Figure 3F:
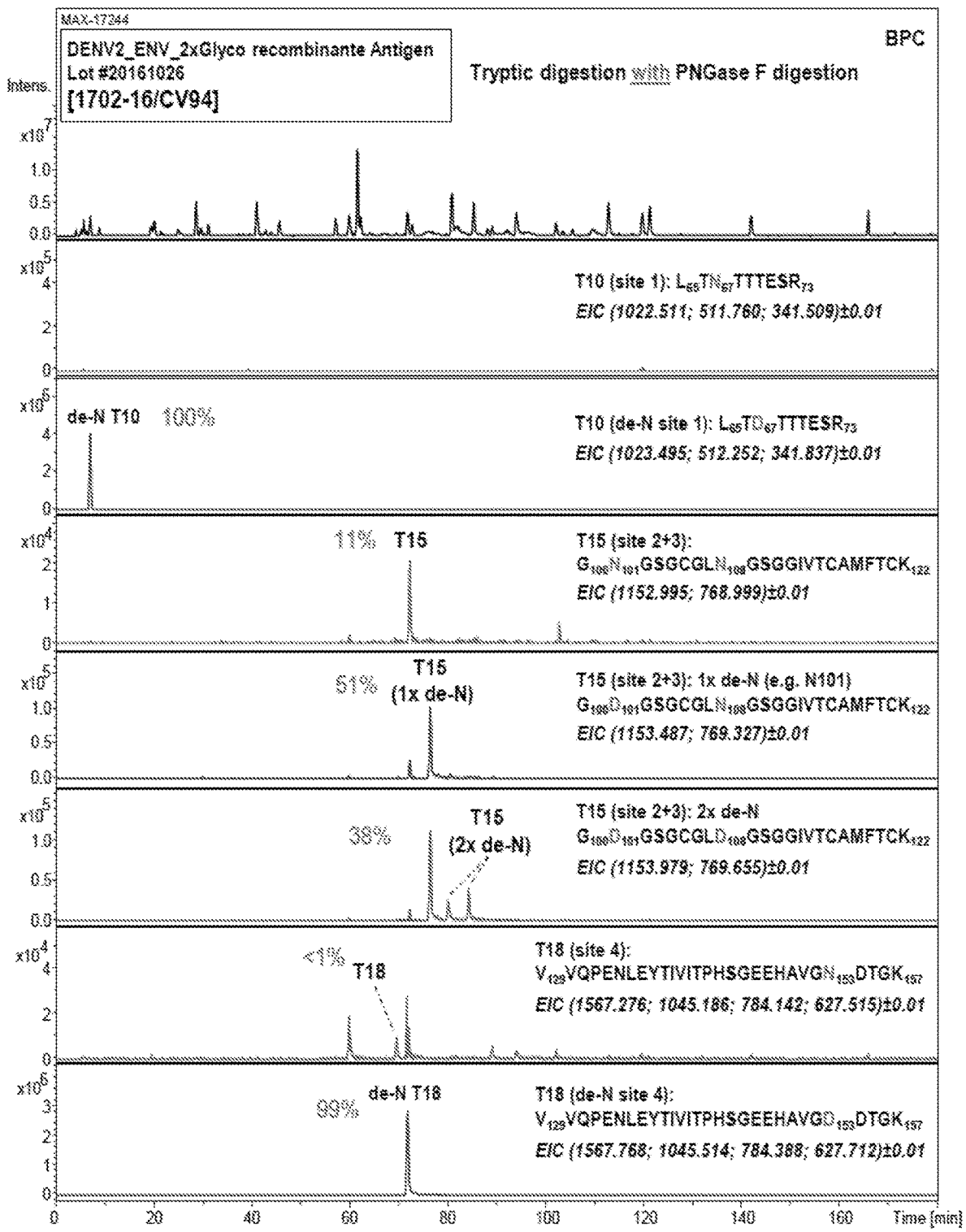

FIG. 3f shows tryptic digestion of dengue-2 (SEQ ID NO: 49) with and without PNGase F digestion: T10 site 1 (SEQ ID NO: 37), T10 de-N site 1 (SEQ ID NO: 38), T15 site 2+3 (SEQ ID NO: 39), T15 site 2+3: 1× de-N(SEQ ID NO: 40), T15 site 2+3: 2× de-N(SEQ ID NO: 42), T18 site 4 (SEQ ID NO: 43), T18 de-N site 4 (SEQ ID NO: 44).

Figure 3G:
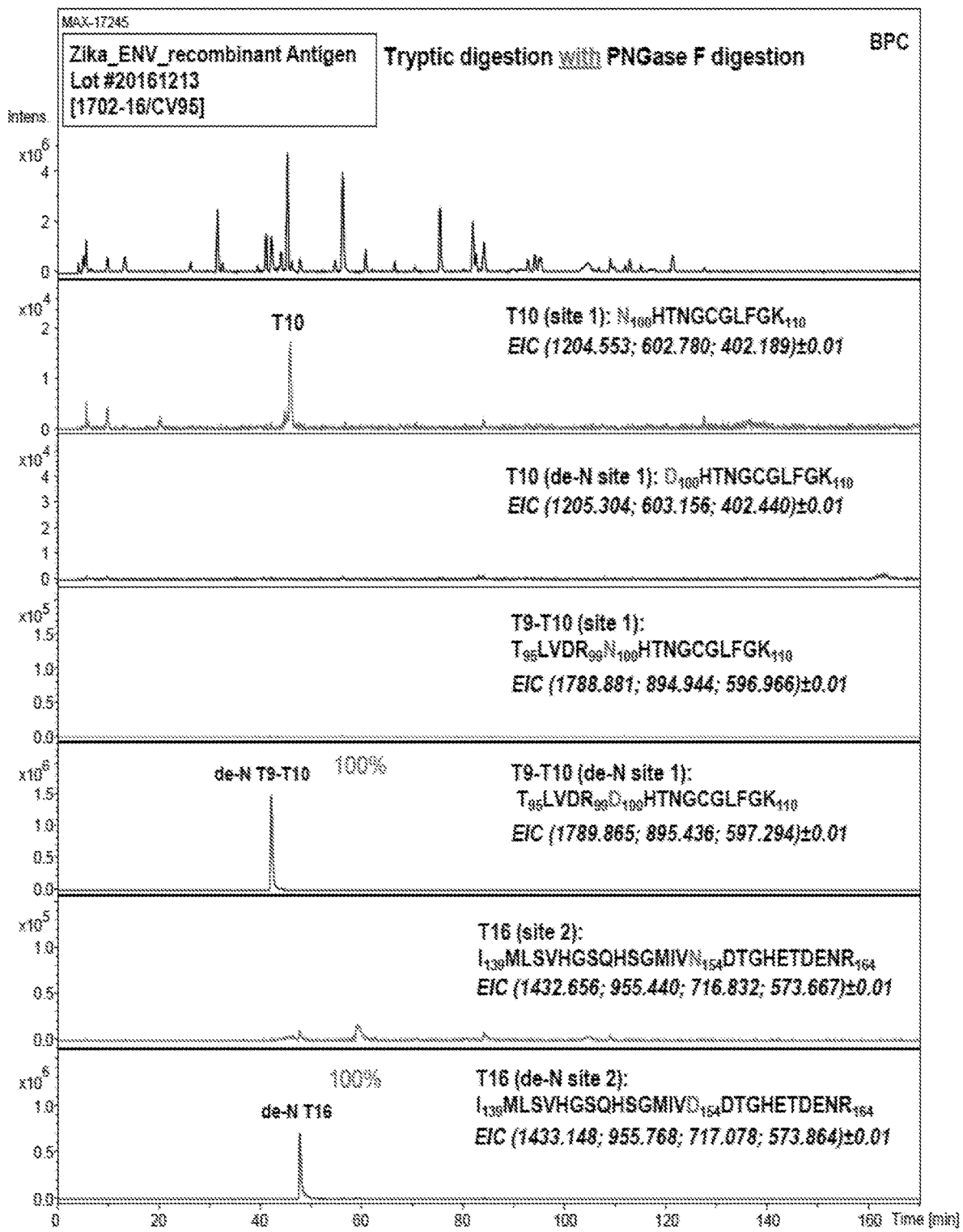

FIG. 3g shows tryptic digestion of Zika (SEQ ID NO: 80) with and without PNGase digestion: T10 site 1 (SEQ ID NO: 88), T10 de-N site 1 (SEQ ID NO: 131), T9-T10 (SEQ ID NO: 132). T9-T10 de-N site 1 (SEQ ID NO: 133), T16 site 2 (SEQ ID NO: 47), T16 de-N site 2 (SEQ ID NO: 48).

Figure 3H:
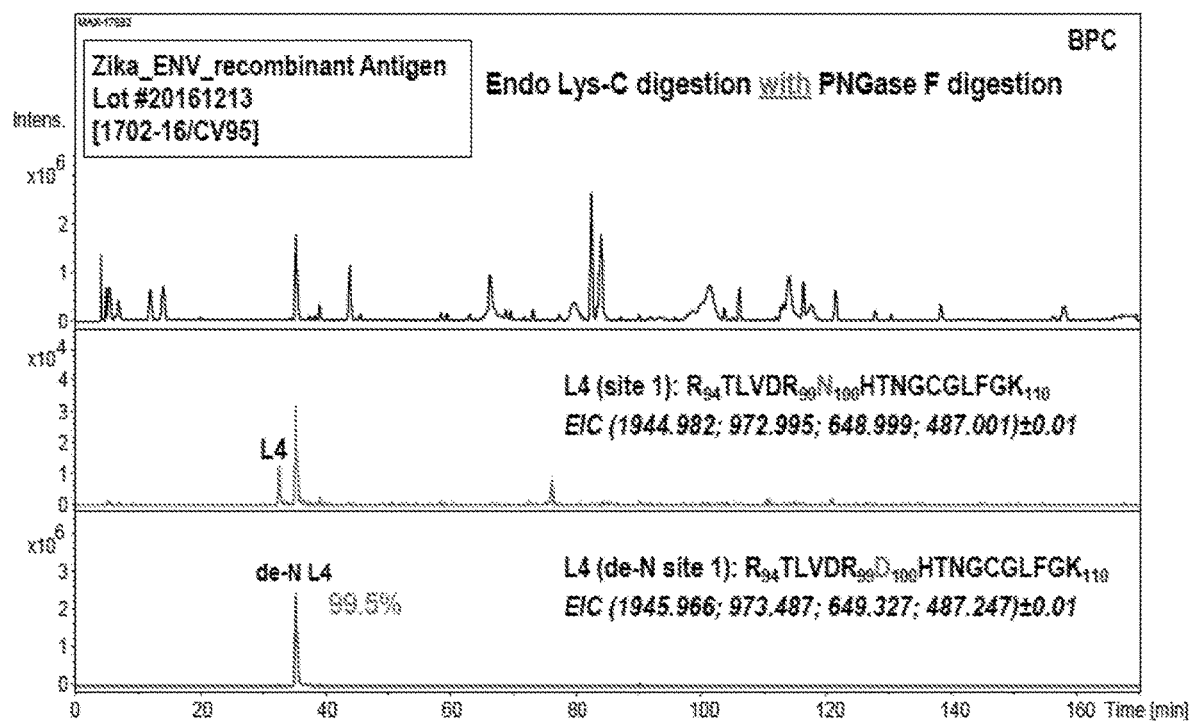

FIG. 3h shows endo-Lys-C digestion of Zika (SEQ ID NO: 80) with and without PNGase digestion: Zika L4 site 1 peptide (SEQ ID NO: 45) and Zika L4 de-N site 1 peptide (SEQ ID NO: 46).

Figure 4:
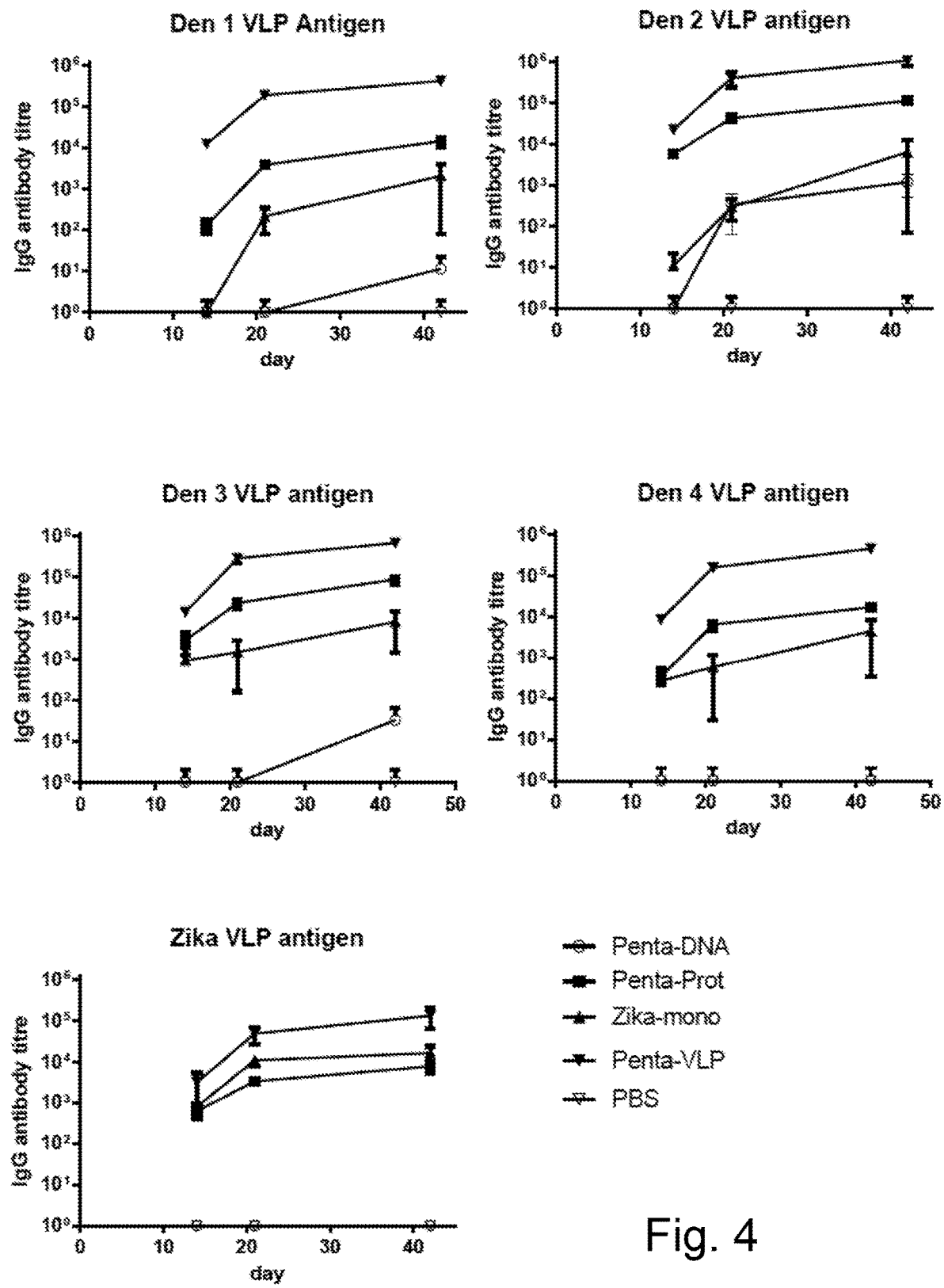

FIG. 4. Immunogenicity of select glycoengineered dengue proteins 1, 2, 3 and 4 and Zika in mice measured by direct ELISA.

The x-axis shows the number of days after immunisation and the y-axis shows the IgG antibody titre. Three doses were given on days 0, 14 and 21. Dosages are indicated in Table 9. Antibody responses were measured in individual mice against all five antigens as wild-type VLPs on the ELISA solid phase as indicted: top row left Den 1 VLP antigen, top row right Den 2 VLP antigen, middle row left Den 3 VLP antigen, middle row right Den 4 VLP antigen, bottom row left Zika VLP antigen. Immunogens (as distinct from antigens uses for assay above) were Penta-DNA (a combination of each of the Den1-4 and Zika DNAs of the invention) shown as an open circle, Penta-Prot (a combination of each of the Den1-4 and Zika proteins of the invention) is shown as an filled square, Monovalent Zika is shown as a filled triangle, Penta VLP (a combination of each of the Den1-4 and Zika VLPs of the invention) is shown as a filled inverted triangle. PBS control is shown as an open inverted triangle.

FIG. 5. Avoidance of recognition of the glycoengineered proteins by fusion loop antibodies and retention of neutralizing epitopes.

In order to further characterize the hyperglycosylated antigens of the present disclosure, comparing them to wild-type equivalent antigens, an ELISA assay was established to measure antibody binding to diverse wild-type and recombinant exodomains (as distinct from the VLP antigens of FIG. 4). Unlike the ELISA used in FIG. 4, which used only wild-type VLPs as antigens this assay used only exodomain-type antigens (recombinant wild-type and recombinant hyperglycosylated forms 'HX' of the invention). In order to ensure the same orientation of each of these materially diverse (non-glycosylated bacterial, insect-glycosylated and human-glycosylated) species, they were anchored to the solid phase by a rabbit anti-His-tag monoclonal antibody, recognizing their C-terminal His tags. Coated plates were blocked and exposed to a constant concentration of the various His-tagged proteins in a 'post-coating' step and were then probed with monoclonal antibodies at various concentrations (FIG. 5*a*, for 4G2) or at a constant concentration (FIG. 5*b*,*c*). Various dengue and Zika antigens and probe antibodies were tested in FIG. 5*b*,*c*, including a human polyclonal anti-Zika convalescent serum sample. Probe antibodies were followed by incubation with a rabbit anti-mouse IgG Fc—horseradish peroxidase (or rabbit-anti-human IgG Fc—horseradish peroxidase) conjugate (as appropriate) and tetramethylbenzidine substrate. A mouse monoclonal anti-human-CD4 antibody served as a control for the mouse monoclonal antibodies.

FIG. 5*a* represents fusion-loop antibody 4G2 (x-axis, ng/ml), which was raised against dengue-2 serotype but is highly cross-reactive among flaviviruses, binding to solid phase wild-type dengue serotype-2 or dengue serotype-4 wild type exodomain antigens, or their hyperglycosylated counterparts containing two additional programmed sequons in the fusion loop ('HX' for hyperglycosylated exodomain). (Asterisks denote absorbance values higher than the read-capability of the ELISA reader), Y Axis shows absorbance at 450 nm. Points are mean of duplicate determinations.

FIG. 5*b* is a photograph of an ELISA plate result of the present assay design, wherein various exodomains were screened for binding to antibodies, including a set of murine monoclonal antibodies, (left to right columns 1 and 2: 4G2 (cross-reactive fusion-loop antibody), columns 3 and 4: Aalto Bioreagents anti-Zika antibody AZ1176-0302156-Lot3889; columns 5 and 6: Z48 anti-Zika antibody, wells 7 and 8: Z67 anti-Zika antibody (these are described as ZV48 and ZV67 Zika-neutralizing antibodies by Zhao et al, Cell 2016 and were obtained from The Native Antigen Company ZV67=MAB12125 and ZV48=MAB12124), wells 9 and 10: anti-human-CD4 control Millipore 024-10D6.B3 2322501; wells 11 and 12: Zika human convalescent serum). Exodomains (all having His-6 C-terminal tag) were as follows (top to bottom): 'Aalto insect'=Sf9 insect-cell produced wild-type recombinant Zika exodomain from Aalto Bioreagents, Dublin, Ireland; Prospec Zika=bacterially produced recombinant wild-type exodomain from Prospec, Israel; NAC WT den-2=HEK293-produced human wild-type dengue-2 exodomain (based on residues 280-675 of NCBI ACA48859.1 followed by a glycine-serine linker of 7 or 8 amino acids in length followed by the His6 tag); 'Excivion HX den-1 (human) cloaked' represents the expressed product of plasmid pCRO21 from HEK 293 cells having two N-glycosylation sequons programmed into the fusion loop; likewise for Excivion HX den-2 through den-4, representing plasmids pCRO22, pCRO23 and pCRO24 respectively. 'Excivion HX Zika human (cloaked)' represents the protein product of plasmid pCRO28 expressed in HEK293 cells, having a single glycosylation programmed into the fusion loop.

FIG. 5*c* shows the absorbance values represented as Excel data bars as % values of the maximum absorbance (which was 3.0 absorbance units), demonstrating the quality of replicates (duplicates). FIG. 5*c* is a graphical representation of the data in FIG. 5*b* and has the same layout as FIG. 5*b*.

FIG. 5*d* shows the ELISA plate depicted in FIG. 5*b* in greater detail.

FIG. 6. Avoidance of generation of fusion-loop antibodies by the glycoengineered proteins. A further ELISA assay was developed, different to those used in FIG. 4 and FIG. 5, to detect antibodies in polyclonal sera from immunized mice, against the fusion loop. This was a competitive binding assay in which biotin-labelled 4G2 was used as a label, and unlabeled 4G2 was used as a standard. Top row left, unconjugated 4G2, x-axis concentration of 4G2 ng/mL; top row middle, Penta DNA, Group 1, Day 42, x-axis dilution of serum; top row right Penta Prot Group 2, Day 42, x-axis dilution of serum; bottom row left Mono Zika, Group 3 Day 42, X-axis dilution of serum; bottom row middle Penta VLPs, Group 4 day 42, x-axis dilution of serum; bottom row right PBS, Group 5 Day 42, x-axis dilution of serum. In each instance the y-axis was % biotinylated (Bt)-4G2 bound.

FIG. 7. Generation of neutralising antibodies by the glycoengineered proteins (PRNT).

FIG. 7*a* shows Dengue PRNT responses for Sample groups 1 to 5 measured in pooled sera: dose response curves against DENV, Top row left Penta DNA (Neutralisation of DENV by Group 1 pool); top row middle Penta Prot (Neutralisation of DENV by Group 2 pool); top row right Mono Zika (Neutralisation of DENV by Group 3 pool); bottom row left Penta VLPs (Neutralisation of DENV by Group 4 pool); Bottom row middle PBS (Neutralisation of DENV by Group 5 pool). In each instance the x-axis is dilution factor and the y-axis shows percentage neutralisation.

FIG. 7*b* shows PRNT responses for Sample groups 1 to 5 measured in pooled sera: dose response curves against ZIKV, Top row left Penta DNA (Neutralisation of ZIKV by Group 1 pool); top row middle Penta Prot (Neutralisation of ZIKV by Group 2 pool); top row right Mono Zika (Neutralisation of ZIKV by Group 3 pool); bottom row left Penta VLPs (Neutralisation of ZIKV by Group 4 pool); Bottom row middle PBS (Neutralisation of ZIKV by Group 5 pool). In each instance the x-axis is dilution factor and the y-axis shows percentage neutralisation.

Figure 8:
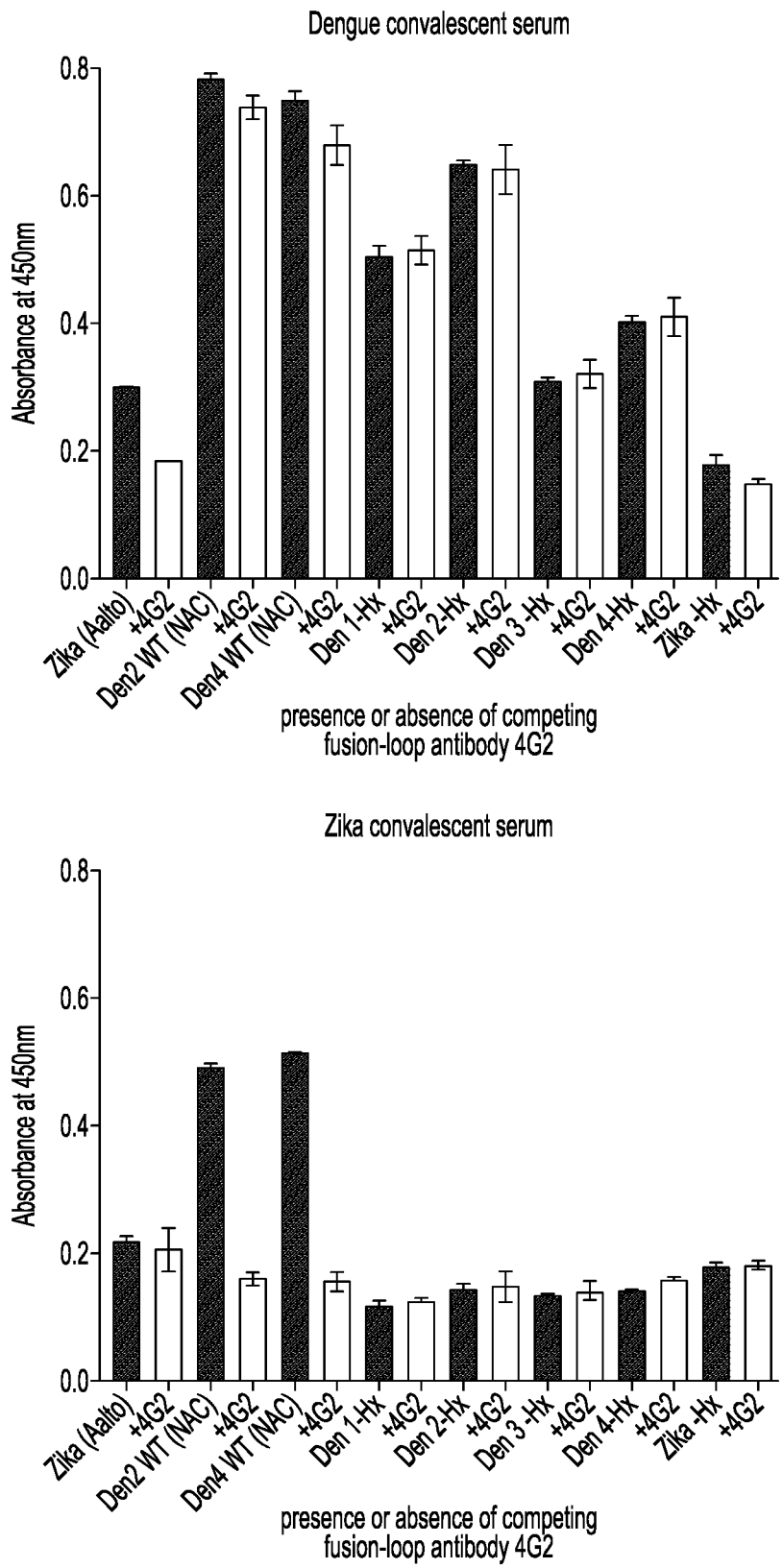

FIG. 8. Reaction of convalescent dengue and Zika sera with immobilized Zika and dengue wild-type (WT) and hyperglycosylated (HX) exodomain proteins Upper panel shows ELISA reactivity of antibodies in a dengue convalescent serum with immobilized Zika and dengue wild-type (WT) and hyperglycosylated (HX) exodomain proteins oriented on the solid phase by capture with a rabbit anti-His-tag monoclonal antibody, in the presence (grey bars, right of each pair) and absence (black bars, left of each pair) of competing mouse monoconal flavivirus fusion loop antibody 4G2 (an anti-dengue-serotype-2 cross-reactive monoclonal antibody) at a concentration of 10 ug/ml during serum incubation. Human sera were tested at a constant concentration of 1/1000.

Lower panel shows ELISA reactivity of antibodies in a Zika convalescent serum with immobilized Zika and Dengue wild-type (WT) and hyperglycosylated (HX) exodomain proteins in the presence (grey bars) and absence (black bars) of competing mouse monoclonal flavivirus fusion loop antibody 4G2. Conditions and labelling are the same as for the upper panel. Error bars are standard error of duplicate determinations.

EXAMPLES

Figure 1:
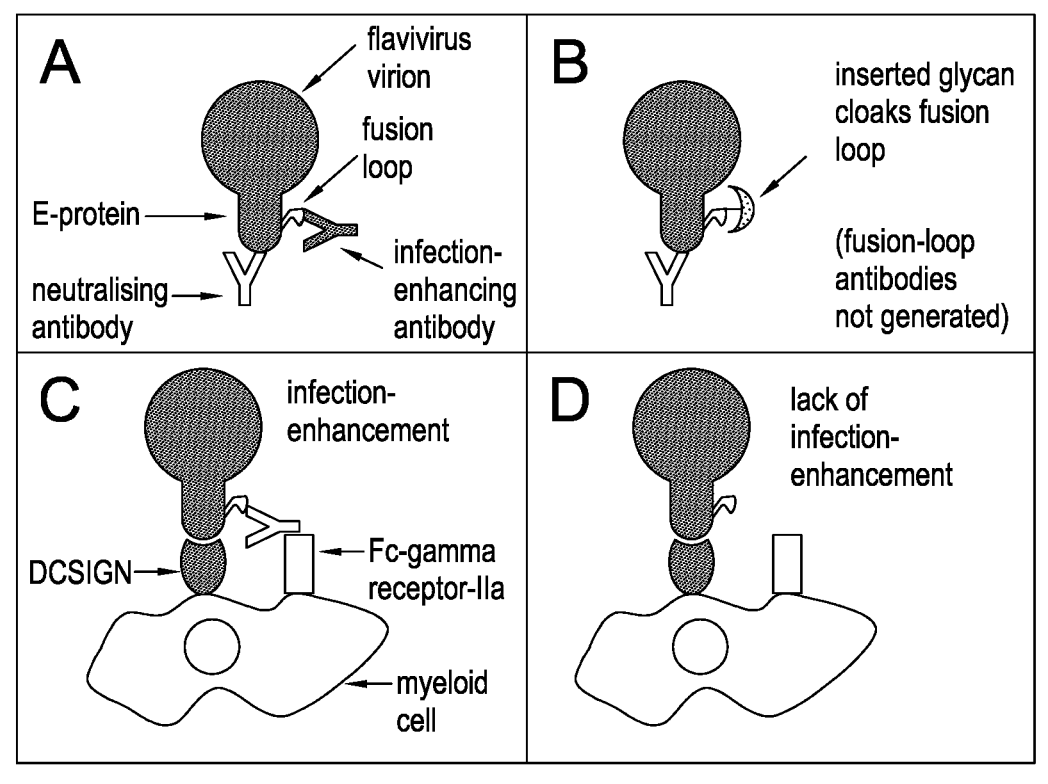

Example 1 Design of New Vaccine Immunogens Designed to Avoid the Elicitation or Stimulation of Infection-Enhancing Antibodies FIG. 1, 'A' shows the effect of vaccination with a flavivirus vaccine, such as a live attenuated vaccine known in the art comprising the four dengue serotypes DEN-1, DEN-2, DEN-3 and DEN-4. The vaccine generates a mixture of antibodies capable of virus neutralisation and other antibodies capable of antibody-dependent enhancement of infection. Antibodies capable of virus neutralisation include those that recognise sites on the receptor-interacting surface of the virion E-protein, i.e., that surface that binds to the DCSIGN lectin/receptor. (For simplicity of illustration, only the DCSIGN receptor is shown, noting that there are other receptors for dengue and flaviviruses generally). 'C' shows how infection-enhancing antibodies against the fusion loop of the E-proteins, when bound to the E-protein of the virion, are able to engage with high affinity the Fc-gamma-receptor-IIa, facilitating infection of myeloid cells. Several types of Fc-gamma receptors have been implicated in this phenomenon, even (paradoxically) including the low-affinity receptor Fc-gamma-receptor-IIb, which is normally inhibitory to myeloid cells and B-cells (Bournazos S, Signaling by Antibodies . . . Ann. Rev. Immunol 2017, 35:285-311). The result of vaccination with a live attenuated vaccine (an example of a vaccine known in the art) is the net effect of two opposing populations of antibody, one set that neutralises dengue virions, and a further set that is capable of infection enhancement. In most subjects of vaccination, neutralising antibodies overcome the effect of the infection-enhancing antibodies, such that the net effect of vaccination is protection against the four dengue serotypes. However, in subjects who do not mount a balanced response to the four serotypes, or who are immunosuppressed e.g., due to measles or HIV infection, flavivirus-infection-enhancing antibodies prevail rendering such subjects predisposed to, rather than protected against, severe infection with dengue and more prone to infection with other flaviviruses. Further, infection-enhancing antibodies in some healthy (non-immunosuppressed) dengue-vaccinated subjects cross-react with Zika virus. Those dengue-immunised subjects are now predisposed to Zika infection upon first being bitten by a Zika-infected mosquito 'C'. Conversely, 'B' illustrates a vaccine immunogen designed in accordance with the invention. The novel immunogen, containing an E-protein wherein the fusion loop sequence has been modified and has been designed to be substituted with a glycan with the aim to generate neutralising antibodies against the E-proteins of the vaccine without generating infection-enhancing antibodies. 'D' represents occasional failure of the vaccine of the invention to elicit a protective level of antibody response in some subjects (e.g., the immunosuppressed), however, unlike other vaccine designs known in the art, the vaccine of the invention is designed to not render immunosuppressed subjects susceptible to enhanced infection with dengue or Zika viruses. Immunogens and vaccines of the present design are thereby designed to be safer on an individual subject basis and moreover to lack the potential to facilitate the epidemic spread of Zika by creating a population of subjects that have Zika-infection-enhancing antibodies, in the absence of neutralising antibodies. (WT=wild type).

Example 2 (FIG. 2) Recombinant Expression of Glycoengineered (Hyperglycosylated) Forms of Dengue and Zika Exodomain Proteins Plasmid inserts encoding various novel recombinant forms of the natural wild type (WT) exodomain sequences representative of the four dengue serotypes and of Zika and containing an *E. coli* origin of replication and a cytomegalovirus (CMV) promoter, as well as a hexahistidine C-terminal tag, were made by de novo gene synthesis (Thermofisher, GeneArt). Where two glycosylation sequons were inserted in the DNA sequence, the sequence was changed 'manually' to avoid the creation of direct DNA sequence repeats that might otherwise allow undesirable homologous recombination events.

Plasmid expression vectors pCRO21 (SEQ ID NO: 13), pCRO22 (SEQ ID NO: 14), pCRO23 (SEQ ID NO: 15), pCRO24 (SEQ ID NO: 16) and pCRO28 (SEQ ID NO: 17), coding for the mutated exodomain of the Envelope proteins of DENV1, DENV2, DENV3, DENV4 and ZIKV, respectively, were ultimately selected and produced by The Native Antigen Company, Oxford, as follows: expression cassettes were synthesized de novo to contain a 5' NotI site followed by a consensus Kozak sequence followed by the coding sequence for the first 17 amino acids of the influenza-A virus haemagglutinin protein acting as secretion signal. The Envelope protein coding sequences used, (numbering relative to the polyprotein), were 280-675 (NCBI ACA48859.1), 281-676 (NCBI ADK37484.1), 281-673 (NCBI AIH13925.1), 280-675 (NCBI ANK35835.1) and 291-696 (NCBI ARB07957.1), respectively. [Elsewhere, for ease of reference, numbering is expressed according to residue number in the E-protein, with W at 101 of the fusion loop as a reference point]. Each construct contained coding sequences for a glycine-serine linker 7 to 8 amino acids in length followed by a 6× His-tag and a stop codon. The stop codon is followed by a NheI site in each expression cassette. The mammalian expression vector pSF-CMV (Oxford Genetics, Oxford) was digested with NotI and NheI, and the 4.2 kb fragment was ligated to the 1.3 kb NotI and NheI fragments of the expression cassette harbouring maintenance vectors (pUC57). In each case, one or two additional sequons of the general formula (NXS/T) was introduced into the fusion loop of the E-protein exodomain, capable (theoretically) of encoding a functional N-linked glycosylation site. The wild-type dengue proteins naturally already have two glycosylation sites, and Zika one. None of the natural glycans are found in the fusion loop.

For small-scale preparation 15 ml aliquots of HEK293FT cells at 3e6/ml were individually transfected with pCRO21, pCRO22, pCRO23, pCRO24 or pCRO25 (SEQ ID NO: 18), 4 control transfections were performed using pSF233, pSF236, pSF237, pSF238 or pSF239. After a day, 15 ml of rescue medium was added to each transfection. At day 3 after transfection each of the 10 transfections was treated the same way as follows: 30 ml of suspension was spun at 4,000 g for 7 minutes. The resulting supernatant was filtered using a 0.22 um disc filter. The pellet was resuspended in 1 ml of PBS. The filtered supernatant was then concentrated using a Vivaspin20 (30,000 Da cutoff) as per manufacturer's instructions. Concentrate volumes ranged from 0.6 ml to 1.2 ml. All concentrates were brought up to 1.2 ml with PBS. The concentrated supernatants were subjected to Talon purification as per manufacturer's instructions using Talon HiTrap Spin (GE). Buffers for Talon capture were: Equilibration Buffer: 50 mM phosphate pH7.8, 300 mM NaCl; Wash Buffer: 50 mM phosphate pH78, 300 mM NaCl, 5 mM imidazole; Elution Buffer: 50 mM phosphate pH7.8, 300 mM NaCl, 150 mM imidazole.

Characterisation of the resulting proteins by coomassie-blue staining (FIG. 2a, FIG. 2d) and by western blot (FIG. 2b, FIG. 2c) of SDS electrophoresis gels is shown in FIG. 2.

FIG. 2c shows a Western blot with anti-His-tag monoclonal antibody of chosen constructs pCRO21 (D1), pCRO22 (D2), pCRO23 (D3), pCRO24 (D4) (for dengue serotypes 1-4 respectively) and pCRO28 for Zika, which gave rise to secreted hyperglycosylated proteins. Molecular weight increments due to glycosylation are apparent, higher for the +2 glycan dengue constructs than for the Zika +1 glycan construct, demonstrating the practical attainment of select theoretically designed constructs as expressible proteins. Wild type forms are shown on the left of each pair.

FIG. 2d shows Coomassie blue stained gels of the purified proteins, hyperglycosylated E protein exodomains from the four dengue virus strains D1, D2, D3, D4 and Zika after cobalt chelate (TALON) chromatography using cobalt chelate. Hyperglycosylated exodomains D1, D2, D3, D4 and Zika correspond to plasmids pCRO21, pCRO22, pCRO23, pCRO24 and pCRO28, respectively.

For scale-up production, the novel hyperglycosylated proteins were expressed recombinantly in human embryonic kidney cells (HEK 293) by transient transfection with linear polyethyleneimine (PEI), and purified by metal chelate affinity chromatography with a cobalt chelate (TALON®, Clontech/GE), as described as follows for the dengue-1 hyperglycosylated construct based on pCRO21. 20×1 L of HEK293 cells were transfected with DENV1_Eexo_2× glyco expression vector pCRO21. 3 days post transfection, the supernatant was harvested by centrifugation, and the cleared supernatant was 0.2 um filtered and concentrated to ~200 ml by tangential flow filtration (TFF). Immobilised metal affinity chromatography (IMAC) was performed on the TFF retentate using 5 ml HiTRAP Talon pre-packed column (GE) according to manufacturer's instructions using 20 mM sodium phosphate pH7.8 based buffer systems. DEN V1_Eexo_2×glyco protein containing fractions were pooled and dialysed against 20 mM TRIS-HCl pH7.8 10 mM NaCl. Ion exchange chromatography was performed using a pre-packed 5 ml HiTrap Q HP column according to manufacturer's instructions. DENV1_Eexo_2×glyco were pooled and dialysed against DPBS pH7.4. The dialysed solution was 0.22 um filtered and vialled under sterile conditions. BCA assay and SDS-PAGE were performed according to manufacturer's instructions (Bio-Rad).

Note that three of the hyperglycosylated constructs express at levels much higher than wild type (these are the hyperglycosylated dengue serotypes 2, 3 and 4 corresponding to plasmids pCRO22, pCRO23 and pCRO24). Zika plasmid, pCRO25 did not give rise to detectable secreted protein (FIG. 2a, lane 20), although significant amounts of cell-associated protein were found (not shown).

Therefore a further round of constructs was made (see FIG. 2b) seeking to improve levels of expression of dengue-1 and Zika hyperglycosylated forms. In this instance nickel chelate chromatography was used for purification. Further constructs of dengue (pCRO26 (SEQ ID NO: 19), and pCRO27 (SEQ ID NO: 20)) and of Zika (pCRO28 (SEQ ID NO: 17), pCRO29 (SEQ ID NO: 21), pCRO30 (SEQ ID NO: 22) and pCRO31 (SEQ ID NO: 23)) were expressed and purified. Favourable expression of the plasmid construct pCRO28 was demonstrated by anti-His-tag Western blot (FIG. 2c) and coomassie staining (FIG. 2d).

The hyperglycosylated forms chosen were pCRO21, pCRO22, pCRO23, pCRO24 (for dengue serotypes 1-4 respectively) and pCRO28 for Zika. Hyperglycosylated exodomains D1, D2, D3, D4 and Zika correspond to plasmids pCRO21, pCRO22, pCRO23, pCRO24 and pCRO28, respectively (SEQ ID NO: 24, 25, 26, 27 and 28 respectively). Molecular weight increments due to glycosylation are apparent, higher for the +2 dengue constructs than for the Zika +1 construct.

In all, eleven plasmid constructs were made and tested for protein expression and five were selected for further investigation, based on equivalent or (in most cases) superior levels of expression compared to wild type (pCRO21, pCRO22, pCRO23, pCRO24 representing the four serotypes of dengue, and pCRO28 representing Zika).

Surprisingly, given the extremely hydrophobic nature of the fusion loop (which features the residues W, F and L exposed at the tip of the E protein in close juxtaposition at its distal end in three dimensional space) in the case of dengue, all four representative serotypes tolerated substitution of two glycans (which are hydrophilic, and radically transform the topography of this part of the protein to an extent that mere amino-acid substitutions cannot) with no penalty to levels of expression (i.e., all expressed as well as the wild type sequence, in some cases markedly better). An objective had been set of 'no less than wild type' for levels of expression in order to ensure that the proteins were not misfolded which would have resulted in eradication from the endoplasmic reticulum via the ERAD channel for proteasomal degradation. Examples of the dengue serotype-1 sequence with a single glycan in the fusion loop were also made, but it did not express any better than wild type or the species with two glycans. In the case of Zika, attempts to generate variants with two glycosylation sites into the fusion loop (following the method established for dengue) were not successful, resulting in less secretion of the recombinant protein into the culture medium than for wild type.

In the case of the Zika E-protein exodomain we therefore explored the generation of variants with a single glycan at various sites in the fusion loop. Substitution of the tryptophan (W101), as for one of the dengue sequons, with an asparagine (the N of the sequon at 101 in place of W), resulted in a level of expression of the construct that was less than for wild type. Likewise, insertion of a glycan at F108 (i.e. the N of the sequon at 108, in place of F), resulted in a level of expression of the construct that was less than for wild type. We concluded that the Zika fusion loop was less tolerant to glycan insertion, and sought a more conservative way to allow it.

Having established, in the case of Zika, that neither the W101 nor the following F of the fusion loop could be replaced with the N of an N-linked glycosylation sequon, an alternative strategy was developed, which was not modeled on the approach taken for dengue. We sought to place a single glycan as near as possible to the end of the fusion loop (based on the 3D structure PDB 51RE). Rather than go through the process of systematically making and testing the hundreds of possible variants that might allow glycan insertion (which would have been arduous by gene synthesis or by library technologies), we contrived a hypothetical solution and tested it. We contrived to straddle the W at the apex of the fusion loop with an N-linked glycosylation sequon. However, we reasoned that may have been infeasible by insertion of the classical NXS/T sequon, because W is not tolerated at the X position of a sequon. However, although W is not tolerated in the 'X' position in the centre of a sequon, H (histidine, a relatively conserved replacement for W, having a hydrophobic-aromatic/cationic dual character) can be tolerated in the X-position. We therefore substituted the 100 position with an N, used a H in place of the W for the X-position, and used a T (which we find works better with H than S), to make a single sequon that read 'NHT' (i.e. residues 100, 101, 102, using the E-protein numbering convention rather than the polyprotein numbering convention). The resulting protein, made from plasmid pCRO28, was found to express as well as wild type, and gave greater yield on purification than wild type, indicating no impediment to expression. The other variants of Zika that we explored gave rise to low level or no secreted protein in the expression systems used.

Example 3 (FIG. 3) Characterisation of Glycans Present on the Glycoengineered Dengue Serotype-2 and Zika Proteins Glycan compositional analysis (GlycoThera, Germany) was performed on two of the selected proteins from Example 2, the dengue-2 serotype product of pCRO22 (representative of the selected dengue constructs that were all designed to carry two glycans in the fusion loop) and that of Zika (the product of pCRO28, designed to carry one glycan in the fusion loop) obtained from transfections of HEK 293.

The results of SDS-PAGE analysis of dengue and Zika samples prior to and after digestion with polypeptide N-glycosidase F (PNGase, Prozyme Inc.) are shown in FIG. 3a. The samples were reduced in 50 mM DTT for 5 min at 95° C. prior to SDS-PAGE analysis (15% polyacrylamide gel after coomassie blue staining) Lane 1: CV94 (pCRO22 protein, dengue-2) prior to PNGase digestion; Lane 2: CV94 after PNGase digestion; Lane 3: CV95 (pCRO28 protein, Zika) prior to PNGase digestion; Lane 4: CV95 after PNGase digestion; Lane 5: molecular weight standard. In this case the degree of decrease in apparent molecular weight (as distinct from the increment in FIG. 2c relative to WT) conforms to theoretical expectation based on the number of additional glycans introduced into the sequence: i.e. dengue-2 has lost four glycans in this digestion (two natural, and two introduced by sequence programming of additional sequons), whereas Zika has lost two glycans (one natural, and one introduced by sequence programming of one additional sequon). Enzymatic digestion with PNGase was conducted according to Tarentino and Plummer, Methods in Enzymology, 1994; 230; 44-57. Glycans were released from the hyperglycosylated protein products and quantified by high-performance anion-exchange chromatography with pulsed amperometric detection (HPAEC-PAD) and normal-phase HPLC with fluorescence detection of 2-AB-labelled N-glycans, along with specific exoglycosidase treatment (FIG. 3b). Table 2 summarizes the results of this analysis.

TABLE 2

| | Sample | |
|---|---|---|
| Structure | DENV2_ENV_2xGlyco recombinant Antigen; Lot #20161026 mol (%) | Zika_ENV_recombinant Antigen; Lot #20161213 mol (%) |
| neutral | 16.9 | 17.0 |
| monosialylated | 30.7 | 36.9 |
| disialylated | 26.6 | 32.0 |
| trisialylated | 15.0 | 8.4 |
| tetrasialylated | 9.5 | 5.1 |
| pentasialylated/sulphated | 1.3 | 0.6 |
| sum | 100.0 | 100.0 |

Quantitative HPAEC-PAD analysis of native oligosaccharides was performed on an ICS 5000+ ion chromatography system of the Thermo Fisher Scientific Inc. (Waltham, Mass., USA; GlycoThera device-ID: HPAEC-7) using high resolution CarboPac PA200 columns. Injection of appropriate oligosaccharide reference standards was included in the analytical sequence.

N-glycans were detected via electrochemical detection. The data were collected and the chromatograms were acquired by using Chromeleon Chromatography Management System Version 6.8. Native N-glycans were analyzed via HPAEC-PAD revealing mainly neutral, monosialylated, disialylated and trisialylated oligosaccharides in both preparations according to GlycoThera's reference oligosaccharide standards. (FIG. 3b, Table 3).

Desialylated N-glycans were analyzed via NP-HPLC after 2-AB labelling revealing predominantly complex-type N-glycans with significant permutational diversity, having proximal a 1,6-linked fucose in both samples (CV94=dengue-2, and CV95=Zika) according to GlycoThera's reference oligosaccharide standards. HPAEC-PAD mapping of native N-glycans released from dengue and Zika preparations CV94 (dengue 2 pCRO22 protein) and CV95 (pCRO28 protein) Zika (as shown in Table 2) revealed the presence of predominantly neutral (16.9% and 17.0%, respectively), monosialylated (30.7% and 36.9%, respectively), disialylated (26.6% and 32.0%, respectively) and trisialylated (15.0% and 8.4%, respectively) oligosaccharides in both samples. Significant amounts of tetrasialylated N-glycans (9.5% and 5.1%, respectively) as well as low proportions of pentasialylated/sulphated oligosaccharides (1.3% and 0.6%, respectively) were found in dengue and Zika samples CV94 and CV95; phosphorylated N-glycan structures such as oligomannosidic Man5-6GlcNAc2 glycan chains with one phosphate residue were not detected in either of the samples analyzed.

TABLE 3

N-glycan mapping of 2-AB labelled desialylated N-glycans, according to standard procedures at GlycoThera, from Dengue and Zika preparations CV94 and CV95 after sialidase treatment using normal-phase HPLC with fluorescence detection revealed the following compositions for the two proteins.

| # | N-glycan structure | Sample code CV94 DENV2_ENV_2xGlyco recombinant Antigen; Lot #20161026 mol (%) | Sample code CV95 Zika_ENV_recombinant Antigen; Lot #20161213 mol (%) |
|---|---|---|---|
|  | complex-type N-glycans | 61.4 | 56.6 |
| 1 | diantennary w/o 2 β-Gal w/o 1 GlcNAc with α1,6-Fuc | 0.1 | 0.2 |
| 2 | diantennary w/o 2 β-Gal with α1,6-Fuc | 0.9 | 1.2 |
| 3 | diantennary w/o 1 β-Gal with α1,6-Fuc | 3.1 | 4.4 |
| 4 | diantennary w/o 1 β-Gal with α1,6-Fuc | 0.4 | 0.8 |
| 5 | diantennary with α1,6-Fuc | 8.1 | 8.8 |
| 6 | diantennary with α1,6-Fuc with 1x α1,3-Fuc | 5.0 | 6.1 |
| 7 | triantennary w/o 3 β-Gal with α1,6-Fuc | 0.6 | 0.4 |
| 8 | triantennary w/o 2 β-Gal with α1,6-Fuc | 1.6 | 2.9 |
| 9 | triantennary w/o 1 β-Gal with α1,6-Fuc | 3.9 | 7.5 |
| 10 | triantennary with α1,6-Fuc with α1,6-Fuc | 8.8 | 7.3 |
| 11 | tetraantennary w/o 4 β-Gal with α1,6-Fuc | 1.0 | 1.9 |
| 12 | tetraantennary w/o 3 β-Gal with α1,6-Fuc | 1.4 | 2.7 |
| 13 | tetraantennary w/o 2 β-Gal with α1,6-Fuc | 3.8 | 6.0 |
| 14 | tetraantennary w/o 1 β-Gal with α1,6-Fuc | 4.9 | 3.3 |
| 15 | tetraantennary with α1,6-Fuc | 15.8 | 2.6 |
| 16 | tetraantennary with one LacNAc repeat | 2.0 | 0.5 |
|  | oligomannosidic N-glycans | 0.1 | 0.8 |
| 17 | Man5GlcNAc2 | 0.1 | 0.8 |
|  | hybrid-type N-glycans | n.d.* | n.d.* |
|  | not identified | 38.5 | 42.6 |
| X1 | — | 0.1 | 0.1 |
| X2 | — | 0.4 | 1.5 |
| X3 | — | 1.0 | 2.3 |
| X4 | — | 3.9 | 8.8 |
| X5 | — | 4.0 | 8.2 |
| X6 | — | 2.5 | 6.5 |
| X7 | — | 1.1 | 1.1 |
| X8 | — | 2.4 | 3.7 |
| X9 | — | 7.4 | 4.4 |
| X10 | — | 12.9 | 5.0 |
| X11 | — | 2.8 | 1.0 |
|  | sum | 100.0 | 100.0 |

*n.d. = not detected.

Site Occupancy Analysis of the Glycans:

Site occupancy was determined by LC-MS measurement of tryptic peptides. The analysis was based on the LC-MS measurement of tryptic or Endo Lys-C generated peptides liberated from proteins de-N-glycosylated enzymatically by PNGase F. Since PNGaseF is a glycoamidase, the asparagine (N) becomes converted to an aspartic acid residue (D). Quantification was done by creation of extracted ion chromatograms (EICs). The EICs were generated using the theoretical m/z values of differently charged target peptides within a mass window of +/−m/z of 0.01. In order to compare the peptide intensity with the specifically modified counterpart generated by de-N-glycosylation, the area of the peak of the EIC was used. The ratio/extent of modification was then calculated as follows: extent of modification=[area under EIC of modified peptide]/([area under EIC of modified peptide]+[area under EIC of unmodified peptide]).

Sequence numbering is by protein rather than the polyprotein sequence numbering convention, with W101 (at the very tip of the fusion loop) as a useful reference point. Sites are numbered according to their appearance in the linear sequence starting at the N-terminus, such that in dengue (pCRO22, GlycoThera sample number CV94) there were two additional sequons comprising sites 2 and 3. The Occupancy of the natural WT N-glycosylation sites was confirmed to be 100% and 99% for site 1 and site 4, respectively. The added N-glycosylation sites 2 and 3 (in the fusion loop) are located on one tryptic peptide (T15) and the occupancy was 38% (both sites) and additional 51% where only one of the two sites were N-glycosylated. In all 89% of the fusion loops had at least one glycan.

In the case of Zika, the occupancy of the N-glycosylation sites was confirmed to be 99.5% and 100% for the added 'site1' (residue 100, fusion loop) and site 2 (residue 154 the glycan naturally present), respectively. Site occupancy of the programmed glycosylation sequons was deduced from PNGase digestion and its effects on the mass of tryptic peptide fragments (whereby the amide $NH_2$ group of the asparagine side chain is lost and converted to a hydroxyl group). (In the following sequences programmed sequons are in bold). In the hyperglycosylated dengue 2 exodomain the relevant tryptic peptide was T15, i.e., the 15$^{th}$ tryptic peptide (GN$_{101}$GSGCGLN$_{108}$GSGGIVTCAMFTCK$_{122}$ (SEQ ID NO: 35)—containing the substituted N residues at 101 and 108. In the hyperglycosylated Zika exodomain (with a single introduced glycosylation sequon 'NHT') the relevant peptide was T10 (N$_{100}$HTNGCGLFGK$_{110}$ (SEQ ID NO: 36)).

These findings of efficient introduction of large and complex glycans into the fusion loop of dengue and Zika exodomain proteins strengthened our expectation that these proteins would neither bind to the fusion loop, nor elicit fusion-loop antibodies, giving confidence that B-cells or antibodies capable of recognising the wild type versions of the fusion loop would not engage with the glycosylated forms of the invention. This scenario is markedly different from mere introduction of mutations into the fusion loop, because by imposing one or more large additional glycan structures into the fusion loop, the resulting variant fusion loop cannot bind antibodies or B-cell receptors or generate fusion loop antibodies reactive with the wild type versions of the fusion loop. This was fully confirmed in later examples. This strategy may also be contrasted to deleting domains I and II from the structure of the protein, as these domains also contribute neutralising epitopes and T-cell epitopes useful for anamnestic immune responses upon encounter with flaviviruses in the wild, while pre-conditioning the immune system in such a way as to avoid the dangerous dominance of the fusion loop in immune responses to natural virus infections or to other vaccines.

TABLE 4 list of m/z values used for creating Extracted-Ion-Chromatograms (EIC) for N-glycosylation-site occupancy for dengue-2

| ID | Amino Acid Range | Amino acid sequence | Theor. mass in Da | m/z values used for EIC $[M + n H]^{n+}$ |
|---|---|---|---|---|
| Site 1 | | | | |
| T10 | [65-73] | L65TN67TTTESR73 (SEQ ID NO: 37) | 1022.511 | 1022.511; |
| T10 | [65-73] | L65TD67TTTESR73 (SEQ ID NO: 38) | 1023.495 | 1023.495; |
| Site 2 + 3 | | | | |
| T15 | [100-122] | G100N101GSGCGLN108GSGGIVTCAMFTCK122 (SEQ ID NO: 39) | 2304.983 | 1152.995; 768.999 |
| T15 1x de-N | [100-122] | G100D101GSGCGLN108GSGGIVTCANIFTCK122 (SEQ ID NO: 40) OR G100N101GSGCGLD108GSGGIVTCANIFTCK122 (SEQ ID NO: 41) | 2305.967 | 1153.487; 769.327 |
| T15 2x de-N | [100-122] | G100D101GSGCGLD108GSGGIVTCANIFTCK122 (SEQ ID NO: 42) | 2306.951 | 1153.979; 769.655 |
| Site 4 | | | | |
| T18 | [129-157] | V129VQPENLEYTIVITPHSGEEHAVGN153DTGK157 (SEQ ID NO: 43) | 3133.544 | 1567.276; 1045.186; 784.142; 627.515 |
| T18 de-N | [129-157] | V129VQPENLEYTIVITPHSGEEHAVGD153DTGK157 (SEQ ID NO: 44) | 3134.528 | 1567.768; 1045.514; 784.388; 627.712 |

TABLE 5 list of m/z values used for creating Extracted-Ion-Chromatograms (EIC) for N-glycosylation-site occupancy for Zika

| ID | Amino Acid Range | Amino acid sequence | Theor. mass in Da | m/z values used for EIC $[M + n H]^{n+}$ |
|---|---|---|---|---|
| Site 1 | | | | |
| L4 | [94-110] | R94TLVDR99N100HTNGCGLFGK110 (SEQ ID NO: 45) | 1944.982 | 1944.982; 972.995; 648.99; |

TABLE 5-continued list of m/z values used for creating Extracted-Ion-Chromatograms (EIC)
for N-glycosylation-site occupancy for Zika

| ID | Amino Acid Range | Amino acid sequence | Theor. mass in Da | m/z values used for EIC $[M + n H]^{n+}$ |
|---|---|---|---|---|
| L4 de-N | [94-110] | R94TLVDR99D100HTNGCGLFGK110 (SEQ ID NO: 46) | 1945.966 | 1945.966; 973.487; 649.327; |
| Site 2 | | | | |
| T16 | [139-164] | I$_{139}$MLSVHGSQHSGMIVN$_{154}$DTGHETDENR$_{164}$ (SEQ ID NO: 47) | 2864.305 | 1432.656; 955.440; 716.832; |
| T16 de-N | [139-164] | I$_{139}$MLSVHGSQHSGMIVD$_{154}$DTGHETDENR164 (SEQ ID NO: 48) | 2865.289 | 1433.148; 955.768; 717.078; |

TABLE 6 site occupancy (% occupation) for dengue-2
(sites 2 and 3 are in the fusion loop)
Rate of N-glycosylation site occupancy [%]

| Sample | GT-code | N-glycosylation site [peptide] | | | |
|---|---|---|---|---|---|
| | | Site 1 N$_{67}$ [T10] | Site 2 + 3 N$_{101}$; N$_{108}$ [T15] | Site 2 or 3 N$_{101}$ or N$_{108}$ [T15] | Site 4 N$_{153}$ [T15] |
| DENV2_ENV | CV94 | 100 | 38 | 51 | 99 |

(collectively, 89% of molecules have a glycan or two in the fusion loop. N101 replaced W101 of the WT sequence; N108 replaced F108 of the wild type sequence)

TABLE 7 site occupancy (% occupation) for Zika (site 1 is in the fusion loop)
Rate of N-glycosylation site occupancy [%]

| Sample | GT-code | N-glycosylation site [peptide] | |
|---|---|---|---|
| | | Site 1 N$_{100}$ [L4] | Site2 N$_{154}$ [T16] |
| Zika_ENV | CV95 | 99.5 | 100 |

(99.5% of molecules have a single glycan in the fusion loop; N100 replaced G100 of the WT sequence)

Example 4 (FIG. 4) Immunogenicity of Select Glycoengineered Dengue Proteins 1, 2, 3 and 4 and Zika in Direct ELISA Female Balb-c mice were immunized with PBS (negative control) and various dengue and Zika formulations of the hyperglycosylated exodomain proteins on Alhydrogel, alone (Zika mono) and in combination (Penta-) and as naked DNA (DNA). Alhydrogel formulations of proteins were injected subcutaneously (s.c.) in a total volume of 200 ul and naked DNA (comprising plasmids pCRO21, pCRO22, pCRO23 and pCRO24 of dengue plus pCRO28 representing Zika) was injected intramuscularly (i.m.) in a total volume of 50 ul for pentavalent DNA (representing 5 micrograms of each plasmid immunogen). Pentavalent protein combinations contained 5 ug amounts per dose of each hyperglycosylated exodomain, and monovalent (Zika) contained 10 ug per dose. Mice were dosed three times, once at each of day 0, day 14 and day 21. The legend at the bottom right of FIG. 4 denotes the composition of each immunogen. The title of each panel denotes the antigen used on the solid phase ELISA plate. (Wild type recombinant VLPs were used both as immunogens, Group 4, and as antigens in FIG. 4). Mice were bled retro-orbitally at the intervals indicated and serum was collected for ELISA and PRNT assays.

The Balb-c Mice were immunized with DNA and protein representations of the glycoengineered exodomains and with the corresponding VLPs (i.e. VLPs representing the wild type sequences) from The Native Antigen Company Ltd, Oxford, UK (with no extra glycans, and exposed fusion loops) as positive control. These VLPs (see Table 8, used as both immunogens and also as test antigens in the ELISA tests of FIG. 4) also contain multiple additional epitopes not present in the exodomains, notably epitopes of the pre-membrane protein prM.

TABLE 8

| Group (n = 5) female Balb-c mice | Immunogen | Route of immunization | Doe | Injectate volume | Alhydrogel* adjuvant (2% w/v aqueous alhydrogel suspension)(ul) |
|---|---|---|---|---|---|
| 1 | Pentavalent glycoengineered DNA ('Penta-DNA' in figures) | i.m., in 10 mM Tris-HCl pH 7.4 | 50 ug of each plasmid (250 ug total) | 50 ul | None |

TABLE 8-continued

| Group (n = 5) female Balb-c mice | Immunogen | Route of immunization | Doe | Injectate volume | Alhydrogel* adjuvant (2% w/v aqueous alhydrogel suspension)(ul) |
|---|---|---|---|---|---|
| 2 | Pentavalent glycoengineered proteins (Penta-Prot) | s.c. | 5 ug of each protein (25 ug in total) | 200 ul | 50 |
| 3 | Monovalent Zika glycoengineered protein (Zika-mono) | s.c. | 10 ug of Zika protein | 80 ul | 20 |
| 4 | Pentavalent wild type VLP (Penta VLP) | s.c. | 5 ug of each VLP (25 ug in total) | 200 ul | 50 |
| 5 | PBS | s.c. | 0 | 200 ul | none |

There was little antibody response to naked DNA representing the five exodomains—as expected in the absence of delivery assistance from liposomal formulation, gene-gun or electroporation technology. Antibody responses to naked DNA were evident against dengue 1, 2 and 3 native VLPs, and not against Zika and dengue 4 VLPs. However these results served to demonstrate the potential utility of these DNA encoded antigens (all of them) with appropriate delivery systems. The assay is naturally more sensitive to detect immune responses to VLPs, due to the presence of additional epitopes (noted above), such that, as expected, antibody responses to the VLP antigens were uniform and very strong in the VLP-immunised 'Group 4'. However, so too were responses to the novel glycoengineered exodomain proteins of the present invention, which gave strong, balanced immune responses against all five components (dengue serotypes 1,2,3 and 4 plus Zika) with the pentavalent immunogen formulation. Responses were uniformly high to the exodomain immunogens (pentavalent protein and monovalent Zika) and there were no non-responders. Also, the response to Zika in the monovalent-Zika-hyperglycosylated-exodomain-immunized group (10 μg dose) was modestly higher than that in the pentavalent protein group where the same exodomain was used at half the dose. This finding indicates a favorable lack of competition among the serotypes in the generation of type specific immune responses (this is a known problem with live attenuated flavivirus vaccine approaches, such as Dengvaxia, where immune responses to dengue serotype 2 are problematically low).

For direct ELISA (FIG. 4) to measure murine antibodies against dengue and Zika viruses Nunc™ Flat 96-Well Microplates, Thermoscientific, Cat. No. 269620, were coated with VLPs (from The Native Antigen Company (Oxford)) at a concentration of 0.5 μg/ml in bicarbonate-carbonate buffer (pH 9.4-9.6) containing sodium bicarbonate at 4.43 g/l and sodium carbonate at 1.59 g/l, at 104 μl/well for 2 h at room temperature. Plates were aspirated and blocked with 2% neutral BSA (SigmaAldrich A7906) in Dulbecco's phosphate buffered saline (PBS, ThermoFisher-Gibco 14190136) (PBS-BSA). The blocking buffer was used as diluent for the testing of mouse sera diluted at concentrations of 1/100 and 1/10,000 (duplicates at each concentration). Plates were washed with PBS containing 0.05% Tween-20 detergent (Sigma-Aldrich) (PBS-Tween) after each incubation (blocking, diluted serum incubation, conjugate incubation) by filling and emptying the wells five times with PBS-Tween. After serum incubation and washing, a secondary antibody conjugate was applied in PBS-BSA (goat anti-mouse IgG HRP conjugate BioRad 103005) at a dilution of 1:4000. After washing the plate a final time, substrate for horseradish peroxidase (HRP) was added (3,3',5,5'-tetramethylbenzidine, TMB, Sigma-Aldrich T00440), and stopped with 0.16 M sulfuric acid after 20 min incubation at room temperature. Incubations were conducted on a mixer (Grant Bio, PMS-1000 at 500 rpm approx.). Absorbance of the stopped reaction was read at 450 nm.

Antibody responses were calibrated against fusion loop antibody 4G2 (The Native Antigen Company Ltd, Oxford) with dengue VLP representing serotype 2 on the solid phase at 0.5 micrograms per ml coating concentration. Units of antibody measurement "IgG antibody titre" are micrograms per ml 4G2-equivalent in undiluted serum, determined by interpolation of the standard curve using a four-component polynomial regression fit (AssayFit, IVD Tools). At day 42, antibody responses reached $10^4$-$10^5$ for the hyperglycosylated exodomain immunogens (a notional 10 mg per ml-100 mg per ml in neat serum). These concentrations (taken literally) are unattainably high since the IgG concentration of mouse serum is only 2-5 mg per ml, and probably reflect the higher affinity or avidity of the antibodies generated compared to the antibody, 4G2, used for standardization, or may reflect better epitope exposure (4G2's fusion loop epitope being semi-cryptic in the structure of VLPs and virions). Nevertheless the 4G2 calibration serves a useful purpose allowing the assay to be run from time to time, controlling for such variables as batch to batch variation in the conjugate—(an anti-IgG-Fc horseradish peroxidase conjugate made from polyclonal antibodies which vary by batch). This is more reliable than quoting antibody 'titres' based on a threshold absorbance value which are very conjugate-batch and antigen-batch dependent, and may vary further among conjugates sourced by different manufacturers.

A further aspect of these observations is that the antibodies generated are of the IgG class demonstrating class-switching (even at day 14) from IgM, for all of the protein immunogens. This is an essential component of the B-cell memory response, important for the development of vaccines. A further aspect of these findings is that the antibodies generated by exodomain protein immunogens (and to some extent the DNA immunogens) strongly recognize the native form of the VLP antigens, which also lack His tags, ruling out the possibility of false positives due to anti-His-tag responses. This proves that both the dengue and Zika exodomain materials represent native epitopes of the exodomain proteins that are immunogenic in generating anti-viral (VLP) antibodies. These results suggest that other nucleic acid encoded forms of the hyperglycosylated exodomain species, e.g., liposomal RNA or lipoplex RNA, would also generate desirable antibody responses against virions (VLPs) and viruses.

There was specificity in the immune response to the Zika monovalent hyperglycosylated exodomain, which generated higher antibody titres against the homologous Zika VLP than to other VLPs, despite the known cross-reactivity of these various viruses with antibodies. This is a favourable result since type-specific anti-Zika antibodies are known to have better neutralizing activity generally than dengue-cross-reactive ones. Also, as seen in the antibody-responses to the Zika-monovalent hyperglycosylated exodomain at the later time points (after two or three doses), there was a degree of cross-reactivity against dengue strains that developed over time, raising the potential for generation of beneficial cross-reactive neutralizing responses, excluding the fusion loop epitope (which was not recognized by antibodies generated by hyperglycosylated exodomain species as demonstrated in the data that follows in later examples).

Example 5 (FIG. 5) Avoidance of Recognition of the Glycoengineered Proteins by Fusion Loop Antibodies, and Retention of Neutralizing Epitopes An ELISA test (of FIG. 5) was devised employing oriented capture of His-6-tagged exodomain proteins on the solid phase (the VLPs of FIG. 4 do not have His-tags).

Unless otherwise specified, conditions were the same as for the ELISA test of Example 4 and FIG. 4. 8-well strip ELISA plates (Dynex) were coated with rabbit monoclonal anti-His-6 tag (Anti-6× His Tag® antibody [HIS.H8] (ab18184) Abcam) for 1 h at room temperature and then overnight at a concentration of 1 µg/ml in bicarbonate-carbonate coating buffer. Plates were washed and then exposed to Starting Block (ThermoFisher 37538) 30 min at room temperature, and then to the various exodomain proteins, all having a C-terminal hexa-histidine tag, at a concentration of 0.5 µg/ml, for 2 h at 37 degrees then at 4 degrees overnight. Antibodies were added to appropriate wells in 0.4% BSA in PBS-Tween and incubated for 2 h at 37 degrees. Next a secondary antibody conjugate (rabbit-anti-mouse-HRP IgG H&L, Abcam ab97046), for mouse antibodies, was applied in 0.4% BSA in PBS-Tween, at a dilution of 1/10,000. For human serum, the dilution factor was 1/1000 in PBS-Tween 0.4% BSA followed by goat anti-human IgG Fc (HRP) preadsorbed (Abcam ab98624) at 1/20,000. Secondary antibody HRP conjugates were incubated for 2 h at 37 degrees. The plate was washed between exposure to successive reagents. Finally TMB substrate was added and stopped after 10 min at room temperature.

Antigens were as follows: wild type dengue exodomains representing dengue serotypes 2 and 4 were from The Native Antigen Company (DENV2-ENV, DENV4-ENV); 'HX' designated exodomains (hyperglycosylated exodomains) were the selected set of Excivion exodomains of the present disclosure (pCRO21-24 for dengue, pCRO28 for Zika). Prospec Zika was a non-glycosylated bacterial exodomain from Prospec of Israel (zkv-007-a), and Aalto Zika was an insect (Sf9 cell) derived Zika exodomain (AZ6312-Lot3909). Mouse monoclonal antibodies against Zika virus exodomain were as follows: Aalto Bioreagents AZ1176-0302156-Lot3889; Z48 and Z67 were neutralizing antibodies described by Zhao et al, Cell 2016 (The Native Antigen Company ZV67 MAB12125 and ZV48 MAB12124). Antibody 4G2 is an anti-dengue-serotype-2 antibody recognizing the fusion loop (The Native Antigen Company AbFLA-VENV-4G2).

Figure 5A:
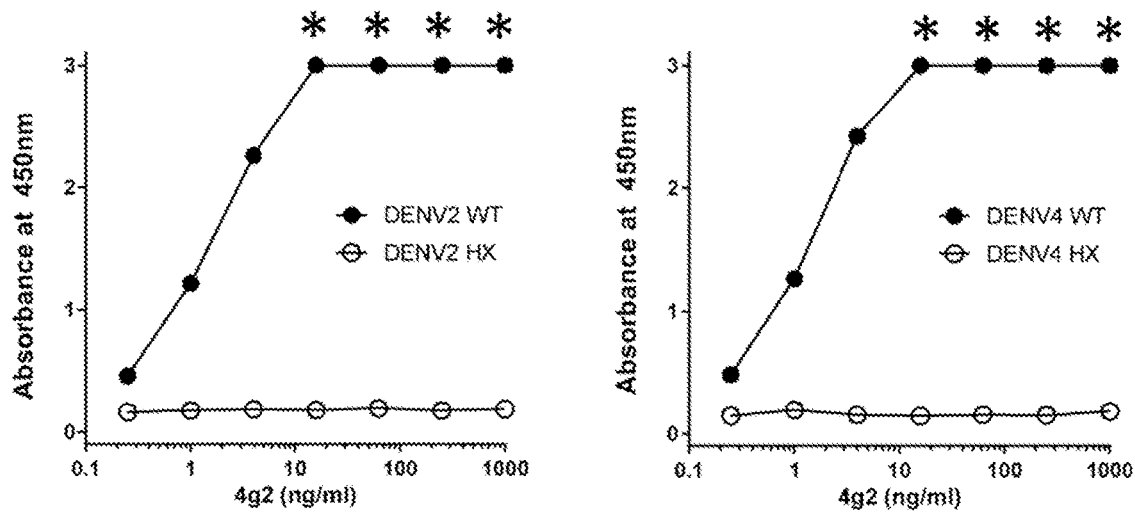

FIG. 5a demonstrates the sensitive detection of wild type exodomains of dengue 2 and 4 by antibody 4G2, giving a signal significantly above background even at very low concentrations (250 pg/ml). In contrast, the hyperglycosylated exodomains gave no detectable signal at any of the concentrations tested (5a). This side-by-side comparison of the wild-type and fusion-loop-glycosylated (HX) exodomains demonstrates that the latter fail to react with this classical fusion loop antibody (which is highly dependent on Leucine 107, Stiasny K et al., J Virol 2006 80:19 9557-68, intolerant of D, T or F at that position), even despite the presence of 11% of non-glycosylated (albeit mutated) fusion loop in the dengue-2 HX exodomain used (refer to example 3 for glycosylation site occupancy data). This demonstrates that the mutations employed, even without the glycans, are sufficient to prevent the binding of this particular fusion loop antibody (4G2). However, given the clonal diversity of human antibodies, ultimately it will be preferable to employ the glycosylated forms as an additional layer of surety that fusion loop antibodies capable of recognizing wild type fusion loops of flaviviruses will not be generated in man with these novel immunogens when used as vaccines.

Figure 5B:
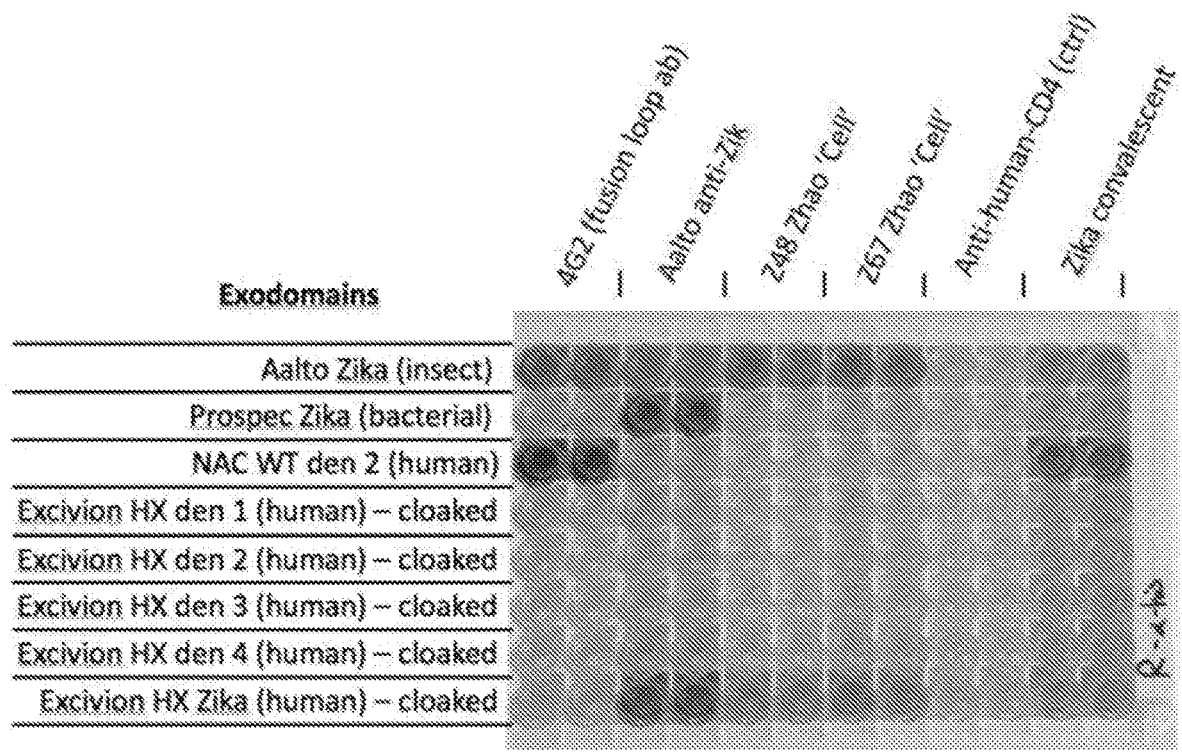
Figure 5C:
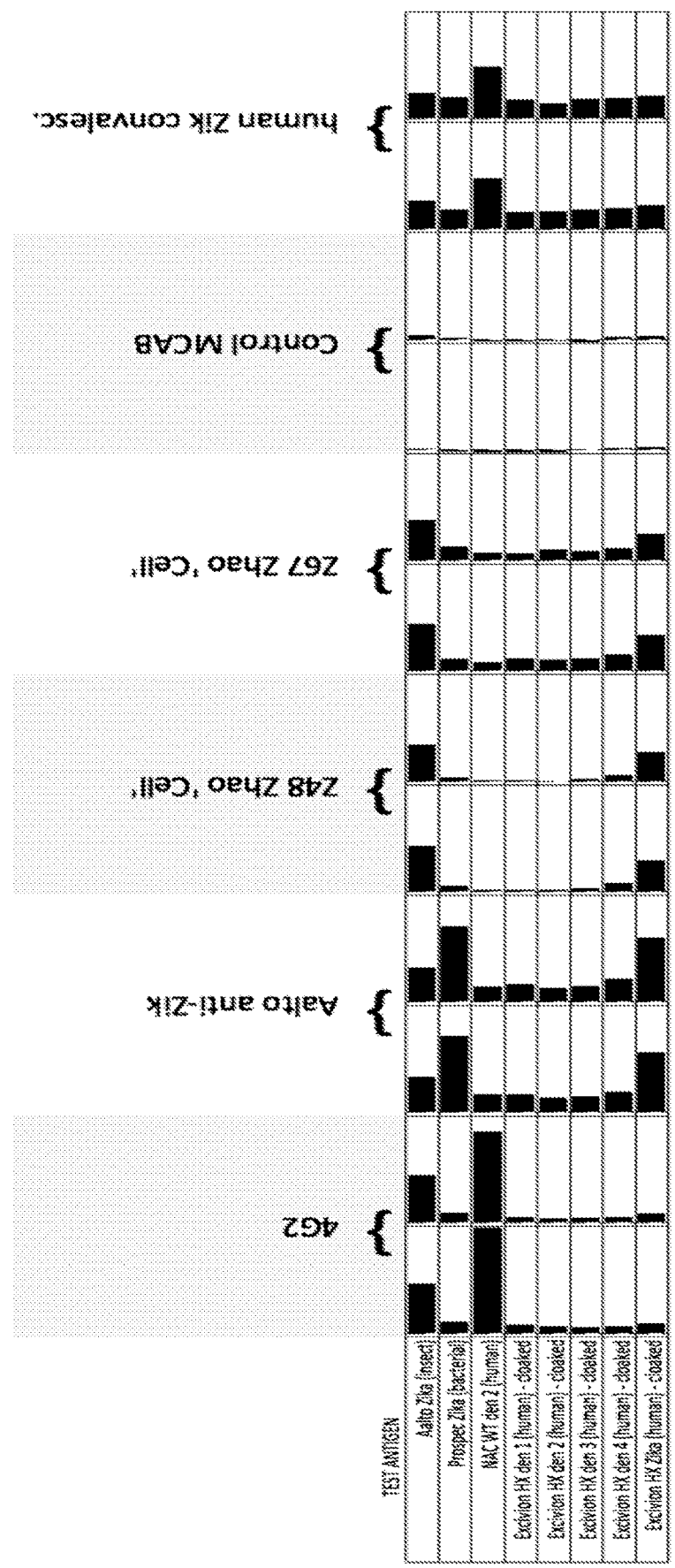
Figure 5D:
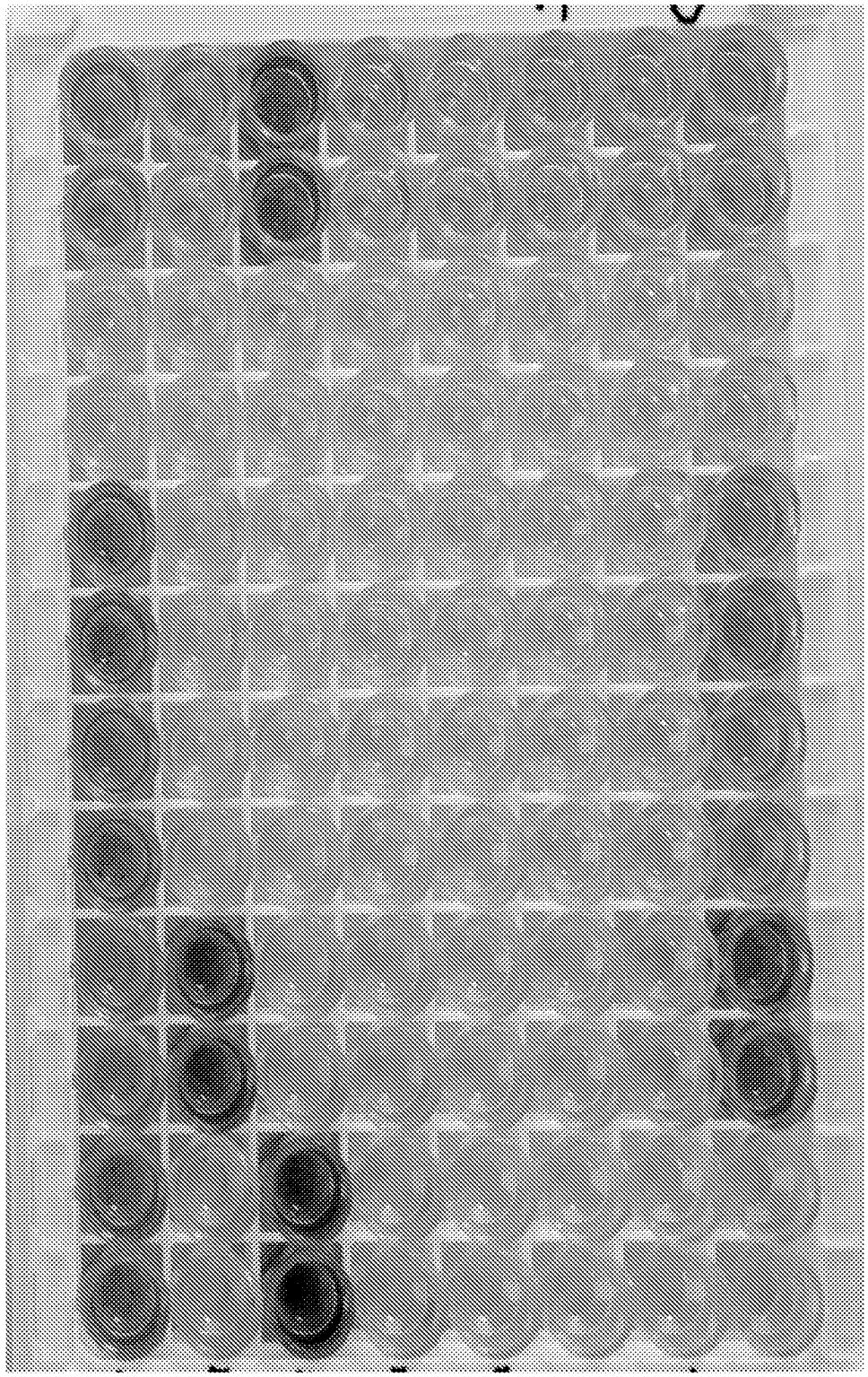

The data of FIG. 5b&c also demonstrate that, in the case of Zika, the HX version of the exodomain reacts with all three Zika monoclonal antibodies, including the two neutralizing epitopes ZV48 (Z48) and ZV67 (Z67). This demonstrates that the Zika HX exodomain has retained these neutralizing epitopes, plus the Aaalto antibody epitope, despite the drastic changes wrought to the structure of the fusion loop by glycan insertion. Moreover, this Zika HX exodomain fails to react with 4G2, as do the four dengue HX exodomains, confirming that this epitope has been effectively cloaked in all five HX proteins.

The data of FIG. 5b&c, with respect to the Zika human convalescent serum tested are also diagnostically informative. This serum was a gift from Mark Page of NIBSC selected for its high PRNT activity against Zika and its high levels of Zika NS1 antibody. The data of FIG. 5b&c demonstrate that this Zika convalescent serum strongly recognizes, indeed prefers the dengue-2 wt exodomain over other antigens in the test. This observation demonstrates the diagnostic utility of the HX series of proteins, and indicates that this patient had previously also been exposed to another flavivirus other than Zika. In fact it suggests that that other flavivirus was not dengue because the Zika convalescent serum (unlike the dengue convalescent serum) fails to react with the hyperglycosylated exodomain forms of dengue. The fusion loop antibodies in the Zika convalescent serum must therefore have originated from exposure to a third flavivirus, such as yellow fever (by vaccination or infection) or West Nile virus, both of which are prevalent in Trinidad where this serum was collected.

A further aspect of the data of FIG. 5b&c are that the Zika HX antigen has the capacity to selectively inform the presence of neutralizing antibodies, since the 4G2 fusion loop epitope has been effectively cloaked, while neutralizing epitopes noted above, have been retained. The HX Zika exodomain protein and likely therefore the dengue HX exodomain proteins will therefore have the capacity to inform the development and deployment of Zika and dengue vaccines. In the case of the latter, the HX antigens of the test will be useful in identifying persons that are naïve to dengue and who might be spared vaccination with the currently licensed DengVaxia® anti-dengue vaccine, in order to reduce the risk of predisposition to subsequent dengue haemorrhagic fever (whereby the vaccine acts as a silent primary dengue infection). Such test may extend the utility of DengVaxia to younger persons (currently it is only licensed to children greater than 9 years of age), or to naïve persons in non-endemic territories such as Europe and the USA (e.g. for use in traveler populations in whom DengVaxia vaccination is not currently advocated).

Example 6 (FIG. 6) Avoidance of Generation of Fusion-Loop Antibodies by the Glycoengineered Proteins An ELISA test was established to measure the binding of polyclonal antibodies against the fusion loop (represented in this example by dengue serotype-3 VLP on solid phase ELISA plates).

A competition ELISA was set up using biotinylated 4G2 (Integrated Biotherapeutics) which was detected using streptavidin-horseradish peroxidase conjugate. Dengue serotype 3 VLP (The Native Antigen Company) which reacts with 4G2 slightly better than the immunizing serotype dengue-2 VLP was used as antigen coated at 0.5 ug per ml on the solid phase. Pooled sera (from the groups of FIG. 4) or unlabeled 4G2 (as standard) were titrated at various dilutions (from 1/10 as the top concentration of the serum pools) to determine their capacity to compete with biotinylated 4G2 for binding to the fusion loop. Similar standard curves were generated (not shown) using Zika VLP and dengue-2 VLP wild type recombinant materials as antigen, underscoring the generality of this phenomenon (cross-reactivity of fusion loop antibodies) across the flaviviruses of interest.

In this assay (FIG. 6) the ability of unlabeled 4G2 to compete for binding to solid phase antigen was demonstrated using biotinylated 4G2 and streptavidin-HRP conjugate (Kirkegaard and Perry KPL KPL 14-30-00 at 1/3000). Unless otherwise specified, conditions were as for Example 4. First, a sample of 4G2 was biotinylated according to manufacturer's instructions using the BioRad EZ-link NHS-PEG4 biotinyation kit (21455) using a molar ratio of reactants of 30:1. Unlabeled antibody and biotinylated antibody were allowed to compete in an overnight room temperature incubation for binding to solid phase antigen. Antigen-coated plates were exposed in parallel to dilutions of standard antibody (four or five-fold serial dilutions of 4G2, unlabeled). Biotinylated antibody was used at a concentration of 100 ng/ml.

Figure 6:
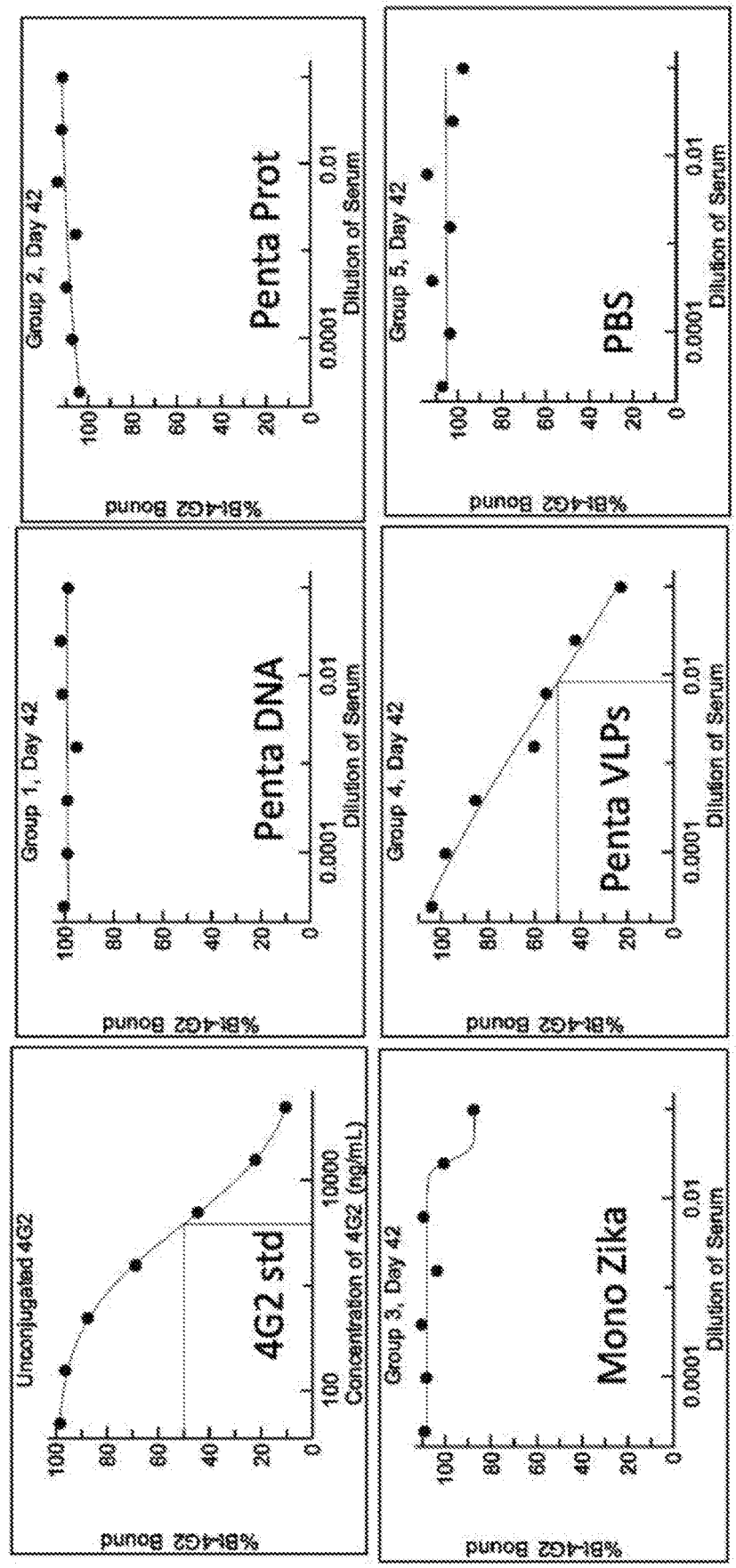

FIG. 6 demonstrates that antibodies raised against pentavalent VLPs on Alhydrogel, containing VLPs of all four dengue serotypes plus Zika, generate abundant fusion loop antibodies. It can be calculated from these data (assuming similar affinities of 4G2 and raised antibodies) that the VLP-immunised sera contain approximately 100 micrograms per ml fusion loop antibody, which is the maximum amount generally for viral antibodies in a polyclonal antiserum. In contrast, none of the other groups generate significant amounts of fusion loop antibodies whose binding is mutually exclusive with 4G2. In particularly the pentavalent (HX) exodomain proteins of the present disclosure do not generate fusion loop antibodies as assessed in this test, and neither does the monovalent Zika (HX) protein, despite generating very substantial antibody responses to the VLP antigens used in the competition ELISA test. In the case of Zika, inhibition was detectable only at the highest concentration tested, indicating a >1000 fold advantage in avoidance of fusion loop antibodies compared to VLP immunogens, if this single point at 1/10 serum dilution is (for the sake of argument) deemed to be significant.

The data of FIG. 6 demonstrate that a dengue vaccine (or a Zika vaccine) of the invention would not prime for antibody responses to the conserved fusion loop. This is in contrast with natural primary dengue infections that prime for subsequent haemorrhagic fever upon encounter with a second serotype of dengue. Such antibody responses to natural primary dengue infections are poorly neutralizing or non-neutralizing at physiological concentrations of antibody and are particularly implicated in the causation of antibody-dependent enhancement of dengue infection and disease by allowing antibody-complexed virions to enter and infect myeloid cells via Fc-receptors, while failing to prevent them infecting other host cells.

Figure 7B:
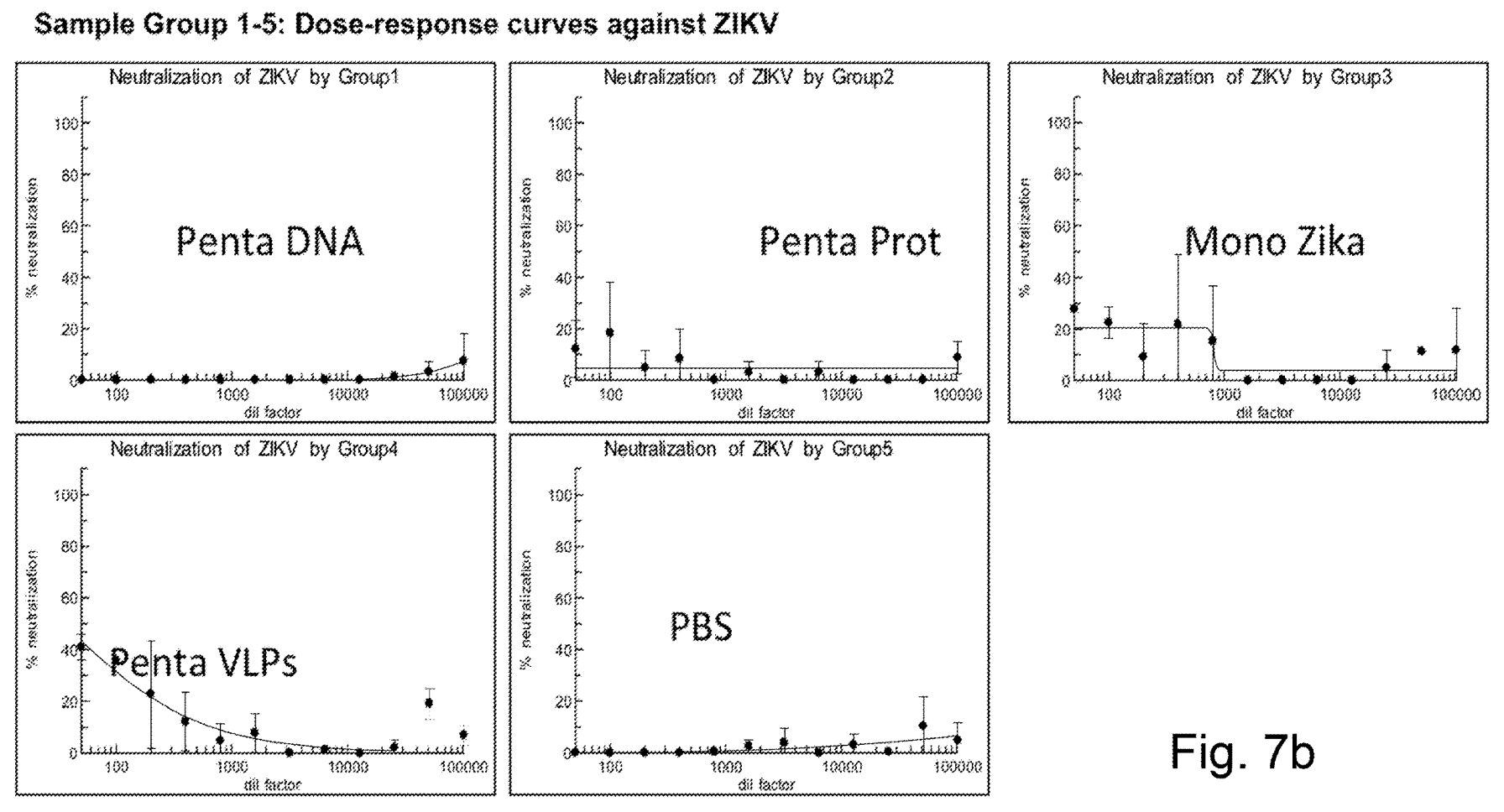

Example 7 (FIG. 7) Generation of Neutralising Antibodies by the Glycoengineered Dengue and Zika Proteins Serum pools from Example 4 were tested for their ability to neutralize dengue serotype 2 and Zika viruses using Vero cells in plaque reduction neutralization tests (PRNT).

In the case of dengue, the dengue serotype 2 strain used to infect the Vero cells (D2Y98P) was a different serotype-2 strain (non-homologous) from the sequence of the immunizing dengue 2 strain of the VLPs and exodomains. In the groups expected (from Example 4) to generate dengue neutralizing antibodies (namely pentavalent protein and pentavalent VLPs, Groups 2 & 4) there was potent neutralization of the 'off target' dengue test virus. In the case of Zika there was significant (albeit partial) neutralization as expected from the results of Example 4, in groups shown to contain antibodies that recognized native Zika VLPs (namely pentavalent protein and pentavalent VLPs, Groups 2, 3 & 4). Due to limitations on sample volume, the maximum concentration of serum that was tested was 1/50, such that in interpreting these results this factor needs to be taken into consideration (i.e. that there would be higher neutralizing capability in the blood of the immunized animals).

TABLE 9

Immunogenicity Study Design

| Group (n = 5) | Vaccine* | Vaccine Schedule | Dosage | Bleeds | Readout |
|---|---|---|---|---|---|
| 1 | Pentavalent glycoengineered DNA | On days 0, 14, & 21 via IM route | 250 µg total DNA (50 µg of each) | Test bleed for serum on Days 14 & 21. Terminal bleed on Day 42. | Measurement of antibodies against ZIKV & DENV 1-4 via ELISA |
| 2 | Pentavalent glycoengineered proteins on Alhydrogel | | 25 µg total protein (5 µg each) | | |

TABLE 9-continued

Immunogenicity Study Design

| Group (n = 5) | Vaccine* | Vaccine Schedule | Dosage | Bleeds | Readout |
|---|---|---|---|---|---|
| 3 | Monovalent Zika glycoengineered protein on Alhydrogel | | 10 μg protein | | |
| 4 | Pentavalent wild type VLP on Alhydrogel | | 25 μg total VLPs (5 μg each) | | |
| 5 | PBS | | — | | |

PRNT Assay was performed as follows. Five mouse serum samples were pooled by taking an equal volume of individual samples in each group (sample description in next slide) and were then tested against ZIKV and DENV, respectively. Twelve two-fold serial dilutions of each serum sample in duplicates starting at 1:50 were prepared for the two-hour inoculation with virus. The serum-virus mix was then added to Vero cells seeded in 24-well culture plates and incubated at 37° C. in a humidified 5% $CO_2$ atmosphere. The Vero cells were fixed on 3 days post incubation (dpi) for ZIKV PRNT and 4 dpi for DENV PRNT. Viral plaque was determined by crystal violet staining.

Potent inhibition of infection by dengue was observed in the group immunized with hyperglycosylated exodomain proteins of the present disclosure (Penta-prot). Zika immunized animals generated antibodies that did not prevent dengue infection of Vero cells, illustrating the type-specific nature of antibodies generated by these novel immunogens. These Zika antibodies (from the Zika monovalent group and from the pentavalent proteins group) were significantly protective of infection of Vero cells by Zika virus. As expected, PBS-sham-immunised animals did not give rise to protective antibodies, nor did pentavalent DNA administered intramuscularly. This latter result may have been due to the low concentrations of antibodies generated by naked DNA, as expected from intramuscular injection (as distinct from gene-gun or electroporation strategies, or strategies incorporating encoded proteins as molecular adjuvants).

The results of Example 6 (generation of neutralizing antibodies) combined with those of Example 5 (lack of recognition by or generation of fusion loop antibodies) by the hyperglycosylated Exodomain proteins of the invention strongly suggest that these proteins can form the basis of a protective vaccine for dengue or Zika viruses (or, in combination, for both viruses) without the generation of fusion loop antibodies, which are particularly implicated in antibody-dependent enhancement of infection.

Example 8 (FIG. 8) Reaction of Convalescent Dengue or Zika Serum with Immobilized Zika and Dengue Wild-Type (WT) and Hyperglycosylated (HX) Exodomain Proteins The ELISA reactivity of antibodies in a dengue convalescent serum with immobilized Zika and dengue wild-type (WT) and hyperglycosylated (HX) exodomain proteins oriented on the solid phase by capture with a rabbit anti-His-tag monoconal antibody (FIG. 8, upper panel), in the presence (grey bars, right of each pair) and absence (black bars, left of each pair) of competing mouse monoconal flavivirus fusion loop antibody 4G2 (an anti-dengue-serotype-2 monoclonal antibody) at a concentration of 10 μg/ml during serum incubation. Human sera were tested at a constant concentration of 1/1000.

The ELISA reactivity of antibodies in a Zika convalescent serum with immobilized Zika and Dengue wild-type (WT) and hyperglycosylated (HX) exodomain proteins (FIG. 8, lower panel) in the presence (grey bars) and absence (black bars) of competing mouse monoclonal flavivirus fusion loop antibody 4G2. Conditions and labelling are the same as for the upper panel. Error bars are standard error.

The results show that:

1) the HX Zika antigen of the invention is not susceptible to the off-target recognition of WT Zika exodomain by the convalescent dengue serum.

2) The off-target recognition of WT Zika exodomain (Aalto) by dengue serum is a fusion-loop directed phenomenon because it is abolished by 4G2 (anti-fusion loop monoclonal antibody) in solution phase at a concentration that causes 80% inhibition against VLPs (10 micrograms per ml). (The antigen on the solid phase in this instance is exodomain rather than VLP).

3) The 'Zika' convalescent serum does not recognize any of three Zika exodomains, but it strongly recognizes WT dengue 2 and WT dengue 4. In the Example 6 the HX Zika antigen of the invention and Aalto's Zika exodomains exhibit reaction with conformation-dependent anti-Zika neutralising antibodies). This demonstrates that this particular Zika serum (positive for Zika plaque neutralisation and Zika NS1 antibodies) is from a subject also exposed to another flavivirus. Because the Zika convalescent serum (unlike the dengue convalescent serum) does not recognize the fusion-loop-cloaked exodomains, it can be concluded that this other flavivirus is not dengue.

4) The off-target recognition of WT dengue-2 and dengue-4 exodomains by the human Zika convalescent serum is not seen with the HX-cloaked dengue exodomains of the invention. This suggests that it is fusion loop directed and would show false positive in other flavivirus diagnostic tests that do not use glycan-cloaked proteins in accordance with the invention.

5) The off-target recognition of WT dengue-2 and dengue-4 exodomains by the human Zika convalescent serum is blocked completely by 4G2 showing that it is a fusion loop directed phenomenon.

6) The dengue convalescent serum recognizes WT 2 & 4 indiscriminately, but clearly prefers the d2 exodomain out of the set of 4. This demonstrates that the fusion loop antigens of the invention have superior selectivity (compared to their wild type equivalent forms) to discriminate between dengue serotypes, due to the glycan cloaking of the fusion loop.

| Sequence Listing Free Text |
|---|

SEQ ID NO: 1   DRGWGNGCGLFGK

SEQ ID NO: 2   DRGNGSGCGLNGS,

SEQ ID NO: 3   DRGNGSGCGLFGK

SEQ ID NO: 4   DRGWGNGCGLNGS

SEQ ID NO: 5   DRNHTNGCGLFGK.

SEQ ID NO: 6   DRGWGNGCGNHTK

SEQ ID NO: 7   pCRO25 fragment CKRTLVDRGNGSGCGLNGSGSLVTCAKFA

SEQ ID NO: 8   pCRO29 fragment CKRTLVDRGWGNGCGNHTKGSLVTCAKFA

SEQ ID NO: 9   pCRO30 fragment CKRTLVDRGNGSGCGLFGKGSLVTCAKFA

SEQ ID NO: 10  pCRO31 fragment CKRTLVDRGWGNGCGLNGSGSLVTCAKFA

SEQ ID NO: 11  DRGWGNNCTLFGK

SEQ ID NO: 12  DRGWGNNCSLFGK pCRI21 (SEQ ID NO: 13)
ORIGIN
```
   1 GCGATCGCGG CTCCCGACAT CTTGGACCAT TAGCTCCACA GGTATCTTCT TCCCTCTAGT
  61 GGTCATAACA GCAGCTTCAG CTACCTCTCA ATTCAAAAAA CCCCTCAAGA CCCGTTTAGA
 121 GGCCCCAAGG GGTTATGCTA TCAATCGTTG CGTTACACAC ACAAAAAACC AACACACATC
 181 CATCTTCGAT GGATAGCGAT TTTATTATCT AACTGCTGAT CGAGTGTAGC CAGATCTAGT
 241 AATCAATTAC GGGGTCATTA GTTCATAGCC CATATATGGA GTTCCGCGTT ACATAACTTA
 301 CGGTAAATGG CCCGCCTGGC TGACCGCCCA ACGACCCCCG CCCATTGACG TCAATAATGA
 361 CGTATGTTCC CATAGTAACG CCAATAGGGA CTTTCCATTG ACGTCAATGG GTGGAGTATT
 421 TACGGTAAAC TGCCCACTTG GCAGTACATC AAGTGTATCA TATGCCAAGT ACGCCCCCTA
 481 TTGACGTCAA TGACGGTAAA TGGCCCGCCT GGCATTATGC CCAGTACATG ACCTTATGGG
 541 ACTTTCCTAC TTGGCAGTAC ATCTACGTAT TAGTCATCGC TATTACCATG CTGATGCGGT
 601 TTTGGCAGTA CATCAATGGG CGTGGATAGC GGTTTGACTC ACGGGGATTT CCAAGTCTCC
 661 ACCCCATTGA CGTCAATGGG AGTTTGTTTT GGCACCAAAA TCAACGGGAC TTTCCAAAAT
 721 GTCGTAACAA CTCCGCCCCA TTGACGCAAA TGGGCGGTAG GCGTGTACGG TGGGAGGTCT
 781 ATATAAGCAG AGCTGGTTTA GTGAACCGTC AGATCAGATC TTTGTCGATC CTACCATCCA
 841 CTCGACACAC CCGCCAGCgg ccgccaccat gaaggccaat ctactggtgt tgctgtgtgc
 901 ccttgcggcg gcagatgcca tgcggtgcgt ggggatcggc aatcgcgatt tgtagaagg
 961 actatctggt gccacgtggg tcgatgtggt tcttgaacac gggtcatgcg tgaccacgat
1021 ggctaaggat aagccgacct tggacatcga actactgaaa ccgaggtca caaaccctgc
1081 tgtgctccgc aagctgtgca tcgaggctaa gatttccaac acaactactg atagccgctg
1141 ccccacccaa ggcgaggcga cctcgttga agagcaggac agcaacttcg tgtgtcgccg
1201 gactttcgtg gaccgcggta atgggtccgg atgcggactt aacggatctg gttccttact
1261 gacttgcgcc aaatttaagt gcgtgactaa gttagagggg aaaatcgttc agtatgagaa
1321 cttaaaatac tcggtgatag ttaccgtgca cacaggcgac cagcatcaag ttgggaacga
1381 aacgacagag cacgggacaa tagcgaccat taccccacag gctccaacga gcgaaattca
1441 gctgacagac tacggtgcac tcaccctgga ctgtagccca cggaccgggc tagactttaa
1501 cgagatggtg ctcctgacta tgaaggaaaa gtcatggttg gtgcacaagc agtggttcct
1561 tgatcttcca ttgccctgga cctctggcgc ttcgacctca caagagactt ggaacaggca
```

| | | | | |
|---|---|---|---|---|
| 1621 | ggacttgctc | gtgacattca | aaacggctca | cgctaaaaag | caagaggtcg tggttctggg |
| 1681 | gagtcaggaa | ggcgctatgc | ataccgcgtt | aacaggggct | acagagatcc agaccagtgg |
| 1741 | aacaaccact | attttcgccg | ggcatcttaa | gtgtaggctg | aagatggata agttgaccct |
| 1801 | gaaaggtatg | tcatatgtga | tgtgcaccgg | tagtttcaaa | ctggagaaag aagtggccga |
| 1861 | aacccagcat | ggaacagtac | tggtgcaagt | caaatatgag | gcaccgatg caccatgtaa |
| 1921 | aatacccttc | agcgcacaag | acgagaaggg | agttacccag | aacggtaggc tgataacagc |
| 1981 | caatccaatc | gtcaccgata | aggagaaacc | agtaaacatc | gaaaccgagc cacccttcgg |
| 2041 | cgaaagctac | atcgtggtcg | gcgctggcga | gaaagcactt | aagctgagct ggtttaagaa |
| 2101 | aggtagcacg | ggcggcggca | gccatcatca | ccatcatcac | tgagctagCT TGACTGACTG |
| 2161 | AGATACAGCG | TACCTTCAGC | TCACAGACAT | GATAAGATAC | ATTGATGAGT TTGGACAAAC |
| 2221 | CACAACTAGA | ATGCAGTGAA | AAAATGCTT | TATTTGTGAA | ATTTGTGATG CTATTGCTTT |
| 2281 | ATTTGTAACC | ATTATAAGCT | GCAATAAACA | AGTTAACAAC | AACAATTGCA TTCATTTTAT |
| 2341 | GTTTCAGGTT | CAGGGGGAGG | TGTGGGAGGT | TTTTTAAAGC | AAGTAAAACC TCTACAAATG |
| 2401 | TGGTATTGGC | CCATCTCTAT | CGGTATCGTA | GCATAACCCC | TTGGGGCCTC TAAACGGGTC |
| 2461 | TTGAGGGGTT | TTTTGTGCCC | CTCGGGCCGG | ATTGCTATCT | ACCGGCATTG GCGCAGAAAA |
| 2521 | AAATGCCTGA | TGCGACGCTG | CGCGTCTTAT | ACTCCACAT | ATGCCAGATT CAGCAACGGA |
| 2581 | TACGGCTTCC | CCAACTTGCC | CACTTCCATA | CGTGTCCTCC | TTACCAGAAA TTTATCCTTA |
| 2641 | AGGTCGTCAG | CTATCCTGCA | GGCGATCTCT | CGATTTCGAT | CAAGACATTC CTTTAATGGT |
| 2701 | CTTTTCTGGA | CACCACTAGG | GGTCAGAAGT | AGTTCATCAA | ACTTTCTTCC CTCCCTAATC |
| 2761 | TCATTGGTTA | CCTTGGGCTA | TCGAAACTTA | ATTAACCAGT | CAAGTCAGCT ACTTGGCGAG |
| 2821 | ATCGACTTGT | CTGGGTTTCG | ACTACGCTCA | GAATTGCGTC | AGTCAAGTTC GATCTGGTCC |
| 2881 | TTGCTATTGC | ACCCGTTCTC | CGATTACGAG | TTTCATTTAA | ATCATGTGAG CAAAAGGCCA |
| 2941 | GCAAAAGGCC | AGGAACCGTA | AAAAGGCCGC | GTTGCTGGCG | TTTTTCCATA GGCTCCGCCC |
| 3001 | CCCTGACGAG | CATCACAAAA | ATCGACGCTC | AAGTCAGAGG | TGGCGAAACC CGACAGGACT |
| 3061 | ATAAAGATAC | CAGGCGTTTC | CCCCTGGAAG | CTCCCTCGTG | CGCTCTCCTG TTCCGACCCT |
| 3121 | GCCGCTTACC | GGATACCTGT | CCGCCTTTCT | CCCTTCGGGA | AGCGTGGCGC TTTCTCATAG |
| 3181 | CTCACGCTGT | AGGTATCTCA | GTTCGGTGTA | GGTCGTTCGC | TCCAAGCTGG GCTGTGTGCA |
| 3241 | CGAACCCCCC | GTTCAGCCCG | ACCGCTGCGC | CTTATCCGGT | AACTATCGTC TTGAGTCCAA |
| 3301 | CCCGGTAAGA | CACGACTTAT | CGCCACTGGC | AGCAGCCACT | GGTAACAGGA TTAGCAGAGC |
| 3361 | GAGGTATGTA | GGCGGTGCTA | CAGAGTTCTT | GAAGTGGTGG | CCTAACTACG GCTACACTAG |
| 3421 | AAGAACAGTA | TTTGGTATCT | GCGCTCTGCT | GAAGCCAGTT | ACCTTCGGAA AAAGAGTTGG |
| 3481 | TAGCTCTTGA | TCCGGCAAAC | AAACCACCGC | TGGTAGCGGT | GGTTTTTTTG TTTGCAAGCA |
| 3541 | GCAGATTACG | CGCAGAAAAA | AAGGATCTCA | AGAAGATCCT | TTGATCTTTT CTACGGGGTC |
| 3601 | TGACGCTCAG | TGGAACGAAA | ACTCACGTTA | AGGGATTTTG | GTCATGAGAT TATCAAAAAG |
| 3661 | GATCTTCACC | TAGATCCTTT | TAAATTAAAA | ATGAAGTTTT | AAATCAATCT AAAGTATATA |
| 3721 | TGAGTAAACT | TGGTCTGACA | GTTACCAATG | CTTAATCAGT | GAGGCACCTA TCTCAGCGAT |
| 3781 | CTGTCTATTT | CGTTCATCCA | TAGTTGCATT | TAAATTTCCG | AACTCTCCAA GGCCCTCGTC |
| 3841 | GGAAAATCTT | CAAACCTTTC | GTCCGATCCA | TCTTGCAGGC | TACCTCTCGA ACGAACTATC |

-continued

| Sequence Listing Free Text |
|---|

```
3901  GCAAGTCTCT TGGCCGGCCT TGCGCCTTGG CTATTGCTTG GCAGCGCCTA TCGCCAGGTA
3961  TTACTCCAAT CCCGAATATC CGAGATCGGG ATCACCCGAG AGAAGTTCAA CCTACATCCT
4021  CAATCCCGAT CTATCCGAGA TCCGAGGAAT ATCGAAATCG GGGCGCGCCT GGTGTACCGA
4081  GAACGATCCT CTCAGTGCGA GTCTCGACGA TCCATATCGT TGCTTGGCAG TCAGCCAGTC
4141  GGAATCCAGC TTGGGACCCA GGAAGTCCAA TCGTCAGATA TTGTACTCAA GCCTGGTCAC
4201  GGCAGCGTAC CGATCTGTTT AAACCTAGAT ATTGATAGTC TGATCGGTCA ACGTATAATC
4261  GAGTCCTAGC TTTTGCAAAC ATCTATCAAG AGACAGGATC AGCAGGAGGC TTTCGCATGA
4321  GTATTCAACA TTTCCGTGTC GCCCTTATTC CCTTTTTTGC GGCATTTTGC CTTCCTGTTT
4381  TTGCTCACCC AGAAACGCTG GTGAAAGTAA AGATGCTGA AGATCAGTTG GGTGCGCGAG
4441  TGGGTTACAT CGAACTGGAT CTCAACAGCG GTAAGATCCT TGAGAGTTTT CGCCCCGAAG
4501  AACGCTTTCC AATGATGAGC ACTTTTAAAG TTCTGCTATG TGGCGCGGTA TTATCCCGTA
4561  TTGACGCCGG GCAAGAGCAA CTCGGTCGCC GCATACACTA TTCTCAGAAT GACTTGGTTG
4621  AGTATTCACC AGTCACAGAA AAGCATCTTA CGGATGGCAT GACAGTAAGA GAATTATGCA
4681  GTGCTGCCAT AACCATGAGT GATAACACTG CGGCCAACTT ACTTCTGACA ACGATTGGAG
4741  GACCGAAGGA GCTAACCGCT TTTTTGCACA ACATGGGGGA TCATGTAACT CGCCTTGATC
4801  GTTGGGAACC GGAGCTGAAT GAAGCCATAC CAAACGACGA GCGTGACACC ACGATGCCTG
4861  TAGCAATGGC AACAACCTTG CGTAAACTAT TAACTGGCGA ACTACTTACT CTAGCTTCCC
4921  GGCAACAGTT GATAGACTGG ATGGAGGCGG ATAAAGTTGC AGGACCACTT CTGCGCTCGG
4981  CCCTTCCGGC TGGCTGGTTT ATTGCTGATA AATCTGGAGC CGGTGAGCGT GGGTCTCGCG
5041  GTATCATTGC AGCACTGGGG CCAGATGGTA AGCCCTCCCG TATCGTAGTT ATCTACACGA
5101  CGGGGAGTCA GGCAACTATG GATGAACGAA ATAGACAGAT CGCTGAGATA GGTGCCTCAC
5161  TGATTAAGCA TTGGTAACCG ATTCTAGGTG CATTGGCGCA GAAAAAAATG CCTGATGCGA
5221  CGCTGCGCGT CTTATACTCC CACATATGCC AGATTCAGCA ACGGATACGG CTTCCCCAAC
5281  TTGCCCACTT CCATACGTGT CCTCCTTACC AGAAATTTAT CCTTAAGATC CCGAATCGTT
5341  TAAACTCGAC TCTGGCTCTA TCGAATCTCC GTCGTTTCGA GCTTACGCGA ACAGCCGTGG
5401  CGCTCATTTG CTCGTCGGGC ATCGAATCTC GTCAGCTATC GTCAGCTTAC CTTTTTGGCA
5461
``` pCRO22 (SEQ ID NO: 14)
ORIGIN
```
   1  GCGATCGCGG CTCCCGACAT CTTGGACCAT TAGCTCCACA GGTATCTTCT TCCCTCTAGT
  61  GGTCATAACA GCAGCTTCAG CTACCTCTCA ATTCAAAAAA CCCCTCAAGA CCCGTTTAGA
 121  GGCCCCAAGG GGTTATGCTA TCAATCGTTG CGTTACACAC ACAAAAAACC AACACACATC
 181  CATCTTCGAT GGATAGCGAT TTTATTATCT AACTGCTGAT CGAGTGTAGC CAGATCTAGT
 241  AATCAATTAC GGGGTCATTA GTTCATAGCC CATATATGGA GTTCCGCGTT ACATAACTTA
 301  CGGTAAATGG CCCGCCTGGC TGACCGCCCA ACGACCCCCG CCCATTGACG TCAATAATGA
 361  CGTATGTTCC CATAGTAACG CCAATAGGGA CTTTCCATTG ACGTCAATGG GTGGAGTATT
 421  TACGGTAAAC TGCCCACTTG GCAGTACATC AAGTGTATCA TATGCCAAGT ACGCCCCCTA
 481  TTGACGTCAA TGACGGTAAA TGGCCCGCCT GGCATTATGC CCAGTACATG ACCTTATGGG
 541  ACTTTCCTAC TTGGCAGTAC ATCTACGTAT TAGTCATCGC TATTACCATG CTGATGCGGT
 601  TTTGGCAGTA CATCAATGGG CGTGGATAGC GGTTTGACTC ACGGGGATTT CCAAGTCTCC
```

| Sequence Listing Free Text |
|---|
| 661 ACCCCATTGA CGTCAATGGG AGTTTGTTTT GGCACCAAAA TCAACGGGAC TTTCCAAAAT |
| 721 GTCGTAACAA CTCCGCCCCA TTGACGCAAA TGGGCGGTAG GCGTGTACGG TGGGAGGTCT |
| 781 ATATAAGCAG AGCTGGTTTA GTGAACCGTC AGATCAGATC TTTGTCGATC CTACCATCCA |
| 841 CTCGACACAC CCGCCAGCgg ccgccaccat gaaggccaat ctactggtgt tgctgtgtgc |
| 901 ccttgcggcg gcagatgcca tgcgctgcat cgggatcagc aatcgcgact ttgtggaagg |
| 961 agtcagcggc ggatcatggg tggacatcgt gcttgagcac ggcagctgcg tgaccactat |
| 1021 ggcaaagaat aagccgactc tggattttga actcattaaa accgaggcga agcagcccgc |
| 1081 aactctgagg aagtactgca tcgaggccaa actgactaac actaccaccg aatcacggtg |
| 1141 cccgacccaa ggcgaaccga gcctgaacga agagcaggat aagagatttg tctgcaagca |
| 1201 ctcaatggtg gaccggggga atggatccgg ctgcggactg aacggatctg ggggcattgt |
| 1261 gacttgcgca atgttcacct gtaaaaagaa catggagggc aaggtcgtgc agccagagaa |
| 1321 cctggaatac accattgtca ttactccaca ttccggagag gaacacgccg tcggcaacga |
| 1381 cactggaaaa catgggaagg aaattaagat caccccgcag tcgtcaatta ccgaggcaga |
| 1441 actcaccggg tacggcactg tcactatgga gtgctcaccg agaactgggt tggatttcaa |
| 1501 tgagatggtg ctcctacaga tggagaacaa ggcatggctc gtgcaccggc aatggtttct |
| 1561 cgacctgccg ctgccttggc tccctggggc cgacactcaa ggctcgaatt ggattcagaa |
| 1621 ggaaacgctg gtcacgttca agaaccccca tgccaagaag caagacgtgg tggtcctggg |
| 1681 ctcgcaagaa ggagctatgc acaccgctct gaccggcgcg accgaaatcc aaatgtcatc |
| 1741 aggcaacctc ctgttcactg gccacctcaa atgccggctg agaatggata agctgcaact |
| 1801 gaaaggtatg tcctactcga tgtgcaccgg taaatttaaa gtggtgaaag agatcgctga |
| 1861 aactcagcac ggtaccatcg tcatcagggt gcagtacgag ggagacggct caccctgcaa |
| 1921 aatcccccttc gaaatcatgg acctcgaaaa gagacacgtg ctgggccgcc tgatcaccgt |
| 1981 taacccgatc gtgaccgaga agacagcccc ggtgaatatt gaagcggaac ctccgttcgg |
| 2041 cgacagctac atcattatcg gcgtggaacc gggccagctg aagcttaatt ggttcaaaaa |
| 2101 ggggtccagc ggcggcggca gccatcatca ccatcatcac tgagctagcT TGACTGACTG |
| 2161 AGATACAGCG TACCTTCAGC TCACAGACAT GATAAGATAC ATTGATGAGT TTGGACAAAC |
| 2221 CACAACTAGA ATGCAGTGAA AAAAATGCTT TATTTGTGAA ATTTGTGATG CTATTGCTTT |
| 2281 ATTTGTAACC ATTATAAGCT GCAATAAACA AGTTAACAAC AACAATTGCA TTCATTTTAT |
| 2341 GTTTCAGGTT CAGGGGGAGG TGTGGGAGGT TTTTTAAAGC AAGTAAAACC TCTACAAATG |
| 2401 TGGTATTGGC CCATCTCTAT CGGTATCGTA GCATAACCCC TTGGGGCCTC TAAACGGGTC |
| 2461 TTGAGGGGTT TTTTGTGCCC CTCGGGCCGG ATTGCTATCT ACCGGCATTG GCGCAGAAAA |
| 2521 AAATGCCTGA TGCGACGCTG CGCGTCTTAT ACTCCCACAT ATGCCAGATT CAGCAACGGA |
| 2581 TACGGCTTCC CCAACTTGCC CACTTCCATA CGTGTCCTCC TTACCAGAAA TTTATCCTTA |
| 2641 AGGTCGTCAG CTATCCTGCA GGCGATCTCT CGATTTCGAT CAAGACATTC CTTTAATGGT |
| 2701 CTTTTCTGGA CACCACTAGG GGTCAGAAGT AGTTCATCAA ACTTTCTTCC CTCCCTAATC |
| 2761 TCATTGGTTA CCTTGGGCTA TCGAAACTTA ATTAACCAGT CAAGTCAGCT ACTTGGCGAG |
| 2821 ATCGACTTGT CTGGGTTTCG ACTACGCTCA GAATTGCGTC AGTCAAGTTC GATCTGGTCC |
| 2881 TTGCTATTGC ACCCGTTCTC CGATTACGAG TTTCATTTAA ATCATGTGAG CAAAAGGCCA |

| | |
|---|---|
| 2941 | GCAAAAGGCC AGGAACCGTA AAAAGGCCGC GTTGCTGGCG TTTTTCCATA GGCTCCGCCC |
| 3001 | CCCTGACGAG CATCACAAAA ATCGACGCTC AAGTCAGAGG TGGCGAAACC CGACAGGACT |
| 3061 | ATAAAGATAC CAGGCGTTTC CCCCTGGAAG CTCCCTCGTG CGCTCTCCTG TTCCGACCCT |
| 3121 | GCCGCTTACC GGATACCTGT CCGCCTTTCT CCCTTCGGGA AGCGTGGCGC TTTCTCATAG |
| 3181 | CTCACGCTGT AGGTATCTCA GTTCGGTGTA GGTCGTTCGC TCCAAGCTGG GCTGTGTGCA |
| 3241 | CGAACCCCCC GTTCAGCCCG ACCGCTGCGC CTTATCCGGT AACTATCGTC TTGAGTCCAA |
| 3301 | CCCGGTAAGA CACGACTTAT CGCCACTGGC AGCAGCCACT GGTAACAGGA TTAGCAGAGC |
| 3361 | GAGGTATGTA GGCGGTGCTA CAGAGTTCTT GAAGTGGTGG CCTAACTACG GCTACACTAG |
| 3421 | AAGAACAGTA TTTGGTATCT GCGCTCTGCT GAAGCCAGTT ACCTTCGGAA AAAGAGTTGG |
| 3481 | TAGCTCTTGA TCCGGCAAAC AAACCACCGC TGGTAGCGGT GGTTTTTTTG TTTGCAAGCA |
| 3541 | GCAGATTACG CGCAGAAAAA AAGGATCTCA AGAAGATCCT TTGATCTTTT CTACGGGGTC |
| 3601 | TGACGCTCAG TGGAACGAAA ACTCACGTTA AGGGATTTTG GTCATGAGAT TATCAAAAAG |
| 3661 | GATCTTCACC TAGATCCTTT TAAATTAAAA ATGAAGTTTT AAATCAATCT AAAGTATATA |
| 3721 | TGAGTAAACT TGGTCTGACA GTTACCAATG CTTAATCAGT GAGGCACCTA TCTCAGCGAT |
| 3781 | CTGTCTATTT CGTTCATCCA TAGTTGCATT TAAATTTCCG AACTCTCCAA GGCCCTCGTC |
| 3841 | GGAAAATCTT CAAACCTTTC GTCCGATCCA TCTTGCAGGC TACCTCTCGA ACGAACTATC |
| 3901 | GCAAGTCTCT TGGCCGGCCT TGCGCCTTGG CTATTGCTTG GCAGCGCCTA TCGCCAGGTA |
| 3961 | TTACTCCAAT CCCGAATATC CGAGATCGGG ATCACCCGAG AGAAGTTCAA CCTACATCCT |
| 4021 | CAATCCCGAT CTATCCGAGA TCCGAGGAAT ATCGAAATCG GGCGCGCCT GGTGTACCGA |
| 4081 | GAACGATCCT CTCAGTGCGA GTCTCGACGA TCCATATCGT TGCTTGGCAG TCAGCCAGTC |
| 4141 | GGAATCCAGC TTGGGACCCA GGAAGTCCAA TCGTCAGATA TTGTACTCAA GCCTGGTCAC |
| 4201 | GGCAGCGTAC CGATCTGTTT AAACCTAGAT ATTGATAGTC TGATCGGTCA ACGTATAATC |
| 4261 | GAGTCCTAGC TTTTGCAAAC ATCTATCAAG AGACAGGATC AGCAGGAGGC TTTCGCATGA |
| 4321 | GTATTCAACA TTTCCGTGTC GCCCTTATTC CCTTTTTTGC GGCATTTTGC CTTCCTGTTT |
| 4381 | TTGCTCACCC AGAAACGCTG GTGAAAGTAA AAGATGCTGA AGATCAGTTG GGTGCGCGAG |
| 4441 | TGGGTTACAT CGAACTGGAT CTCAACAGCG GTAAGATCCT TGAGAGTTTT CGCCCCGAAG |
| 4501 | AACGCTTTCC AATGATGAGC ACTTTTAAAG TTCTGCTATG TGGCGCGGTA TTATCCCGTA |
| 4561 | TTGACGCCGG GCAAGAGCAA CTCGGTCGCC GCATACACTA TTCTCAGAAT GACTTGGTTG |
| 4621 | AGTATTCACC AGTCACAGAA AAGCATCTTA CGGATGGCAT GACAGTAAGA GAATTATGCA |
| 4681 | GTGCTGCCAT AACCATGAGT GATAACACTG CGGCCAACTT ACTTCTGACA ACGATTGGAG |
| 4741 | GACCGAAGGA GCTAACCGCT TTTTTGCACA ACATGGGGGA TCATGTAACT CGCCTTGATC |
| 4801 | GTTGGGAACC GGAGCTGAAT GAAGCCATAC CAAACGACGA GCGTGACACC ACGATGCCTG |
| 4861 | TAGCAATGGC AACAACCTTG CGTAAACTAT TAACTGGCGA ACTACTTACT CTAGCTTCCC |
| 4921 | GGCAACAGTT GATAGACTGG ATGGAGGCGG ATAAAGTTGC AGGACCACTT CTGCGCTCGG |
| 4981 | CCCTTCCGGC TGGCTGGTTT ATTGCTGATA AATCTGGAGC CGGTGAGCGT GGGTCTCGCG |
| 5041 | GTATCATTGC AGCACTGGGG CCAGATGGTA AGCCCTCCCG TATCGTAGTT ATCTACACGA |
| 5101 | CGGGGAGTCA GGCAACTATG GATGAACGAA ATAGACAGAT CGCTGAGATA GGTGCCTCAC |
| 5161 | TGATTAAGCA TTGGTAACCG ATTCTAGGTG CATTGGCGCA GAAAAAAATG CCTGATGCGA |
| 5221 | CGCTGCGCGT CTTATACTCC CACATATGCC AGATTCAGCA ACGGATACGG CTTCCCCAAC |

| Sequence Listing Free Text |
| --- |

```
5281  TTGCCCACTT CCATACGTGT CCTCCTTACC AGAAATTTAT CCTTAAGATC CCGAATCGTT

5341  TAAACTCGAC TCTGGCTCTA TCGAATCTCC GTCGTTTCGA GCTTACGCGA ACAGCCGTGG

5401  CGCTCATTTG CTCGTCGGGC ATCGAATCTC GTCAGCTATC GTCAGCTTAC CTTTTTGGCA

5461
``` pCRO23 (SEQ ID NO: 15)
ORIGIN

```
   1  GCGATCGCGG CTCCCGACAT CTTGGACCAT TAGCTCCACA GGTATCTTCT TCCCTCTAGT

61  GGTCATAACA GCAGCTTCAG CTACCTCTCA ATTCAAAAAA CCCCTCAAGA CCCGTTTAGA

121  GGCCCCAAGG GGTTATGCTA TCAATCGTTG CGTTACACAC ACAAAAAACC AACACACATC

181  CATCTTCGAT GGATAGCGAT TTTATTATCT AACTGCTGAT CGAGTGTAGC CAGATCTAGT

241  AATCAATTAC GGGGTCATTA GTTCATAGCC CATATATGGA GTTCCGCGTT ACATAACTTA

301  CGGTAAATGG CCCGCCTGGC TGACCGCCCA ACGACCCCCG CCCATTGACG TCAATAATGA

361  CGTATGTTCC CATAGTAACG CCAATAGGGA CTTTCCATTG ACGTCAATGG GTGGAGTATT

421  TACGGTAAAC TGCCCACTTG GCAGTACATC AAGTGTATCA TATGCCAAGT ACGCCCCCTA

481  TTGACGTCAA TGACGGTAAA TGGCCCGCCT GGCATTATGC CCAGTACATG ACCTTATGGG

541  ACTTTCCTAC TTGGCAGTAC ATCTACGTAT TAGTCATCGC TATTACCATG CTGATGCGGT

601  TTTGGCAGTA CATCAATGGG CGTGGATAGC GGTTTGACTC ACGGGGATTT CCAAGTCTCC

661  ACCCCATTGA CGTCAATGGG AGTTTGTTTT GGCACCAAAA TCAACGGGAC TTTCCAAAAT

721  GTCGTAACAA CTCCGCCCCA TTGACGCAAA TGGGCGGTAG GCGTGTACGG TGGGAGGTCT

781  ATATAAGCAG AGCTGGTTTA GTGAACCGTC AGATCAGATC TTTGTCGATC CTACCATCCA

841  CTCGACACAC CCGCCAGCgg ccgccaccat gaaggccaat ctactggtgt tgctgtgtgc 901  ccttgcggcg gcagatgcca tgagatgtgt gggcgtgggg aaccgcgact tgtcgaagg 961  attaagtggc gcgacctggg tagacgtcgt gctggagcac ggagggtgcg tcacaaccat 1021  ggccaagaac aagcccaccc ttgacattga acttcaaaag acagaagcta ctcagctggc 1081  tacactgcgc aagctgtgca tagagggaaa aatcaccaac ataactacgg actcgaggtg 1141  tcccacacag ggtgaagcgg tcttgcctga gaacaggat cagaattatg tttgtaaaca 1201  tacttatgta gacaggggga atggatccgg gtgcggtctg aacggatctg gttccctagt 1261  cacatgcgct aagttccagt gcctcgagcc tatcgaaggt aaagtggtcc agtacgagaa 1321  tcttaagtac accgtgatca tcacggtcca tacaggagat caacaccagg ttggaaacga 1381  gacccaagga gtcactgccg aaatcacacc gcaggccagc acgacggagg ctattttgcc 1441  ggagtatggg acactgggac tggaatgctc ccctaggacg ggactagatt ttaatgagat 1501  gattctgctg acaatgaaga acaaggcttg gatggtgcat cgtcaatggt tctttgatct 1561  gccactgccg tgggccagcg gcgccacgac agagaccca acctggaatc gaaaagagct 1621  gctggtcaca ttcaaaaacg cacacgccaa aaagcaagaa gtggtagtgc ttggctccca 1681  ggaaggtgcc atgcacactg cactcacagg ggctactgaa attcagaatt caggaggcac 1741  ttctattttc gccggccacc tcaaatgccg gttaaagatg acaagctgg aactgaaagg 1801  tatgtcgtac gcaatgtgca ctaatacatt tgtgctaaag aaggaagtct ccgagactca 1861  gcacgggaca atactgatta aggtggaata caaaggtgag gatgctccct gtaagatccc 1921  cttctctact gaggatggtc agggcaaagc tcataatggt cggttgatca cagcgaatcc
```

| | |
|---|---|
| 1981 | agtggttaca aagaaggagg agccagtgaa tatcgaagca gaacctccct tcggtgagtc |
| 2041 | aaacattgtc atcggtatcg gagataacgc tcttaagata aactggtaca aaaagggatc |
| 2101 | tagcggcggc ggcagccatc atcaccatca tcactgagct agCTTGACTG ACTGAGATAC |
| 2161 | AGCGTACCTT CAGCTCACAG ACATGATAAG ATACATTGAT GAGTTTGGAC AAACCACAAC |
| 2221 | TAGAATGCAG TGAAAAAAAT GCTTTATTTG TGAAATTTGT GATGCTATTG CTTTATTTGT |
| 2281 | AACCATTATA AGCTGCAATA AACAAGTTAA CAACAACAAT TGCATTCATT TTATGTTTCA |
| 2341 | GGTTCAGGGG GAGGTGTGGG AGGTTTTTTA AAGCAAGTAA AACCTCTACA AATGTGGTAT |
| 2401 | TGGCCCATCT CTATCGGTAT CGTAGCATAA CCCCTTGGGG CCTCTAAACG GGTCTTGAGG |
| 2461 | GGTTTTTTGT GCCCCTCGGG CCGGATTGCT ATCTACCGGC ATTGGCGCAG AAAAAAATGC |
| 2521 | CTGATGCGAC GCTGCGCGTC TTATACTCCC ACATATGCCA GATTCAGCAA CGGATACGGC |
| 2581 | TTCCCCAACT TGCCCACTTC CATACGTGTC CTCCTTACCA GAAATTTATC CTTAAGGTCG |
| 2641 | TCAGCTATCC TGCAGGCGAT CTCTCGATTT CGATCAAGAC ATTCCTTTAA TGGTCTTTTC |
| 2701 | TGGACACCAC TAGGGGTCAG AAGTAGTTCA TCAAACTTTC TTCCCTCCCT AATCTCATTG |
| 2761 | GTTACCTTGG GCTATCGAAA CTTAATTAAC CAGTCAAGTC AGCTACTTGG CGAGATCGAC |
| 2821 | TTGTCTGGGT TTCGACTACG CTCAGAATTG CGTCAGTCAA GTTCGATCTG GTCCTTGCTA |
| 2881 | TTGCACCCGT TCTCCGATTA CGAGTTTCAT TTAAATCATG TGAGCAAAAG GCCAGCAAAA |
| 2941 | GGCCAGGAAC CGTAAAAAGG CCGCGTTGCT GGCGTTTTTC CATAGGCTCC GCCCCCCTGA |
| 3001 | CGAGCATCAC AAAAATCGAC GCTCAAGTCA GAGGTGGCGA AACCCGACAG GACTATAAAG |
| 3061 | ATACCAGGCG TTTCCCCCTG GAAGCTCCCT CGTGCGCTCT CCTGTTCCGA CCCTGCCGCT |
| 3121 | TACCGGATAC CTGTCCGCCT TTCTCCCTTC GGGAAGCGTG GCGCTTTCTC ATAGCTCACG |
| 3181 | CTGTAGGTAT CTCAGTTCGG TGTAGGTCGT TCGCTCCAAG CTGGGCTGTG TGCACGAACC |
| 3241 | CCCCGTTCAG CCCGACCGCT GCGCCTTATC CGGTAACTAT CGTCTTGAGT CCAACCCGGT |
| 3301 | AAGACACGAC TTATCGCCAC TGGCAGCAGC CACTGGTAAC AGGATTAGCA GAGCGAGGTA |
| 3361 | TGTAGGCGGT GCTACAGAGT TCTTGAAGTG GTGGCCTAAC TACGGCTACA CTAGAAGAAC |
| 3421 | AGTATTTGGT ATCTGCGCTC TGCTGAAGCC AGTTACCTTC GGAAAAAGAG TTGGTAGCTC |
| 3481 | TTGATCCGGC AAACAAACCA CCGCTGGTAG CGGTGGTTTT TTTGTTTGCA AGCAGCAGAT |
| 3541 | TACGCGCAGA AAAAAAGGAT CTCAAGAAGA TCCTTTGATC TTTTCTACGG GGTCTGACGC |
| 3601 | TCAGTGGAAC GAAAACTCAC GTTAAGGGAT TTTGGTCATG AGATTATCAA AAAGGATCTT |
| 3661 | CACCTAGATC CTTTTAAATT AAAAATGAAG TTTTAAATCA ATCTAAAGTA TATATGAGTA |
| 3721 | AACTTGGTCT GACAGTTACC AATGCTTAAT CAGTGAGGCA CCTATCTCAG CGATCTGTCT |
| 3781 | ATTTCGTTCA TCCATAGTTG CATTTAAATT TCCGAACTCT CCAAGGCCCT CGTCGGAAAA |
| 3841 | TCTTCAAACC TTTCGTCCGA TCCATCTTGC AGGCTACCTC TCGAACGAAC TATCGCAAGT |
| 3901 | CTCTTGGCCG GCCTTGCGCC TTGGCTATTG CTTGGCAGCG CCTATCGCCA GGTATTACTC |
| 3961 | CAATCCCGAA TATCCGAGAT CGGGATCACC CGAGAGAAGT TCAACCTACA TCCTCAATCC |
| 4021 | CGATCTATCC GAGATCCGAG GAATATCGAA ATCGGGGCGC GCCTGGTGTA CCGAGAACGA |
| 4081 | TCCTCTCAGT GCGAGTCTCG ACGATCCATA TCGTTGCTTG GCAGTCAGCC AGTCGGAATC |
| 4141 | CAGCTTGGGA CCCAGGAAGT CCAATCGTCA GATATTGTAC TCAAGCCTGG TCACGGCAGC |
| 4201 | GTACCGATCT GTTTAAACCT AGATATTGAT AGTCTGATCG GTCAACGTAT AATCGAGTCC |
| 4261 | TAGCTTTTGC AAACATCTAT CAAGAGACAG GATCAGCAGG AGGCTTTCGC ATGAGTATTC |

-continued

| Sequence Listing Free Text |
| --- |

```
4321  AACATTTCCG TGTCGCCCTT ATTCCCTTTT TTGCGGCATT TTGCCTTCCT GTTTTTGCTC
4381  ACCCAGAAAC GCTGGTGAAA GTAAAAGATG CTGAAGATCA GTTGGGTGCG CGAGTGGGTT
4441  ACATCGAACT GGATCTCAAC AGCGGTAAGA TCCTTGAGAG TTTTCGCCCC GAAGAACGCT
4501  TTCCAATGAT GAGCACTTTT AAAGTTCTGC TATGTGGCGC GGTATTATCC CGTATTGACG
4561  CCGGGCAAGA GCAACTCGGT CGCCGCATAC ACTATTCTCA GAATGACTTG GTTGAGTATT
4621  CACCAGTCAC AGAAAAGCAT CTTACGGATG GCATGACAGT AAGAGAATTA TGCAGTGCTG
4681  CCATAACCAT GAGTGATAAC ACTGCGGCCA ACTTACTTCT GACAACGATT GGAGGACCGA
4741  AGGAGCTAAC CGCTTTTTTG CACAACATGG GGATCATGT AACTCGCCTT GATCGTTGGG
4801  AACCGGAGCT GAATGAAGCC ATACCAAACG ACGAGCGTGA CACCACGATG CCTGTAGCAA
4861  TGGCAACAAC CTTGCGTAAA CTATTAACTG GCGAACTACT TACTCTAGCT TCCCGGCAAC
4921  AGTTGATAGA CTGGATGGAG GCGGATAAAG TTGCAGGACC ACTTCTGCGC TCGGCCCTTC
4981  CGGCTGGCTG GTTTATTGCT GATAAATCTG GAGCCGGTGA GCGTGGGTCT CGCGGTATCA
5041  TTGCAGCACT GGGGCCAGAT GGTAAGCCCT CCCGTATCGT AGTTATCTAC ACGACGGGGA
5101  GTCAGGCAAC TATGGATGAA CGAAATAGAC AGATCGCTGA GATAGGTGCC TCACTGATTA
5161  AGCATTGGTA ACCGATTCTA GGTGCATTGG CGCAGAAAAA AATGCCTGAT GCGACGCTGC
5221  GCGTCTTATA CTCCCACATA TGCCAGATTC AGCAACGGAT ACGGCTTCCC CAACTTGCCC
5281  ACTTCCATAC GTGTCCTCCT TACCAGAAAT TTATCCTTAA GATCCCGAAT CGTTTAAACT
5341  CGACTCTGGC TCTATCGAAT CTCCGTCGTT TCGAGCTTAC GCGAACAGCC GTGGCGCTCA
5401  TTTGCTCGTC GGGCATCGAA TCTCGTCAGC TATCGTCAGC TTACCTTTTT GGCA
// pCRO24 (SEQ ID NO: 16) ORIGIN
   1  GCGATCGCGG CTCCCGACAT CTTGGACCAT TAGCTCCACA GGTATCTTCT TCCCTCTAGT
  61  GGTCATAACA GCAGCTTCAG CTACCTCTCA ATTCAAAAAA CCCCTCAAGA CCCGTTTAGA
 121  GGCCCCAAGG GGTTATGCTA TCAATCGTTG CGTTACACAC ACAAAAAACC AACACACATC
 181  CATCTTCGAT GGATAGCGAT TTTATTATCT AACTGCTGAT CGAGTGTAGC CAGATCTAGT
 241  AATCAATTAC GGGGTCATTA GTTCATAGCC CATATATGGA GTTCCGCGTT ACATAACTTA
 301  CGGTAAATGG CCCGCCTGGC TGACCGCCCA ACGACCCCCG CCCATTGACG TCAATAATGA
 361  CGTATGTTCC CATAGTAACG CCAATAGGGA CTTTCCATTG ACGTCAATGG GTGGAGTATT
 421  TACGGTAAAC TGCCCACTTG GCAGTACATC AAGTGTATCA TATGCCAAGT ACGCCCCCTA
 481  TTGACGTCAA TGACGGTAAA TGGCCCGCCT GGCATTATGC CCAGTACATG ACCTTATGGG
 541  ACTTTCCTAC TTGGCAGTAC ATCTACGTAT TAGTCATCGC TATTACCATG CTGATGCGGT
 601  TTTGGCAGTA CATCAATGGG CGTGGATAGC GGTTTGACTC ACGGGGATTT CCAAGTCTCC
 661  ACCCCATTGA CGTCAATGGG AGTTTGTTTT GGCACCAAAA TCAACGGGAC TTTCCAAAAT
 721  GTCGTAACAA CTCCGCCCCA TTGACGCAAA TGGGCGGTAG GCGTGTACGG TGGGAGGTCT
 781  ATATAAGCAG AGCTGGTTTA GTGAACCGTC AGATCAGATC TTTGTCGATC CTACCATCCA
 841  CTCGACACAC CGCCAGCgg ccgccaccat gaaggccaat ctactggtgt tgctgtgtgc
 901  ccttgcggcg gcagatgcca tgcgatgcgt gggggtgggc aatagagatt tcgtggaagg
 961  ggtgtctgga ggggcatggg tggatctggt gctggagcac ggcggatgtg tcacaactat
1021  ggcccagggg aagccaaccc tggatttcga gctaactaag accacagcta aggaggtagc
```

-continued

Sequence Listing Free Text

```
1081  cctgcttcgg acttactgta ttgaggcatc catctctaac atcaccaccg ccacgagatg
1141  cccgacacag ggcgaaccct acttgaagga agaacaggat cagcagtaca tttgccggcg
1201  cgatgttgtt gatagaggca atggctccgg gtgtggcctc aacggctctg gtggggtggt
1261  cacctgtgcc aagttcagct gttctggcaa gatcacggga atctggtgc aaattgaaaa
1321  tttggaatat acggtcgttg tgactgtcca caatggcgat acacatgctg tgggcaacga
1381  taccagtaac cacggcgtca ccgcgatgat aactccccgg agcccatctg ttgaagttaa
1441  actgcccgat tacgagagt tgcactcga ctgcgaaccg aggtctggaa tagatttcaa
1501  cgagatgata cttatgaaaa tgaagaaaaa gacctggctc gtacacaagc agtggttttt
1561  ggatttgccc ctcccttgga ccgcagggc cgataccagc gaggtgcatt ggaattacaa
1621  agagcgcatg gtgactttca aagtgcccca cgcaaagcgg caagatgtga ctgtattagg
1681  atcacaggaa ggcgctatgc attccgccct ggctggtgcc acggaggtgg attcaggaga
1741  cggtaaccat atgtttgctg ccacctcaa atgtaaggtc cgcatggaaa aacttcgcat
1801  taaaggaatg tcctacacga tgtgctcagg aaagttctct atcgacaagg aaatggccga
1861  gactcagcat ggaacgactg tagtcaaggt gaaatatgaa ggtgccgggg cgccttgcaa
1921  ggtgccaatc gaaatccgag acgttaacaa ggagaaggtg gttgggagga ttataagtag
1981  cactccgctc gcagagaaca ccaatagcgt gactaacata gaactggagc cccttttgg
2041  ggatagctac attgtgattg gagtagggaa tagtgcacta acattgcact ggttcagaaa
2101  agggtcttca ggcggcggca gccatcatca ccatcatcac tgagctagCT TGACTGACTG
2161  AGATACAGCG TACCTTCAGC TCACAGACAT GATAAGATAC ATTGATGAGT TTGGACAAAC
2221  CACAACTAGA ATGCAGTGAA AAAATGCTT TATTTGTGAA ATTTGTGATG CTATTGCTTT
2281  ATTTGTAACC ATTATAAGCT GCAATAAACA AGTTAACAAC AACAATTGCA TTCATTTTAT
2341  GTTTCAGGTT CAGGGGGAGG TGTGGGAGGT TTTTTAAAGC AAGTAAAACC TCTACAAATG
2401  TGGTATTGGC CCATCTCTAT CGGTATCGTA GCATAACCCC TTGGGGCCTC TAAACGGGTC
2461  TTGAGGGGTT TTTTGTGCCC CTCGGGCCGG ATTGCTATCT ACCGGCATTG GCGCAGAAAA
2521  AAATGCCTGA TGCGACGCTG CGCGTCTTAT ACTCCCACAT ATGCCAGATT CAGCAACGGA
2581  TACGGCTTCC CCAACTTGCC CACTTCCATA CGTGTCCTCC TTACCAGAAA TTTATCCTTA
2641  AGGTCGTCAG CTATCCTGCA GGCGATCTCT CGATTTCGAT CAAGACATTC CTTTAATGGT
2701  CTTTTCTGGA CACCACTAGG GGTCAGAAGT AGTTCATCAA ACTTTCTTCC CTCCCTAATC
2761  TCATTGGTTA CCTTGGGCTA TCGAAACTTA ATTAACCAGT CAAGTCAGCT ACTTGGCGAG
2821  ATCGACTTGT CTGGGTTTCG ACTACGCTCA GAATTGCGTC AGTCAAGTTC GATCTGGTCC
2881  TTGCTATTGC ACCCGTTCTC CGATTACGAG TTTCATTTAA ATCATGTGAG CAAAAGGCCA
2941  GCAAAGGCC AGGAACCGTA AAAAGGCCGC GTTGCTGGCG TTTTTCCATA GGCTCCGCCC
3001  CCCTGACGAG CATCACAAAA ATCGACGCTC AAGTCAGAGG TGGCGAAACC CGACAGGACT
3061  ATAAAGATAC CAGGCGTTTC CCCCTGGAAG CTCCCTCGTG CGCTCTCCTG TTCCGACCCT
3121  GCCGCTTACC GGATACCTGT CCGCCTTTCT CCCTTCGGGA AGCGTGGCGC TTTCTCATAG
3181  CTCACGCTGT AGGTATCTCA GTTCGGTGTA GGTCGTTCGC TCCAAGCTGG GCTGTGTGCA
3241  CGAACCCCCC GTTCAGCCCG ACCGCTGCGC CTTATCCGGT AACTATCGTC TTGAGTCCAA
3301  CCCGGTAAGA CACGACTTAT CGCCACTGGC AGCAGCCACT GGTAACAGGA TTAGCAGAGC
```

| | Sequence Listing Free Text |
|---|---|
| 3361 | GAGGTATGTA GGCGGTGCTA CAGAGTTCTT GAAGTGGTGG CCTAACTACG GCTACACTAG |
| 3421 | AAGAACAGTA TTTGGTATCT GCGCTCTGCT GAAGCCAGTT ACCTTCGGAA AAAGAGTTGG |
| 3481 | TAGCTCTTGA TCCGGCAAAC AAACCACCGC TGGTAGCGGT GGTTTTTTTG TTTGCAAGCA |
| 3541 | GCAGATTACG CGCAGAAAAA AAGGATCTCA AGAAGATCCT TTGATCTTTT CTACGGGGTC |
| 3601 | TGACGCTCAG TGGAACGAAA ACTCACGTTA AGGGATTTTG GTCATGAGAT TATCAAAAAG |
| 3661 | GATCTTCACC TAGATCCTTT TAAATTAAAA ATGAAGTTTT AAATCAATCT AAAGTATATA |
| 3721 | TGAGTAAACT TGGTCTGACA GTTACCAATG CTTAATCAGT GAGGCACCTA TCTCAGCGAT |
| 3781 | CTGTCTATTT CGTTCATCCA TAGTTGCATT TAAATTTCCG AACTCTCCAA GGCCCTCGTC |
| 3841 | GGAAAATCTT CAAACCTTTC GTCCGATCCA TCTTGCAGGC TACCTCTCGA ACGAACTATC |
| 3901 | GCAAGTCTCT TGGCCGGCCT TGCGCCTTGG CTATTGCTTG GCAGCGCCTA TCGCCAGGTA |
| 3961 | TTACTCCAAT CCCGAATATC CGAGATCGGG ATCACCCGAG AGAAGTTCAA CCTACATCCT |
| 4021 | CAATCCCGAT CTATCCGAGA TCCGAGGAAT ATCGAAATCG GGCGCGCCT GGTGTACCGA |
| 4081 | GAACGATCCT CTCAGTGCGA GTCTCGACGA TCCATATCGT TGCTTGGCAG TCAGCCAGTC |
| 4141 | GGAATCCAGC TTGGGACCCA GGAAGTCCAA TCGTCAGATA TTGTACTCAA GCCTGGTCAC |
| 4201 | GGCAGCGTAC CGATCTGTTT AAACCTAGAT ATTGATAGTC TGATCGGTCA ACGTATAATC |
| 4261 | GAGTCCTAGC TTTTGCAAAC ATCTATCAAG AGACAGGATC AGCAGGAGGC TTTCGCATGA |
| 4321 | GTATTCAACA TTTCCGTGTC GCCCTTATTC CCTTTTTTGC GGCATTTTGC CTTCCTGTTT |
| 4381 | TTGCTCACCC AGAAACGCTG GTGAAAGTAA AAGATGCTGA AGATCAGTTG GGTGCGCGAG |
| 4441 | TGGGTTACAT CGAACTGGAT CTCAACAGCG GTAAGATCCT TGAGAGTTTT CGCCCCGAAG |
| 4501 | AACGCTTTCC AATGATGAGC ACTTTTAAAG TTCTGCTATG TGGCGCGGTA TTATCCCGTA |
| 4561 | TTGACGCCGG GCAAGAGCAA CTCGGTCGCC GCATACACTA TTCTCAGAAT GACTTGGTTG |
| 4621 | AGTATTCACC AGTCACAGAA AAGCATCTTA CGGATGGCAT GACAGTAAGA GAATTATGCA |
| 4681 | GTGCTGCCAT AACCATGAGT GATAACACTG CGGCCAACTT ACTTCTGACA ACGATTGGAG |
| 4741 | GACCGAAGGA GCTAACCGCT TTTTTGCACA ACATGGGGGA TCATGTAACT CGCCTTGATC |
| 4801 | GTTGGGAACC GGAGCTGAAT GAAGCCATAC CAAACGACGA GCGTGACACC ACGATGCCTG |
| 4861 | TAGCAATGGC AACAACCTTG CGTAAACTAT TAACTGGCGA ACTACTTACT CTAGCTTCCC |
| 4921 | GGCAACAGTT GATAGACTGG ATGGAGGCGG ATAAAGTTGC AGGACCACTT CTGCGCTCGG |
| 4981 | CCCTTCCGGC TGGCTGGTTT ATTGCTGATA AATCTGGAGC CGGTGAGCGT GGGTCTCGCG |
| 5041 | GTATCATTGC AGCACTGGGG CCAGATGGTA AGCCCTCCCG TATCGTAGTT ATCTACACGA |
| 5101 | CGGGGAGTCA GGCAACTATG GATGAACGAA ATAGACAGAT CGCTGAGATA GGTGCCTCAC |
| 5161 | TGATTAAGCA TTGGTAACCG ATTCTAGGTG CATTGGCGCA GAAAAAAATG CCTGATGCGA |
| 5221 | CGCTGCGCGT CTTATACTCC CACATATGCC AGATTCAGCA ACGGATACGG CTTCCCCAAC |
| 5281 | TTGCCCACTT CCATACGTGT CCTCCTTACC AGAAATTTAT CCTTAAGATC CCGAATCGTT |
| 5341 | TAAACTCGAC TCTGGCTCTA TCGAATCTCC GTCGTTTCGA GCTTACGCGA ACAGCCGTGG |
| 5401 | CGCTCATTTG CTCGTCGGGC ATCGAATCTC GTCAGCTATC GTCAGCTTAC CTTTTTGGCA |
| 5461 | |

// pCRO28 (SEQ ID NO: 17)
ORIGIN
    1 GCGATCGCGG CTCCCGACAT CTTGGACCAT TAGCTCCACA GGTATCTTCT TCCCTCTAGT

| | |
|---|---|
| 61 | GGTCATAACA GCAGCTTCAG CTACCTCTCA ATTCAAAAAA CCCCTCAAGA CCCGTTTAGA |
| 121 | GGCCCCAAGG GGTTATGCTA TCAATCGTTG CGTTACACAC ACAAAAAACC AACACACATC |
| 181 | CATCTTCGAT GGATAGCGAT TTTATTATCT AACTGCTGAT CGAGTGTAGC CAGATCTAGT |
| 241 | AATCAATTAC GGGGTCATTA GTTCATAGCC CATATATGGA GTTCCGCGTT ACATAACTTA |
| 301 | CGGTAAATGG CCCGCCTGGC TGACCGCCCA ACGACCCCCG CCCATTGACG TCAATAATGA |
| 361 | CGTATGTTCC CATAGTAACG CCAATAGGGA CTTTCCATTG ACGTCAATGG GTGGAGTATT |
| 421 | TACGGTAAAC TGCCCACTTG GCAGTACATC AAGTGTATCA TATGCCAAGT ACGCCCCCTA |
| 481 | TTGACGTCAA TGACGGTAAA TGGCCCGCCT GGCATTATGC CCAGTACATG ACCTTATGGG |
| 541 | ACTTTCCTAC TTGGCAGTAC ATCTACGTAT TAGTCATCGC TATTACCATG CTGATGCGGT |
| 601 | TTTGGCAGTA CATCAATGGG CGTGGATAGC GGTTTGACTC ACGGGGATTT CCAAGTCTCC |
| 661 | ACCCCATTGA CGTCAATGGG AGTTTGTTTT GGCACCAAAA TCAACGGGAC TTTCCAAAAT |
| 721 | GTCGTAACAA CTCCGCCCCA TTGACGCAAA TGGGCGGTAG CGTGTACGG TGGGAGGTCT |
| 781 | ATATAAGCAG AGCTGGTTTA GTGAACCGTC AGATCAGATC TTTGTCGATC CTACCATCCA |
| 841 | CTCGACACAC CCGCCAGCgg ccgccaccat gaaggccaat ctactggtgt tgctgtgtgc |
| 901 | ccttgcggcg gcagatgccA TCAGGTGCAT TGGAGTCAGC AACAGGGACT TCGTCGAAGG |
| 961 | CATGTCCGGC GGCACCTGGG TGGATGTGGT GCTCGAACAC GGCGGATGCG TGACCGTCAT |
| 1021 | GGCCCAGGAC AAGCCTACCG TCGATATTGA GCTGGTGACC ACCACAGTGA GCAACATGGC |
| 1081 | CGAAGTGAGA AGCTACTGCT ATGAGGCCTC CATCAGCGAT ATGGCTTCCG ATTCCAGATG |
| 1141 | CCCCACACAG GGAGAGGCTT ATCTGGACAA ACAGTCCGAC ACCCAGTACG TCTGCAAAAG |
| 1201 | AACCCTGGTG GACAGAaacc acaccAACGG ATGCGGCCTG TTCGGCAAAG GCAGCCTCGT |
| 1261 | GACATGTGCC AAGTTCGCCT GCAGCAAAAA GATGACCGGC AAGTCCATCC AGCCCGAGAA |
| 1321 | CCTGGAATAC AGGATCATGC TGTCCGTGCA TGGATCCCAG CACTCCGGCA TGATCGTCAA |
| 1381 | CGATACCGGC CACGAGACCG ACGAGAACAG GGCTAAAGTG GAGATCACCC CAACAGCCC |
| 1441 | TAGAGCCGAA GCTACACTGG GCGGCTTCGG AAGCCTGGGC CTGGATTGCG AACCCAGGAC |
| 1501 | CGGCCTGGAT TTCAGCGACC TGTATTACCT GACCATGAAC AATAAGCACT GGCTGGTGCA |
| 1561 | CAAGGAATGG TTCCACGACA TCCCCCTGCC TTGGCATGCT GGCGCCGATA CCGGCACACC |
| 1621 | TCACTGGAAC AATAAGGAAG CCCTGGTCGA GTTTAAGGAC GCCCACGCCA AAGACAGAC |
| 1681 | CGTGGTGGTG CTGGAAGCCA AGGAGGGAGC TGTCCACACA GCCCTGGCCG GAGCTCTGGA |
| 1741 | AGCCGAGATG GATGGCGCCA AGGGCAGGCT GAGCTCCGGC CACCTGAAAT GCAGGCTCAA |
| 1801 | GATGGACAAG CTGAGGCTGA AGGGCGTGAG CTACAGCCTG TGCACCGCCG CTTTCACCTT |
| 1861 | TACCAAGATC CCTGCCGAGA CACTGCACGG CACCGTCACC GTGGAGGTGC AATACGCCGG |
| 1921 | AACCGATGGA CCTTGCAAAG TGCCTGCCCA GATGGCTGTG GATATGCAGA CCCTCACACC |
| 1981 | CGTCGGCAGG CTGATCACCG CCAATCCCGT CATTACCGAG TCCACCGAGA ACAGCAAGAT |
| 2041 | GATGCTcGAG CTCGATCCCC CCTTTGGCGA CAGCTACATT GTGATCGGCG TGGGCGAGAA |
| 2101 | GAAGATCACC CACCATTGGC ACAGAAGCGG CTCCACAggg ggtagcggtg gtagcggagg |
| 2161 | tagccatcac caccatcacc actgagctag CTTGACTGAC TGAGATACAG CGTACCTTCA |
| 2221 | GCTCACAGAC ATGATAAGAT ACATTGATGA GTTTGGACAA ACCACAACTA GAATGCAGTG |
| 2281 | AAAAAAATGC TTTATTTGTG AAATTTGTGA TGCTATTGCT TATTTGTAA CCATTATAAG |

| | |
|---|---|
| 2341 | CTGCAATAAA CAAGTTAACA ACAACAATTG CATTCATTTT ATGTTTCAGG TTCAGGGGGA |
| 2401 | GGTGTGGGAG GTTTTTTAAA GCAAGTAAAA CCTCTACAAA TGTGGTATTG GCCCATCTCT |
| 2461 | ATCGGTATCG TAGCATAACC CCTTGGGGCC TCTAAACGGG TCTTGAGGGG TTTTTTGTGC |
| 2521 | CCCTCGGGCC GGATTGCTAT CTACCGGCAT TGGCGCAGAA AAAAATGCCT GATGCGACGC |
| 2581 | TGCGCGTCTT ATACTCCCAC ATATGCCAGA TTCAGCAACG GATACGGCTT CCCCAACTTG |
| 2641 | CCCACTTCCA TACGTGTCCT CCTTACCAGA AATTTATCCT TAAGGTCGTC AGCTATCCTG |
| 2701 | CAGGCGATCT CTCGATTTCG ATCAAGACAT TCCTTTAATG GTCTTTTCTG GACACCACTA |
| 2761 | GGGGTCAGAA GTAGTTCATC AAACTTTCTT CCCTCCCTAA TCTCATTGGT TACCTTGGGC |
| 2821 | TATCGAAACT TAATTAACCA GTCAAGTCAG CTACTTGGCG AGATCGACTT GTCTGGGTTT |
| 2881 | CGACTACGCT CAGAATTGCG TCAGTCAAGT TCGATCTGGT CCTTGCTATT GCACCCGTTC |
| 2941 | TCCGATTACG AGTTTCATTT AAATCATGTG AGCAAAAGGC CAGCAAAAGG CCAGGAACCG |
| 3001 | TAAAAAGGCC GCGTTGCTGG CGTTTTTCCA TAGGCTCCGC CCCCCTGACG AGCATCACAA |
| 3061 | AAATCGACGC TCAAGTCAGA GGTGGCGAAA CCCGACAGGA CTATAAAGAT ACCAGGCGTT |
| 3121 | TCCCCCTGGA AGCTCCCTCG TGCGCTCTCC TGTTCCGACC CTGCCGCTTA CCGGATACCT |
| 3181 | GTCCGCCTTT CTCCCTTCGG GAAGCGTGGC GCTTTCTCAT AGCTCACGCT GTAGGTATCT |
| 3241 | CAGTTCGGTG TAGGTCGTTC GCTCCAAGCT GGGCTGTGTG CACGAACCCC CCGTTCAGCC |
| 3301 | CGACCGCTGC GCCTTATCCG GTAACTATCG TCTTGAGTCC AACCCGGTAA GACACGACTT |
| 3361 | ATCGCCACTG GCAGCAGCCA CTGGTAACAG GATTAGCAGA GCGAGGTATG TAGGCGGTGC |
| 3421 | TACAGAGTTC TTGAAGTGGT GGCCTAACTA CGGCTACACT AGAAGAACAG TATTTGGTAT |
| 3481 | CTGCGCTCTG CTGAAGCCAG TTACCTTCGG AAAAAGAGTT GGTAGCTCTT GATCCGGCAA |
| 3541 | ACAAACCACC GCTGGTAGCG GTGGTTTTTT TGTTTGCAAG CAGCAGATTA CGCGCAGAAA |
| 3601 | AAAAGGATCT CAAGAAGATC CTTTGATCTT TTCTACGGGG TCTGACGCTC AGTGGAACGA |
| 3661 | AAACTCACGT TAAGGGATTT TGGTCATGAG ATTATCAAAA AGGATCTTCA CCTAGATCCT |
| 3721 | TTTAAATTAA AAATGAAGTT TTAAATCAAT CTAAAGTATA TATGAGTAAA CTTGGTCTGA |
| 3781 | CAGTTACCAA TGCTTAATCA GTGAGGCACC TATCTCAGCG ATCTGTCTAT TTCGTTCATC |
| 3841 | CATAGTTGCA TTTAAATTTC CGAACTCTCC AAGGCCCTCG TCGAAAATC TTCAAACCTT |
| 3901 | TCGTCCGATC CATCTTGCAG GCTACCTCTC GAACGAACTA TCGCAAGTCT CTTGGCCGGC |
| 3961 | CTTGCGCCTT GGCTATTGCT TGGCAGCGCC TATCGCCAGG TATTACTCCA ATCCCGAATA |
| 4021 | TCCGAGATCG GGATCACCCG AGAGAAGTTC AACCTACATC CTCAATCCCG ATCTATCCGA |
| 4081 | GATCCGAGGA ATATCGAAAT CGGGGCGCGC CTGGTGTACC GAGAACGATC CTCTCAGTGC |
| 4141 | GAGTCTCGAC GATCCATATC GTTGCTTGGC AGTCAGCCAG TCGGAATCCA GCTTGGGACC |
| 4201 | CAGGAAGTCC AATCGTCAGA TATTGTACTC AAGCCTGGTC ACGGCAGCGT ACCGATCTGT |
| 4261 | TTAAACCTAG ATATTGATAG TCTGATCGGT CAACGTATAA TCGAGTCCTA GCTTTTGCAA |
| 4321 | ACATCTATCA AGAGACAGGA TCAGCAGGAG CTTTCGCAT GAGTATTCAA CATTTCCGTG |
| 4381 | TCGCCCTTAT TCCCTTTTTT GCGGCATTTT GCCTTCCTGT TTTTGCTCAC CCAGAAACGC |
| 4441 | TGGTGAAAGT AAAAGATGCT GAAGATCAGT TGGGTGCGCG AGTGGGTTAC ATCGAACTGG |
| 4501 | ATCTCAACAG CGGTAAGATC CTTGAGAGTT TTCGCCCCGA AGAACGCTTT CCAATGATGA |
| 4561 | GCACTTTTAA AGTTCTGCTA TGTGGCGCGG TATTATCCCG TATTGACGCC GGGCAAGAGC |
| 4621 | AACTCGGTCG CCGCATACAC TATTCTCAGA ATGACTTGGT TGAGTATTCA CCAGTCACAG |

TABLE-continued

Sequence Listing Free Text

```
4681  AAAAGCATCT TACGGATGGC ATGACAGTAA GAGAATTATG CAGTGCTGCC ATAACCATGA
4741  GTGATAACAC TGCGGCCAAC TTACTTCTGA CAACGATTGG AGGACCGAAG GAGCTAACCG
4801  CTTTTTTGCA CAACATGGGG GATCATGTAA CTCGCCTTGA TCGTTGGGAA CCGGAGCTGA
4861  ATGAAGCCAT ACCAAACGAC GAGCGTGACA CCACGATGCC TGTAGCAATG GCAACAACCT
4921  TGCGTAAACT ATTAACTGGC GAACTACTTA CTCTAGCTTC CCGGCAACAG TTGATAGACT
4981  GGATGGAGGC GGATAAAGTT GCAGGACCAC TTCTGCGCTC GGCCCTTCCG GCTGGCTGGT
5041  TTATTGCTGA TAAATCTGGA GCCGGTGAGC GTGGGTCTCG CGGTATCATT GCAGCACTGG
5101  GGCCAGATGG TAAGCCCTCC CGTATCGTAG TTATCTACAC GACGGGGAGT CAGGCAACTA
5161  TGGATGAACG AAATAGACAG ATCGCTGAGA TAGGTGCCTC ACTGATTAAG CATTGGTAAC
5221  CGATTCTAGG TGCATTGGCG CAGAAAAAAA TGCCTGATGC GACGCTGCGC GTCTTATACT
5281  CCCACATATG CCAGATTCAG CAACGGATAC GGCTTCCCCA ACTTGCCCAC TTCCATACGT
5341  GTCCTCCTTA CCAGAAATTT ATCCTTAAGA TCCCGAATCG TTTAAACTCG ACTCTGGCTC
5401  TATCGAATCT CCGTCGTTTC GAGCTTACGC GAACAGCCGT GGCGCTCATT TGCTCGTCGG
5461  GCATCGAATC TCGTCAGCTA TCGTCAGCTT ACCTTTTTGG CA
pCRO25 (SEQ ID NO: 18) ORIGIN
   1  GCGATCGCGG CTCCCGACAT CTTGGACCAT TAGCTCCACA GGTATCTTCT TCCCTCTAGT
  61  GGTCATAACA GCAGCTTCAG CTACCTCTCA ATTCAAAAAA CCCCTCAAGA CCCGTTTAGA
 121  GGCCCCAAGG GGTTATGCTA TCAATCGTTG CGTTACACAC ACAAAAAACC AACACACATC
 181  CATCTTCGAT GGATAGCGAT TTTATTATCT AACTGCTGAT CGAGTGTAGC CAGATCTAGT
 241  AATCAATTAC GGGGTCATTA GTTCATAGCC CATATATGGA GTTCCGCGTT ACATAACTTA
 301  CGGTAAATGG CCCGCCTGGC TGACCGCCCA ACGACCCCCG CCCATTGACG TCAATAATGA
 361  CGTATGTTCC CATAGTAACG CCAATAGGGA CTTTCCATTG ACGTCAATGG GTGGAGTATT
 421  TACGGTAAAC TGCCCACTTG GCAGTACATC AAGTGTATCA TATGCCAAGT ACGCCCCCTA
 481  TTGACGTCAA TGACGGTAAA TGGCCCGCCT GGCATTATGC CCAGTACATG ACCTTATGGG
 541  ACTTTCCTAC TTGGCAGTAC ATCTACGTAT TAGTCATCGC TATTACCATG CTGATGCGGT
 601  TTTGGCAGTA CATCAATGGG CGTGGATAGC GGTTTGACTC ACGGGGATTT CCAAGTCTCC
 661  ACCCCATTGA CGTCAATGGG AGTTTGTTTT GGCACCAAAA TCAACGGGAC TTTCCAAAAT
 721  GTCGTAACAA CTCCGCCCCA TTGACGCAAA TGGGCGGTAG CGTGTACGG TGGGAGGTCT
 781  ATATAAGCAG AGCTGGTTTA GTGAACCGTC AGATCAGATC TTTGTCGATC CTACCATCCA
 841  CTCGACACAC CCGCCAGCgg ccgccaccat gaaggccaat ctactggtgt tgctgtgtgc
 901  ccttgcggcg gcagatgcca tcaggtgcat tggagtcagc aacagggact tcgtcgaagg
 961  catgtccggc ggcacctggg tggatgtggt gctcgaacac ggcggatgcg tgaccgtcat
1021  ggcccaggac aagcctaccg tcgatattga gctggtgacc accacagtga gcaacatggc
1081  cgaagtgaga agctactgct atgaggcctc catcagcgat atggcttccg attccagatg
1141  ccccacacag ggagaggctt atctggacaa acagtccgac acccagtacg tctgcaaaag
1201  aaccctggtg gacagaggca atggatccgg atgcggcctg aacggctctg gcagcctcgt
1261  gacatgtgcc aagttcgcct gcagcaaaaa gatgaccggc aagtccatcc agcccgagaa
1321  cctggaatac aggatcatgc tgtccgtgca tggatcccag cactccggca tgatcgtcaa
1381  cgataccggc cacgagaccg acgagaacag ggctaaagtg agatcaccc ccaacagccc
```

-continued

| | Sequence Listing Free Text | | | | |
|---|---|---|---|---|---|
| 1441 | tagagccgaa | gctacactgg | gcggcttcgg | aagcctgggc | ctggattgcg | aacccaggac |
| 1501 | cggcctggat | ttcagcgacc | tgtattacct | gaccatgaac | aataagcact | ggctggtgca |
| 1561 | caaggaatgg | ttccacgaca | tcccctgcc | ttggcatgct | ggcgccgata | ccggcacacc |
| 1621 | tcactggaac | aataaggaag | ccctggtcga | gtttaaggac | gcccacgcca | aagacagac |
| 1681 | cgtggtggtg | ctgggaagcc | aggagggagc | tgtccacaca | gccctggccg | gagctctgga |
| 1741 | agccgagatg | gatggcgcca | agggcaggct | gagctccggc | cacctgaaat | gcaggctcaa |
| 1801 | gatggacaag | ctgaggctga | agggcgtgag | ctacagcctg | tgcaccgccg | ctttcacctt |
| 1861 | taccaagatc | cctgccgaga | cactgcacgg | caccgtcacc | gtggaggtgc | aatacgccgg |
| 1921 | aaccgatgga | ccttgcaaag | tgcctgccca | gatggctgtg | gatatgcaga | ccctcacacc |
| 1981 | cgtcggcagg | ctgatcaccg | ccaatcccgt | cattaccgag | tccaccgaga | cagcaagat |
| 2041 | gatgctcgag | ctcgatcccc | cctttggcga | cagctacatt | gtgatcggcg | tgggcgagaa |
| 2101 | gaagatcacc | caccattggc | acagaagcgg | ctccacaggg | ggtagcggtg | gtagcggagg |
| 2161 | tagccatcac | caccatcacc | actgagctag | CTTGACTGAC | TGAGATACAG | CGTACCTTCA |
| 2221 | GCTCACAGAC | ATGATAAGAT | ACATTGATGA | GTTTGGACAA | ACCACAACTA | GAATGCAGTG |
| 2281 | AAAAAAATGC | TTTATTTGTG | AAATTTGTGA | TGCTATTGCT | TTATTTGTAA | CCATTATAAG |
| 2341 | CTGCAATAAA | CAAGTTAACA | ACAACAATTG | CATTCATTTT | ATGTTTCAGG | TTCAGGGGGA |
| 2401 | GGTGTGGGAG | GTTTTTTAAA | GCAAGTAAAA | CCTCTACAAA | TGTGGTATTG | GCCCATCTCT |
| 2461 | ATCGGTATCG | TAGCATAACC | CCTTGGGGCC | TCTAAACGGG | TCTTGAGGGG | TTTTTTGTGC |
| 2521 | CCCTCGGGCC | GGATTGCTAT | CTACCGGCAT | GGCGCAGAA | AAAAATGCCT | GATGCGACGC |
| 2581 | TGCGCGTCTT | ATACTCCCAC | ATATGCCAGA | TTCAGCAACG | GATACGGCTT | CCCCAACTTG |
| 2641 | CCCACTTCCA | TACGTGTCCT | CCTTACCAGA | AATTTATCCT | TAAGGTCGTC | AGCTATCCTG |
| 2701 | CAGGCGATCT | CTCGATTTCG | ATCAAGACAT | TCCTTTAATG | GTCTTTTCTG | GACACCACTA |
| 2761 | GGGGTCAGAA | GTAGTTCATC | AAACTTTCTT | CCCTCCCTAA | TCTCATTGGT | TACCTTGGGC |
| 2821 | TATCGAAACT | TAATTAACCA | GTCAAGTCAG | CTACTTGGCG | AGATCGACTT | GTCTGGGTTT |
| 2881 | CGACTACGCT | CAGAATTGCG | TCAGTCAAGT | TCGATCTGGT | CCTTGCTATT | GCACCCGTTC |
| 2941 | TCCGATTACG | AGTTTCATTT | AAATCATGTG | AGCAAAAGGC | CAGCAAAAGG | CCAGGAACCG |
| 3001 | TAAAAAGGCC | GCGTTGCTGG | CGTTTTTCCA | TAGGCTCCGC | CCCCCTGACG | AGCATCACAA |
| 3061 | AAATCGACGC | TCAAGTCAGA | GGTGGCGAAA | CCCGACAGGA | CTATAAAGAT | ACCAGGCGTT |
| 3121 | TCCCCCTGGA | AGCTCCCTCG | TGCGCTCTCC | TGTTCCGACC | CTGCCGCTTA | CCGGATACCT |
| 3181 | GTCCGCCTTT | CTCCCTTCGG | GAAGCGTGGC | GCTTTCTCAT | AGCTCACGCT | GTAGGTATCT |
| 3241 | CAGTTCGGTG | TAGGTCGTTC | GCTCCAAGCT | GGGCTGTGTG | CACGAACCCC | CCGTTCAGCC |
| 3301 | CGACCGCTGC | GCCTTATCCG | GTAACTATCG | TCTTGAGTCC | AACCCGGTAA | GACACGACTT |
| 3361 | ATCGCCACTG | GCAGCAGCCA | CTGGTAACAG | GATTAGCAGA | GCGAGGTATG | TAGGCGGTGC |
| 3421 | TACAGAGTTC | TTGAAGTGGT | GGCCTAACTA | CGGCTACACT | AGAAGAACAG | TATTTGGTAT |
| 3481 | CTGCGCTCTG | CTGAAGCCAG | TTACCTTCGG | AAAAAGAGTT | GGTAGCTCTT | GATCCGGCAA |
| 3541 | ACAAACCACC | GCTGGTAGCG | GTGGTTTTTT | TGTTTGCAAG | CAGCAGATTA | CGCGCAGAAA |
| 3601 | AAAAGGATCT | CAAGAAGATC | CTTTGATCTT | TTCTACGGGG | TCTGACGCTC | AGTGGAACGA |
| 3661 | AAACTCACGT | TAAGGGATTT | TGGTCATGAG | ATTATCAAAA | AGGATCTTCA | CCTAGATCCT |

| Sequence Listing Free Text |
|---|
| 3721 TTTAAATTAA AAATGAAGTT TTAAATCAAT CTAAAGTATA TATGAGTAAA CTTGGTCTGA |
| 3781 CAGTTACCAA TGCTTAATCA GTGAGGCACC TATCTCAGCG ATCTGTCTAT TTCGTTCATC |
| 3841 CATAGTTGCA TTTAAATTTC CGAACTCTCC AAGGCCCTCG TCGGAAAATC TTCAAACCTT |
| 3901 TCGTCCGATC CATCTTGCAG GCTACCTCTC GAACGAACTA TCGCAAGTCT CTTGGCCGGC |
| 3961 CTTGCGCCTT GGCTATTGCT TGGCAGCGCC TATCGCCAGG TATTACTCCA ATCCCGAATA |
| 4021 TCCGAGATCG GGATCACCCG AGAGAAGTTC AACCTACATC CTCAATCCCG ATCTATCCGA |
| 4081 GATCCGAGGA ATATCGAAAT CGGGGCGCGC CTGGTGTACC GAGAACGATC CTCTCAGTGC |
| 4141 GAGTCTCGAC GATCCATATC GTTGCTTGGC AGTCAGCCAG TCGGAATCCA GCTTGGGACC |
| 4201 CAGGAAGTCC AATCGTCAGA TATTGTACTC AAGCCTGGTC ACGGCAGCGT ACCGATCTGT |
| 4261 TTAAACCTAG ATATTGATAG TCTGATCGGT CAACGTATAA TCGAGTCCTA GCTTTTGCAA |
| 4321 ACATCTATCA AGAGACAGGA TCAGCAGGAG GCTTTCGCAT GAGTATTCAA CATTTCCGTG |
| 4381 TCGCCCTTAT TCCCTTTTTT GCGGCATTTT GCCTTCCTGT TTTTGCTCAC CCAGAAACGC |
| 4441 TGGTGAAAGT AAAAGATGCT GAAGATCAGT TGGGTGCGCG AGTGGGTTAC ATCGAACTGG |
| 4501 ATCTCAACAG CGGTAAGATC CTTGAGAGTT TTCGCCCCGA AGAACGCTTT CCAATGATGA |
| 4561 GCACTTTTAA AGTTCTGCTA TGTGGCGCGG TATTATCCCG TATTGACGCC GGGCAAGAGC |
| 4621 AACTCGGTCG CCGCATACAC TATTCTCAGA ATGACTTGGT TGAGTATTCA CCAGTCACAG |
| 4681 AAAAGCATCT TACGGATGGC ATGACAGTAA GAGAATTATG CAGTGCTGCC ATAACCATGA |
| 4741 GTGATAACAC TGCGGCCAAC TTACTTCTGA CAACGATTGG AGGACCGAAG GAGCTAACCG |
| 4801 CTTTTTTGCA CAACATGGGG GATCATGTAA CTCGCCTTGA TCGTTGGGAA CCGGAGCTGA |
| 4861 ATGAAGCCAT ACCAAACGAC GAGCGTGACA CCACGATGCC TGTAGCAATG GCAACAACCT |
| 4921 TGCGTAAACT ATTAACTGGC GAACTACTTA CTCTAGCTTC CCGGCAACAG TTGATAGACT |
| 4981 GGATGGAGGC GGATAAAGTT GCAGGACCAC TTCTGCGCTC GGCCCTTCCG GCTGGCTGGT |
| 5041 TTATTGCTGA TAAATCTGGA GCCGGTGAGC GTGGGTCTCG CGGTATCATT GCAGCACTGG |
| 5101 GGCCAGATGG TAAGCCCTCC CGTATCGTAG TTATCTACAC GACGGGGAGT CAGGCAACTA |
| 5161 TGGATGAACG AAATAGACAG ATCGCTGAGA TAGGTGCCTC ACTGATTAAG CATTGGTAAC |
| 5221 CGATTCTAGG TGCATTGGCG CAGAAAAAAA TGCCTGATGC GACGCTGCGC GTCTTATACT |
| 5281 CCCACATATG CCAGATTCAG CAACGGATAC GGCTTCCCCA ACTTGCCCAC TTCCATACGT |
| 5341 GTCCTCCTTA CCAGAAATTT ATCCTTAAGA TCCCGAATCG TTTAAACTCG ACTCTGGCTC |
| 5401 TATCGAATCT CCGTCGTTTC GAGCTTACGC GAACAGCCGT GGCGCTCATT TGCTCGTCGG |
| 5461 GCATCGAATC TCGTCAGCTA TCGTCAGCTT ACCTTTTGG CA | pCR026 (SEQ ID NO: 19)
ORIGIN
| 1 GCGATCGCGG CTCCCGACAT CTTGGACCAT TAGCTCCACA GGTATCTTCT TCCCTCTAGT |
|---|
| 61 GGTCATAACA GCAGCTTCAG CTACCTCTCA ATTCAAAAAA CCCCTCAAGA CCCGTTTAGA |
| 121 GGCCCCAAGG GGTTATGCTA TCAATCGTTG CGTTACACAC ACAAAAAACC AACACACATC |
| 181 CATCTTCGAT GGATAGCGAT TTTATTATCT AACTGCTGAT CGAGTGTAGC CAGATCTAGT |
| 241 AATCAATTAC GGGGTCATTA GTTCATAGCC CATATATGGA GTTCCGCGTT ACATAACTTA |
| 301 CGGTAAATGG CCCGCCTGGC TGACCGCCCA ACGACCCCCG CCCATTGACG TCAATAATGA |
| 361 CGTATGTTCC CATAGTAACG CCAATAGGGA CTTTCCATTG ACGTCAATGG GTGGAGTATT |
| 421 TACGGTAAAC TGCCCACTTG GCAGTACATC AAGTGTATCA TATGCCAAGT ACGCCCCCTA |

-continued

Sequence Listing Free Text

```
 481   TTGACGTCAA TGACGGTAAA TGGCCCGCCT GGCATTATGC CCAGTACATG ACCTTATGGG
 541   ACTTTCCTAC TTGGCAGTAC ATCTACGTAT TAGTCATCGC TATTACCATG CTGATGCGGT
 601   TTTGGCAGTA CATCAATGGG CGTGGATAGC GGTTTGACTC ACGGGGATTT CCAAGTCTCC
 661   ACCCCATTGA CGTCAATGGG AGTTTGTTTT GGCACCAAAA TCAACGGGAC TTTCCAAAAT
 721   GTCGTAACAA CTCCGCCCCA TTGACGCAAA TGGGCGGTAG CGTGTACGG TGGGAGGTCT
 781   ATATAAGCAG AGCTGGTTTA GTGAACCGTC AGATCAGATC TTTGTCGATC CTACCATCCA
 841   CTCGACACAC CCGCCAGCgg ccgccaccat gaaggccaat ctactggtgt tgctgtgtgc
 901   ccttgcggcg gcagatgcca tgcggtgcgt ggggatcggc aatcgcgatt ttgtagaagg
 961   actatctggt gccacgtggg tcgatgtggt tcttgaacac gggtcatgcg tgaccacgat
1021   ggctaaggat aagccgacct tggacatcga actactgaaa accgaggtca caaaccctgc
1081   tgtgctccgc aagctgtgca tcgaggctaa gatttccaac acaactactg atagccgctg
1141   ccccacccaa ggcgaggcga ccctcgttga agagcaggac agcaacttcg tgtgtcgccg
1201   gactttcgtg daccgcggta atgggtccgg atgcggactt TTTGGAAAGg gttccttact
1261   gacttgcgcc aaatttaagt gcgtgactaa gttagagggg aaaatcgttc agtatgagaa
1321   cttaaaatac tcggtgatag ttaccgtgca cacaggcgac cagcatcaag ttgggaacga
1381   aacgacagag cacgggacaa tagcgaccat taccccacag gctccaacga gcgaaattca
1441   gctgacagac tacggtgcac tcaccctgga ctgtagccca cggaccgggc tagactttaa
1501   cgagatggtg ctcctgacta tgaaggaaaa gtcatggttg gtgcacaagc agtggttcct
1561   tgatcttcca ttgccctgga cctctggcgc ttcgacctca caagagactt ggaacaggca
1621   ggacttgctc gtgacattca aaacggctca cgctaaaaag caagaggtcg tggttctggg
1681   gagtcaggaa ggcgctatgc ataccgcgtt aacagggggct acagagatcc agaccagtgg
1741   aacaaccact attttcgccg ggcatcttaa gtgtaggctg aagatggata agttgaccct
1801   gaaaggtatg tcatatgtga tgtgcaccgg tagtttcaaa ctggagaaag aagtggccga
1861   aacccagcat ggaacagtac tggtgcaagt caaatatgag ggcaccgatg caccatgtaa
1921   aatacccttc agcgcacaag acgagaaggg agttacccag aacggtaggc tgataacagc
1981   caatccaatc gtcaccgata aggagaaacc agtaaacatc gaaaccgagc caccttcgg
2041   cgaaagctac atcgtggtcg gcgctggcga gaaagcactt aagctgagct ggtttaagaa
2101   aggtagcacg ggcggcggca gccatcatca ccatcatcac tgagctagCT TGACTGACTG
2161   AGATACAGCG TACCTTCAGC TCACAGACAT GATAAGATAC ATTGATGAGT TTGGACAAAC
2221   CACAACTAGA ATGCAGTGAA AAAATGCTT TATTTGTGAA ATTTGTGATG CTATTGCTTT
2281   ATTTGTAACC ATTATAAGCT GCAATAAACA AGTTAACAAC AACAATTGCA TTCATTTTAT
2341   GTTTCAGGTT CAGGGGGAGG TGTGGGAGGT TTTTTAAAGC AAGTAAAACC TCTACAAATG
2401   TGGTATTGGC CCATCTCTAT CGGTATCGTA GCATAACCCC TTGGGGCCTC TAAACGGGTC
2461   TTGAGGGGTT TTTTGTGCCC CTCGGGCCGG ATTGCTATCT ACCGGCATTG GCGCAGAAAA
2521   AAATGCCTGA TGCGACGCTG CGCGTCTTAT ACTCCCACAT ATGCCAGATT CAGCAACGGA
2581   TACGGCTTCC CCAACTTGCC CACTTCCATA CGTGTCCTCC TTACCAGAAA TTTATCCTTA
2641   AGGTCGTCAG CTATCCTGCA GGCGATCTCT CGATTTCGAT CAAGACATTC CTTTAATGGT
2701   CTTTTCTGGA CACCACTAGG GGTCAGAAGT AGTTCATCAA ACTTTCTTCC CTCCCTAATC
```

-continued

| | Sequence Listing Free Text |
|---|---|
| 2761 | TCATTGGTTA CCTTGGGCTA TCGAAACTTA ATTAACCAGT CAAGTCAGCT ACTTGGCGAG |
| 2821 | ATCGACTTGT CTGGGTTTCG ACTACGCTCA GAATTGCGTC AGTCAAGTTC GATCTGGTCC |
| 2881 | TTGCTATTGC ACCCGTTCTC CGATTACGAG TTTCATTTAA ATCATGTGAG CAAAAGGCCA |
| 2941 | GCAAAAGGCC AGGAACCGTA AAAAGGCCGC GTTGCTGGCG TTTTTCCATA GGCTCCGCCC |
| 3001 | CCCTGACGAG CATCACAAAA ATCGACGCTC AAGTCAGAGG TGGCGAAACC CGACAGGACT |
| 3061 | ATAAAGATAC CAGGCGTTTC CCCCTGGAAG CTCCCTCGTG CGCTCTCCTG TTCCGACCCT |
| 3121 | GCCGCTTACC GGATACCTGT CCGCCTTTCT CCCTTCGGGA AGCGTGGCGC TTTCTCATAG |
| 3181 | CTCACGCTGT AGGTATCTCA GTTCGGTGTA GGTCGTTCGC TCCAAGCTGG GCTGTGTGCA |
| 3241 | CGAACCCCCC GTTCAGCCCG ACCGCTGCGC CTTATCCGGT AACTATCGTC TTGAGTCCAA |
| 3301 | CCCGGTAAGA CACGACTTAT CGCCACTGGC AGCAGCCACT GGTAACAGGA TTAGCAGAGC |
| 3361 | GAGGTATGTA GGCGGTGCTA CAGAGTTCTT GAAGTGGTGG CCTAACTACG GCTACACTAG |
| 3421 | AAGAACAGTA TTTGGTATCT GCGCTCTGCT GAAGCCAGTT ACCTTCGGAA AAAGAGTTGG |
| 3481 | TAGCTCTTGA TCCGGCAAAC AAACCACCGC TGGTAGCGGT GGTTTTTTTG TTTGCAAGCA |
| 3541 | GCAGATTACG CGCAGAAAAA AAGGATCTCA AGAAGATCCT TTGATCTTTT CTACGGGGTC |
| 3601 | TGACGCTCAG TGGAACGAAA ACTCACGTTA AGGGATTTTG GTCATGAGAT TATCAAAAAG |
| 3661 | GATCTTCACC TAGATCCTTT TAAATTAAAA ATGAAGTTTT AAATCAATCT AAAGTATATA |
| 3721 | TGAGTAAACT TGGTCTGACA GTTACCAATG CTTAATCAGT GAGGCACCTA TCTCAGCGAT |
| 3781 | CTGTCTATTT CGTTCATCCA TAGTTGCATT TAAATTTCCG AACTCTCCAA GGCCCTCGTC |
| 3841 | GGAAAATCTT CAAACCTTTC GTCCGATCCA TCTTGCAGGC TACCTCTCGA ACGAACTATC |
| 3901 | GCAAGTCTCT TGGCCGGCCT TGCGCCTTGG CTATTGCTTG GCAGCGCCTA TCGCCAGGTA |
| 3961 | TTACTCCAAT CCCGAATATC CGAGATCGGG ATCACCCGAG AGAAGTTCAA CCTACATCCT |
| 4021 | CAATCCCGAT CTATCCGAGA TCCGAGGAAT ATCGAAATCG GGGCGCGCCT GGTGTACCGA |
| 4081 | GAACGATCCT CTCAGTGCGA GTCTCGACGA TCCATATCGT TGCTTGGCAG TCAGCCAGTC |
| 4141 | GGAATCCAGC TTGGGACCCA GGAAGTCCAA TCGTCAGATA TTGTACTCAA GCCTGGTCAC |
| 4201 | GGCAGCGTAC CGATCTGTTT AAACCTAGAT ATTGATAGTC TGATCGGTCA ACGTATAATC |
| 4261 | GAGTCCTAGC TTTTGCAAAC ATCTATCAAG AGACAGGATC AGCAGGAGGC TTTCGCATGA |
| 4321 | GTATTCAACA TTTCCGTGTC GCCCTTATTC CCTTTTTTGC GGCATTTTGC CTTCCTGTTT |
| 4381 | TTGCTCACCC AGAAACGCTG GTGAAAGTAA AAGATGCTGA AGATCAGTTG GGTGCGCGAG |
| 4441 | TGGGTTACAT CGAACTGGAT CTCAACAGCG GTAAGATCCT TGAGAGTTTT CGCCCCGAAG |
| 4501 | AACGCTTTCC AATGATGAGC ACTTTTAAAG TTCTGCTATG TGGCGCGGTA TTATCCCGTA |
| 4561 | TTGACGCCGG GCAAGAGCAA CTCGGTCGCC GCATACACTA TTCTCAGAAT GACTTGGTTG |
| 4621 | AGTATTCACC AGTCACAGAA AAGCATCTTA CGGATGGCAT GACAGTAAGA GAATTATGCA |
| 4681 | GTGCTGCCAT AACCATGAGT GATAACACTG CGGCCAACTT ACTTCTGACA ACGATTGGAG |
| 4741 | GACCGAAGGA GCTAACCGCT TTTTTGCACA ACATGGGGGA TCATGTAACT CGCCTTGATC |
| 4801 | GTTGGGAACC GGAGCTGAAT GAAGCCATAC CAAACGACGA GCGTGACACC ACGATGCCTG |
| 4861 | TAGCAATGGC AACAACCTTG CGTAAACTAT TAACTGGCGA ACTACTTACT CTAGCTTCCC |
| 4921 | GGCAACAGTT GATAGACTGG ATGGAGGCGG ATAAAGTTGC AGGACCACTT CTGCGCTCGG |
| 4981 | CCCTTCCGGC TGGCTGGTTT ATTGCTGATA AATCTGGAGC CGGTGAGCGT GGGTCTCGCG |
| 5041 | GTATCATTGC AGCACTGGGG CCAGATGGTA AGCCCTCCCG TATCGTAGTT ATCTACACGA |

| | | | | |
|---|---|---|---|---|
| 5101 | CGGGGAGTCA | GGCAACTATG | GATGAACGAA | ATAGACAGAT | CGCTGAGATA | GGTGCCTCAC |
| 5161 | TGATTAAGCA | TTGGTAACCG | ATTCTAGGTG | CATTGGCGCA | GAAAAAAATG | CCTGATGCGA |
| 5221 | CGCTGCGCGT | CTTATACTCC | CACATATGCC | AGATTCAGCA | ACGGATACGG | CTTCCCCAAC |
| 5281 | TTGCCCACTT | CCATACGTGT | CCTCCTTACC | AGAAATTTAT | CCTTAAGATC | CCGAATCGTT |
| 5341 | TAAACTCGAC | TCTGGCTCTA | TCGAATCTCC | GTCGTTTCGA | GCTTACGCGA | ACAGCCGTGG |
| 5401 | CGCTCATTTG | CTCGTCGGGC | ATCGAATCTC | GTCAGCTATC | GTCAGCTTAC | CTTTTTGGCA |
| 5461 | | | | | | | pCRO27 (SEQ ID NO: 20)
RIGIN

| | | | | | |
|---|---|---|---|---|---|
| 1 | GCGATCGCGG | CTCCCGACAT | CTTGGACCAT | TAGCTCCACA | GGTATCTTCT | TCCCTCTAGT |
| 61 | GGTCATAACA | GCAGCTTCAG | CTACCTCTCA | ATTCAAAAAA | CCCCTCAAGA | CCCGTTTAGA |
| 121 | GGCCCCAAGG | GGTTATGCTA | TCAATCGTTG | CGTTACACAC | ACAAAAAACC | AACACACATC |
| 181 | CATCTTCGAT | GGATAGCGAT | TTTATTATCT | AACTGCTGAT | CGAGTGTAGC | CAGATCTAGT |
| 241 | AATCAATTAC | GGGGTCATTA | GTTCATAGCC | CATATATGGA | GTTCCGCGTT | ACATAACTTA |
| 301 | CGGTAAATGG | CCCGCCTGGC | TGACCGCCCA | ACGACCCCCG | CCCATTGACG | TCAATAATGA |
| 361 | CGTATGTTCC | CATAGTAACG | CCAATAGGGA | CTTTCCATTG | ACGTCAATGG | GTGGAGTATT |
| 421 | TACGGTAAAC | TGCCCACTTG | GCAGTACATC | AAGTGTATCA | TATGCCAAGT | ACGCCCCCTA |
| 481 | TTGACGTCAA | TGACGGTAAA | TGGCCCGCCT | GGCATTATGC | CCAGTACATG | ACCTTATGGG |
| 541 | ACTTTCCTAC | TTGGCAGTAC | ATCTACGTAT | TAGTCATCGC | TATTACCATG | CTGATGCGGT |
| 601 | TTTGGCAGTA | CATCAATGGG | CGTGGATAGC | GGTTTGACTC | ACGGGGATTT | CCAAGTCTCC |
| 661 | ACCCCATTGA | CGTCAATGGG | AGTTTGTTTT | GGCACCAAAA | TCAACGGGAC | TTTCCAAAAT |
| 721 | GTCGTAACAA | CTCCGCCCCA | TTGACGCAAA | TGGGCGGTAG | GCGTGTACGG | TGGGAGGTCT |
| 781 | ATATAAGCAG | AGCTGGTTTA | GTGAACCGTC | AGATCAGATC | TTTGTCGATC | CTACCATCCA |
| 841 | CTCGACACAC | CCGCCAGCgg | ccgccaccat | gaaggccaat | ctactggtgt | tgctgtgtgc |
| 901 | ccttgcggcg | gcagatgcca | tgcggtgcgt | ggggatcggc | aatcgcgatt | ttgtagaagg |
| 961 | actatctggt | gccacgtggg | tcgatgtggt | tcttgaacac | gggtcatgcg | tgaccacgat |
| 1021 | ggctaaggat | aagccgacct | tggacatcga | actactgaaa | accgaggtca | caaaccctgc |
| 1081 | tgtgctccgc | aagctgtgca | tcgaggctaa | gatttccaac | acaactactg | atagccgctg |
| 1141 | ccccaccccaa | ggcgaggcga | ccctcgttga | agagcaggac | agcaacttcg | tgtgtcgccg |
| 1201 | gactttcgtg | gaccgcggtT | GGGGGAATgg | atgcggactt | aacggatctg | gttccttact |
| 1261 | gacttgcgcc | aaatttaagt | gcgtgactaa | gttagagggg | aaaatcgttc | agtatgagaa |
| 1321 | cttaaaatac | tcggtgatag | ttaccgtgca | cacaggcgac | cagcatcaag | ttgggaacga |
| 1381 | aacgacagag | cacgggacaa | tagcgaccat | taccccacag | gctccaacga | gcgaaattca |
| 1441 | gctgacagac | tacggtgcac | tcaccctgga | ctgtagccca | cggaccgggc | tagactttaa |
| 1501 | cgagatggtg | ctcctgacta | tgaaggaaaa | gtcatggttg | tgcacaagc | agtggttcct |
| 1561 | tgatcttcca | ttgccctgga | cctctggcgc | ttcgacctca | caagagactt | ggaacaggca |
| 1621 | ggacttgctc | gtgacattca | aaacggctca | cgctaaaaag | caagaggtcg | tggttctggg |
| 1681 | gagtcaggaa | ggcgctatgc | ataccgcgtt | aacagggggct | acagagatcc | agaccagtgg |
| 1741 | aacaaccact | attttcgccg | ggcatcttaa | gtgtaggctg | aagatggata | agttgaccct |

-continued

| | | | | | |
|---|---|---|---|---|---|
| 1801 | gaaaggtatg | tcatatgtga | tgtgcaccgg | tagtttcaaa | ctggagaaag aagtggccga |
| 1861 | aacccagcat | ggaacagtac | tggtgcaagt | caaatatgag | ggcaccgatg caccatgtaa |
| 1921 | aataccctcc | agcgcacaag | acgagaaggg | agttacccag | aacggtaggc tgataacagc |
| 1981 | caatccaatc | gtcaccgata | aggagaaacc | agtaaacatc | gaaaccgagc caccttcgg |
| 2041 | cgaaagctac | atcgtggtcg | gcgctggcga | gaaagcactt | aagctgagct ggtttaagaa |
| 2101 | aggtagcacg | ggcggcggca | gccatcatca | ccatcatcac | tgagctagCT TGACTGACTG |
| 2161 | AGATACAGCG | TACCTTCAGC | TCACAGACAT | GATAAGATAC | ATTGATGAGT TTGGACAAAC |
| 2221 | CACAACTAGA | ATGCAGTGAA | AAAATGCTT | TATTTGTGAA | ATTTGTGATG CTATTGCTTT |
| 2281 | ATTTGTAACC | ATTATAAGCT | GCAATAAACA | AGTTAACAAC | AACAATTGCA TTCATTTTAT |
| 2341 | GTTTCAGGTT | CAGGGGGAGG | TGTGGGAGGT | TTTTTAAAGC | AAGTAAAACC TCTACAAATG |
| 2401 | TGGTATTGGC | CCATCTCTAT | CGGTATCGTA | GCATAACCCC | TTGGGGCCTC TAAACGGGTC |
| 2461 | TTGAGGGGTT | TTTTGTGCCC | CTCGGGCCGG | ATTGCTATCT | ACCGGCATTG GCGCAGAAAA |
| 2521 | AAATGCCTGA | TGCGACGCTG | CGCGTCTTAT | ACTCCCACAT | ATGCCAGATT CAGCAACGGA |
| 2581 | TACGGCTTCC | CCAACTTGCC | CACTTCCATA | CGTGTCCTCC | TTACCAGAAA TTTATCCTTA |
| 2641 | AGGTCGTCAG | CTATCCTGCA | GGCGATCTCT | CGATTTCGAT | CAAGACATTC CTTTAATGGT |
| 2701 | CTTTTCTGGA | CACCACTAGG | GGTCAGAAGT | AGTTCATCAA | ACTTTCTTCC CTCCCTAATC |
| 2761 | TCATTGGTTA | CCTTGGGCTA | TCGAAACTTA | ATTAACCAGT | CAAGTCAGCT ACTTGGCGAG |
| 2821 | ATCGACTTGT | CTGGGTTTCG | ACTACGCTCA | GAATTGCGTC | AGTCAAGTTC GATCTGGTCC |
| 2881 | TTGCTATTGC | ACCCGTTCTC | CGATTACGAG | TTTCATTTAA | ATCATGTGAG CAAAAGGCCA |
| 2941 | GCAAAAGGCC | AGGAACCGTA | AAAAGGCCGC | GTTGCTGGCG | TTTTTCCATA GGCTCCGCCC |
| 3001 | CCCTGACGAG | CATCACAAAA | ATCGACGCTC | AAGTCAGAGG | TGGCGAAACC CGACAGGACT |
| 3061 | ATAAAGATAC | CAGGCGTTTC | CCCCTGGAAG | CTCCCTCGTG | CGCTCTCCTG TTCCGACCCT |
| 3121 | GCCGCTTACC | GGATACCTGT | CCGCCTTTCT | CCCTTCGGGA | AGCGTGGCGC TTTCTCATAG |
| 3181 | CTCACGCTGT | AGGTATCTCA | GTTCGGTGTA | GGTCGTTCGC | TCCAAGCTGG GCTGTGTGCA |
| 3241 | CGAACCCCCC | GTTCAGCCCG | ACCGCTGCGC | CTTATCCGGT | AACTATCGTC TTGAGTCCAA |
| 3301 | CCCGGTAAGA | CACGACTTAT | CGCCACTGGC | AGCAGCCACT | GGTAACAGGA TTAGCAGAGC |
| 3361 | GAGGTATGTA | GGCGGTGCTA | CAGAGTTCTT | GAAGTGGTGG | CCTAACTACG GCTACACTAG |
| 3421 | AAGAACAGTA | TTTGGTATCT | GCGCTCTGCT | GAAGCCAGTT | ACCTTCGGAA AAAGAGTTGG |
| 3481 | TAGCTCTTGA | TCCGGCAAAC | AAACCACCGC | TGGTAGCGGT | GGTTTTTTTG TTTGCAAGCA |
| 3541 | GCAGATTACG | CGCAGAAAAA | AAGGATCTCA | AGAAGATCCT | TTGATCTTTT CTACGGGGTC |
| 3601 | TGACGCTCAG | TGGAACGAAA | ACTCACGTTA | AGGGATTTTG | GTCATGAGAT TATCAAAAAG |
| 3661 | GATCTTCACC | TAGATCCTTT | TAAATTAAAA | ATGAAGTTTT | AAATCAATCT AAAGTATATA |
| 3721 | TGAGTAAACT | TGGTCTGACA | GTTACCAATG | CTTAATCAGT | GAGGCACCTA TCTCAGCGAT |
| 3781 | CTGTCTATTT | CGTTCATCCA | TAGTTGCATT | TAAATTTCCG | AACTCTCCAA GGCCCTCGTC |
| 3841 | GGAAAATCTT | CAAACCTTTC | GTCCGATCCA | TCTTGCAGGC | TACCTCTCGA ACGAACTATC |
| 3901 | GCAAGTCTCT | TGGCCGGCCT | TGCGCCTTGG | CTATTGCTTG | GCAGCGCCTA TCGCCAGGTA |
| 3961 | TTACTCCAAT | CCCGAATATC | CGAGATCGGG | ATCACCCGAG | AGAAGTTCAA CCTACATCCT |
| 4021 | CAATCCCGAT | CTATCCGAGA | TCCGAGGAAT | ATCGAAATCG | GGGCGCGCCT GGTGTACCGA |
| 4081 | GAACGATCCT | CTCAGTGCGA | GTCTCGACGA | TCCATATCGT | TGCTTGGCAG TCAGCCAGTC |

| Sequence Listing Free Text |
|---|
| 4141 GGAATCCAGC TTGGGACCCA GGAAGTCCAA TCGTCAGATA TTGTACTCAA GCCTGGTCAC |
| 4201 GGCAGCGTAC CGATCTGTTT AAACCTAGAT ATTGATAGTC TGATCGGTCA ACGTATAATC |
| 4261 GAGTCCTAGC TTTTGCAAAC ATCTATCAAG AGACAGGATC AGCAGGAGGC TTTCGCATGA |
| 4321 GTATTCAACA TTTCCGTGTC GCCCTTATTC CCTTTTTTGC GGCATTTTGC CTTCCTGTTT |
| 4381 TTGCTCACCC AGAAACGCTG GTGAAAGTAA AAGATGCTGA AGATCAGTTG GGTGCGCGAG |
| 4441 TGGGTTACAT CGAACTGGAT CTCAACAGCG GTAAGATCCT TGAGAGTTTT CGCCCCGAAG |
| 4501 AACGCTTTCC AATGATGAGC ACTTTTAAAG TTCTGCTATG TGGCGCGGTA TTATCCCGTA |
| 4561 TTGACGCCGG GCAAGAGCAA CTCGGTCGCC GCATACACTA TTCTCAGAAT GACTTGGTTG |
| 4621 AGTATTCACC AGTCACAGAA AAGCATCTTA CGGATGGCAT GACAGTAAGA GAATTATGCA |
| 4681 GTGCTGCCAT AACCATGAGT GATAACACTG CGGCCAACTT ACTTCTGACA ACGATTGGAG |
| 4741 GACCGAAGGA GCTAACCGCT TTTTTGCACA ACATGGGGGA TCATGTAACT CGCCTTGATC |
| 4801 GTTGGGAACC GGAGCTGAAT GAAGCCATAC CAAACGACGA GCGTGACACC ACGATGCCTG |
| 4861 TAGCAATGGC AACAACCTTG CGTAAACTAT TAACTGGCGA ACTACTTACT CTAGCTTCCC |
| 4921 GGCAACAGTT GATAGACTGG ATGGAGGCGG ATAAAGTTGC AGGACCACTT CTGCGCTCGG |
| 4981 CCCTTCCGGC TGGCTGGTTT ATTGCTGATA AATCTGGAGC CGGTGAGCGT GGGTCTCGCG |
| 5041 GTATCATTGC AGCACTGGGG CCAGATGGTA AGCCCTCCCG TATCGTAGTT ATCTACACGA |
| 5101 CGGGGAGTCA GGCAACTATG GATGAACGAA ATAGACAGAT CGCTGAGATA GGTGCCTCAC |
| 5161 TGATTAAGCA TTGGTAACCG ATTCTAGGTG CATTGGCGCA GAAAAAAATG CCTGATGCGA |
| 5221 CGCTGCGCGT CTTATACTCC CACATATGCC AGATTCAGCA ACGGATACGG CTTCCCCAAC |
| 5281 TTGCCCACTT CCATACGTGT CCTCCTTACC AGAAATTTAT CCTTAAGATC CCGAATCGTT |
| 5341 TAAACTCGAC TCTGGCTCTA TCGAATCTCC GTCGTTTCGA GCTTACGCGA ACAGCCGTGG |
| 5401 CGCTCATTTG CTCGTCGGGC ATCGAATCTC GTCAGCTATC GTCAGCTTAC CTTTTTGGCA |
| 5461 |

//

```
pCRO29 (SEQ ID NO: 21)
ORIGIN
    1 GCGATCGCGG CTCCCGACAT CTTGGACCAT TAGCTCCACA GGTATCTTCT TCCCTCTAGT
   61 GGTCATAACA GCAGCTTCAG CTACCTCTCA ATTCAAAAAA CCCCTCAAGA CCCGTTTAGA
  121 GGCCCCAAGG GGTTATGCTA TCAATCGTTG CGTTACACAC ACAAAAAACC AACACACATC
  181 CATCTTCGAT GGATAGCGAT TTTATTATCT AACTGCTGAT CGAGTGTAGC CAGATCTAGT
  241 AATCAATTAC GGGGTCATTA GTTCATAGCC CATATATGGA GTTCCGCGTT ACATAACTTA
  301 CGGTAAATGG CCCGCCTGGC TGACCGCCCA ACGACCCCG CCCATTGACG TCAATAATGA
  361 CGTATGTTCC CATAGTAACG CCAATAGGGA CTTTCCATTG ACGTCAATGG GTGGAGTATT
  421 TACGGTAAAC TGCCCACTTG GCAGTACATC AAGTGTATCA TATGCCAAGT ACGCCCCCTA
  481 TTGACGTCAA TGACGGTAAA TGGCCCGCCT GGCATTATGC CCAGTACATG ACCTTATGGG
  541 ACTTTCCTAC TTGGCAGTAC ATCTACGTAT TAGTCATCGC TATTACCATG CTGATGCGGT
  601 TTTGGCAGTA CATCAATGGG CGTGGATAGC GGTTTGACTC ACGGGGATTT CCAAGTCTCC
  661 ACCCCATTGA CGTCAATGGG AGTTTGTTTT GGCACCAAAA TCAACGGGAC TTTCCAAAAT
  721 GTCGTAACAA CTCCGCCCCA TTGACGCAAA TGGGCGGTAG GCGTGTACGG TGGGAGGTCT
```

-continued

| | Sequence Listing Free Text |
|---|---|
| 781 | ATATAAGCAG AGCTGGTTTA GTGAACCGTC AGATCAGATC TTTGTCGATC CTACCATCCA |
| 841 | CTCGACACAC CCGCCAGCgg ccgccaccat gaaggccaat ctactggtgt tgctgtgtgc |
| 901 | ccttgcggcg gcagatgccA TCAGGTGCAT TGGAGTCAGC AACAGGGACT TCGTCGAAGG |
| 961 | CATGTCCGGC GGCACCTGGG TGGATGTGGT GCTCGAACAC GGCGGATGCG TGACCGTCAT |
| 1021 | GGCCCAGGAC AAGCCTACCG TCGATATTGA GCTGGTGACC ACCACAGTGA GCAACATGGC |
| 1081 | CGAAGTGAGA AGCTACTGCT ATGAGGCCTC CATCAGCGAT ATGGCTTCCG ATTCCAGATG |
| 1141 | CCCCACACAG GGAGAGGCTT ATCTGGACAA ACAGTCCGAC ACCCAGTACG TCTGCAAAAG |
| 1201 | AACCCTGGTG GACAGAGGCT GGGGAAACGG ATGCGGCaac cacaccAAAG GCAGCCTCGT |
| 1261 | GACATGTGCC AAGTTCGCCT GCAGCAAAAA GATGACCGGC AAGTCCATCC AGCCCGAGAA |
| 1321 | CCTGGAATAC AGGATCATGC TGTCCGTGCA TGGATCCCAG CACTCCGGCA TGATCGTCAA |
| 1381 | CGATACCGGC CACGAGACCG ACGAGAACAG GGCTAAAGTG GAGATCACCC CCAACAGCCC |
| 1441 | TAGAGCCGAA GCTACACTGG GCGGCTTCGG AAGCCTGGGC CTGGATTGCG AACCCAGGAC |
| 1501 | CGGCCTGGAT TTCAGCGACC TGTATTACCT GACCATGAAC AATAAGCACT GGCTGGTGCA |
| 1561 | CAAGGAATGG TTCCACGACA TCCCCCTGCC TTGGCATGCT GGCGCCGATA CCGGCACACC |
| 1621 | TCACTGGAAC AATAAGGAAG CCCTGGTCGA GTTTAAGGAC GCCCACGCCA AAGACAGAC |
| 1681 | CGTGGTGGTG CTGGAAGCCA AGGAGGGAGC TGTCCACACA GCCCTGGCCG GAGCTCTGGA |
| 1741 | AGCCGAGATG GATGGCGCCA AGGGCAGGCT GAGCTCCGGC CACCTGAAAT GCAGGCTCAA |
| 1801 | GATGGACAAG CTGAGGCTGA AGGGCGTGAG CTACAGCCTG TGCACCGCCG CTTTCACCTT |
| 1861 | TACCAAGATC CCTGCCGAGA CACTGCACGG CACCGTCACC GTGGAGGTGC AATACGCCGG |
| 1921 | AACCGATGGA CCTTGCAAAG TGCCTGCCCA GATGGCTGTG GATATGCAGA CCCTCACACC |
| 1981 | CGTCGGCAGG CTGATCACCG CCAATCCCGT CATTACCGAG TCCACCGAGA ACAGCAAGAT |
| 2041 | GATGCTcGAG CTCGATCCCC CCTTTGGCGA CAGCTACATT GTGATCGGCG TGGGCGAGAA |
| 2101 | GAAGATCACC CACCATTGGC ACAGAAGCGG CTCCACAggg ggtagcggtg gtagcggagg |
| 2161 | tagccatcac caccatcacc actgagctag CTTGACTGAC TGAGATACAG CGTACCTTCA |
| 2221 | GCTCACAGAC ATGATAAGAT ACATTGATGA GTTTGGACAA ACCACAACTA GAATGCAGTG |
| 2281 | AAAAAAATGC TTTATTTGTG AAATTTGTGA TGCTATTGCT TTATTTGTAA CCATTATAAG |
| 2341 | CTGCAATAAA CAAGTTAACA ACAACAATTG CATTCATTTT ATGTTTCAGG TTCAGGGGGA |
| 2401 | GGTGTGGGAG GTTTTTTAAA GCAAGTAAAA CCTCTACAAA TGTGGTATTG GCCCATCTCT |
| 2461 | ATCGGTATCG TAGCATAACC CCTTGGGGCC TCTAAACGGG TCTTGAGGGG TTTTTTGTGC |
| 2521 | CCCTCGGGCC GGATTGCTAT CTACCGGCAT GGCGCAGAA AAAATGCCT GATGCGACGC |
| 2581 | TGCGCGTCTT ATACTCCCAC ATATGCCAGA TTCAGCAACG GATACGGCTT CCCCAACTTG |
| 2641 | CCCACTTCCA TACGTGTCCT CCTTACCAGA AATTTATCCT TAAGGTCGTC AGCTATCCTG |
| 2701 | CAGGCGATCT CTCGATTTCG ATCAAGACAT TCCTTTAATG GTCTTTTCTG GACACCACTA |
| 2761 | GGGGTCAGAA GTAGTTCATC AAACTTTCTT CCCTCCCTAA TCTCATTGGT TACCTTGGGC |
| 2821 | TATCGAAACT TAATTAACCA GTCAAGTCAG CTACTTGGCG AGATCGACTT GTCTGGGTTT |
| 2881 | CGACTACGCT CAGAATTGCG TCAGTCAAGT TCGATCTGGT CCTTGCTATT GCACCCGTTC |
| 2941 | TCCGATTACG AGTTTCATTT AAATCATGTG AGCAAAAGGC CAGCAAAGG CCAGGAACCG |
| 3001 | TAAAAAGGCC GCGTTGCTGG CGTTTTTCCA TAGGCTCCGC CCCCCTGACG AGCATCACAA |
| 3061 | AAATCGACGC TCAAGTCAGA GGTGGCGAAA CCCGACAGGA CTATAAAGAT ACCAGGCGTT |

-continued

Sequence Listing Free Text

| | |
|---|---|
| 3121 | TCCCCCTGGA AGCTCCCTCG TGCGCTCTCC TGTTCCGACC CTGCCGCTTA CCGGATACCT |
| 3181 | GTCCGCCTTT CTCCCTTCGG GAAGCGTGGC GCTTTCTCAT AGCTCACGCT GTAGGTATCT |
| 3241 | CAGTTCGGTG TAGGTCGTTC GCTCCAAGCT GGGCTGTGTG CACGAACCCC CCGTTCAGCC |
| 3301 | CGACCGCTGC GCCTTATCCG GTAACTATCG TCTTGAGTCC AACCCGGTAA GACACGACTT |
| 3361 | ATCGCCACTG GCAGCAGCCA CTGGTAACAG GATTAGCAGA GCGAGGTATG TAGGCGGTGC |
| 3421 | TACAGAGTTC TTGAAGTGGT GGCCTAACTA CGGCTACACT AGAAGAACAG TATTTGGTAT |
| 3481 | CTGCGCTCTG CTGAAGCCAG TTACCTTCGG AAAAAGAGTT GGTAGCTCTT GATCCGGCAA |
| 3541 | ACAAACCACC GCTGGTAGCG GTGGTTTTTT TGTTTGCAAG CAGCAGATTA CGCGCAGAAA |
| 3601 | AAAAGGATCT CAAGAAGATC CTTTGATCTT TTCTACGGGG TCTGACGCTC AGTGGAACGA |
| 3661 | AAACTCACGT TAAGGGATTT TGGTCATGAG ATTATCAAAA AGGATCTTCA CCTAGATCCT |
| 3721 | TTTAAATTAA AAATGAAGTT TTAAATCAAT CTAAAGTATA TATGAGTAAA CTTGGTCTGA |
| 3781 | CAGTTACCAA TGCTTAATCA GTGAGGCACC TATCTCAGCG ATCTGTCTAT TTCGTTCATC |
| 3841 | CATAGTTGCA TTTAAATTTC CGAACTCTCC AAGGCCCTCG TCGGAAAATC TTCAAACCTT |
| 3901 | TCGTCCGATC CATCTTGCAG GCTACCTCTC GAACGAACTA TCGCAAGTCT CTTGGCCGGC |
| 3961 | CTTGCGCCTT GGCTATTGCT TGGCAGCGCC TATCGCCAGG TATTACTCCA ATCCCGAATA |
| 4021 | TCCGAGATCG GGATCACCCG AGAGAAGTTC AACCTACATC CTCAATCCCG ATCTATCCGA |
| 4081 | GATCCGAGGA ATATCGAAAT CGGGGCGCGC CTGGTGTACC GAGAACGATC CTCTCAGTGC |
| 4141 | GAGTCTCGAC GATCCATATC GTTGCTTGGC AGTCAGCCAG TCGGAATCCA GCTTGGGACC |
| 4201 | CAGGAAGTCC AATCGTCAGA TATTGTACTC AAGCCTGGTC ACGGCAGCGT ACCGATCTGT |
| 4261 | TTAAACCTAG ATATTGATAG TCTGATCGGT CAACGTATAA TCGAGTCCTA GCTTTTGCAA |
| 4321 | ACATCTATCA AGAGACAGGA TCAGCAGGAG GCTTTCGCAT GAGTATTCAA CATTTCCGTG |
| 4381 | TCGCCCTTAT TCCCTTTTTT GCGGCATTTT GCCTTCCTGT TTTTGCTCAC CCAGAAACGC |
| 4441 | TGGTGAAAGT AAAAGATGCT GAAGATCAGT TGGGTGCGCG AGTGGGTTAC ATCGAACTGG |
| 4501 | ATCTCAACAG CGGTAAGATC CTTGAGAGTT TTCGCCCCGA AGAACGCTTT CCAATGATGA |
| 4561 | GCACTTTTAA AGTTCTGCTA TGTGGCGCGG TATTATCCCG TATTGACGCC GGGCAAGAGC |
| 4621 | AACTCGGTCG CCGCATACAC TATTCTCAGA ATGACTTGGT TGAGTATTCA CCAGTCACAG |
| 4681 | AAAAGCATCT TACGGATGGC ATGACAGTAA GAGAATTATG CAGTGCTGCC ATAACCATGA |
| 4741 | GTGATAACAC TGCGGCCAAC TTACTTCTGA CAACGATTGG AGGACCGAAG GAGCTAACCG |
| 4801 | CTTTTTTGCA CAACATGGGG GATCATGTAA CTCGCCTTGA TCGTTGGGAA CCGGAGCTGA |
| 4861 | ATGAAGCCAT ACCAAACGAC GAGCGTGACA CCACGATGCC TGTAGCAATG GCAACAACCT |
| 4921 | TGCGTAAACT ATTAACTGGC GAACTACTTA CTCTAGCTTC CCGGCAACAG TTGATAGACT |
| 4981 | GGATGGAGGC GGATAAAGTT GCAGGACCAC TTCTGCGCTC GGCCCTTCCG GCTGGCTGGT |
| 5041 | TTATTGCTGA TAAATCTGGA GCCGGTGAGC GTGGGTCTCG CGGTATCATT GCAGCACTGG |
| 5101 | GGCCAGATGG TAAGCCCTCC CGTATCGTAG TTATCTACAC GACGGGAGT CAGGCAACTA |
| 5161 | TGGATGAACG AAATAGACAG ATCGCTGAGA TAGGTGCCTC ACTGATTAAG CATTGGTAAC |
| 5221 | CGATTCTAGG TGCATTGGCG CAGAAAAAAA TGCCTGATGC GACGCTGCGC GTCTTATACT |
| 5281 | CCCACATATG CCAGATTCAG CAACGGATAC GGCTTCCCCA ACTTGCCCAC TTCCATACGT |
| 5341 | GTCCTCCTTA CCAGAAATTT ATCCTTAAGA TCCCGAATCG TTTAAACTCG ACTCTGGCTC |

| | Sequence Listing Free Text |
|---|---|
| 5401 | TATCGAATCT CCGTCGTTTC GAGCTTACGC GAACAGCCGT GGCGCTCATT TGCTCGTCGG |
| 5461 | GCATCGAATC TCGTCAGCTA TCGTCAGCTT ACCTTTTTGG CA |

// pCRO30 (SEQ ID NO: 22)
ORIGIN

| 1 | GCGATCGCGG CTCCCGACAT CTTGGACCAT TAGCTCCACA GGTATCTTCT TCCCTCTAGT |
|---|---|
| 61 | GGTCATAACA GCAGCTTCAG CTACCTCTCA ATTCAAAAAA CCCCTCAAGA CCCGTTTAGA |
| 121 | GGCCCCAAGG GGTTATGCTA TCAATCGTTG CGTTACACAC ACAAAAAACC AACACACATC |
| 181 | CATCTTCGAT GGATAGCGAT TTTATTATCT AACTGCTGAT CGAGTGTAGC CAGATCTAGT |
| 241 | AATCAATTAC GGGGTCATTA GTTCATAGCC CATATATGGA GTTCCGCGTT ACATAACTTA |
| 301 | CGGTAAATGG CCCGCCTGGC TGACCGCCCA ACGACCCCCG CCCATTGACG TCAATAATGA |
| 361 | CGTATGTTCC CATAGTAACG CCAATAGGGA CTTTCCATTG ACGTCAATGG GTGGAGTATT |
| 421 | TACGGTAAAC TGCCCACTTG GCAGTACATC AAGTGTATCA TATGCCAAGT ACGCCCCCTA |
| 481 | TTGACGTCAA TGACGGTAAA TGGCCCGCCT GGCATTATGC CCAGTACATG ACCTTATGGG |
| 541 | ACTTTCCTAC TTGGCAGTAC ATCTACGTAT TAGTCATCGC TATTACCATG CTGATGCGGT |
| 601 | TTTGGCAGTA CATCAATGGG CGTGGATAGC GGTTTGACTC ACGGGGATTT CCAAGTCTCC |
| 661 | ACCCCATTGA CGTCAATGGG AGTTTGTTTT GGCACCAAAA TCAACGGGAC TTTCCAAAAT |
| 721 | GTCGTAACAA CTCCGCCCCA TTGACGCAAA TGGGCGGTAG CGTGTACGG TGGGAGGTCT |
| 781 | ATATAAGCAG AGCTGGTTTA GTGAACCGTC AGATCAGATC TTTGTCGATC CTACCATCCA |
| 841 | CTCGACACAC CCGCCAGCgg ccgccaccat gaaggccaat ctactggtgt tgctgtgtgc |
| 901 | ccttgcggcg gcagatgccA TCAGGTGCAT TGGAGTCAGC AACAGGGACT TCGTCGAAGG |
| 961 | CATGTCCGGC GGCACCTGGG TGGATGTGGT GCTCGAACAC GGCGGATGCG TGACCGTCAT |
| 1021 | GGCCCAGGAC AAGCCTACCG TCGATATTGA GCTGGTGACC ACCACAGTGA GCAACATGGC |
| 1081 | CGAAGTGAGA AGCTACTGCT ATGAGGCCTC CATCAGCGAT ATGGCTTCCG ATTCCAGATG |
| 1141 | CCCCACACAG GGAGAGGCTT ATCTGGACAA ACAGTCCGAC ACCCAGTACG TCTGCAAAAG |
| 1201 | AACCCTGGTG GACAGAGGCa acggatccGG ATGCGGCCTG TTCGGCAAAG GCAGCCTCGT |
| 1261 | GACATGTGCC AAGTTCGCCT GCAGCAAAAA GATGACCGGC AAGTCCATCC AGCCCGAGAA |
| 1321 | CCTGGAATAC AGGATCATGC TGTCCGTGCA TGGATCCCAG CACTCCGGCA TGATCGTCAA |
| 1381 | CGATACCGGC CACGAGACCG ACGAGAACAG GGCTAAAGTG GAGATCACCC CAACAGCCC |
| 1441 | TAGAGCCGAA GCTACACTGG GCGGCTTCGG AAGCCTGGGC CTGGATTGCG AACCCAGGAC |
| 1501 | CGGCCTGGAT TTCAGCGACC TGTATTACCT GACCATGAAC AATAAGCACT GGCTGGTGCA |
| 1561 | CAAGGAATGG TTCCACGACA TCCCCCTGCC TTGGCATGCT GGCGCCGATA CCGGCACACC |
| 1621 | TCACTGGAAC AATAAGGAAG CCCTGGTCGA GTTTAAGGAC GCCCACGCCA AAGACAGAC |
| 1681 | CGTGGTGGTG CTGGGAAGCC AGGAGGGAGC TGTCCACACA GCCCTGGCCG GAGCTCTGGA |
| 1741 | AGCCGAGATG GATGGCGCCA AGGGCAGGCT GAGCTCCGGC CACCTGAAAT GCAGGCTCAA |
| 1801 | GATGGACAAG CTGAGGCTGA AGGGCGTGAG CTACAGCCTG TGCACCGCCG CTTTCACCTT |
| 1861 | TACCAAGATC CCTGCCGAGA CACTGCACGG CACCGTCACC GTGGAGGTGC AATACGCCGG |
| 1921 | AACCGATGGA CCTTGCAAAG TGCCTGCCCA GATGGCTGTG GATATGCAGA CCCTCACACC |
| 1981 | CGTCGGCAGG CTGATCACCG CCAATCCCGT CATTACCGAG TCCACCGAGA ACAGCAAGAT |
| 2041 | GATGCTcGAG CTCGATCCCC CCTTTGGCGA CAGCTACATT GTGATCGGCG TGGGCGAGAA |

| Sequence Listing Free Text |
|---|
| 2101 GAAGATCACC CACCATTGGC ACAGAAGCGG CTCCACAggg ggtagcggtg gtagcggagg |
| 2161 tagccatcac caccatcacc actgagctag CTTGACTGAC TGAGATACAG CGTACCTTCA |
| 2221 GCTCACAGAC ATGATAAGAT ACATTGATGA GTTTGGACAA ACCACAACTA GAATGCAGTG |
| 2281 AAAAAAATGC TTTATTTGTG AAATTTGTGA TGCTATTGCT TTATTTGTAA CCATTATAAG |
| 2341 CTGCAATAAA CAAGTTAACA ACAACAATTG CATTCATTTT ATGTTTCAGG TTCAGGGGGA |
| 2401 GGTGTGGGAG GTTTTTTAAA GCAAGTAAAA CCTCTACAAA TGTGGTATTG GCCCATCTCT |
| 2461 ATCGGTATCG TAGCATAACC CCTTGGGGCC TCTAAACGGG TCTTGAGGGG TTTTTTGTGC |
| 2521 CCCTCGGGCC GGATTGCTAT CTACCGGCAT TGGCGCAGAA AAAATGCCT GATGCGACGC |
| 2581 TGCGCGTCTT ATACTCCCAC ATATGCCAGA TTCAGCAACG GATACGGCTT CCCCAACTTG |
| 2641 CCCACTTCCA TACGTGTCCT CCTTACCAGA AATTTATCCT TAAGGTCGTC AGCTATCCTG |
| 2701 CAGGCGATCT CTCGATTTCG ATCAAGACAT TCCTTTAATG GTCTTTTCTG ACACCACTA |
| 2761 GGGGTCAGAA GTAGTTCATC AAACTTTCTT CCCTCCCTAA TCTCATTGGT TACCTTGGGC |
| 2821 TATCGAAACT TAATTAACCA GTCAAGTCAG CTACTTGGCG AGATCGACTT GTCTGGGTTT |
| 2881 CGACTACGCT CAGAATTGCG TCAGTCAAGT TCGATCTGGT CCTTGCTATT GCACCCGTTC |
| 2941 TCCGATTACG AGTTTCATTT AAATCATGTG AGCAAAAGGC CAGCAAAAGG CCAGGAACCG |
| 3001 TAAAAAGGCC GCGTTGCTGG CGTTTTTCCA TAGGCTCCGC CCCCCTGACG AGCATCACAA |
| 3061 AAATCGACGC TCAAGTCAGA GGTGGCGAAA CCCGACAGGA CTATAAAGAT ACCAGGCGTT |
| 3121 TCCCCCTGGA AGCTCCCTCG TGCGCTCTCC TGTTCCGACC CTGCCGCTTA CCGGATACCT |
| 3181 GTCCGCCTTT CTCCCTTCGG GAAGCGTGGC GCTTTCTCAT AGCTCACGCT GTAGGTATCT |
| 3241 CAGTTCGGTG TAGGTCGTTC GCTCCAAGCT GGGCTGTGTG CACGAACCCC CCGTTCAGCC |
| 3301 CGACCGCTGC GCCTTATCCG GTAACTATCG TCTTGAGTCC AACCCGGTAA GACACGACTT |
| 3361 ATCGCCACTG GCAGCAGCCA CTGGTAACAG GATTAGCAGA GCGAGGTATG TAGGCGGTGC |
| 3421 TACAGAGTTC TTGAAGTGGT GGCCTAACTA CGGCTACACT AGAAGAACAG TATTTGGTAT |
| 3481 CTGCGCTCTG CTGAAGCCAG TTACCTTCGG AAAAAGAGTT GGTAGCTCTT GATCCGGCAA |
| 3541 ACAAACCACC GCTGGTAGCG GTGGTTTTTT TGTTTGCAAG CAGCAGATTA CGCGCAGAAA |
| 3601 AAAAGGATCT CAAGAAGATC CTTTGATCTT TTCTACGGGG TCTGACGCTC AGTGGAACGA |
| 3661 AAACTCACGT TAAGGGATTT TGGTCATGAG ATTATCAAAA AGGATCTTCA CCTAGATCCT |
| 3721 TTTAAATTAA AAATGAAGTT TTAAATCAAT CTAAAGTATA TATGAGTAAA CTTGGTCTGA |
| 3781 CAGTTACCAA TGCTTAATCA GTGAGGCACC TATCTCAGCG ATCTGTCTAT TTCGTTCATC |
| 3841 CATAGTTGCA TTTAAATTTC CGAACTCTCC AAGGCCCTCG TCGGAAAATC TTCAAACCTT |
| 3901 TCGTCCGATC CATCTTGCAG GCTACCTCTC GAACGAACTA TCGCAAGTCT CTTGGCCGGC |
| 3961 CTTGCGCCTT GGCTATTGCT TGGCAGCGCC TATCGCCAGG TATTACTCCA ATCCCGAATA |
| 4021 TCCGAGATCG GGATCACCCG AGAGAAGTTC AACCTACATC CTCAATCCCG ATCTATCCGA |
| 4081 GATCCGAGGA ATATCGAAAT CGGGGCGCGC CTGGTGTACC GAGAACGATC CTCTCAGTGC |
| 4141 GAGTCTCGAC GATCCATATC GTTGCTTGGC AGTCAGCCAG TCGGAATCCA GCTTGGGACC |
| 4201 CAGGAAGTCC AATCGTCAGA TATTGTACTC AAGCCTGGTC ACGGCAGCGT ACCGATCTGT |
| 4261 TTAAACCTAG ATATTGATAG TCTGATCGGT CAACGTATAA TCGAGTCCTA GCTTTTGCAA |
| 4321 ACATCTATCA AGAGACAGGA TCAGCAGGAG GCTTTCGCAT GAGTATTCAA CATTTCCGTG |

-continued

| | Sequence Listing Free Text |
|---|---|
| 4381 | TCGCCCTTAT TCCCTTTTTT GCGGCATTTT GCCTTCCTGT TTTTGCTCAC CCAGAAACGC |
| 4441 | TGGTGAAAGT AAAAGATGCT GAAGATCAGT TGGGTGCGCG AGTGGGTTAC ATCGAACTGG |
| 4501 | ATCTCAACAG CGGTAAGATC CTTGAGAGTT TTCGCCCCGA AGAACGCTTT CCAATGATGA |
| 4561 | GCACTTTTAA AGTTCTGCTA TGTGGCGCGG TATTATCCCG TATTGACGCC GGGCAAGAGC |
| 4621 | AACTCGGTCG CCGCATACAC TATTCTCAGA ATGACTTGGT TGAGTATTCA CCAGTCACAG |
| 4681 | AAAAGCATCT TACGGATGGC ATGACAGTAA GAGAATTATG CAGTGCTGCC ATAACCATGA |
| 4741 | GTGATAACAC TGCGGCCAAC TTACTTCTGA CAACGATTGG AGGACCGAAG GAGCTAACCG |
| 4801 | CTTTTTTGCA CAACATGGGG GATCATGTAA CTCGCCTTGA TCGTTGGGAA CCGGAGCTGA |
| 4861 | ATGAAGCCAT ACCAAACGAC GAGCGTGACA CCACGATGCC TGTAGCAATG GCAACAACCT |
| 4921 | TGCGTAAACT ATTAACTGGC GAACTACTTA CTCTAGCTTC CCGGCAACAG TTGATAGACT |
| 4981 | GGATGGAGGC GGATAAAGTT GCAGGACCAC TTCTGCGCTC GGCCCTTCCG GCTGGCTGGT |
| 5041 | TTATTGCTGA TAAATCTGGA GCCGGTGAGC GTGGGTCTCG CGGTATCATT GCAGCACTGG |
| 5101 | GGCCAGATGG TAAGCCCTCC CGTATCGTAG TTATCTACAC GACGGGGAGT CAGGCAACTA |
| 5161 | TGGATGAACG AAATAGACAG ATCGCTGAGA TAGGTGCCTC ACTGATTAAG CATTGGTAAC |
| 5221 | CGATTCTAGG TGCATTGGCG CAGAAAAAAA TGCCTGATGC GACGCTGCGC GTCTTATACT |
| 5281 | CCCACATATG CCAGATTCAG CAACGGATAC GGCTTCCCCA ACTTGCCCAC TTCCATACGT |
| 5341 | GTCCTCCTTA CCAGAAATTT ATCCTTAAGA TCCCGAATCG TTTAAACTCG ACTCTGGCTC |
| 5401 | TATCGAATCT CCGTCGTTTC GAGCTTACGC GAACAGCCGT GGCGCTCATT TGCTCGTCGG |
| 5461 | GCATCGAATC TCGTCAGCTA TCGTCAGCTT ACCTTTTTGG CA |

// pCR031 (SEQ ID NO: 23)
RIGIN

| 1 | GCGATCGCGG CTCCCGACAT CTTGGACCAT TAGCTCCACA GGTATCTTCT TCCCTCTAGT |
|---|---|
| 61 | GGTCATAACA GCAGCTTCAG CTACCTCTCA ATTCAAAAAA CCCCTCAAGA CCCGTTTAGA |
| 121 | GGCCCCAAGG GGTTATGCTA TCAATCGTTG CGTTACACAC ACAAAAAACC AACACACATC |
| 181 | CATCTTCGAT GGATAGCGAT TTTATTATCT AACTGCTGAT CGAGTGTAGC CAGATCTAGT |
| 241 | AATCAATTAC GGGGTCATTA GTTCATAGCC CATATATGGA GTTCCGCGTT ACATAACTTA |
| 301 | CGGTAAATGG CCCGCCTGGC TGACCGCCCA ACGACCCCCG CCCATTGACG TCAATAATGA |
| 361 | CGTATGTTCC CATAGTAACG CCAATAGGGA CTTTCCATTG ACGTCAATGG GTGGAGTATT |
| 421 | TACGGTAAAC TGCCCACTTG GCAGTACATC AAGTGTATCA TATGCCAAGT ACGCCCCCTA |
| 481 | TTGACGTCAA TGACGGTAAA TGGCCCGCCT GGCATTATGC CCAGTACATG ACCTTATGGG |
| 541 | ACTTTCCTAC TTGGCAGTAC ATCTACGTAT TAGTCATCGC TATTACCATG CTGATGCGGT |
| 601 | TTTGGCAGTA CATCAATGGG CGTGGATAGC GGTTTGACTC ACGGGGATTT CCAAGTCTCC |
| 661 | ACCCCATTGA CGTCAATGGG AGTTTGTTTT GGCACCAAAA TCAACGGGAC TTTCCAAAAT |
| 721 | GTCGTAACAA CTCCGCCCCA TTGACGCAAA TGGGCGGTAG CGTGTACGG TGGGAGGTCT |
| 781 | ATATAAGCAG AGCTGGTTTA GTGAACCGTC AGATCAGATC TTTGTCGATC CTACCATCCA |
| 841 | CTCGACACAC CCGCCAGCgg ccgccaccat gaaggccaat ctactggtgt tgctgtgtgc |
| 901 | ccttgcggcg gcagatgccA TCAGGTGCAT TGGAGTCAGC AACAGGGACT TCGTCGAAGG |
| 961 | CATGTCCGGC GGCACCTGGG TGGATGTGGT GCTCGAACAC GGCGGATGCG TGACCGTCAT |
| 1021 | GGCCCAGGAC AAGCCTACCG TCGATATTGA GCTGGTGACC ACCACAGTGA GCAACATGGC |

Sequence Listing Free Text

```
1081  CGAAGTGAGA AGCTACTGCT ATGAGGCCTC CATCAGCGAT ATGGCTTCCG ATTCCAGATG

1141  CCCCACACAG GGAGAGGCTT ATCTGGACAA ACAGTCCGAC ACCCAGTACG TCTGCAAAAG

1201  AACCCTGGTG GACAGAGGCT GGGGAAACGG ATGCGGCCTG aacggatccG GCAGCCTCGT

1261  GACATGTGCC AAGTTCGCCT GCAGCAAAAA GATGACCGGC AAGTCCATCC AGCCCGAGAA

1321  CCTGGAATAC AGGATCATGC TGTCCGTGCA TGGATCCCAG CACTCCGGCA TGATCGTCAA

1381  CGATACCGGC CACGAGACCG ACGAGAACAG GGCTAAAGTG GAGATCACCC CCAACAGCCC

1441  TAGAGCCGAA GCTACACTGG GCGGCTTCGG AAGCCTGGGC CTGGATTGCG AACCCAGGAC

1501  CGGCCTGGAT TTCAGCGACC TGTATTACCT GACCATGAAC AATAAGCACT GGCTGGTGCA

1561  CAAGGAATGG TTCCACGACA TCCCCCTGCC TTGGCATGCT GGCGCCGATA CCGGCACACC

1621  TCACTGGAAC AATAAGGAAG CCCTGGTCGA GTTTAAGGAC GCCCACGCCA AAGACAGAC

1681  CGTGGTGGTG CTGGGAAGCC AGGAGGGAGC TGTCCACACA GCCCTGGCCG GAGCTCTGGA

1741  AGCCGAGATG GATGGCGCCA AGGGCAGGCT GAGCTCCGGC CACCTGAAAT GCAGGCTCAA

1801  GATGGACAAG CTGAGGCTGA AGGGCGTGAG CTACAGCCTG TGCACCGCCG CTTTCACCTT

1861  TACCAAGATC CCTGCCGAGA CACTGCACGG CACCGTCACC GTGGAGGTGC AATACGCCGG

1921  AACCGATGGA CCTTGCAAAG TGCCTGCCCA GATGGCTGTG GATATGCAGA CCCTCACACC

1981  CGTCGGCAGG CTGATCACCG CCAATCCCGT CATTACCGAG TCCACCGAGA ACAGCAAGAT

2041  GATGCTcGAG CTCGATCCCC CCTTTGGCGA CAGCTACATT GTGATCGGCG TGGGCGAGAA

2101  GAAGATCACC CACCATTGGC ACAGAAGCGG CTCCACAggg ggtagcggtg gtagcggagg 2161  tagccatcac caccatcacc actgagctag CTTGACTGAC TGAGATACAG CGTACCTTCA

2221  GCTCACAGAC ATGATAAGAT ACATTGATGA GTTTGGACAA ACCACAACTA GAATGCAGTG

2281  AAAAAAATGC TTTATTTGTG AAATTTGTGA TGCTATTGCT TTATTTGTAA CCATTATAAG

2341  CTGCAATAAA CAAGTTAACA ACAACAATTG CATTCATTTT ATGTTTCAGG TTCAGGGGGA

2401  GGTGTGGGAG GTTTTTTAAA GCAAGTAAAA CCTCTACAAA TGTGGTATTG GCCCATCTCT

2461  ATCGGTATCG TAGCATAACC CCTTGGGGCC TCTAAACGGG TCTTGAGGGG TTTTTTGTGC

2521  CCCTCGGGCC GGATTGCTAT CTACCGGCAT GGCGCAGAA AAAATGCCT GATGCGACGC

2581  TGCGCGTCTT ATACTCCCAC ATATGCCAGA TTCAGCAACG GATACGGCTT CCCCAACTTG

2641  CCCACTTCCA TACGTGTCCT CCTTACCAGA AATTTATCCT TAAGGTCGTC AGCTATCCTG

2701  CAGGCGATCT CTCGATTTCG ATCAAGACAT TCCTTTAATG GTCTTTTCTG GACACCACTA

2761  GGGGTCAGAA GTAGTTCATC AAACTTTCTT CCCTCCCTAA TCTCATTGGT TACCTTGGGC

2821  TATCGAAACT TAATTAACCA GTCAAGTCAG CTACTTGGCG AGATCGACTT GTCTGGGTTT

2881  CGACTACGCT CAGAATTGCG TCAGTCAAGT TCGATCTGGT CCTTGCTATT GCACCCGTTC

2941  TCCGATTACG AGTTTCATTT AAATCATGTG AGCAAAAGGC CAGCAAAGG CCAGGAACCG

3001  TAAAAAGGCC GCGTTGCTGG CGTTTTTCCA TAGGCTCCGC CCCCCTGACG AGCATCACAA

3061  AAATCGACGC TCAAGTCAGA GGTGGCGAAA CCCGACAGGA CTATAAAGAT ACCAGGCGTT

3121  TCCCCCTGGA AGCTCCCTCG TGCGCTCTCC TGTTCCGACC CTGCCGCTTA CCGGATACCT

3181  GTCCGCCTTT CTCCCTTCGG GAAGCGTGGC GCTTTCTCAT AGCTCACGCT GTAGGTATCT

3241  CAGTTCGGTG TAGGTCGTTC GCTCCAAGCT GGGCTGTGTG CACGAACCCC CCGTTCAGCC

3301  CGACCGCTGC GCCTTATCCG GTAACTATCG TCTTGAGTCC AACCCGGTAA GACACGACTT
```

-continued

| | Sequence Listing Free Text |
|---|---|
| 3361 | ATCGCCACTG GCAGCAGCCA CTGGTAACAG GATTAGCAGA GCGAGGTATG TAGGCGGTGC |
| 3421 | TACAGAGTTC TTGAAGTGGT GGCCTAACTA CGGCTACACT AGAAGAACAG TATTTGGTAT |
| 3481 | CTGCGCTCTG CTGAAGCCAG TTACCTTCGG AAAAAGAGTT GGTAGCTCTT GATCCGGCAA |
| 3541 | ACAAACCACC GCTGGTAGCG GTGGTTTTTT TGTTTGCAAG CAGCAGATTA CGCGCAGAAA |
| 3601 | AAAAGGATCT CAAGAAGATC CTTTGATCTT TTCTACGGGG TCTGACGCTC AGTGGAACGA |
| 3661 | AAACTCACGT TAAGGGATTT TGGTCATGAG ATTATCAAAA AGGATCTTCA CCTAGATCCT |
| 3721 | TTTAAATTAA AAATGAAGTT TTAAATCAAT CTAAAGTATA TATGAGTAAA CTTGGTCTGA |
| 3781 | CAGTTACCAA TGCTTAATCA GTGAGGCACC TATCTCAGCG ATCTGTCTAT TTCGTTCATC |
| 3841 | CATAGTTGCA TTTAAATTTC CGAACTCTCC AAGGCCCTCG TCGGAAAATC TTCAAACCTT |
| 3901 | TCGTCCGATC CATCTTGCAG GCTACCTCTC GAACGAACTA TCGCAAGTCT CTTGGCCGGC |
| 3961 | CTTGCGCCTT GGCTATTGCT TGGCAGCGCC TATCGCCAGG TATTACTCCA ATCCCGAATA |
| 4021 | TCCGAGATCG GGATCACCCG AGAGAAGTTC AACCTACATC CTCAATCCCG ATCTATCCGA |
| 4081 | GATCCGAGGA ATATCGAAAT CGGGGCGCGC CTGGTGTACC GAGAACGATC CTCTCAGTGC |
| 4141 | GAGTCTCGAC GATCCATATC GTTGCTTGGC AGTCAGCCAG TCGGAATCCA GCTTGGGACC |
| 4201 | CAGGAAGTCC AATCGTCAGA TATTGTACTC AAGCCTGGTC ACGGCAGCGT ACCGATCTGT |
| 4261 | TTAAACCTAG ATATTGATAG TCTGATCGGT CAACGTATAA TCGAGTCCTA GCTTTTGCAA |
| 4321 | ACATCTATCA AGAGACAGGA TCAGCAGGAG GCTTTCGCAT GAGTATTCAA CATTTCCGTG |
| 4381 | TCGCCCTTAT TCCCTTTTTT GCGGCATTTT GCCTTCCTGT TTTTGCTCAC CCAGAAACGC |
| 4441 | TGGTGAAAGT AAAAGATGCT GAAGATCAGT TGGGTGCGCG AGTGGGTTAC ATCGAACTGG |
| 4501 | ATCTCAACAG CGGTAAGATC CTTGAGAGTT TTCGCCCCGA AGAACGCTTT CCAATGATGA |
| 4561 | GCACTTTTAA AGTTCTGCTA TGTGGCGCGG TATTATCCCG TATTGACGCC GGGCAAGAGC |
| 4621 | AACTCGGTCG CCGCATACAC TATTCTCAGA ATGACTTGGT TGAGTATTCA CCAGTCACAG |
| 4681 | AAAAGCATCT TACGGATGGC ATGACAGTAA GAGAATTATG CAGTGCTGCC ATAACCATGA |
| 4741 | GTGATAACAC TGCGGCCAAC TTACTTCTGA CAACGATTGG AGGACCGAAG GAGCTAACCG |
| 4801 | CTTTTTTGCA CAACATGGGG GATCATGTAA CTCGCCTTGA TCGTTGGGAA CCGGAGCTGA |
| 4861 | ATGAAGCCAT ACCAAACGAC GAGCGTGACA CCACGATGCC TGTAGCAATG GCAACAACCT |
| 4921 | TGCGTAAACT ATTAACTGGC GAACTACTTA CTCTAGCTTC CCGGCAACAG TTGATAGACT |
| 4981 | GGATGGAGGC GGATAAAGTT GCAGGACCAC TTCTGCGCTC GGCCCTTCCG GCTGGCTGGT |
| 5041 | TTATTGCTGA TAAATCTGGA GCCGGTGAGC GTGGGTCTCG CGGTATCATT GCAGCACTGG |
| 5101 | GGCCAGATGG TAAGCCCTCC CGTATCGTAG TTATCTACAC GACGGGGAGT CAGGCAACTA |
| 5161 | TGGATGAACG AAATAGACAG ATCGCTGAGA TAGGTGCCTC ACTGATTAAG CATTGGTAAC |
| 5221 | CGATTCTAGG TGCATTGGCG CAGAAAAAAA TGCCTGATGC GACGCTGCGC GTCTTATACT |
| 5281 | CCCACATATG CCAGATTCAG CAACGGATAC GGCTTCCCCA ACTTGCCCAC TTCCATACGT |
| 5341 | GTCCTCCTTA CCAGAAATTT ATCCTTAAGA TCCCGAATCG TTTAAACTCG ACTCTGGCTC |
| 5401 | TATCGAATCT CCGTCGTTTC GAGCTTACGC GAACAGCCGT GGCGCTCATT TGCTCGTCGG |
| 5461 | GCATCGAATC TCGTCAGCTA TCGTCAGCTT ACCTTTTTGG CA |

//

Hyperglycosylated exodomain D1 (from pCRO21) (SEQ ID NO: 24)

Hyperglycosylated exodomain D2 (from pCRO22) (SEQ ID NO: 25)

Sequence Listing Free Text

Hyperglycosylated exodomain D3 (from pCRO23) (SEQ ID NO: 26)

Hyperglycosylated exodomain D4 (from pCRO24) (SEQ ID NO: 27)

Hyperglycosylated exodomain Zika (from pCRO28) (SEQ ID NO: 28)

SEQ ID NO: 24 >DENV1_Eexo = pCRO21
MRCVGIGNRDFVEGLSGATWVDVVLEHGSCVTTMAKDKPTLDIELLKTEVTNPAVLRKLCIEAKISNTTTDSRC
PTQGEATLVEEQDSNFVCRRTFVDRGNGSGCGLNGSGSLLTCAKFKCVTKLEGKIVQYENLKYSVIVTVHTGDQ
HQVGNETTEHGTIATITPQAPTSEIQLTDYGALTLDCSPRTGLDFNEMVLLTMKEKSWLVHKQWFLDLPLPWTS
GASTSQETWNRQDLLVTFKTAHAKKQEVVVLGSQEGAMHTALTGATEIQTSGTTTIFAGHLKCRLKMDKLTLKG
MSYVMCTGSFKLEKEVAETQHGTVLVQVKYEGTDAPCKIPFSAQDEKGVTQNGRLITANPIVTDKEKPVNIETE
PPFGESYIVVGAGEKALKLSWFKKGSTGGGSHHHHHH SEQ ID NO: 25 >DENV2_Eexo = pCRO22
MRCIGISNRDFVEGVSGGSWVDIVLEHGSCVTTMAKNKPTLDFELIKTEAKQPATLRKYCIEAKLTNTTTESRC
PTQGEPSLNEEQDKRFVCKHSMVDRGNGSGCGLNGSGGIVTCAMFTCKKNMEGKVVQPENLEYTIVITPHSGEE
HAVGNDTGKHGKEIKITPQSSITEAELTGYGTVTMECSPRTGLDFNEMVLLQMENKAWLVHRQWFLDLPLPWLP
GADTQGSNWIQKETLVTFKNPHAKKQDVVVLGSQEGAMHTALTGATEIQMSSGNLLFTGHLKCRLRMDKLQLKG
MSYSMCTGKFKVVKEIAETQHGTIVIRVQYEGDGSPCKIPFEIMDLEKRHVLGRLITVNPIVTEKDSPVNIEAE
PPFGDSYIIIGVEPGQLKLNWFKKGSSGGGSHHHHHH SEQ ID NO: 26 >DENV3_Eexo = pCRO23
MRCVGVGNRDFVEGLSGATWVDVVLEHGGCVTTMAKNKPTLDIELQKTEATQLATLRKLCIEGKITNITTDSRC
PTQGEAVLPEEQDQNYVCKHTYVDRGNGSGCGLNGSGSLVTCAKFQCLEPIEGKVVQYENLKYTVIITVHTGDQ
HQVGNETQGVTAEITPQASTTEAILPEYGTLGLECSPRTGLDFNEMILLTMKNKAWMVHRQWFFDLPLPWASGA
TTETPTWNRKELLVTFKNAHAKKQEVVVLGSQEGAMHTALTGATEIQNSGGTSIFAGHLKCRLKMDKLELKGMS
YAMCTNTFVLKKEVSETQHGTILIKVEYKGEDAPCKIPFSTEDGQGKAHNGRLITANPVVTKKEEPVNIEAEPP
FGESNIVIGIGDNALKINWYKKGSSGGGSHHHHHH SEQ ID NO: 27 >DENV4_Eexo = pCRO24
MRCVGVGNRDFVEGVSGGAWVDLVLEHGGCVTTMAQGKPTLDFELTKTTAKEVALLRTYCIEASISNITTATRC
PTQGEPYLKEEQDQQYICRRDVVDRGNGSGCGLNGSGGVVTCAKFSCSGKITGNLVQIENLEYTVVVTVHNGDT
HAVGNDTSNHGVTAMITPRSPSVEVKLPDYGELTLDCEPRSGIDFNEMILMKMKKKTWLVHKQWFLDLPLPWTA
GADTSEVHWNYKERMVTFKVPHAKRQDVTVLGSQEGAMHSALAGATEVDSGDGNHMFAGHLKCKVRMEKLRIKG
MSYTMCSGKFSIDKEMAETQHGTTVVKVKYEGAGAPCKVPIEIRDVNKEKVVGRIISSTPLAENTNSVTNIELE
PPFGDSYIVIGVGNSALTLHWFRKGSSGGGSHHHHHH SEQ ID NO: 28 >ZIKV_Eexo = pCRO25
IRCIGVSNRDFVEGMSGGTWVDVVLEHGGCVTVMAQDKPTVDIELVTTTVSNMAEVRSYCYEASISDMASDSRC
PTQGEAYLDKQSDTQYVCKRTLVDRGNGSGCGLNGSGSLVTCAKFACSKKMTGKSIQPENLEYRIMLSVHGSQH
SGMIVNDTGHETDENRAKVEITPNSPRAEATLGGFGSLGLDCEPRTGLDFSDLYYLTMNNKHWLVHKEWFHDIP
LPWHAGADTGTPHWNNKEALVEFKDAHAKRQTVVVLGSQEGAVHTALAGALEAEMDGAKGRLSSGHLKCRLKMD
KLRLKGVSYSLCTAAFTFTKIPAETLHGTVTVEVQYAGTDGPCKVPAQMAVDMQTLTPVGRLITANPVITESTE
NSKMMLELDPPFGDSYIVIGVGEKKITHHWHRSGSTGGSGGSGGSHHHHHH SEQ ID NO: 29 >DENV1_Eexo 2.1 (single sequon W101N; N103S) [= insert for pCRO26 plasmid]
MRCVGIGNRDFVEGLSGATWVDVVLEHGSCVTTMAKDKPTLDIELLKTEVTNPAVLRKLCIEAKISNTTTDSRC
PTQGEATLVEEQDSNFVCRRTFVDRGNGSGCGLFGKGSLLTCAKFKCVTKLEGKIVQYENLKYSVIVTVHTGDQ
HQVGNETTEHGTIATITPQAPTSEIQLTDYGALTLDCSPRTGLDFNEMVLLTMKEKSWLVHKQWFLDLPLPWTS
GASTSQETWNRQDLLVTFKTAHAKKQEVVVLGSQEGAMHTALTGATEIQTSGTTTIFAGHLKCRLKMDKLTLKG
MSYVMCTGSFKLEKEVAETQHGTVLVQVKYEGTDAPCKIPFSAQDEKGVTQNGRLITANPIVTDKEKPVNIETE
PPFGESYIVVGAGEKALKLSWFKKGSTGGGSHHHHHH SEQ ID NO: 30 >DENV1_Eexo 2.2 (single sequon F108N; K110S) [= insert for pCRO27 plasmid]
MRCVGIGNRDFVEGLSGATWVDVVLEHGSCVTTMAKDKPTLDIELLKTEVTNPAVLRKLCIEAKISNTTTDSRC
PTQGEATLVEEQDSNFVCRRTFVDRGWGNGCGLNGSGSLLTCAKFKCVTKLEGKIVQYENLKYSVIVTVHTGDQ
HQVGNETTEHGTIATITPQAPTSEIQLTDYGALTLDCSPRTGLDFNEMVLLTMKEKSWLVHKQWFLDLPLPWTS
GASTSQETWNRQDLLVTFKTAHAKKQEVVVLGSQEGAMHTALTGATEIQTSGTTTIFAGHLKCRLKMDKLTLKG
MSYVMCTGSFKLEKEVAETQHGTVLVQVKYEGTDAPCKIPFSAQDEKGVTQNGRLITANPIVTDKEKPVNIETE
PPFGESYIVVGAGEKALKLSWFKKGSTGGGSHHHHHH SEQ ID NO: 31 >ZIKV_Eexo 2.1 (single sequon G100N; W101H; G102T) [= insert for pCRO28 plasmid]
IRCIGVSNRDFVEGMSGGTWVDVVLEHGGCVTVMAQDKPTVDIELVTTTVSNMAEVRSYCYEASISDMASDSRC
PTQGEAYLDKQSDTQYVCKRTLVDRNHTNGCGLFGKGSLVTCAKFACSKKMTGKSIQPENLEYRIMLSVHGSQH
SGMIVNDTGHETDENRAKVEITPNSPRAEATLGGFGSLGLDCEPRTGLDFSDLYYLTMNNKHWLVHKEWFHDIP
LPWHAGADTGTPHWNNKEALVEFKDAHAKRQTVVVLGSQEGAVHTALAGALEAEMDGAKGRLSSGHLKCRLKMD
KLRLKGVSYSLCTAAFTFTKIPAETLHGTVTVEVQYAGTDGPCKVPAQMAVDMQTLTPVGRLITANPVITESTE
NSKMMLELDPPFGDSYIVIGVGEKKITHHWHRSGSTGGSGGSGGSHHHHHH SEQ ID NO: 32 >ZIKV_Eexo 2.2 (single sequon L107N; F108H; G109T) [= insert for pCRO29 plasmid]
IRCIGVSNRDFVEGMSGGTWVDVVLEHGGCVTVMAQDKPTVDIELVTTTVSNMAEVRSYCYEASISDMASDSRC -continued

Sequence Listing Free Text

```
PTQGEAYLDKQSDTQYVCKRTLVDRGWGNGCGNHTKGSLVTCAKFACSKKMTGKSIQPENLEYRIMLSVHGSQH
SGMIVNDTGHETDENRAKVEITPNSPRAEATLGGFGSLGLDCEPRTGLDFSDLYYLTMNNKHWLVHKEWFHDIP
LPWHAGADTGTPHWNNKEALVEFKDAHAKRQTVVVLGSQEGAVHTALAGALEAEMDGAKGRLSSGHLKCRLKMD
KLRLKGVSYSLCTAAFTFTKIPAETLHGTVTVEVQYAGTDGPCKVPAQMAVDMQTLTPVGRLITANPVITESTE
NSKMMLELDPPFGDSYIVIGVGEKKITHHWHRSGSTGGSGGSGGSHHHHHH

SEQ ID NO: 33 >ZIKV_Eexo 2.3 (single sequon W101N; N103S) [= insert for
pCRO30 plasmid]
IRC

SEQUENCE LISTING

<160> NUMBER OF SEQ ID NOS: 130

<210> SEQ ID NO 1
<211> LENGTH: 13
<212> TYPE: PRT
<213> ORGANISM: Flavivirus

<400> SEQUENCE: 1

Asp Arg Gly Trp Gly Asn Gly Cys Gly Leu Phe Gly Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 2

Asp Arg Gly Asn Gly Ser Gly Cys Gly Leu Asn Gly Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 3

Asp Arg Gly Asn Gly Ser Gly Cys Gly Leu Phe Gly Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 4

Asp Arg Gly Trp Gly Asn Gly Cys Gly Leu Asn Gly Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 5

Asp Arg Asn His Thr Asn Gly Cys Gly Leu Phe Gly Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Modified Flavivirus E protein fusion loop
      98-110 fragment

<400> SEQUENCE: 6

```
Asp Arg Gly Trp Gly Asn Gly Cys Gly Asn His Thr Lys
1               5                   10
```

<210> SEQ ID NO 7
<211> LENGTH: 29
<212> TYPE: PRT
<213> ORGANISM: Artificial Sequence
<220> FEATURE:
<223> OTHER INFORMATION: pCRO25-encoded amino acid sequence containing
      recombinant analogue of flavivirus E protein fusion loop 98-110 of
      SEQ ID NO:2

<400> SEQUENCE: 7

```
Cys Lys Arg Thr Leu Val Asp Arg Gly Asn Gly Ser Gly Cys Gly Leu
1               5                   10                  15

Asn Gly Ser Gly Ser Leu Val Thr Cys Ala Lys Phe Ala
            20                  25
```

<210> SEQ ID NO 8
<211> LENGTH: 29
<212> TYPE: PRT
<213> ORGANISM: Artificial Sequence
<220> FEATURE:
<223> OTHER INFORMATION: pCRO29 -encoded amino acid sequence containing
      recombinant analogue of flavivirus E protein fusion loop 98-110
      fragment of SEQ ID NO: 6

<400> SEQUENCE: 8

```
Cys Lys Arg Thr Leu Val Asp Arg Gly Trp Gly Asn Gly Cys Gly Asn
1               5                   10                  15

His Thr Lys Gly Ser Leu Val Thr Cys Ala Lys Phe Ala
            20                  25
```

<210> SEQ ID NO 9
<211> LENGTH: 29
<212> TYPE: PRT
<213> ORGANISM: Artificial Sequence
<220> FEATURE:
<223> OTHER INFORMATION: pCRO30-encoded amino acid sequence containing
      recombinant analogue of flavivirus E protein fusion loop 98-110
      fragment of SEQ ID NO: 3

<400> SEQUENCE: 9

```
Cys Lys Arg Thr Leu Val Asp Arg Gly Asn Gly Ser Gly Cys Gly Leu
1               5                   10                  15

Phe Gly Lys Gly Ser Leu Val Thr Cys Ala Lys Phe Ala
            20                  25
```

<210> SEQ ID NO 10
<211> LENGTH: 29
<212> TYPE: PRT
<213> ORGANISM: Artificial Sequence
<220> FEATURE:
<223> OTHER INFORMATION: pCRO31-encoded amino acid sequence containing
      recombinant analogue of flavivirus E protein fusion loop 98-110
      fragment of SEQ ID NO: 4

<400> SEQUENCE: 10

```
Cys Lys Arg Thr Leu Val Asp Arg Gly Trp Gly Asn Gly Cys Gly Leu
1               5                   10                  15

Asn Gly Ser Gly Ser Leu Val Thr Cys Ala Lys Phe Ala
            20                  25
```

<210> SEQ ID NO 11
<211> LENGTH: 13

```
<212> TYPE: PRT
<213> ORGANISM: Artificial Sequence
<220> FEATURE:
<223> OTHER INFORMATION: Modified flavivirus E protein fusion loop
      98-110 fragment

<400> SEQUENCE: 11

Asp Arg Gly Trp Gly Asn Asn Cys Thr Leu Phe Gly Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Modified flavivirus E protein fusion loop
      98-110 fragment

<400> SEQUENCE: 12

Asp Arg Gly Trp Gly Asn Asn Cys Ser Leu Phe Gly Lys
1               5                   10

<210> SEQ ID NO 13
<211> LENGTH: 5460
<212> TYPE: DNA
<213> ORGANISM: Artificial Sequence
<220> FEATURE:
<223> OTHER INFORMATION: Plasmid expression vector pCRO21

<400> SEQUENCE: 13
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga     360
cgtatgttcc catagtaacg ccaatagggga ctttccattg acgtcaatgg gtggagtatt     420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac ccgccagcgg ccgccaccat gaaggccaat ctactggtgt gctgtgtgc      900
ccttgcggcg gcagatgcca tcgggtgcgt gggaatcggc aatcgcgatt ttgtagaagg     960
actatctggt gccacgtggg tcgatgtggt tcttgaacac gggtcatgcg tgaccacgat    1020
ggctaaggat aagccgacct tggacatcga actactgaaa accgaggtca caaaccctgc    1080
tgtgctccgc aagctgtgca tcgaggctaa gattccaaac acaactactg atagccgctg    1140
ccccacccaa ggcgaggcga ccctcgttga agagcaggac agcaacttcg tgtgtcgccg    1200
gactttcgtg gaccgcggta atgggtccgg atgcggactt aacggatctg gttcccttact    1260
gacttgcgcc aaatttaagt gcgtgactaa gttagagggg aaaatcgttc agtatgagaa    1320
```

```
cttaaaatac tcggtgatag ttaccgtgca cacaggcgac cagcatcaag ttgggaacga    1380
aacgacagag cacgggacaa tagcgaccat tacccccacag gctccaacga gcgaaattca    1440
gctgacagac tacggtgcac tcaccctgga ctgtagccca cggaccgggc tagactttaa    1500
cgagatggtg ctcctgacta tgaaggaaaa gtcatggttg gtgcacaagc agtggttcct    1560
tgatcttcca ttgccctgga cctctggcgc ttcgacctca caagagactt ggaacaggca    1620
ggacttgctc gtgacattca aaacggctca cgctaaaaag caagaggtcg tggttctggg    1680
gagtcaggaa ggcgctatgc ataccgcgtt aacaggggct acagagatcc agaccagtgg    1740
aacaaccact attttcgccg ggcatcttaa gtgtaggctg aagatggata agttgaccct    1800
gaaaggtatg tcatatgtga tgtgcaccgg tagtttcaaa ctggagaaag aagtggccga    1860
aacccagcat ggaacagtac tggtgcaagt caaatatgag ggcaccgatg caccatgtaa    1920 aataccttc agcgcacaag acgagaaggg agttacccag aacggtaggc tgataacagc    1980
caatccaatc gtcaccgata aggagaaacc agtaaacatc gaaaccgagc cacccttcgg    2040
cgaaagctac atcgtggtcg gcgctggcga gaaagcactt aagctgagct ggtttaagaa    2100
aggtagcacg ggcggcggca gccatcatca ccatcatcac tgagctagct tgactgactg    2160
agatacagcg taccttcagc tcacagacat gataagatac attgatgagt ttggacaaac    2220
cacaactaga atgcagtgaa aaaaatgctt tatttgtgaa atttgtgatg ctattgcttt    2280
atttgtaacc attataagct gcaataaaca agttaacaac aacaattgca ttcattttat    2340
gtttcaggtt cagggggagg tgtgggaggt tttttaaagc aagtaaaacc tctacaaatg    2400
tggtattggc ccatctctat cggtatcgta gcataacccc ttggggcctc taaacgggtc    2460
ttgaggggtt ttttgtgccc ctcgggccgg attgctatct accggcattg gcgcagaaaa    2520 aaaatgcctga tgcgacgctg cgcgtcttat actcccacat atgccagatt cagcaacgga    2580
tacggcttcc ccaacttgcc cacttccata cgtgtcctcc ttaccagaaa tttatcctta    2640
aggtcgtcag ctatcctgca ggcgatctct cgatttcgat caagacattc ctttaatggt    2700 ctttctctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940
gcaaaaggcc aggaaccgta aaaaggccgc gttgctggcg ttttttccata ggctccgccc    3000 ccctgacgag catcacaaaa atcgacgctc aagtcagagg tggcgaaacc cgacaggact    3060
ataaagatac caggcgtttc ccctggaag ctccctcgtg cgctctcctg ttccgaccct    3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240 cgaaccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
gcagattacg cgcagaaaaa aaggatctca agaagatcct ttgatctttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
```

```
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga acgaactatc    3900
gcaagtctct tggccggcct tgcgccttgg ctattgcttg cagcgccta tcgccaggta    3960 ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cctttttgc ggcattttgc cttcctgttt    4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct tttttgcaca acatggggga tcatgtaact cgccttgatc    4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata aatctggagc cggtgagcgt gggtctcgcg    5040
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaatg cctgatgcga    5220 cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
cgctcatttg ctcgtcgggc atcgaatctc gtcagctatc gtcagcttac cttttttggca    5460
```

<210> SEQ ID NO 14
<211> LENGTH: 5460
<212> TYPE: DNA
<213> ORGANISM: Artificial Sequence
<220> FEATURE:
<223> OTHER INFORMATION: Plasmid expression vector pCRO22

<400> SEQUENCE: 14

```
gcgatcgcgg ctccccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
```

-continued

```
cggtaaatgg cccgcctggc tgaccgccca acgaccccg cccattgacg tcaataatga   360
cgtatgttcc catagtaacg ccaataggga cttccattg acgtcaatgg gtggagtatt   420
tacggtaaac tgcccacttg gcagtacatc aagtgtatca tatgccaagt acgcccccta   480
ttgacgtcaa tgacggtaaa tggcccgcct ggcattatgc ccagtacatg accttatggg   540
actttcctac ttggcagtac atctacgtat tagtcatcgc tattaccatg ctgatgcggt   600
tttggcagta catcaatggg cgtggatagc ggtttgactc acggggattt ccaagtctcc   660
accccattga cgtcaatggg agtttgtttt ggcaccaaaa tcaacgggac tttccaaaat   720
gtcgtaacaa ctccgcccca ttgacgcaaa tgggcggtag cgtgtacgg tgggaggtct   780
atataagcag agctggttta gtgaaccgtc agatcagatc tttgtcgatc ctaccatcca   840
ctcgacacac cgccagcgg ccgccaccat gaaggccaat ctactggtgt tgctgtgtgc   900
ccttgcggcg gcagatgcca tgcgctgcat cgggatcagc aatcgcgact tgtggaagg   960
agtcagcggc ggatcatggg tggacatcgt gcttgagcac ggcagctgcg tgaccactat  1020
ggcaaagaat aagccgactc tggattttga actcattaaa accgaggcga agcagcccgc  1080
aactctgagg aagtactgca tcgaggccaa actgactaac actaccaccg aatcacggtg  1140
cccgacccaa ggcgaaccga gcctgaacga agagcaggat aagagatttg tctgcaagca  1200
ctcaatggtg gaccggggga atggatccgg ctgcggactg aacggatctg ggggcattgt  1260
gacttgcgca atgttcacct gtaaaaagaa catggagggc aaggtcgtgc agccagagaa  1320
cctggaatac accattgtca ttactccaca ttccggagag aacacgccg tcggcaacga  1380
cactggaaaa catgggaagg aaattaagat caccccgcag tcgtcaatta ccgaggcaga  1440
actcaccggg tacggcactg tcactatgga gtgctcaccg agaactgggt tggatttcaa  1500
tgagatggtg ctcctacaga tggagaacaa ggcatggctc gtgcacccggc aatggtttct  1560
cgacctgccg ctgccttggc tcctggggc cgacactcaa gctcgaatt ggattcagaa  1620
ggaaacgctg gtcacgttca agaaccccca tgccaagaag caagacgtgg tggtcctggg  1680
ctcgcaagaa ggagctatgc acaccgctct gaccggcgcg accgaaatcc aaatgtcatc  1740
aggcaacctc ctgttcactg gccacctcaa atgccggctg agaatggata agctgcaact  1800
gaaaggtatg tcctactcga tgtgcaccgg taaatttaaa gtggtgaaag agatcgctga  1860
aactcagcac ggtaccatcg tcatcagggt gcagtacgag ggagacgct cacctgcaa  1920
aatcccctc gaaatcatgg acctcgaaaa agagacacgtg ctgggccgcc tgatcaccgt  1980
taacccgatc gtgaccgaga agacagccc ggtgaatatt gaagcggaac tccgttcgg  2040
cgacagctac atcattatcg gcgtggaacc gggccagctg aagcttaatt ggttcaaaaa  2100
ggggtccagc ggcggcggca gccatcatca ccatcatcac tgagctagct tgactgactg  2160
agatacagcg taccttcagc tcacagacat gataagatac attgatgagt ttggacaaac  2220
cacaactaga atgcagtgaa aaaaatgctt tatttgtgaa atttgtgatg ctattgcttt  2280
atttgtaacc attataagct gcaataaaca agttaacaac acaattgca ttcattttat  2340
gtttcaggtt caggggggagg tgtgggaggt tttttaaagc aagtaaaacc tctacaaatg  2400
tggtattggc ccatctctat cggtatcgta gcataacccc ttggggcctc taaacgggtc  2460
ttgaggggtt ttttgtgccc ctcgggccgg attgctatct accggcattg gcgcagaaaa  2520
aaatgcctga tgcgacgctg cgcgtcttat actcccacat atgccagatt cagcaacgga  2580
tacggcttcc ccaacttgcc cacttccata cgtgtcctcc ttaccagaaa tttatcctta  2640
aggtcgtcag ctatcctgca ggcgatctct cgatttcgat caagacattc ctttaatggt  2700
```

```
cttttctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940
gcaaaaggcc aggaaccgta aaaaggccgc gttgctggcg ttttccata ggctccgccc     3000 ccctgacgag catcacaaaa atcgacgctc aagtcagagg tggcgaaacc cgacaggact    3060
ataaagatac caggcgtttc ccctggaag ctccctcgtg cgctctcctg ttccgaccct     3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240
cgaacccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
gcagattacg cgcagaaaaa aaggatctca agaagatcct ttgatctttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga cgaactatc     3900 gcaagtctct tggccggcct tgcgccttgg ctattgcttg cagcgcctta tcgccaggta    3960
ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc ccttttttgc ggcattttgc cttcctgttt    4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500 aacgcttttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct tttttgcaca acatggggga tcatgtaact cgccttgatc    4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata aatctggagc cggtgagcgt gggtctcgcg    5040
```

```
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaaatg cctgatgcga    5220
cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
cgctcatttg ctcgtcgggc atcgaatctc gtcagctatc gtcagcttac ctttttggca    5460
```

<210> SEQ ID NO 15
<211> LENGTH: 5454
<212> TYPE: DNA
<213> ORGANISM: Artificial Sequence
<220> FEATURE:
<223> OTHER INFORMATION: Plasmid expression vector pCRO23

<400> SEQUENCE: 15

```
gcgatcgcgg ctcccgacat cttgaccat  tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgacccccg cccattgacg tcaataatga     360
cgtatgttcc catagtaacg ccaatagggA cttccattg acgtcaatgg gtggagtatt     420
tacggtaaac tgcccacttg gcagtacatc aagtgtatca tatgccaagt acgccccta     480 ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac ccgccagcgg ccgccaccat gaaggccaat ctactggtgt tgctgtgtgc     900
ccttgcggcg gcagatgcca tgagatgtgt gggcgtgggg aaccgcgact tgtcgaagg     960 attaagtggc gcgacctggg tagacgtcgt gctggagcac ggagggtgcg tcacaaccat    1020
ggccaagaac aagcccaccc ttgacattga acttcaaaag acagaagcta ctcagctggc    1080
tacactgcgc aagctgtgca tagagggaaa aatcaccaac ataactacgg actcgaggtg    1140
tcccacacag ggtgaagcgg tcttgcctga gaacaggat cagaattatg tttgtaaaca    1200
tacttatgta gacaggggga atggatccgg gtgcggtctg aacggatctg gttccctagt    1260
cacatgcgct aagttccagt gcctcgagcc tatcgaaggt aaagtggtcc agtacgagaa    1320
tcttaagtac accgtgatca tcacggtcca tacaggagat caacaccagg ttggaaacga    1380
gacccaagga gtcactgccg aaatcacacc gcaggcagc acgacggagg ctattttgcc    1440
ggagtatggg acactgggac tggaatgctc ccctaggacg ggactagatt ttaatgagat    1500
gattctgctg acaatgaaga acaaggcttg gatggtgcat cgtcaatggt tctttgatct    1560
gccactgccg tggccagcg cgccacgac agagaccca acctggaatc gaaaagagct    1620
gctggtcaca ttcaaaaacg cacacgccaa aaagcaagaa gtggtagtgc ttggctccca    1680
```

```
ggaaggtgcc atgcacactg cactcacagg ggctactgaa attcagaatt caggaggcac    1740
ttctattttc gccggccacc tcaaatgccg gttaaagatg gacaagctgg aactgaaagg    1800
tatgtcgtac gcaatgtgca ctaatacatt tgtgctaaag aaggaagtct ccgagactca    1860
gcacgggaca atactgatta aggtggaata caaaggtgag gatgctccct gtaagatccc    1920
cttctctact gaggatggtc agggcaaagc tcataatggt cggttgatca cagcgaatcc    1980
agtggttaca aagaaggagg agccagtgaa tatcgaagca gaacctccct tcggtgagtc    2040
aaacattgtc atcggtatcg gagataacgc tcttaagata aactggtaca aaaagggatc    2100
tagcggcggc ggcagccatc atcaccatca tcactgagct agcttgactg actgagatac    2160
agcgtacctt cagctcacag acatgataag atacattgat gagtttggac aaaccacaac    2220
tagaatgcag tgaaaaaaat gctttatttg tgaaatttgt gatgctattg ctttatttgt    2280
aaccattata agctgcaata acaagttaa caacaacaat tgcattcatt ttatgtttca    2340
ggttcagggg gaggtgtggg aggttttta aagcaagtaa aacctctaca aatgtggtat    2400
tggcccatct ctatcggtat cgtagcataa ccccttgggg cctctaaacg ggtcttgagg    2460
ggttttttgt gcccctcggg ccggattgct atctaccggc attggcgcag aaaaaaatgc    2520
ctgatgcgac gctgcgcgtc ttatactccc acatatgcca gattcagcaa cggatacggc    2580
ttccccaact tgcccacttc catacgtgtc ctccttacca gaaatttatc cttaaggtcg    2640
tcagctatcc tgcaggcgat ctctcgattt cgatcaagac attcctttaa tggtcttttc    2700
tggacaccac taggggtcag aagtagttca tcaaactttc ttccctccct aatctcattg    2760
gttaccttgg gctatcgaaa cttaattaac cagtcaagtc agctacttgg cgagatcgac    2820
ttgtctgggt ttcgactacg ctcagaattg cgtcagtcaa gttcgatctg gtccttgcta    2880
ttgcacccgt tctccgatta cgagtttcat ttaaatcatg tgagcaaaag gccagcaaaa    2940
ggccaggaac cgtaaaaagg ccgcgttgct ggcgttttc cataggctcc gcccccctga    3000
cgagcatcac aaaaatcgac gctcaagtca gaggtggcga aacccgacag gactataaag    3060
ataccaggcg tttccccctg gaagctccct cgtgcgctct cctgttccga ccctgccgct    3120
taccggatac ctgtccgcct ttctcccttc gggaagcgtg gcgctttctc atagctcacg    3180
ctgtaggtat ctcagttcgg tgtaggtcgt tcgctccaag ctgggctgtg tgcacgaacc    3240
ccccgttcag cccgaccgct gcgccttatc cggtaactat cgtcttgagt ccaacccggt    3300
aagacacgac ttatcgccac tggcagcagc cactggtaac aggattagca gagcgaggta    3360
tgtaggcggt gctacagagt tcttgaagtg gtggcctaac tacggctaca ctagaagaac    3420
agtatttggt atctgcgctc tgctgaagcc agttaccttc ggaaaaagag ttggtagctc    3480
ttgatccggc aaacaaacca ccgctggtag cggtggtttt tttgtttgca agcagcagat    3540
tacgcgcaga aaaaaggat ctcaagaaga tcctttgatc ttttctacgg ggtctgacgc    3600
tcagtggaac gaaaactcac gttaagggat tttggtcatg agattatcaa aaaggatctt    3660
cacctagatc cttttaaatt aaaaatgaag ttttaaatca atctaaagta tatatgagta    3720
aacttggtct gacagttacc aatgcttaat cagtgaggca cctatctcag cgatctgtct    3780
atttcgttca tccatagttg catttaaatt tccgaactct ccaaggccct cgtcggaaaa    3840
tcttcaaacc tttcgtccga tccatcttgc aggctacctc tcgaacgaac tatcgcaagt    3900
ctcttggccg gccttgcgcc ttggctattg cttggcagcg cctatcgcca ggtattactc    3960
caatcccgaa tatccgagat cgggatcacc cgagagaagt tcaacctaca tcctcaatcc    4020
```

```
cgatctatcc gagatccgag gaatatcgaa atcggggcgc gcctggtgta ccgagaacga    4080
tcctctcagt gcgagtctcg acgatccata tcgttgcttg gcagtcagcc agtcggaatc    4140
cagcttggga cccaggaagt ccaatcgtca gatattgtac tcaagcctgg tcacggcagc    4200
gtaccgatct gtttaaacct agatattgat agtctgatcg gtcaacgtat aatcgagtcc    4260
tagcttttgc aaacatctat caagagacag gatcagcagg aggctttcgc atgagtattc    4320
aacatttccg tgtcgccctt attccctttt ttgcggcatt ttgccttcct gttttgctc     4380 acccagaaac gctggtgaaa gtaaaagatg ctgaagatca gttgggtgcg cgagtgggtt    4440
acatcgaact ggatctcaac agcggtaaga tccttgagag ttttcgcccc gaagaacgct    4500
ttccaatgat gagcactttt aaagttctgc tatgtggcgc ggtattatcc cgtattgacg    4560
ccgggcaaga gcaactcggt cgccgcatac actattctca gaatgacttg gttgagtatt    4620
caccagtcac agaaaagcat cttacggatg gcatgacagt aagagaatta tgcagtgctg    4680
ccataaccat gagtgataac actgcggcca acttacttct gacaacgatt ggaggaccga    4740
aggagctaac cgcttttttg cacaacatgg ggatcatgt aactcgcctt gatcgttggg     4800
aaccggagct gaatgaagcc ataccaaacg acgagcgtga caccacgatg cctgtagcaa    4860
tggcaacaac cttgcgtaaa ctattaactg gcgaactact tactctagct tcccggcaac    4920
agttgataga ctggatggag gcggataaag ttgcaggacc acttctgcgc tcggcccttc    4980
cggctggctg gtttattgct gataaatctg agccggtga gcgtgggtct cgcggtatca     5040
ttgcagcact ggggccagat ggtaagccct cccgtatcgt agttatctac acgacgggga    5100
gtcaggcaac tatggatgaa cgaaatagac agatcgctga gataggtgcc tcactgatta    5160
agcattggta accgattcta ggtgcattgg cgcagaaaaa aatgcctgat gcgacgctgc    5220
gcgtcttata ctcccacata tgccagattc agcaacggat acggcttccc caacttgccc    5280
acttccatac gtgtcctcct taccagaaat ttatccttaa gatcccgaat cgtttaaact    5340
cgactctggc tctatcgaat ctccgtcgtt tcgagcttac gcgaacagcc gtggcgctca    5400
tttgctcgtc gggcatcgaa tctcgtcagc tatcgtcagc ttacctttt ggca           5454
```

<210> SEQ ID NO 16
<211> LENGTH: 5460
<212> TYPE: DNA
<213> ORGANISM: Artificial Sequence
<220> FEATURE:
<223> OTHER INFORMATION: Plasmid expression vector pCRO24

<400> SEQUENCE: 16

```
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgacccccg cccattgacg tcaataatga    360
cgtatgttcc catagtaacg ccaataggga ctttccattg acgtcaatgg gtggagtatt    420
tacggtaaac tgcccacttg gcagtacatc aagtgtatca tatgccaagt acgccccta    480 ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
```

```
acccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcgg ccgccaccat gaaggccaat ctactggtgt tgctgtgtgc    900
ccttgcggcg gcagatgcca tgcgatgcgt ggggtgggc aatagagatt cgtggaagg     960
ggtgtctgga ggggcatggg tggatctggt gctggagcac ggcggatgtg tcacaactat   1020
ggcccagggg aagccaaccc tggatttcga gctaactaag accacagcta aggaggtagc   1080
cctgcttcgg acttactgta ttgaggcatc catctctaac atcaccaccg ccacgagatg   1140
cccgacacag ggcgaaccct acttgaagga agaacaggat cagcagtaca tttgccggcg   1200
cgatgttgtt gatagaggca atggctccgg gtgtggcctc aacggctctg gtggggtggt   1260
cacctgtgcc aagttcagct gttctggcaa gatcacggga aatctggtgc aaattgaaaa   1320
tttggaatat acggtcgttg tgactgtcca caatggcgat acacatgctg tgggcaacga   1380
taccagtaac cacggcgtca ccgcgatgat aactccccgg agcccatctg ttgaagttaa   1440
actgcccgat tacggagagt tgacactcga ctgcgaaccg aggtctggaa tagatttcaa   1500
cgagatgata cttatgaaaa tgaagaaaaa gacctggctc gtacacaagc agtggttttt   1560
ggatttgccc ctcccttgga ccgcaggggc cgataccagc gaggtgcatt ggaattacaa   1620
agagcgcatg gtgactttca aagtgcccca cgcaaagcgg caagatgtga ctgtattagg   1680
atcacaggaa ggcgctatgc attccgccct ggctggtgcc acggaggtgg attcaggaga   1740
cggtaaccat atgtttgctg ccacctcaa atgtaaggtc cgcatggaaa aacttcgcat    1800
taaaggaatg tcctacacga tgtgctcagg aaagttctct atcgacaagg aaatggccga   1860
gactcagcat ggaacgactg tagtcaaggt gaaatatgaa ggtgccgggg cgccttgcaa   1920
ggtgccaatc gaaatccgag acgttaacaa ggagaaggtg gttgggagga ttataagtag   1980
cactccgctc gcagagaaca ccaatagcgt gactaacata gaactggagc cccttttgg    2040
ggatagctac attgtgattg gagtagggaa tagtgcacta acattgcact ggttcagaaa   2100
agggtcttca ggcggcggca gccatcatca ccatcatcac tgagctagct tgactgactg   2160
agatacagcg taccttcagc tcacagacat gataagatac attgatgagt ttggacaaac   2220
cacaactaga atgcagtgaa aaaatgctt tatttgtgaa atttgtgatg ctattgcttt    2280
atttgtaacc attataagct gcaataaaca agttaacaac aacaattgca ttcatttat    2340
gtttcaggtt caggggagg tgtgggaggt tttttaaagc aagtaaaacc tctacaaatg   2400
tggtattggc ccatctctat cggtatcgta gcataacccc ttgggccctc taaacgggtc   2460
ttgaggggtt ttttgtgccc ctcgggccgg attgctatct accggcattg gcgcagaaaa   2520
aaatgcctga tgcgacgctg cgcgtcttat actcccacat atgccagatt cagcaacgga   2580
tacggcttcc ccaacttgcc cacttccata cgtgtcctcc ttaccagaaa tttatcctta   2640
aggtcgtcag ctatcctgca ggcgatctct cgatttcgat caagacattc ctttaatggt   2700
cttttctgga caccactagg ggtcagaagt agttcatcaa actttcttcc ctccctaatc   2760
tcattggtta ccttgggcta tcgaaactta attaaccagt caagtcagct acttggcgag   2820
atcgacttgt ctgggtttcg actacgctca gaattgcgtc agtcaagttc gatctggtcc   2880
ttgctattgc acccgttctc cgattacgag tttcatttaa atcatgtgag caaaaggcca   2940
gcaaaaggcc aggaaccgta aaaaggccgc gttgctggcg ttttccata ggctccgccc    3000
```

```
ccctgacgag catcacaaaa atcgacgctc aagtcagagg tggcgaaacc cgacaggact    3060
ataaagatac caggcgtttc ccctggaag ctccctcgtg cgctctcctg ttccgaccct     3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240
cgaacccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggttttttg tttgcaagca     3540
gcagattacg cgcagaaaaa aaggatctca agaagatcct ttgatctttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga acgaactatc    3900
gcaagtctct tggccggcct tgcgccttgg ctattgcttg cagcgcccta tcgccaggta    3960
ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cctttttgc ggcattttgc cttcctgttt     4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
ttgacgccgg gcaagagcaa ctcggtcgcc gcatacacta ttctcagaat gacttggttg    4620
agtattcacc agtcacagaa aagcatctta cggatggcat gacagtaaga gaattatgca    4680
gtgctgccat aaccatgagt gataacactg cggccaactt acttctgaca acgattggag    4740
gaccgaagga gctaaccgct tttttgcaca acatgggga tcatgtaact cgccttgatc     4800
gttgggaacc ggagctgaat gaagccatac caaacgacga gcgtgacacc acgatgcctg    4860
tagcaatggc aacaaccttg cgtaaactat taactggcga actacttact ctagcttccc    4920
ggcaacagtt gatagactgg atggaggcgg ataaagttgc aggaccactt ctgcgctcgg    4980
cccttccggc tggctggttt attgctgata atctggagc cggtgagcgt gggtctcgcg      5040
gtatcattgc agcactgggg ccagatggta agccctcccg tatcgtagtt atctacacga    5100
cggggagtca ggcaactatg gatgaacgaa atagacagat cgctgagata ggtgcctcac    5160
tgattaagca ttggtaaccg attctaggtg cattggcgca gaaaaaatg cctgatgcga     5220
cgctgcgcgt cttatactcc cacatatgcc agattcagca acggatacgg cttccccaac    5280
ttgcccactt ccatacgtgt cctccttacc agaaatttat ccttaagatc ccgaatcgtt    5340
taaactcgac tctggctcta tcgaatctcc gtcgtttcga gcttacgcga acagccgtgg    5400
```

-continued

| | |
|---|---|
| cgctcatttg ctcgtcgggc atcgaatctc gtcagctatc gtcagcttac cttttttggca | 5460 |

<210> SEQ ID NO 17
<211> LENGTH: 5502
<212> TYPE: DNA
<213> ORGANISM: Artificial Sequence
<220> FEATURE:
<223> OTHER INFORMATION: Plasmid expression vector pCRO28

<400> SEQUENCE: 17

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctagt | 240 |
| aatcaattac ggggtcatta gttcatagcc catatatgga gttccgcgtt acataactta | 300 |
| cggtaaatgg cccgcctggc tgaccgccca acgaccccg cccattgacg tcaataatga | 360 |
| cgtatgttcc catagtaacg ccaatagggg cttTCCATtg acgtcaatgg gtggagtatt | 420 |
| tacggtaaac tgcccacttg gcagtacatc aagtgtatca tatgccaagt acgccccta | 480 |
| ttgacgtcaa tgacggtaaa tggcccgcct ggcattatgc ccagtacatg accttatggg | 540 |
| actttcctac ttggcagtac atctacgtat tagtcatcgc tattaccatg ctgatgcgt | 600 |
| tttggcagta catcaatggg cgtggatagc ggtttgactc acggggattt ccaagtctcc | 660 |
| accccattga cgtcaatggg agtttgtttt ggcaccaaaa tcaacgggac tttccaaaat | 720 |
| gtcgtaacaa ctccgcccca ttgacgcaaa tgggcggtag gcgtgtacgg tgggaggtct | 780 |
| atataagcag agctggttta gtgaaccgtc agatcagatc tttgtcgatc ctaccatcca | 840 |
| ctcgacacac ccgccagcgg ccgccaccat gaaggccaat ctactggtgt gctgtgtgc | 900 |
| ccttgcggcg gcagatgcca tcaggtgcat tggagtcagc aacagggact tcgtcgaagg | 960 |
| catgtccggc ggcacctggg tggatgtggt gctcgaacac ggcggatgcg tgaccgtcat | 1020 |
| ggcccaggac aagcctaccg tcgatattga gctggtgacc accacagtga gcaacatggc | 1080 |
| cgaagtgaga agctactgct atgaggcctc catcagcgat atggcttccg attccagatg | 1140 |
| ccccacacag ggagaggctt atctggacaa acagtccgac acccagtacg tctgcaaaag | 1200 |
| aaccctggtg gacagaaacc acaccaacgg atgcggcctg ttcggcaaag gcagcctcgt | 1260 |
| gacatgtgcc aagttcgcct gcagcaaaaa gatgaccggc aagtccatcc agcccgagaa | 1320 |
| cctggaatac aggatcatgc tgtccgtgca tggatcccag cactccggca tgatcgtcaa | 1380 |
| cgataccggc cacgagaccg acgagaacag ggctaaagtg gagatcaccc ccaacagccc | 1440 |
| tagagccgaa gctacactgg gcggcttcgg aagcctgggc ctggattgcg aacccaggac | 1500 |
| cggcctggat ttcagcgacc tgtattacct gaccatgaac aataagcact ggctggtgca | 1560 |
| caaggaatgg ttccacgaca tccccctgcc ttggcatgct ggcgccgata ccggcacacc | 1620 |
| tcactggaac aataaggaag ccctggtcga gtttaaggac gcccacgcca aagacagac | 1680 |
| cgtggtggtg ctgggaagcc aggagggagc tgtccacaca gccctggccg gagctctgga | 1740 |
| agccgagatg atggcgcca agggcaggct gagctccggc cacctgaaat gcaggctcaa | 1800 |
| gatggacaag ctgaggctga agggcgtgag ctacagcctg tgcaccgccg ctttcacctt | 1860 |
| taccaagatc cctgccgaga cactgcacgg caccgtcacc gtggaggtgc aatacgccgg | 1920 |
| aaccgatgga ccttgcaaag tgcctgccca gatggctgtg gatatgcaga ccctcacacc | 1980 |

```
cgtcggcagg ctgatcaccg ccaatcccgt cattaccgag tccaccgaga acagcaagat    2040
gatgctcgag ctcgatcccc cctttggcga cagctacatt gtgatcggcg tgggcgagaa    2100
gaagatcacc caccattggc acagaagcgg ctccacaggg ggtagcggtg gtagcggagg    2160
tagccatcac caccatcacc actgagctag cttgactgac tgagatacag cgtaccttca    2220
gctcacagac atgataagat acattgatga gtttggacaa accacaacta gaatgcagtg    2280
aaaaaaatgc tttatttgtg aaatttgtga tgctattgct ttatttgtaa ccattataag    2340
ctgcaataaa caagttaaca acaacaattg cattcatttt atgtttcagg ttcagggggga   2400 ggtgtgggag gttttttaaa gcaagtaaaa cctctacaaa tgtggtattg gcccatctct    2460
atcggtatcg tagcataacc ccttggggcc tctaaacggg tcttgagggg ttttttgtgc    2520
ccctcgggcc ggattgctat ctaccggcat ggcgcagaa aaaatgcct gatgcgacgc      2580 tgcgcgtctt atactcccac atatgccaga ttcagcaacg gatacggctt ccccaacttg    2640
cccacttcca tacgtgtcct ccttaccaga aatttatcct taaggtcgtc agctatcctg    2700
caggcgatct ctcgatttcg atcaagacat tcctttaatg gtcttttctg gacaccacta    2760
ggggtcagaa gtagttcatc aaactttctt ccctccctaa tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttttcca taggctccgc ccccctgacg agcatcacaa    3060
aaatcgacgc tcaagtcaga ggtggcgaaa cccgacagga ctataaagat accaggcgtt    3120
tccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc ccgttcagcc    3300
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaaagagtt ggtagctctt gatccggcaa    3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc tggtgtacc gagaacgatc ctctcagtgc     4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag gctttcgcat gagtattcaa catttccgtg    4380
```

```
tcgcccttat tcccttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560
gcacttttaa agttctgcta tgtggcgcgg tattatcccg tattgacgcc gggcaagagc    4620
aactcggtcg ccgcatacac tattctcaga atgacttggt tgagtattca ccagtcacag    4680
aaaagcatct tacggatggc atgacagtaa gagaattatg cagtgctgcc ataaccatga    4740
gtgataacac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
ggccagatgg taagccctcc cgtatcgtag ttatctacac gacggggagt caggcaacta    5160
tggatgaacg aaatagacag atcgctgaga taggtgcctc actgattaag cattggtaac    5220
cgattctagg tgcattggcg cagaaaaaaa tgcctgatgc gacgctgcgc gtcttatact    5280
cccacatatg ccagattcag caacggatac ggcttcccca acttgcccac ttccatacgt    5340
gtcctcctta ccagaaattt atccttaaga tcccgaatcg tttaaactcg actctggctc    5400
tatcgaatct ccgtcgtttc gagcttacgc gaacagccgt ggcgctcatt tgctcgtcgg    5460
gcatcgaatc tcgtcagcta tcgtcagctt accttttggg ca                      5502

<210> SEQ ID NO 18
<211> LENGTH: 5502
<212> TYPE: DNA
<213> ORGANISM: Artificial Sequence
<220> FEATURE:
<223> OTHER INFORMATION: Plasmid expression vector pCRO25

<400> SEQUENCE: 18
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga     360
cgtatgttcc catagtaacg ccaatagga ctttccattg acgtcaatgg gtggagtatt     420
tacggtaaac tgcccacttg gcagtacatc aagtgtatca tatgccaagt acgccccta     480 ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac ccgccagcgg ccgccaccat gaaggccaat ctactggtgt tgctgtgtgc     900
```

```
ccttgcggcg gcagatgcca tcaggtgcat tggagtcagc aacagggact tcgtcgaagg   960
catgtccggc ggcacctggg tggatgtggt gctcgaacac ggcggatgcg tgaccgtcat  1020
ggcccaggac aagcctaccg tcgatattga gctggtgacc accacagtga gcaacatggc  1080
cgaagtgaga agctactgct atgaggcctc catcagcgat atggcttccg attccagatg  1140
ccccacacag ggagaggctt atctggacaa acagtccgac acccagtacg tctgcaaaag  1200
aaccctggtg gacagaggca atggatccgg atgcggcctg aacggctctg gcagcctcgt  1260
gacatgtgcc aagttcgcct gcagcaaaaa gatgaccggc aagtccatcc agcccgagaa  1320
cctggaatac aggatcatgc tgtccgtgca tggatcccag cactccggca tgatcgtcaa  1380
cgataccggc cacgagaccg acgagaacag ggctaaagtg gagatcaccc ccaacagccc  1440
tagagccgaa gctacactgg gcggcttcgg aagcctgggc ctggattgcg aacccaggac  1500
cggcctggat ttcagcgacc tgtattacct gaccatgaac aataagcact ggctggtgca  1560
caaggaatgg ttccacgaca tcccctgcc ttggcatgct ggcgccgata ccggcacacc  1620
tcactggaac aataaggaag ccctggtcga gtttaaggac gcccacgcca aaagacagac  1680
cgtggtggtg ctgggaagcc aggagggagc tgtccacaca gccctggccg gagctctgga  1740
agccgagatg gatggcgcca agggcaggct gagctccggc cacctgaaat gcaggctcaa  1800
gatggacaag ctgaggctga agggcgtgag ctacagcctg tgcaccgccg ctttcacctt  1860
taccaagatc cctgccgaga cactgcacgg caccgtcacc gtggaggtgc aatacgccgg  1920
aaccgatgga ccttgcaaag tgcctgccca gatggctgtg gatatgcaga ccctcacacc  1980
cgtcggcagg ctgatcaccg ccaatcccgt cattaccgag tccaccgaga cagcaagat   2040
gatgctcgag ctcgatcccc cctttggcga cagctacatt gtgatcggcg tgggcgagaa  2100
gaagatcacc caccattggc acagaagcgg ctccacaggg ggtagcggtg gtagcggagg  2160
tagccatcac caccatcacc actgagctag cttgactgac tgagatacag cgtaccttca  2220
gctcacagac atgataagat acattgatga gtttggacaa accacaacta gaatgcagtg  2280
aaaaaaatgc tttatttgtg aaatttgtga tgctattgct ttatttgtaa ccattataag  2340
ctgcaataaa caagttaaca acaacaattg cattcatttt atgtttcagg ttcaggggga  2400
ggtgtgggag gttttttaaa gcaagtaaaa cctctacaaa tgtggtattg gcccatctct  2460
atcggtatcg tagcataacc ccttggggcc tctaaacggg tcttgagggg ttttttgtgc  2520
ccctcgggcc ggattgctat ctaccggcat ggcgcagaa aaaatgcct gatgcgacgc   2580
tgcgcgtctt atactcccac atatgccaga ttcagcaacg gatacggctt ccccaacttg  2640
cccacttcca tacgtgtcct ccttaccaga aatttatcct taaggtcgtc agctatcctg  2700
caggcgatct ctcgatttcg atcaagacat tcctttaatg gtcttttctg gacaccacta  2760
ggggtcagaa gtagttcatc aaactttctt ccctccctaa tctcattggt taccttgggc  2820
tatcgaaact taattaacca gtcaagtcag ctacttggcg agatcgactt gtctgggttt  2880
cgactacgct cagaattgcg tcagtcaagt tcgatctggt ccttgctatt gcacccgttc  2940
tccgattacg agtttcattt aaatcatgtg agcaaaaggc cagcaaaagg ccaggaaccg  3000
taaaaaggcc gcgttgctgg cgttttccca taggctccgc cccctgacg agcatcacaa   3060
aaatcgacgc tcaagtcaga ggtggcgaaa cccgacagga ctataaagat accaggcgtt  3120
tccccctgga agctccctcg tgcgctctcc tgttccgacc ctgccgctta ccggatacct  3180
gtccgccttt ctcccttcgg gaagcgtggc gctttctcat agctcacgct gtaggtatct  3240
cagttcggtg taggtcgttc gctccaagct gggctgtgtg cacgaacccc ccgttcagcc  3300
```

```
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttccttcgg aaaaagagtt ggtagctctt gatccggcaa     3540
acaaaccacc gctggtagcg gtggttttt tgtttgcaag cagcagatta cgcgcagaaa     3600
aaaggatct caagaagatc ctttgatctt ttctacgggg tctgacgctc agtggaacga     3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag gctttcgcat gagtattcaa catttccgtg    4380
tcgcccttat tccctttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560
gcacttttaa agttctgcta tgtggcgcgg tattatcccg tattgacgcc gggcaagagc    4620
aactcggtcg ccgcatacac tattctcaga atgacttggt tgagtattca ccagtcacag    4680
aaaagcatct tacggatggc atgacagtaa gagaattatg cagtgctgcc ataaccatga    4740
gtgataacac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
ggccagatgg taagccctcc cgtatcgtag ttatctacac gacggggagt caggcaacta    5160
tggatgaacg aaatagacag atcgctgaga taggtgcctc actgattaag cattggtaac    5220
cgattctagg tgcattggcg cagaaaaaaa tgcctgatgc gacgctgcgc gtcttatact    5280
cccacatatg ccagattcag caacggatac ggcttcccca acttgcccac ttccatacgt    5340
gtcctcctta ccagaaattt atccttaaga tcccgaatcg tttaaactcg actctggctc    5400
tatcgaatct ccgtcgtttc gagcttacgc gaacagccgt ggcgctcatt tgctcgtcgg    5460
gcatcgaatc tcgtcagcta tcgtcagctt acctttttgg ca                      5502
```

<210> SEQ ID NO 19
<211> LENGTH: 5460
<212> TYPE: DNA

<213> ORGANISM: Artificial Sequence
<220> FEATURE:
<223> OTHER INFORMATION: Plasmid expression vector pCRO26

<400> SEQUENCE: 19

```
gcgatcgcgg ctcccgacat cttggaccat tagctccaca ggtatcttct tccctctagt    60
ggtcataaca gcagcttcag ctacctctca attcaaaaaa cccctcaaga cccgtttaga   120
ggccccaagg ggttatgcta tcaatcgttg cgttacacac acaaaaaacc aacacacatc   180
catcttcgat ggatagcgat tttattatct aactgctgat cgagtgtagc cagatctagt   240
aatcaattac ggggtcatta gttcatagcc catatatgga gttccgcgtt acataactta   300
cggtaaatgg cccgcctggc tgaccgccca acgaccccccg cccattgacg tcaataatga   360
cgtatgttcc catagtaacg ccaatagggat ctttccattg acgtcaatgg gtggagtatt   420
tacggtaaac tgcccacttg gcagtacatc aagtgtatca tatgccaagt acgccccta    480
ttgacgtcaa tgacggtaaa tggcccgcct ggcattatgc ccagtacatg accttatggg   540
actttcctac ttggcagtac atctacgtat tagtcatcgc tattaccatg ctgatgcggt   600
tttggcagta catcaatggg cgtggatagc ggtttgactc acggggattt ccaagtctcc   660
accccattga cgtcaatggg agtttgtttt ggcaccaaaa tcaacgggac tttccaaaat   720
gtcgtaacaa ctccgcccca ttgacgcaaa tgggcggtag cgtgtacgg tgggaggtct   780
atataagcag agctggttta gtgaaccgtc agatcagatc tttgtcgatc ctaccatcca   840
ctcgacacac ccgccagcgg ccgccaccat gaaggccaat ctactggtgt gctgtgtgc   900
ccttgcggcg gcagatgcca tgcggtgcgt ggggatcggc aatcgcgatt ttgtagaagg   960
actatctggt gccacgtggg tcgatgtggt tcttgaacac gggtcatgcg tgaccacgat  1020
ggctaaggat aagccgacct tggacatcga actactgaaa accgaggtca caaaccctgc  1080
tgtgctccgc aagctgtgca tcgaggctaa gatttccaac acaactactg atagccgctg  1140
ccccaccccaa ggcgaggcga ccctcgttga agagcaggac agcaacttcg tgtgtcgccg  1200
gactttcgtg gaccgcggta atgggtccgg atgcggactt tttggaaagg gttccttact  1260
gacttgcgcc aaatttaagt gcgtgactaa gttagagggg aaaatcgttc agtatgagaa  1320
cttaaaatac tcggtgatag ttaccgtgca cacaggcgac cagcatcaag ttgggaacga  1380
aacgacagag cacgggacaa tagcgaccat taccccacag gctccaacga gcgaaattca  1440
gctgacagac tacggtgcac tcaccctgga ctgtagccca cggaccgggc tagactttaa  1500
cgagatggtg ctcctgacta tgaaggaaaa gtcatggttg gtgcacaagc agtggttcct  1560
tgatcttcca ttgccctgga cctctggcgc ttcgacctca aagagactt ggaacaggca  1620
ggacttgctc gtgacattca aaacggctca cgctaaaaag caagaggtcg tggttctggg  1680
gagtcaggaa ggcgctatgc ataccgcgtt aacagggget acagagatcc agaccagtgg  1740
aacaaccact atttttcgccg ggcatcttaa gtgtaggctg aagatggata agttgaccct  1800
gaaaggtatg tcatatgtga tgtgcaccgg tagtttcaaa ctggagaaag aagtggccga  1860
aacccagcat ggaacagtac tggtgcaagt caaatatgag ggcaccgatg caccatgtaa  1920
aataccccttc agcgcacaag acgagaaggg agttacccag aacggtaggc tgataacagc  1980
caatccaatc gtcaccgata aggagaaacc agtaaacatc gaaaccgagc cacccttcgg  2040
cgaaagctac atcgtggtcg gcgctggcga gaaagcactt aagctgagct ggtttaagaa  2100
aggtagcacg ggcggcggca gccatcatca ccatcatcac tgagctagct tgactgactg  2160
agatacagcg taccttcagc tcacagacat gataagatac attgatgagt ttggacaaac  2220
```

```
cacaactaga atgcagtgaa aaaaatgctt tatttgtgaa atttgtgatg ctattgcttt    2280
atttgtaacc attataagct gcaataaaca agttaacaac aacaattgca ttcattttat    2340
gtttcaggtt caggggggagg tgtgggaggt tttttaaagc aagtaaaacc tctacaaatg    2400
tggtattggc ccatctctat cggtatcgta gcataacccc ttggggcctc taaacgggtc    2460
ttgaggggtt ttttgtgccc ctcgggccgg attgctatct accggcattg gcgcagaaaa    2520
aaatgcctga tgcgacgctg cgcgtcttat actcccacat atgccagatt cagcaacgga    2580
tacggcttcc ccaacttgcc cacttccata cgtgtcctcc ttaccagaaa tttatcctta    2640
aggtcgtcag ctatcctgca ggcgatctct cgatttcgat caagacattc ctttaatggt    2700
cttttctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940
gcaaaaggcc aggaaccgta aaaaggccgc gttgctggcg ttttttccata ggctccgccc    3000 ccctgacgag catcacaaaa atcgacgctc aagtcagagg tggcgaaacc cgacaggact    3060
ataaagatac caggcgtttc cccctggaag ctccctcgtg cgctctcctg ttccgaccct    3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240
cgaacccccc gttcagcccg accgctgcgc cttatccggt aactatcgtc ttgagtccaa    3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
gcagattacg cgcagaaaaa aaggatctca agaagatcct ttgatctttt ctacggggtc    3600
tgacgctcag tggaacgaaa actcacgtta agggattttg gtcatgagat tatcaaaaag    3660
gatcttcacc tagatccttt taaattaaaa atgaagtttt aaatcaatct aaagtatata    3720
tgagtaaact tggtctgaca gttaccaatg cttaatcagt gaggcaccta tctcagcgat    3780
ctgtctattt cgttcatcca tagttgcatt taaatttccg aactctccaa ggccctcgtc    3840
ggaaaatctt caaacctttc gtccgatcca tcttgcaggc tacctctcga acgaactatc    3900
gcaagtctct tggccggcct tgcgccttgg ctattgcttg cagcgcctta tcgccaggta    3960
ttactccaat cccgaatatc cgagatcggg atcacccgag agaagttcaa cctacatcct    4020
caatcccgat ctatccgaga tccgaggaat atcgaaatcg gggcgcgcct ggtgtaccga    4080
gaacgatcct ctcagtgcga gtctcgacga tccatatcgt tgcttggcag tcagccagtc    4140
ggaatccagc ttgggaccca ggaagtccaa tcgtcagata ttgtactcaa gcctggtcac    4200
ggcagcgtac cgatctgttt aaacctagat attgatagtc tgatcggtca acgtataatc    4260
gagtcctagc ttttgcaaac atctatcaag agacaggatc agcaggaggc tttcgcatga    4320
gtattcaaca tttccgtgtc gcccttattc cctttttttgc ggcattttgc cttcctgttt    4380
ttgctcaccc agaaacgctg gtgaaagtaa aagatgctga agatcagttg ggtgcgcgag    4440
tgggttacat cgaactggat ctcaacagcg gtaagatcct tgagagtttt cgccccgaag    4500
aacgctttcc aatgatgagc acttttaaag ttctgctatg tggcgcggta ttatcccgta    4560
```

| | |
|---|---|
| ttgacgccgg gcaagagcaa ctcggtcgcc gcatacacta ttctcagaat gacttggttg | 4620 |
| agtattcacc agtcacagaa aagcatctta cggatggcat gacagtaaga gaattatgca | 4680 |
| gtgctgccat aaccatgagt gataacactg cggccaactt acttctgaca acgattggag | 4740 |
| gaccgaagga gctaaccgct tttttgcaca acatggggga tcatgtaact cgccttgatc | 4800 |
| gttgggaacc ggagctgaat gaagccatac caaacgacga gcgtgacacc acgatgcctg | 4860 |
| tagcaatggc aacaaccttg cgtaaactat taactggcga actacttact ctagcttccc | 4920 |
| ggcaacagtt gatagactgg atggaggcgg ataaagttgc aggaccactt ctgcgctcgg | 4980 |
| cccttccggc tggctggttt attgctgata aatctggagc cggtgagcgt gggtctcgcg | 5040 |
| gtatcattgc agcactgggg ccagatggta agccctcccg tatcgtagtt atctacacga | 5100 |
| cggggagtca ggcaactatg gatgaacgaa atagacagat cgctgagata ggtgcctcac | 5160 |
| tgattaagca ttggtaaccg attctaggtg cattggcgca gaaaaaaatg cctgatgcga | 5220 |
| cgctgcgcgt cttatactcc cacatatgcc agattcagca acggatacgg cttccccaac | 5280 |
| ttgcccactt ccatacgtgt cctccttacc agaaatttat ccttaagatc ccgaatcgtt | 5340 |
| taaactcgac tctggctcta tcgaatctcc gtcgtttcga gcttacgcga acagccgtgg | 5400 |
| cgctcatttg ctcgtcgggc atcgaatctc gtcagctatc gtcagcttac ctttttggca | 5460 |

<210> SEQ ID NO 20
<211> LENGTH: 5460
<212> TYPE: DNA
<213> ORGANISM: Artificial Sequence
<220> FEATURE:
<223> OTHER INFORMATION: Plasmid expression vector pCRO27

<400> SEQUENCE: 20

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctagt | 240 |
| aatcaattac ggggtcatta gttcatagcc catatatgga gttccgcgtt acataactta | 300 |
| cggtaaatgg cccgcctggc tgaccgccca acgacccccg cccattgacg tcaataatga | 360 |
| cgtatgttcc catagtaacg ccaatagggA ctttccattg acgtcaatgg gtggagtatt | 420 |
| tacggtaaac tgcccacttg gcagtacatc aagtgtatca tatgccaagt acgccccta | 480 |
| ttgacgtcaa tgacggtaaa tggcccgcct ggcattatgc ccagtacatg accttatggg | 540 |
| actttcctac ttggcagtac atctacgtat tagtcatcgc tattaccatg ctgatgcggt | 600 |
| tttggcagta catcaatggg cgtggatagc ggtttgactc acggggattt ccaagtctcc | 660 |
| accccattga cgtcaatggg agtttgtttt ggcaccaaaa tcaacgggac tttccaaaat | 720 |
| gtcgtaacaa ctccgcccca ttgacgcaaa tgggcggtag gcgtgtacgg tgggaggtct | 780 |
| atataagcag agctggttta gtgaaccgtc agatcagatc tttgtcgatc ctaccatcca | 840 |
| ctcgacacac ccgccagcgg ccgccaccat gaaggccaat ctactggtgt gctgtgtgc | 900 |
| ccttgcggcg gcagatgcca tcggtcgt ggggatcggc aatcgcgatt tgtagaagg | 960 |
| actatctggt gccacgtggg tcgatgtggt tcttgaacac gggtcatgcg tgaccacgat | 1020 |
| ggctaaggat aagccgacct tggacatcga actactgaaa accgaggtca caaaccctgc | 1080 |
| tgtgctccgc aagctgtgca tcgaggctaa gattccaac acaactactg atagccgctg | 1140 |
| ccccacccaa ggcgaggcga ccctcgttga agagcaggac agcaacttcg tgtgtcgccg | 1200 |

-continued

```
gactttcgtg gaccgcggtt gggggaatgg atgcggactt aacgatctg gttccttact    1260 gacttgcgcc aaatttaagt gcgtgactaa gttagagggg aaaatcgttc agtatgagaa    1320
cttaaaatac tcggtgatag ttaccgtgca cacaggcgac cagcatcaag ttgggaacga    1380
aacgacagag cacgggacaa tagcgaccat taccccacag gctccaacga gcgaaattca    1440
gctgacagac tacggtgcac tcaccctgga ctgtagccca cggaccgggc tagactttaa    1500
cgagatggtg ctcctgacta tgaaggaaaa gtcatggttg gtgcacaagc agtggttcct    1560
tgatcttcca ttgccctgga cctctggcgc ttcgacctca caagagactt ggaacaggca    1620
ggacttgctc gtgacattca aaacggctca cgctaaaaag caagaggtcg tggttctggg    1680
gagtcaggaa ggcgctatgc ataccgcgtt aacagggct acagagatcc agaccagtgg     1740
aacaaccact attttcgccg ggcatcttaa gtgtaggctg aagatggata agttgaccct    1800
gaaaggtatg tcatatgtga tgtgcaccgg tagtttcaaa ctggagaaag aagtggccga    1860
aacccagcat ggaacagtac tggtgcaagt caaatatgag gcaccgatg caccatgtaa     1920 aatacccttc agcgcacaag acgagaaggg agttacccag aacggtaggc tgataacagc    1980
caatccaatc gtcaccgata aggagaaacc agtaaacatc gaaaccgagc cacccttcgg    2040
cgaaagctac atcgtggtcg gcgctggcga gaaagcactt aagctgagct ggtttaagaa    2100
aggtagcacg ggcggcggca gccatcatca ccatcatcac tgagctagct tgactgactg    2160
agatacagcg taccttcagc tcacagacat gataagatac attgatgagt ttggacaaac    2220
cacaactaga atgcagtgaa aaaaatgctt tatttgtgaa atttgtgatg ctattgcttt    2280
atttgtaacc attataagct gcaataaaca agttaacaac acaattgca ttcattttat     2340 gtttcaggtt caggggggagg tgtgggaggt tttttaaagc aagtaaaacc tctacaaatg    2400
tggtattggc ccatctctat cggtatcgta gcataacccc ttggggcctc taaacgggtc    2460
ttgaggggtt ttttgtgccc ctcgggccgg attgctatct accggcattg gcgcagaaaa    2520
aaatgcctga tgcgacgctg cgcgtcttat actcccacat atgccagatt cagcaacgga    2580
tacggcttcc ccaacttgcc cacttccata cgtgtcctcc ttaccagaaa tttatcctta    2640
aggtcgtcag ctatcctgca ggcgatctct cgatttcgat caagacattc ctttaatggt    2700
cttttctgga caccactagg ggtcagaagt agttcatcaa actttcttcc ctccctaatc    2760
tcattggtta ccttgggcta tcgaaactta attaaccagt caagtcagct acttggcgag    2820
atcgacttgt ctgggtttcg actacgctca gaattgcgtc agtcaagttc gatctggtcc    2880
ttgctattgc acccgttctc cgattacgag tttcatttaa atcatgtgag caaaaggcca    2940
gcaaaaggcc aggaaccgta aaaaggccgc gttgctggcg ttttttccata ggctccgccc    3000 ccctgacgag catcacaaaa atcgacgctc aagtcagagg tggcgaaacc cgacaggact    3060
ataaagatac caggcgtttc cccctggaag ctccctcgtg cgctctcctg ttccgaccct    3120
gccgcttacc ggatacctgt ccgcctttct cccttcggga agcgtggcgc tttctcatag    3180
ctcacgctgt aggtatctca gttcggtgta ggtcgttcgc tccaagctgg gctgtgtgca    3240 cgaaccccc gttcagcccg accgctgcgc cttatccggt aactatcgtc ttgagtccaa     3300
cccggtaaga cacgacttat cgccactggc agcagccact ggtaacagga ttagcagagc    3360
gaggtatgta ggcggtgcta cagagttctt gaagtggtgg cctaactacg gctacactag    3420
aagaacagta tttggtatct gcgctctgct gaagccagtt accttcggaa aaagagttgg    3480
tagctcttga tccggcaaac aaaccaccgc tggtagcggt ggtttttttg tttgcaagca    3540
```

| | |
|---|---|
| gcagattacg cgcagaaaaa aaggatctca agaagatcct ttgatctttt ctacggggtc | 3600 |
| tgacgctcag tggaacgaaa actcacgtta agggattttg gtcatgagat tatcaaaaag | 3660 |
| gatcttcacc tagatccttt taaattaaaa atgaagtttt aaatcaatct aaagtatata | 3720 |
| tgagtaaact tggtctgaca gttaccaatg cttaatcagt gaggcaccta tctcagcgat | 3780 |
| ctgtctattt cgttcatcca tagttgcatt taaatttccg aactctccaa ggccctcgtc | 3840 |
| ggaaaatctt caaacctttc gtccgatcca tcttgcaggc tacctctcga acgaactatc | 3900 |
| gcaagtctct tggccggcct tgcgccttgg ctattgcttg gcagcgccta tcgccaggta | 3960 |
| ttactccaat cccgaatatc cgagatcggg atcacccgag agaagttcaa cctacatcct | 4020 |
| caatcccgat ctatccgaga tccgaggaat atcgaaatcg gggcgcgcct ggtgtaccga | 4080 |
| gaacgatcct ctcagtgcga gtctcgacga tccatatcgt tgcttggcag tcagccagtc | 4140 |
| ggaatccagc ttgggaccca ggaagtccaa tcgtcagata ttgtactcaa gcctggtcac | 4200 |
| ggcagcgtac cgatctgttt aaacctagat attgatagtc tgatcggtca acgtataatc | 4260 |
| gagtcctagc ttttgcaaac atctatcaag agacaggatc agcaggaggc tttcgcatga | 4320 |
| gtattcaaca tttccgtgtc gcccttattc cctttttgc ggcattttgc cttcctgttt | 4380 |
| ttgctcaccc agaaacgctg gtgaaagtaa aagatgctga agatcagttg ggtgcgcgag | 4440 |
| tgggttacat cgaactggat ctcaacagcg gtaagatcct tgagagtttt cgccccgaag | 4500 |
| aacgctttcc aatgatgagc acttttaaag ttctgctatg tggcgcggta ttatcccgta | 4560 |
| ttgacgccgg gcaagagcaa ctcggtcgcc gcatacacta ttctcagaat gacttggttg | 4620 |
| agtattcacc agtcacagaa aagcatctta cggatggcat gacagtaaga gaattatgca | 4680 |
| gtgctgccat aaccatgagt gataacactg cggccaactt acttctgaca acgattggag | 4740 |
| gaccgaagga gctaaccgct tttttgcaca acatggggga tcatgtaact cgccttgatc | 4800 |
| gttgggaacc ggagctgaat gaagccatac caaacgacga gcgtgacacc acgatgcctg | 4860 |
| tagcaatggc aacaaccttg cgtaaactat taactggcga actacttact ctagcttccc | 4920 |
| ggcaacagtt gatagactgg atggaggcgg ataaagttgc aggaccactt ctgcgctcgg | 4980 |
| cccttccggc tggctggttt attgctgata aatctggagc cggtgagcgt gggtctcgcg | 5040 |
| gtatcattgc agcactgggg ccagatggta agccctcccg tatcgtagtt atctacacga | 5100 |
| cggggagtca ggcaactatg gatgaacgaa atagacagat cgctgagata ggtgcctcac | 5160 |
| tgattaagca ttggtaaccg attctaggtg cattggcgca gaaaaaaatg cctgatgcga | 5220 |
| cgctgcgcgt cttatactcc cacatatgcc agattcagca acggatacgg cttccccaac | 5280 |
| ttgcccactt ccatacgtgt cctccttacc agaaatttat ccttaagatc ccgaatcgtt | 5340 |
| taaactcgac tctggctcta tcgaatctcc gtcgtttcga gcttacgcga acagccgtgg | 5400 |
| cgctcatttg ctcgtcgggc atcgaatctc gtcagctatc gtcagcttac cttttttggca | 5460 |

<210> SEQ ID NO 21
<211> LENGTH: 5502
<212> TYPE: DNA
<213> ORGANISM: Artificial Sequence
<220> FEATURE:
<223> OTHER INFORMATION: Plasmid expression vector pCRO29

<400> SEQUENCE: 21

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |

```
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgaccccg cccattgacg tcaataatga    360
cgtatgttcc catagtaacg ccaatagga ctttccattg acgtcaatgg gtggagtatt    420
tacggtaaac tgcccacttg gcagtacatc aagtgtatca tatgccaagt acgcccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag cgtgtacgg tgggaggtct    780
atataagcag agctggttta gtgaaccgtc agatcagatc tttgtcgatc ctaccatcca    840
ctcgacacac cgccagcgg ccgccaccat gaaggccaat ctactggtgt tgctgtgtgc    900
ccttgcggcg gcagatgcca tcaggtgcat tggagtcagc aacagggact tcgtcgaagg    960
catgtccggc ggcaccctgg tggatgtggt gctcgaacac ggcggatgcg tgaccgtcat   1020
ggcccaggac aagcctaccg tcgatattga gctggtgacc accacagtga gcaacatggc   1080
cgaagtgaga agctactgct atgaggcctc catcagcgat atggcttccg attccagatg   1140
ccccacacag ggagaggctt atctggacaa acagtccgac acccagtacg tctgcaaaag   1200
aaccctggtg gacagaggct ggggaaacgg atgcggcaac cacaccaaag gcagcctcgt   1260
gacatgtgcc aagttcgcct gcagcaaaaa gatgaccggc aagtccatcc agcccgagaa   1320
cctggaatac aggatcatgc tgtccgtgca tggatcccag cactccggca tgatcgtcaa   1380
cgataccggc cacgagaccg acgagaacag ggctaaagtg gagatcaccc ccaacagccc   1440
tagagccgaa gctacactgg gcggcttcgg aagcctgggc ctggattgcg aacccaggac   1500
cggcctggat ttcagcgacc tgtattacct gaccatgaac aataagcact ggctggtgca   1560
caaggaatgg ttccacgaca tcccctgcc ttggcatgct ggcgccgata ccggcacacc   1620
tcactggaac aataaggaag ccctggtcga gtttaaggac gcccacgcca aaagacagac   1680
cgtggtggtg ctgggaagcc aggagggagc tgtccacaca gccctggccg gagctctgga   1740
agccgagatg gatggcgcca agggcaggct gagctccggc cacctgaaat gcaggctcaa   1800
gatggacaag ctgaggctga gggcgtgag ctacagcctg tgcaccgccg ctttcacctt   1860
taccaagatc cctgccgaga cactgcacgg caccgtcacc gtggaggtgc aatacgccgg   1920
aaccgatgga ccttgcaaag tgcctgccca gatggctgtg gatatgcaga ccctcacacc   1980
cgtcggcagg ctgatcaccg ccaatcccgt cattaccgag tccaccgaga acagcaagat   2040
gatgctcgag ctcgatcccc cctttggcga cagctacatt gtgatcggcg tgggcgagaa   2100
gaagatcacc accattggc acagaagcgg ctccacaggg ggtagcggtg gtagcggagg   2160
tagccatcac caccatcacc actgagctag cttgactgac tgagatacag cgtaccttca   2220
gctcacagac atgataagat acattgatga gtttggacaa accacaacta gaatgcagtg   2280
aaaaaaatgc tttatttgtg aaatttgtga tgctattgct ttatttgtaa ccattataag   2340
ctgcaataaa caagttaaca acaacaattg cattcatttt atgtttcagg ttcaggggga   2400
ggtgtgggag gttttttaaa gcaagtaaaa cctctacaaa tgtggtattg gcccatctct   2460
atcggtatcg tagcataacc ccttggggcc tctaaacggg tcttgagggg ttttttgtgc   2520
```

```
ccctcgggcc ggattgctat ctaccggcat tggcgcagaa aaaaatgcct gatgcgacgc    2580
tgcgcgtctt atactcccac atatgccaga ttcagcaacg gatacggctt ccccaacttg    2640
cccacttcca tacgtgtcct ccttaccaga aatttatcct taaggtcgtc agctatcctg    2700
caggcgatct ctcgatttcg atcaagacat tcctttaatg gtcttttctg acaccacta     2760 ggggtcagaa gtagttcatc aaactttctt ccctccctaa tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttttcca taggctccgc ccccctgacg agcatcacaa   3060
aaatcgacgc tcaagtcaga ggtggcgaaa cccgacagga ctataaagat accaggcgtt    3120 tcccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc cgttcagcc     3300 cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaaagagtt ggtagctctt gatccggcaa    3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag gctttcgcat gagtattcaa catttccgtg    4380
tcgcccttat tcccttttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560
gcacttttaa agttctgcta tgtggcgcgg tattatcccg tattgacgcc gggcaagagc    4620
aactcggtcg ccgcatacac tattctcaga atgacttggt tgagtattca ccagtcacag    4680
aaaagcatct tacggatggc atgacagtaa gagaattatg cagtgctgcc ataaccatga    4740
gtgataacac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
```

```
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
ggccagatgg taagccctcc cgtatcgtag ttatctacac gacggggagt caggcaacta    5160
tggatgaacg aaatagacag atcgctgaga taggtgcctc actgattaag cattggtaac    5220
cgattctagg tgcattggcg cagaaaaaaa tgcctgatgc gacgctgcgc gtcttatact    5280
cccacatatg ccagattcag caacggatac ggcttcccca acttgcccac ttccatacgt    5340
gtcctcctta ccagaaattt atccttaaga tcccgaatcg tttaaactcg actctggctc    5400
tatcgaatct ccgtcgtttc gagcttacgc gaacagccgt ggcgtcatt tgctcgtcgg     5460 gcatcgaatc tcgtcagcta tcgtcagctt acctttttgg ca                      5502

<210> SEQ ID NO 22
<211> LENGTH: 5502
<212> TYPE: DNA
<213> ORGANISM: Artificial Sequence
<220> FEATURE:
<223> OTHER INFORMATION: Plasmid expression vector pCRO30

<400> SEQUENCE: 22
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga     360
cgtatgttcc catagtaacg ccaataggga ctttccattg acgtcaatgg gtggagtatt     420
tacggtaaac tgcccacttg gcagtacatc aagtgtatca tatgccaagt acgccccta     480 ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag gcgtgtacgg tgggaggtct     780
atataagcag agctggttta gtgaaccgtc agatcagatc tttgtcgatc ctaccatcca     840
ctcgacacac cgccagcgg ccgccaccat gaaggccaat ctactggtgt gctgtgtgc     900 ccttgcggcg gcagatgcca tcaggtgcat tggagtcagc aacagggact tcgtcgaagg     960
catgtccggc ggcacctggg tggatgtggt gctcgaacac ggcggatgcg tgaccgtcat    1020
ggcccaggac aagcctaccg tcgatattga gctggtgacc accacagtga gcaacatggc    1080
cgaagtgaga agctactgct atgaggcctc catcagcgat atggcttccg attccagatg    1140
ccccacacag ggagaggctt atctggacaa acagtccgac acccagtacg tctgcaaaag    1200
aaccctggtg gacagaggca acggatccgg atgcggcctg ttcggcaaag gcagcctcgt    1260
gacatgtgcc aagttcgcct gcagcaaaaa gatgaccggc aagtccatcc agcccgagaa    1320
cctggaatac aggatcatgc tgtccgtgca tggatcccag cactccggca tgatcgtcaa    1380
cgataccggc cacgagaccg acgagaacag ggctaaagtg gagatcaccc ccaacagccc    1440
```

```
tagagccgaa gctacactgg gcggcttcgg aagcctgggc ctggattgcg aacccaggac   1500
cggcctggat ttcagcgacc tgtattacct gaccatgaac aataagcact ggctggtgca   1560
caaggaatgg ttccacgaca tccccctgcc ttggcatgct ggcgccgata ccggcacacc   1620
tcactggaac aataaggaag ccctggtcga gtttaaggac gcccacgcca aaagacagac   1680
cgtggtggtg ctgggaagcc aggagggagc tgtccacaca gccctggccg gagctctgga   1740
agccgagatg gatggcgcca agggcaggct gagctccggc cacctgaaat gcaggctcaa   1800
gatggacaag ctgaggctga agggcgtgag ctacagcctg tgcaccgccg ctttcacctt   1860
taccaagatc cctgccgaga cactgcacgg caccgtcacc gtggaggtgc aatacgccgg   1920
aaccgatgga ccttgcaaag tgcctgccca gatggctgtg gatatgcaga ccctcacacc   1980
cgtcggcagg ctgatcaccg ccaatcccgt cattaccgag tccaccgaga cagcaagat    2040 gatgctcgag ctcgatcccc cctttggcga cagctacatt gtgatcggcg tgggcgagaa   2100
gaagatcacc caccattggc acagaagcgg ctccacaggg ggtagcggtg gtagcggagg   2160
tagccatcac caccatcacc actgagctag cttgactgac tgagatacag cgtaccttca   2220
gctcacagac atgataagat acattgatga gtttggacaa accacaacta gaatgcagtg   2280
aaaaaaatgc tttatttgtg aaatttgtga tgctattgct ttatttgtaa ccattataag   2340
ctgcaataaa caagttaaca acaacaattg cattcatttt atgtttcagg ttcagggga    2400 ggtgtgggag gttttttaaa gcaagtaaaa cctctacaaa tgtggtattg gcccatctct   2460
atcggtatcg tagcataacc ccttggggcc tctaaacggg tcttgagggg ttttttgtgc   2520
ccctcgggcc ggattgctat ctaccggcat ggcgcagaa aaaaatgcct gatgcgacgc     2580
tgcgcgtctt atactcccac atatgccaga ttcagcaacg gatacggctt ccccaacttg   2640
cccacttcca tacgtgtcct ccttaccaga aatttatcct taaggtcgtc agctatcctg   2700
caggcgatct ctcgatttcg atcaagacat tcctttaatg gtcttttctg gacaccacta   2760
ggggtcagaa gtagttcatc aaactttctt ccctccctaa tctcattggt taccttgggc   2820
tatcgaaact taattaacca gtcaagtcag ctacttggcg agatcgactt gtctgggttt   2880
cgactacgct cagaattgcg tcagtcaagt tcgatctggt ccttgctatt cacccgttc    2940 tccgattacg agtttcattt aaatcatgtg agcaaaaggc cagcaaaagg ccaggaaccg   3000
taaaaaggcc gcgttgctgg cgttttccca taggctccgc cccctgacg agcatcacaa    3060 aaatcgacgc tcaagtcaga ggtggcgaaa cccgacagga ctataaagat accaggcgtt   3120
tccccctgga agctccctcg tgcgctctcc tgttccgacc ctgccgctta ccggatacct   3180
gtccgccttt ctcccttcgg gaagcgtggc gctttctcat agctcacgct gtaggtatct   3240
cagttcggtg taggtcgttc gctccaagct gggctgtgtg cacgaacccc ccgttcagcc   3300
cgaccgctgc gccttatccg gtaactatcg tcttgagtcc aacccggtaa gacacgactt   3360
atcgccactg gcagcagcca ctggtaacag gattagcaga gcgaggtatg taggcggtgc   3420
tacagagttc ttgaagtggt ggcctaacta cggctacact agaagaacag tatttggtat   3480
ctgcgctctg ctgaagccag ttaccttcgg aaaaagagtt ggtagctctt gatccggcaa   3540
acaaaccacc gctggtagcg gtggtttttt tgtttgcaag cagcagatta cgcgcagaaa   3600
aaaaggatct caagaagatc ctttgatctt ttctacgggg tctgacgctc agtggaacga   3660
aaactcacgt taagggattt tggtcatgag attatcaaaa aggatcttca cctagatcct   3720
tttaaattaa aaatgaagtt ttaaatcaat ctaaagtata tatgagtaaa cttggtctga   3780
cagttaccaa tgcttaatca gtgaggcacc tatctcagcg atctgtctat ttcgttcatc   3840
```

-continued

| | |
|---|---|
| catagttgca tttaaatttc cgaactctcc aaggccctcg tcggaaaatc ttcaaacctt | 3900 |
| tcgtccgatc catcttgcag gctacctctc gaacgaacta tcgcaagtct cttggccggc | 3960 |
| cttgcgcctt ggctattgct tggcagcgcc tatcgccagg tattactcca atcccgaata | 4020 |
| tccgagatcg ggatcacccg agagaagttc aacctacatc ctcaatcccg atctatccga | 4080 |
| gatccgagga atatcgaaat cggggcgcgc ctggtgtacc gagaacgatc ctctcagtgc | 4140 |
| gagtctcgac gatccatatc gttgcttggc agtcagccag tcggaatcca gcttgggacc | 4200 |
| caggaagtcc aatcgtcaga tattgtactc aagcctggtc acggcagcgt accgatctgt | 4260 |
| ttaaacctag atattgatag tctgatcggt caacgtataa tcgagtccta gcttttgcaa | 4320 |
| acatctatca agagacagga tcagcaggag ctttcgcat gagtattcaa catttccgtg | 4380 |
| tcgcccttat tcccttttt gcggcatttt gccttcctgt ttttgctcac ccagaaacgc | 4440 |
| tggtgaaagt aaaagatgct gaagatcagt tgggtgcgcg agtgggttac atcgaactgg | 4500 |
| atctcaacag cggtaagatc cttgagagtt tcgcccccga agaacgcttt ccaatgatga | 4560 |
| gcacttttaa agttctgcta tgtggcgcgg tattatcccg tattgacgcc gggcaagagc | 4620 |
| aactcggtcg ccgcatacac tattctcaga atgacttggt tgagtattca ccagtcacag | 4680 |
| aaaagcatct tacggatggc atgacagtaa gagaattatg cagtgctgcc ataaccatga | 4740 |
| gtgataacac tgcggccaac ttacttctga caacgattgg aggaccgaag gagctaaccg | 4800 |
| cttttttgca caacatgggg gatcatgtaa ctcgccttga tcgttgggaa ccggagctga | 4860 |
| atgaagccat accaaacgac gagcgtgaca ccacgatgcc tgtagcaatg caacaacct | 4920 |
| tgcgtaaact attaactggc gaactactta ctctagcttc ccggcaacag ttgatagact | 4980 |
| ggatggaggc ggataaagtt gcaggaccac ttctgcgctc ggcccttccg gctggctggt | 5040 |
| ttattgctga taaatctgga gccggtgagc gtgggtctcg cggtatcatt gcagcactgg | 5100 |
| ggccagatgg taagccctcc cgtatcgtag ttatctacac gacggggagt caggcaacta | 5160 |
| tggatgaacg aaatagacag atcgctgaga taggtgcctc actgattaag cattggtaac | 5220 |
| cgattctagg tgcattggcg cagaaaaaaa tgcctgatgc gacgctgcgc gtcttatact | 5280 |
| cccacatatg ccagattcag caacggatac ggcttcccca acttgccac ttccatacgt | 5340 |
| gtcctcctta ccagaaattt atccttaaga tcccgaatcg tttaaactcg actctggctc | 5400 |
| tatcgaatct ccgtcgtttc gagcttacgc gaacagccgt ggcgctcatt tgctcgtcgg | 5460 |
| gcatcgaatc tcgtcagcta tcgtcagctt accttttggg ca | 5502 |

<210> SEQ ID NO 23
<211> LENGTH: 5502
<212> TYPE: DNA
<213> ORGANISM: Artificial Sequence
<220> FEATURE:
<223> OTHER INFORMATION: Plasmid expression vector pCRO31

<400> SEQUENCE: 23

| | |
|---|---|
| gcgatcgcgg ctcccgacat cttggaccat tagctccaca ggtatcttct tccctctagt | 60 |
| ggtcataaca gcagcttcag ctacctctca attcaaaaaa cccctcaaga cccgtttaga | 120 |
| ggccccaagg ggttatgcta tcaatcgttg cgttacacac acaaaaaacc aacacacatc | 180 |
| catcttcgat ggatagcgat tttattatct aactgctgat cgagtgtagc cagatctagt | 240 |
| aatcaattac ggggtcatta gttcatagcc catatatgga gttccgcgtt acataactta | 300 |
| cggtaaatgg cccgcctggc tgaccgccca acgacccccg cccattgacg tcaataatga | 360 |

```
cgtatgttcc catagtaacg ccaataggga ctttccattg acgtcaatgg gtggagtatt    420
tacggtaaac tgcccacttg gcagtacatc aagtgtatca tatgccaagt acgccccta     480 ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcgg ccgccaccat gaaggccaat ctactggtgt tgctgtgtgc    900
ccttgcggcg gcagatgcca tcaggtgcat tggagtcagc aacagggact cgtcgaagg     960 catgtccggc ggcacctggg tggatgtggt gctcgaacac ggcggatgcg tgaccgtcat    1020
ggcccaggac aagcctaccg tcgatattga gctggtgacc accacagtga gcaacatggc    1080
cgaagtgaga agctactgct atgaggcctc catcagcgat atggcttccg attccagatg    1140
ccccacacag ggagaggctt atctggacaa acagtccgac acccagtacg tctgcaaaag    1200 aacccctggtg gacagaggct ggggaaacgg atgcggcctg aacggatccg gcagcctcgt    1260
gacatgtgcc aagttcgcct gcagcaaaaa gatgaccggc aagtccatcc agcccgagaa    1320
cctggaatac aggatcatgc tgtccgtgca tggatcccag cactccggca tgatcgtcaa    1380
cgataccggc cacgagaccg acgagaacag ggctaaagtg gagatcaccc ccaacagccc    1440
tagagccgaa gctacactgg gcggcttcgg aagcctgggc ctggattgcg aacccaggac    1500
cggcctggat ttcagcgacc tgtattacct gaccatgaac aataagcact ggctggtgca    1560
caaggaatgg ttccacgaca tcccctgcc ttggcatgct ggcgccgata ccggcacacc     1620
tcactggaac aataaggaag ccctggtcga gtttaaggac gcccacgcca aagacagac     1680 cgtggtggtg ctgggaagcc aggagggagc tgtccacaca gccctggccg agctctgga    1740 agccgagatg gatggcgcca agggcaggct gagctccggc cacctgaaat gcaggctcaa    1800
gatggacaag ctgaggctga agggcgtgag ctacagcctg tgcaccgccg ctttcacctt    1860
taccaagatc cctgccgaga cactgcacgg caccgtcacc gtggaggtgc aatacgccgg    1920
aaccgatgga ccttgcaaag tgcctgccca gatggctgtg gatatgcaga ccctcacacc    1980
cgtcggcagg ctgatcaccg ccaatcccgt cattaccgag tccaccgaga acagcaagat    2040
gatgctcgag ctcgatcccc cctttggcga cagctacatt gtgatcggcg tgggcgagaa    2100
gaagatcacc caccattggc acagaagcgg ctccacaggg ggtagcggtg gtagcggagg    2160
tagccatcac caccatcacc actgagctag cttgactgac tgagatacag cgtaccttca    2220
gctcacagac atgataagat acattgatga gtttggacaa accacaacta gaatgcagtg    2280
aaaaaaatgc tttatttgtg aaatttgtga tgctattgct ttatttgtaa ccattataag    2340
ctgcaataaa caagttaaca acaacaattg cattcatttt atgtttcagg ttcaggggga    2400
ggtgtgggag gttttttaaa gcaagtaaaa cctctacaaa tgtggtattg gcccatctct    2460
atcggtatcg tagcataacc ccttgggggcc tctaaacggg tcttgagggg ttttttgtgc    2520
ccctcgggcc ggattgctat ctaccggcat ggcgcagaa aaaatgcct gatgcgacgc      2580 tgcgcgtctt atactcccac atatgccaga ttcagcaacg gatacggctt ccccaacttg    2640
cccacttcca tacgtgtcct ccttaccaga aattatcct taaggtcgtc agctatcctg     2700
caggcgatct ctcgatttcg atcaagacat tcctttaatg gtcttttctg gacaccacta    2760
```

-continued

```
ggggtcagaa gtagttcatc aaactttctt ccctccctaa tctcattggt taccttgggc    2820
tatcgaaact taattaacca gtcaagtcag ctacttggcg agatcgactt gtctgggttt    2880
cgactacgct cagaattgcg tcagtcaagt tcgatctggt ccttgctatt gcacccgttc    2940
tccgattacg agtttcattt aaatcatgtg agcaaaaggc cagcaaaagg ccaggaaccg    3000
taaaaaggcc gcgttgctgg cgttttttcca taggctccgc cccctgacg agcatcacaa    3060 aaatcgacgc tcaagtcaga ggtggcgaaa cccgacagga ctataaagat accaggcgtt    3120
tccccctgga agctccctcg tgcgctctcc tgttccgacc ctgccgctta ccggatacct    3180
gtccgccttt ctcccttcgg gaagcgtggc gctttctcat agctcacgct gtaggtatct    3240
cagttcggtg taggtcgttc gctccaagct gggctgtgtg cacgaacccc ccgttcagcc    3300
cgaccgctgc gccttatccg gtaactatcg tcttgagtcc aacccggtaa gacacgactt    3360
atcgccactg gcagcagcca ctggtaacag gattagcaga gcgaggtatg taggcggtgc    3420
tacagagttc ttgaagtggt ggcctaacta cggctacact agaagaacag tatttggtat    3480
ctgcgctctg ctgaagccag ttaccttcgg aaaaagagtt ggtagctctt gatccggcaa    3540
acaaaccacc gctggtagcg gtggtttttt tgtttgcaag cagcagatta cgcgcagaaa    3600
aaaaggatct caagaagatc ctttgatctt ttctacgggg tctgacgctc agtggaacga    3660
aaactcacgt taagggattt tggtcatgag attatcaaaa aggatcttca cctagatcct    3720
tttaaattaa aaatgaagtt ttaaatcaat ctaaagtata tatgagtaaa cttggtctga    3780
cagttaccaa tgcttaatca gtgaggcacc tatctcagcg atctgtctat ttcgttcatc    3840
catagttgca tttaaatttc cgaactctcc aaggccctcg tcggaaaatc ttcaaacctt    3900
tcgtccgatc catcttgcag gctacctctc gaacgaacta tcgcaagtct cttggccggc    3960
cttgcgcctt ggctattgct tggcagcgcc tatcgccagg tattactcca atcccgaata    4020
tccgagatcg ggatcacccg agagaagttc aacctacatc ctcaatcccg atctatccga    4080
gatccgagga atatcgaaat cggggcgcgc ctggtgtacc gagaacgatc ctctcagtgc    4140
gagtctcgac gatccatatc gttgcttggc agtcagccag tcggaatcca gcttgggacc    4200
caggaagtcc aatcgtcaga tattgtactc aagcctggtc acggcagcgt accgatctgt    4260
ttaaacctag atattgatag tctgatcggt caacgtataa tcgagtccta gcttttgcaa    4320
acatctatca agagacagga tcagcaggag gctttcgcat gagtattcaa catttccgtg    4380
tcgcccttat tcccttttttt gcggcatttt gccttcctgt ttttgctcac ccagaaacgc    4440
tggtgaaagt aaaagatgct gaagatcagt tgggtgcgcg agtgggttac atcgaactgg    4500
atctcaacag cggtaagatc cttgagagtt ttcgccccga agaacgcttt ccaatgatga    4560
gcacttttaa agttctgcta tgtggcgcgg tattatcccg tattgacgcc gggcaagagc    4620
aactcggtcg ccgcatacac tattctcaga atgacttggt tgagtattca ccagtcacag    4680
aaaagcatct tacggatggc atgacagtaa gagaattatg cagtgctgcc ataaccatga    4740
gtgataacac tgcggccaac ttacttctga caacgattgg aggaccgaag gagctaaccg    4800
cttttttgca caacatgggg gatcatgtaa ctcgccttga tcgttgggaa ccggagctga    4860
atgaagccat accaaacgac gagcgtgaca ccacgatgcc tgtagcaatg gcaacaacct    4920
tgcgtaaact attaactggc gaactactta ctctagcttc ccggcaacag ttgatagact    4980
ggatggaggc ggataaagtt gcaggaccac ttctgcgctc ggcccttccg gctggctggt    5040
ttattgctga taaatctgga gccggtgagc gtgggtctcg cggtatcatt gcagcactgg    5100
```

-continued

```
ggccagatgg taagccctcc cgtatcgtag ttatctacac gacggggagt caggcaacta    5160
tggatgaacg aaatagacag atcgctgaga taggtgcctc actgattaag cattggtaac    5220
cgattctagg tgcattggcg cagaaaaaaa tgcctgatgc gacgctgcgc gtcttatact    5280
cccacatatg ccagattcag caacggatac ggcttcccca acttgcccac ttccatacgt    5340
gtcctcctta ccagaaattt atccttaaga tcccgaatcg tttaaactcg actctggctc    5400
tatcgaatct ccgtcgtttc gagcttacgc gaacagccgt ggcgctcatt tgctcgtcgg    5460
gcatcgaatc tcgtcagcta tcgtcagctt acctttttgg ca                       5502
```

<210> SEQ ID NO 24
<211> LENGTH: 407
<212> TYPE: PRT
<213> ORGANISM: Artificial Sequence
<220> FEATURE:
<223> OTHER INFORMATION: Hyperglycosylated exodomain D1 (from pCRO21)

<400> SEQUENCE: 24

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ser Asn Phe Val Cys Arg Arg Thr Phe
                85                  90                  95

Val Asp Arg Gly Asn Gly Ser Gly Cys Gly Leu Asn Gly Ser Gly Ser
            100                 105                 110

Leu Leu Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
```

```
                  290                 295                 300

Ser Phe Lys Leu Glu Lys Glu Val Ala Glu Thr Gln His Gly Thr Val
305                 310                 315                 320

Leu Val Gln Val Lys Tyr Gly Thr Asp Ala Pro Cys Lys Ile Pro
                325                 330                 335

Phe Ser Ala Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
                355                 360                 365

Thr Glu Pro Pro Phe Gly Glu Ser Tyr Ile Val Val Gly Ala Gly Glu
                370                 375                 380

Lys Ala Leu Lys Leu Ser Trp Phe Lys Lys Gly Ser Thr Gly Gly Gly
385                 390                 395                 400

Ser His His His His His His
                405

<210> SEQ ID NO 25
<211> LENGTH: 407
<212> TYPE: PRT
<213> ORGANISM: Artificial Sequence
<220> FEATURE:
<223> OTHER INFORMATION: Hyperglycosylated exodomain D2 (from pCRO22)

<400> SEQUENCE: 25

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
                35                  40                  45

Glu Ala Lys Gln Pro Ala Thr Leu Arg Lys Tyr Cys Ile Glu Ala Lys
            50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Asn Gly Ser Gly Cys Gly Leu Asn Gly Ser Gly Gly
                100                 105                 110

Ile Val Thr Cys Ala Met Phe Thr Cys Lys Lys Asn Met Glu Gly Lys
            115                 120                 125

Val Val Gln Pro Glu Asn Leu Glu Tyr Thr Ile Val Ile Thr Pro His
            130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
            210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
```

-continued

```
                    245                 250                 255
Glu Gly Ala Met His Thr Ala Leu Thr Gly Ala Thr Glu Ile Gln Met
                260                 265                 270
Ser Ser Gly Asn Leu Leu Phe Thr Gly His Leu Lys Cys Arg Leu Arg
            275                 280                 285
Met Asp Lys Leu Gln Leu Lys Gly Met Ser Tyr Ser Met Cys Thr Gly
        290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Met Asp Leu Glu Lys Arg His Val Leu Gly Arg Leu Ile
                340                 345                 350
Thr Val Asn Pro Ile Val Thr Glu Lys Asp Ser Pro Val Asn Ile Glu
            355                 360                 365
Ala Glu Pro Pro Phe Gly Asp Ser Tyr Ile Ile Gly Val Glu Pro
        370                 375                 380
Gly Gln Leu Lys Leu Asn Trp Phe Lys Lys Gly Ser Ser Gly Gly
385                 390                 395                 400
Ser His His His His His His
            405
```

<210> SEQ ID NO 26
<211> LENGTH: 405
<212> TYPE: PRT
<213> ORGANISM: Artificial Sequence
<220> FEATURE:
<223> OTHER INFORMATION: Hyperglycosylated exodomain D3 (from pCRO23)

<400> SEQUENCE: 26

```
Met Arg Cys Val Gly Val Gly Asn Arg Asp Phe Val Glu Gly Leu Ser
1               5                   10                  15
Gly Ala Thr Trp Val Asp Val Val Leu Glu His Gly Gly Cys Val Thr
                20                  25                  30
Thr Met Ala Lys Asn Lys Pro Thr Leu Asp Ile Glu Leu Gln Lys Thr
            35                  40                  45
Glu Ala Thr Gln Leu Ala Thr Leu Arg Lys Leu Cys Ile Glu Gly Lys
        50                  55                  60
Ile Thr Asn Ile Thr Thr Asp Ser Arg Cys Pro Thr Gln Gly Glu Ala
65                  70                  75                  80
Val Leu Pro Glu Glu Gln Asp Gln Asn Tyr Val Cys Lys His Thr Tyr
                85                  90                  95
Val Asp Arg Gly Asn Gly Ser Gly Cys Gly Leu Asn Gly Ser Gly Ser
            100                 105                 110
Leu Val Thr Cys Ala Lys Phe Gln Cys Leu Glu Pro Ile Glu Gly Lys
        115                 120                 125
Val Val Gln Tyr Glu Asn Leu Lys Tyr Thr Val Ile Ile Thr Val His
    130                 135                 140
Thr Gly Asp Gln His Gln Val Gly Asn Glu Thr Gln Gly Val Thr Ala
145                 150                 155                 160
Glu Ile Thr Pro Gln Ala Ser Thr Thr Glu Ala Ile Leu Pro Glu Tyr
                165                 170                 175
Gly Thr Leu Gly Leu Glu Cys Ser Pro Arg Thr Gly Leu Asp Phe Asn
            180                 185                 190
Glu Met Ile Leu Leu Thr Met Lys Asn Lys Ala Trp Met Val His Arg
```

```
                195                 200                 205
Gln Trp Phe Asp Leu Pro Leu Pro Trp Ala Ser Gly Ala Thr Thr
210                 215                 220
Glu Thr Pro Thr Trp Asn Arg Lys Glu Leu Leu Val Thr Phe Lys Asn
225                 230                 235                 240
Ala His Ala Lys Lys Gln Glu Val Val Leu Gly Ser Gln Glu Gly
                245                 250                 255
Ala Met His Thr Ala Leu Thr Gly Ala Thr Glu Ile Gln Asn Ser Gly
            260                 265                 270
Gly Thr Ser Ile Phe Ala Gly His Leu Lys Cys Arg Leu Lys Met Asp
            275                 280                 285
Lys Leu Glu Leu Lys Gly Met Ser Tyr Ala Met Cys Thr Asn Thr Phe
290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                325                 330                 335
Thr Glu Asp Gly Gln Gly Lys Ala His Asn Gly Arg Leu Ile Thr Ala
            340                 345                 350
Asn Pro Val Val Thr Lys Lys Glu Glu Pro Val Asn Ile Glu Ala Glu
            355                 360                 365
Pro Pro Phe Gly Glu Ser Asn Ile Val Ile Gly Ile Gly Asp Asn Ala
        370                 375                 380
Leu Lys Ile Asn Trp Tyr Lys Lys Gly Ser Ser Gly Gly Gly Ser His
385                 390                 395                 400
His His His His His
            405

<210> SEQ ID NO 27
<211> LENGTH: 407
<212> TYPE: PRT
<213> ORGANISM: Artificial Sequence
<220> FEATURE:
<223> OTHER INFORMATION: Hyperglycosylated exodomain D4 (from pCRO24)

<400> SEQUENCE: 27

Met Arg Cys Val Gly Val Gly Asn Arg Asp Phe Val Glu Gly Val Ser
1               5                   10                  15
Gly Gly Ala Trp Val Asp Leu Val Leu Glu His Gly Gly Cys Val Thr
            20                  25                  30
Thr Met Ala Gln Gly Lys Pro Thr Leu Asp Phe Glu Leu Thr Lys Thr
        35                  40                  45
Thr Ala Lys Glu Val Ala Leu Leu Arg Thr Tyr Cys Ile Glu Ala Ser
    50                  55                  60
Ile Ser Asn Ile Thr Thr Ala Thr Arg Cys Pro Thr Gln Gly Glu Pro
65                  70                  75                  80
Tyr Leu Lys Glu Glu Gln Asp Gln Gln Tyr Ile Cys Arg Arg Asp Val
                85                  90                  95
Val Asp Arg Gly Asn Gly Ser Gly Cys Gly Leu Asn Gly Ser Gly Gly
            100                 105                 110
Val Val Thr Cys Ala Lys Phe Ser Cys Ser Gly Lys Ile Thr Gly Asn
        115                 120                 125
Leu Val Gln Ile Glu Asn Leu Glu Tyr Thr Val Val Val Thr Val His
    130                 135                 140
Asn Gly Asp Thr His Ala Val Gly Asn Asp Thr Ser Asn His Gly Val
```

```
145                 150                 155                 160
Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
                180                 185                 190

Phe Asn Glu Met Ile Leu Met Lys Met Lys Lys Thr Trp Leu Val
                195                 200                 205

His Lys Gln Trp Phe Leu Asp Leu Pro Leu Pro Trp Thr Ala Gly Ala
            210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
                260                 265                 270

Gly Asp Gly Asn His Met Phe Ala Gly His Leu Lys Cys Lys Val Arg
            275                 280                 285

Met Glu Lys Leu Arg Ile Lys Gly Met Ser Tyr Thr Met Cys Ser Gly
            290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
                340                 345                 350

Ser Ser Thr Pro Leu Ala Glu Asn Thr Asn Ser Val Thr Asn Ile Glu
            355                 360                 365

Leu Glu Pro Pro Phe Gly Asp Ser Tyr Ile Val Ile Gly Val Gly Asn
            370                 375                 380

Ser Ala Leu Thr Leu His Trp Phe Arg Lys Gly Ser Ser Gly Gly Gly
385                 390                 395                 400

Ser His His His His His His
                405

<210> SEQ ID NO 28
<211> LENGTH: 421
<212> TYPE: PRT
<213> ORGANISM: Artificial Sequence
<220> FEATURE:
<223> OTHER INFORMATION: Hyperglycosylated exodomain Zika (from pCRO25)

<400> SEQUENCE: 28

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
50              55                  60

Ile Ser Asp Met Ala Ser Asp Ser Arg Cys Pro Thr Gln Gly Glu Ala
65              70                  75                  80

Tyr Leu Asp Lys Gln Ser Asp Thr Gln Tyr Val Cys Lys Arg Thr Leu
                85                  90                  95

Val Asp Arg Gly Asn Gly Ser Gly Cys Gly Leu Asn Gly Ser Gly Ser
```

```
                  100                 105                 110
Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
        130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Gly Ser Gly Ser Gly Ser Gly Ser Gly His
                405                 410                 415

His His His His
        420

<210> SEQ ID NO 29
<211> LENGTH: 407
<212> TYPE: PRT
<213> ORGANISM: Artificial Sequence
<220> FEATURE:
<223> OTHER INFORMATION: DENV1_Eexo 2.1 (single sequon W101N;N103S)
      insert for pCRO26 plasmid

<400> SEQUENCE: 29

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30
```

```
Thr Met Ala Lys Asp Lys Pro Thr Leu Asp Ile Glu Leu Leu Lys Thr
             35                  40                  45

Glu Val Thr Asn Pro Ala Val Leu Arg Lys Leu Cys Ile Glu Ala Lys
 50                  55                  60

Ile Ser Asn Thr Thr Thr Asp Ser Arg Cys Pro Thr Gln Gly Glu Ala
 65                  70                  75                  80

Thr Leu Val Glu Glu Gln Asp Ser Asn Phe Val Cys Arg Arg Thr Phe
                 85                  90                  95

Val Asp Arg Gly Asn Gly Ser Gly Cys Gly Leu Phe Gly Lys Gly Ser
                100                 105                 110

Leu Leu Thr Cys Ala Lys Phe Lys Cys Val Thr Lys Leu Glu Gly Lys
                115                 120                 125

Ile Val Gln Tyr Glu Asn Leu Lys Tyr Ser Val Ile Val Thr Val His
                130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Val Leu Leu Thr Met Lys Glu Lys Ser Trp Leu Val
                195                 200                 205

His Lys Gln Trp Phe Leu Asp Leu Pro Leu Pro Trp Thr Ser Gly Ala
                210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
                275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ala Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
                355                 360                 365

Thr Glu Pro Pro Phe Gly Glu Ser Tyr Ile Val Val Gly Ala Gly Glu
370                 375                 380

Lys Ala Leu Lys Leu Ser Trp Phe Lys Lys Gly Ser Thr Gly Gly Gly
385                 390                 395                 400

Ser His His His His His His
                405

<210> SEQ ID NO 30
<211> LENGTH: 407
<212> TYPE: PRT
<213> ORGANISM: Artificial Sequence
<220> FEATURE:
<223> OTHER INFORMATION: DENV1_Eexo 2.2 (single sequon F108N;K110S)
``` insert for pCRO27 plasmid

<400> SEQUENCE: 30

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Asp Ser Arg Cys Pro Thr Gln Gly Glu Ala
65                  70                  75                  80

Thr Leu Val Glu Glu Gln Asp Ser Asn Phe Val Cys Arg Arg Thr Phe
                85                  90                  95

Val Asp Arg Gly Trp Gly Asn Gly Cys Gly Leu Asn Gly Ser Gly Ser
            100                 105                 110

Leu Leu Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ala Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Thr Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Thr Gly Gly Gly
385                 390                 395                 400
```

Ser His His His His His His
              405

<210> SEQ ID NO 31
<211> LENGTH: 421
<212> TYPE: PRT
<213> ORGANISM: Artificial Sequence
<220> FEATURE:
<223> OTHER INFORMATION: ZIKV_EEexo 2.1 (single sequon
      G100N;W101H;G102T) insert for pCRO28 plasmid

<400> SEQUENCE: 31

Ile Arg Cys Ile Gly Val Ser Asn Arg Asp Phe Val Gl

```
Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Gly Gly Ser Gly Gly Ser Gly Gly Ser His
                405                 410                 415

His His His His His
            420

<210> SEQ ID NO 32
<211> LENGTH: 421
<212> TYPE: PRT
<213> ORGANISM: Artificial Sequence
<220> FEATURE:
<223> OTHER INFORMATION: ZIKV_Eexo 2.2 (single sequon L107N;F108H;G109T)
      insert for pCRO29 plasmid

<400> SEQUENCE: 32

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Asn His Thr Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
```

```
                275                 280                 285
Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Gly Gly Ser Gly Gly Ser Gly Gly Ser His
                405                 410                 415

His His His His His
            420

<210> SEQ ID NO 33
<211> LENGTH: 421
<212> TYPE: PRT
<213> ORGANISM: Artificial Sequence
<220> FEATURE:
<223> OTHER INFORMATION: ZIKV_Eexo 2.3 (single sequon W101N;N103S)
      insert for pCRO30 plasmid

<400> SEQUENCE: 33

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Asn Gly Ser Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205
```

```
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Gly Gly Ser Gly Gly Ser Gly Gly Ser His
                405                 410                 415
His His His His
        420

<210> SEQ ID NO 34
<211> LENGTH: 421
<212> TYPE: PRT
<213> ORGANISM: Artificial Sequence
<220> FEATURE:
<223> OTHER INFORMATION: ZIKV_Eexo 2.4 (single sequon F108N;K110S)
      insert for pCRO31 plasmid

<400> SEQUENCE: 34

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
                20                  25                  30
Val Met Ala Gln Asp Lys Pro Thr Val Asp Ile Glu Leu Val Thr Thr
            35                  40                  45
Thr Val Ser Asn Met Ala Glu Val Arg Ser Tyr Cys Tyr Glu Ala Ser
        50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Asn Gly Ser Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
```

-continued

```
Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
            165                 170                 175

Glu Ala Thr Leu Gly Gly Phe Gly Ser Leu Gly Leu Asp Cys Glu Pro
        180                 185                 190

Arg Thr Gly Leu Asp Phe Ser Asp Leu Tyr Tyr Leu Thr Met Asn Asn
    195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Gly Gly Ser Gly Gly Ser Gly Gly Ser His
                405                 410                 415

His His His His His
            420

<210> SEQ ID NO 35
<211> LENGTH: 23
<212> TYPE: PRT
<213> ORGANISM: Artificial Sequence
<220> FEATURE:
<223> OTHER INFORMATION: Hyperglycosylated dengue 2 exodomain tryptic
      peptide T15 (15

```
<223> OTHER INFORMATION: Hyperglycosylated Zika exodomain peptide T10
      with single introduced glycosylation sequon NHT

<400> SEQUENCE: 36

Asn His Thr Asn Gly Cys Gly Leu Phe Gly Lys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Dengue-2 (65-73) T10 peptide

<400> SEQUENCE: 37

Leu Thr Asn Thr Thr Thr Glu Ser Arg
1               5

<210> SEQ ID NO 38
<211> LENGTH: 9
<212> TYPE: PRT
<213> ORGANISM: Artificial Sequence
<220> FEATURE:
<223> OTHER INFORMATION: Dengue-2 (65-73) T10 peptide de-N glycosylated
      at position 67 (N67D)

<400> SEQUENCE: 38

Leu Thr Asp Thr Thr Thr Glu Ser Arg
1               5

<210> SEQ ID NO 39
<211> LENGTH: 23
<212> TYPE: PRT
<213> ORGANISM: Artificial Sequence
<220> FEATURE:
<223> OTHER INFORMATION: Dengue-2 (100-122)  T15 peptide

<400> SEQUENCE: 39

Gly Asn Gly Ser Gly Cys Gly Leu Asn Gly Ser Gly Gly Ile Val Thr
1               5                   10                  15

Cys Ala Met Phe Thr Cys Lys
            20

<210> SEQ ID NO 40
<211> LENGTH: 23
<212> TYPE: PRT
<213> ORGANISM: Artificial Sequence
<220> FEATURE:
<223> OTHER INFORMATION: Dengue-2 (100-122) T15 peptide with single de-N
      glycosylation at position 101 (N101D)

<400> SEQUENCE: 40

Gly Asp Gly Ser Gly Cys Gly Leu Asn Gly Ser Gly Gly Ile Val Thr
1               5                   10                  15

Cys Ala Met Phe Thr Cys Lys
            20

<210> SEQ ID NO 41
<211> LENGTH: 23
<212> TYPE: PRT
<213> ORGANISM: Artificial Sequence
<220> FEATURE:
<223> OTHER INFORMATION: Dengue-2 (100-122) T15 peptide with single de-N
      glycosylation at position 108 (N108D)

<400> SEQUENCE: 41
```

Gly Asn Gly Ser Gly Cys Gly Leu Asp Gly Ser Gly Gly Ile Val Thr
1               5                   10                  15

Cys Ala Met Phe Thr Cys Lys
            20

<210> SEQ ID NO 42
<211> LENGTH: 23
<212> TYPE: PRT
<213> ORGANISM: Artificial Sequence
<220> FEATURE:
<223> OTHER INFORMATION: Dengue-2 (100-122) T15 peptide with de-N
      glycosylation at positions 101 and 108 (N101D; N108D)

<400> SEQUENCE: 42

Gly Asp Gly Ser Gly Cys Gly Leu Asp Gly Ser Gly Gly Ile Val Thr
1               5                   10                  15

Cys Ala Met Phe Thr Cys Lys
            20

<210> SEQ ID NO 43
<211> LENGTH: 29
<212> TYPE: PRT
<213> ORGANISM: Artificial Sequence
<220> FEATURE:
<223> OTHER INFORMATION: Dengue-2 (129-157) T18 peptide

<400> SEQUENCE: 43

Val Val Gln Pro Glu Asn Leu Glu Tyr Thr Ile Val Ile Thr Pro His
1               5                   10                  15

Ser Gly Glu Glu His Ala Val Gly Asn Asp Thr Gly Lys
            20                  25

<210> SEQ ID NO 44
<211> LENGTH: 29
<212> TYPE: PRT
<213> ORGANISM: Artificial Sequence
<220> FEATURE:
<223> OTHER INFORMATION: Dengue-2 (129-157) T18 peptide with de-N
      glycosylation at position 153 (N153D)

<400> SEQUENCE: 44

Val Val Gln Pro Glu Asn Leu Glu Tyr Thr Ile Val Ile Thr Pro His
1               5                   10                  15

Ser Gly Glu Glu His Ala Val Gly Asp Asp Thr Gly Lys
            20                  25

<210> SEQ ID NO 45
<211> LENGTH: 17
<212> TYPE: PRT
<213> ORGANISM: Artificial Sequence
<220> FEATURE:
<223> OTHER INFORMATION: Zika (94-110) L4 peptide

<400> SEQUENCE: 45

Arg Thr Leu Val Asp Arg Asn His Thr Asn Gly Cys Gly Leu Phe Gly
1               5                   10                  15

Lys

<210> SEQ ID NO 46
<211> LENGTH: 17
<212> TYPE: PRT
<213> ORGANISM: Artificial Sequence
<220> FEATURE:
<223> OTHER INFORMATION: Zika (94-110) L4 peptide with de-N
      glycosylation at position 100 (N100D)

-continued

<400> SEQUENCE: 46

Arg Thr Leu Val Asp Arg Asp His Thr Asn Gly Cys Gly Leu Phe Gly
1               5                   10                  15

Lys

<210> SEQ ID NO 47
<211> LENGTH: 26
<212> TYPE: PRT
<213> ORGANISM: Artificial Sequence
<220> FEATURE:
<223> OTHER INFORMATION: Zika (139-164) T16 peptide

<400> SEQUENCE: 47

Ile Met Leu Ser Val His Gly Ser Gln His Ser Gly Met Ile Val Asn
1               5                   10                  15

Asp Thr Gly His Glu Thr Asp Glu Asn Arg
            20                  25

<210> SEQ ID NO 48
<211> LENGTH: 26
<212> TYPE: PRT
<213> ORGANISM: Artificial Sequence
<220> FEATURE:
<223> OTHER INFORMATION: Zika (139 - 164) peptide deglycosylated at
      position 154 (N154D)

<400> SEQUENCE: 48

Ile Met Leu Ser Val His Gly Ser Gln His Ser Gly Met Ile Val Asp
1               5                   10                  15

Asp Thr Gly His Glu Thr Asp Glu Asn Arg
            20                  25

<210> SEQ ID NO 49
<211> LENGTH: 407
<212> TYPE: PRT
<213> ORGANISM: Artificial
<220> FEATURE:
<223> OTHER INFORMATION: Dengue-2 serotype product of expression from
      pCRO22

<400> SEQUENCE: 49

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Asn Gly Ser Gly Cys Gly Leu Asn Gly Ser Gly Gly
            100                 105                 110

Ile Val Thr Cys Ala Met Phe Thr Cys Lys Lys Asn Met Glu Gly Lys
        115                 120                 125

Val Val Gln Pro Glu Asn Leu Glu Tyr Thr Ile Val Ile Thr Pro His
    130                 135                 140

-continued

```
Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Ser Gly Gly Gly
385                 390                 395                 400

Ser His His His His His His
                405
```

<210> SEQ ID NO 50
<211> LENGTH: 7
<212> TYPE: PRT
<213> ORGANISM: Artificial Sequence
<220> FEATURE:
<223> OTHER INFORMATION: pCRO22 Dengue-2 T2 peptide

<400> SEQUENCE: 50

```
Cys Ile Gly Ile Ser Asn Arg
1               5
```

<210> SEQ ID NO 51
<211> LENGTH: 27
<212> TYPE: PRT
<213> ORGANISM: Artificial Sequence
<220> FEATURE:
<223> OTHER INFORMATION: pCRO22 Dengue-2 T3 peptide

<400> SEQUENCE: 51

```
Asp Phe Val Glu Gly Val Ser Gly Gly Ser Trp Val Asp Ile Val Leu
1               5                   10                  15

Glu His Gly Ser Cys Val Thr Thr Met Ala Lys
            20                  25
```

<210> SEQ ID NO 52
<211> LENGTH: 9
<212> TYPE: PRT
<213> ORGANISM: Artificial Sequence
<220> FEATURE:
<223> OTHER INFORMATION: pCRO22 Dengue-2 T5 peptide

<400> SEQUENCE: 52

Pro Thr Leu Asp Phe Glu Leu Ile Lys
1               5

<210> SEQ ID NO 53
<211> LENGTH: 4
<212> TYPE: PRT
<213> ORGANISM: Artificial Sequence
<220> FEATURE:
<223> OTHER INFORMATION: pCRO22 Dengue-2 T6 peptide

<400> SEQUENCE: 53

Thr Glu Ala Lys
1

<210> SEQ ID NO 54
<211> LENGTH: 6
<212> TYPE: PRT
<213> ORGANISM: Artificial Sequence
<220> FEATURE:
<223> OTHER INFORMATION: pCRO22 Dengue-2 T7 peptide

<400> SEQUENCE: 54

Gln Pro Ala Thr Leu Arg
1               5

<210> SEQ ID NO 55
<211> LENGTH: 6
<212> TYPE: PRT
<213> ORGANISM: Artificial Sequence
<220> FEATURE:
<223> OTHER INFORMATION: pCRO22 Dengue-2 T9 peptide

<400> SEQUENCE: 55

Tyr Cys Ile Glu Ala Lys
1               5

<210> SEQ ID NO 56
<211> LENGTH: 9
<212> TYPE: PRT
<213> ORGANISM: Artificial Sequence
<220> FEATURE:
<223> OTHER INFORMATION: pCRO22 Dengue-2 T10 peptide

<400> SEQUENCE: 56

Leu Thr Asn Thr Thr Thr Glu Ser Arg
1               5

<210> SEQ ID NO 57
<211> LENGTH: 15
<212> TYPE: PRT
<213> ORGANISM: Artificial Sequence
<220> FEATURE:
<223> OTHER INFORMATION: pCRO22 Dengue-2 T11 peptide

<400> SEQUENCE: 57

Cys Pro Thr Gln Gly Glu Pro Ser Leu Asn Glu Glu Gln Asp Lys
1               5                   10                  15

<210> SEQ ID NO 58
<211> LENGTH: 4
<212> TYPE: PRT
<213> ORGANISM: Artificial Sequence
<220> FEATURE:
<223> OTHER INFORMATION: Dengue-2 T13 peptide

<400> SEQUENCE: 58

Phe Val Cys Lys
1

<210> SEQ ID NO 59
<211> LENGTH: 6
<212> TYPE: PRT
<213> ORGANISM: Artificial Sequence
<220> FEATURE:
<223> OTHER INFORMATION: pCRO22 Dengue-2 T14 peptide

<400> SEQUENCE: 59

His Ser Met Val Asp Arg
1               5

<210> SEQ ID NO 60
<211> LENGTH: 23
<212> TYPE: PRT
<213> ORGANISM: Artificial Sequence
<220> FEATURE:
<223> OTHER INFORMATION: pCRO22 Dengue-2 T15 peptide

<400> SEQUENCE: 60

Gly Asn Gly Ser Gly Cys Gly Leu Asn Gly Ser Gly Gly Ile Val Thr
1               5                   10                  15

Cys Ala Met Phe Thr Cys Lys
            20

<210> SEQ ID NO 61
<211> LENGTH: 5
<212> TYPE: PRT
<213> ORGANISM: Artificial Sequence
<220> FEATURE:
<223> OTHER INFORMATION: pCRO22 Dengue-2 T17 peptide

<400> SEQUENCE: 61

Asn Met Glu Gly Lys
1               5

<210> SEQ ID NO 62
<211> LENGTH: 29
<212> TYPE: PRT
<213> ORGANISM: Artificial Sequence
<220> FEATURE:
<223> OTHER INFORMATION: pCRO22 Dengue-2 T18 peptide

<400> SEQUENCE: 62

Val Val Gln Pro Glu Asn Leu Glu Tyr Thr Ile Val Ile Thr Pro His
1               5                   10                  15

Ser Gly Glu Glu His Ala Val Gly Asn Asp Thr Gly Lys
            20                  25

<210> SEQ ID NO 63
<211> LENGTH: 25
<212> TYPE: PRT
<213> ORGANISM: Artificial Sequence
<220> FEATURE:
<223> OTHER INFORMATION: pCRO22 Dengue-2 T21 peptide

```
<400> SEQUENCE: 63

Ile Thr Pro Gln Ser Ser Ile Thr Glu Ala Glu Leu Thr Gly Tyr Gly
1               5                   10                  15

Thr Val Thr Met Glu Cys Ser Pro Arg
            20                  25

<210> SEQ ID NO 64
<211> LENGTH: 16
<212> TYPE: PRT
<213> ORGANISM: Artificial Sequence
<220> FEATURE:
<223> OTHER INFORMATION: Dengue-2 T22 peptide

<400> SEQUENCE: 64

Thr Gly Leu Asp Phe Asn Glu Met Val Leu Leu Gln Met Glu Asn Lys
1               5                   10                  15

<210> SEQ ID NO 65
<211> LENGTH: 6
<212> TYPE: PRT
<213> ORGANISM: Artificial Sequence
<220> FEATURE:
<223> OTHER INFORMATION: pCRO22 Dengue-2 T23 peptide

<400> SEQUENCE: 65

Ala Trp Leu Val His Arg
1               5

<210> SEQ ID NO 66
<211> LENGTH: 24
<212> TYPE: PRT
<213> ORGANISM: Artificial Sequence
<220> FEATURE:
<223> OTHER INFORMATION: pCRO22 Dengue-2 T24 peptide

<400> SEQUENCE: 66

Gln Trp Phe Leu Asp Leu Pro Leu Pro Trp Leu Pro Gly Ala Asp Thr
1               5                   10                  15

Gln Gly Ser Asn Trp Ile Gln Lys
            20

<210> SEQ ID NO 67
<211> LENGTH: 7
<212> TYPE: PRT
<213> ORGANISM: Artificial Sequence
<220> FEATURE:
<223> OTHER INFORMATION: pCRO22 Dengue-2 T25 peptide

<400> SEQUENCE: 67

Glu Thr Leu Val Thr Phe Lys
1               5

<210> SEQ ID NO 68
<211> LENGTH: 5
<212> TYPE: PRT
<213> ORGANISM: Artificial Sequence
<220> FEATURE:
<223> OTHER INFORMATION: pCRO22 Dengue-2 T26 peptide

<400> SEQUENCE: 68

Asn Pro His Ala Lys
1               5

<210> SEQ ID NO 69
<211> LENGTH: 37
```

<212> TYPE: PRT
<213> ORGANISM: Artificial Sequence
<220> FEATURE:
<223> OTHER INFORMATION: pCRO22 Dengue-2 T28 peptide

<400> SEQUENCE: 69

Gln Asp Val Val Val Leu Gly Ser Gln Glu Gly Ala Met His Thr Ala
1 5 10 15

Leu Thr Gly Ala Thr Glu Ile Gln Met Ser Ser Gly Asn Leu Leu Phe
20 25 30

Thr Gly His Leu Lys
35

<210> SEQ ID NO 70
<211> LENGTH: 4
<212> TYPE: PRT
<213> ORGANISM: Artificial Sequence
<220> FEATURE:
<223> OTHER INFORMATION: pCRO22 Dengue-2 T32 peptide

<400> SEQUENCE: 70

Leu Gln Leu Lys
1

<210> SEQ ID NO 71
<211> LENGTH: 10
<212> TYPE: PRT
<213> ORGANISM: Artificial Sequence
<220> FEATURE:
<223> OTHER INFORMATION: pCRO22 Dengue-2 T33 peptide

<400> SEQUENCE: 71

Gly Met Ser Tyr Ser Met Cys Thr Gly Lys
1 5 10

<210> SEQ ID NO 72
<211> LENGTH: 13
<212> TYPE: PRT
<213> ORGANISM: Artificial Sequence
<220> FEATURE:
<223> OTHER INFORMATION: pCRO22 Dengue-2 T36 peptide

<400> SEQUENCE: 72

Glu Ile Ala Glu Thr Gln His Gly Thr Ile Val Ile Arg
1 5 10

<210> SEQ ID NO 73
<211> LENGTH: 11
<212> TYPE: PRT
<213> ORGANISM: Artificial Sequence
<220> FEATURE:
<223> OTHER INFORMATION: pCRO22 Dengue-2 T37 peptide

<400> SEQUENCE: 73

Val Gln Tyr Glu Gly Asp Gly Ser Pro Cys Lys
1 5 10

<210> SEQ ID NO 74
<211> LENGTH: 10
<212> TYPE: PRT
<213> ORGANISM: Artificial Sequence
<220> FEATURE:
<223> OTHER INFORMATION: pCRO22 Dengue-2 T38 peptide

<400> SEQUENCE: 74

Ile Pro Phe Glu Ile Met Asp Leu Glu Lys

<210> SEQ ID NO 75
<211> LENGTH: 5
<212> TYPE: PRT
<213> ORGANISM: Artificial Sequence
<220> FEATURE:
<223> OTHER INFORMATION: pCRO22 Dengue-2 T40 peptide

<400> SEQUENCE: 75

His Val Leu Gly Arg
1               5

<210> SEQ ID NO 76
<211> LENGTH: 11
<212> TYPE: PRT
<213> ORGANISM: Artificial Sequence
<220> FEATURE:
<223> OTHER INFORMATION: pCRO22 Dengue-2 T41 peptide

<400> SEQUENCE: 76

Leu Ile Thr Val Asn Pro Ile Val Thr Glu Lys
1               5                   10

<210> SEQ ID NO 77
<211> LENGTH: 27
<212> TYPE: PRT
<213> ORGANISM: Artificial Sequence
<220> FEATURE:
<223> OTHER INFORMATION: pCRO22 Dengue-2 T42 peptide

<400> SEQUENCE: 77

Asp Ser Pro Val Asn Ile Glu Ala Glu Pro Pro Phe Gly Asp Ser Tyr
1               5                   10                  15

Ile Ile Ile Gly Val Glu Pro Gly Gln Leu Lys
            20                  25

<210> SEQ ID NO 78
<211> LENGTH: 5
<212> TYPE: PRT
<213> ORGANISM: Artificial Sequence
<220> FEATURE:
<223> OTHER INFORMATION: pCRO22 Dengue-2 T43 peptide

<400> SEQUENCE: 78

Leu Asn Trp Phe Lys
1               5

<210> SEQ ID NO 79
<211> LENGTH: 13
<212> TYPE: PRT
<213> ORGANISM: Artificial Sequence
<220> FEATURE:
<223> OTHER INFORMATION: pCRO22 Dengue-2 T45 peptide

<400> SEQUENCE: 79

Gly Ser Ser Gly Gly Gly Ser His His His His His His
1               5                   10

<210> SEQ ID NO 80
<211> LENGTH: 421
<212> TYPE: PRT
<213> ORGANISM: Artificial Sequence
<220> FEATURE:
<223> OTHER INFORMATION: Zika product of expression from pCRO28

<400> SEQUENCE: 80

```
Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
    50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Asn His Thr Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Gly Ser Gly Gly Ser Gly Gly Ser His
                405                 410                 415
```

His His His His His
            420

<210> SEQ ID NO 81
<211> LENGTH: 7
<212> TYPE: PRT
<213> ORGANISM: Artificial Sequence
<220> FEATURE:
<223> OTHER INFORMATION: pCRO28 Zika T2 peptide

<400> SEQUENCE: 81

Cys Ile Gly Val Ser Asn Arg
1               5

<210> SEQ ID NO 82
<211> LENGTH: 29
<212> TYPE: PRT
<213> ORGANISM: Artificial Sequence
<220> FEATURE:
<223> OTHER INFORMATION: pCRO28 Zika T3 peptide

<400> SEQUENCE: 82

Asp Phe Val Glu Gly Met Ser Gly Gly Thr Trp Val Asp Val Val Leu
1               5                   10                  15

Glu His Gly Gly Cys Val Thr Val Met Ala Gln Asp Lys
            20                  25

<210> SEQ ID NO 83
<211> LENGTH: 19
<212> TYPE: PRT
<213> ORGANISM: Artificial Sequence
<220> FEATURE:
<223> OTHER INFORMATION: pCRO28 Zika T4 peptide

<400> SEQUENCE: 83

Pro Thr Val Asp Ile Glu Leu Val Thr Thr Thr Val Ser Asn Met Ala
1               5                   10                  15

Glu Val Arg

<210> SEQ ID NO 84
<211> LENGTH: 16
<212> TYPE: PRT
<213> ORGANISM: Artificial Sequence
<220> FEATURE:
<223> OTHER INFORMATION: pCRO28 Zika T5 peptide

<400> SEQUENCE: 84

Ser Tyr Cys Tyr Glu Ala Ser Ile Ser Asp Met Ala Ser Asp Ser Arg
1               5                   10                  15

<210> SEQ ID NO 85
<211> LENGTH: 11
<212> TYPE: PRT
<213> ORGANISM: Artificial Sequence
<220> FEATURE:
<223> OTHER INFORMATION: pCRO28 Zika T6 peptide

<400> SEQUENCE: 85

Cys Pro Thr Gln Gly Glu Ala Tyr Leu Asp Lys
1               5                   10

<210> SEQ ID NO 86
<211> LENGTH: 9
<212> TYPE: PRT
<213> ORGANISM: Artificial Sequence
<220> FEATURE:

<223> OTHER INFORMATION: pCRO28 Zika T7 peptide

<400> SEQUENCE: 86

Gln Ser Asp Thr Gln Tyr Val Cys Lys
1 5

<210> SEQ ID NO 87
<211> LENGTH: 5
<212> TYPE: PRT
<213> ORGANISM: Artificial Sequence
<220> FEATURE:
<223> OTHER INFORMATION: pCRO28 Zika T9 peptide

<400> SEQUENCE: 87

Thr Leu Val Asp Arg
1 5

<210> SEQ ID NO 88
<211> LENGTH: 11
<212> TYPE: PRT
<213> ORGANISM: Artificial Sequence
<220> FEATURE:
<223> OTHER INFORMATION: pCRO28 Zika T10 peptide

<400> SEQUENCE: 88

Asn His Thr Asn Gly Cys Gly Leu Phe Gly Lys
1 5 10

<210> SEQ ID NO 89
<211> LENGTH: 8
<212> TYPE: PRT
<213> ORGANISM: Artificial Sequence
<220> FEATURE:
<223> OTHER INFORMATION: pCRO28 Zika T11 peptide

<400> SEQUENCE: 89

Gly Ser Leu Val Thr Cys Ala Lys
1 5

<210> SEQ ID NO 90
<211> LENGTH: 5
<212> TYPE: PRT
<213> ORGANISM: Artificial Sequence
<220> FEATURE:
<223> OTHER INFORMATION: pCRO28 Zika T12 peptide

<400> SEQUENCE: 90

Phe Ala Cys Ser Lys
1 5

<210> SEQ ID NO 91
<211> LENGTH: 4
<212> TYPE: PRT
<213> ORGANISM: Artificial Sequence
<220> FEATURE:
<223> OTHER INFORMATION: pCRO28 Zika T14 peptide

<400> SEQUENCE: 91

Met Thr Gly Lys
1

<210> SEQ ID NO 92
<211> LENGTH: 10
<212> TYPE: PRT
<213> ORGANISM: Artificial Sequence
<220> FEATURE:
<223> OTHER INFORMATION: pCRO28 Zika T15 peptide

<400> SEQUENCE: 92

Ser Ile Gln Pro Glu Asn Leu Glu Tyr Arg
1               5                   10

<210> SEQ ID NO 93
<211> LENGTH: 26
<212> TYPE: PRT
<213> ORGANISM: Artificial Sequence
<220> FEATURE:
<223> OTHER INFORMATION: pCRO28 Zika T16 peptide

<400> SEQUENCE: 93

Ile Met Leu Ser Val His Gly Ser Gln His Ser Gly Met Ile Val Asn
1               5                   10                  15

Asp Thr Gly His Glu Thr Asp Glu Asn Arg
            20                  25

<210> SEQ ID NO 94
<211> LENGTH: 9
<212> TYPE: PRT
<213> ORGANISM: Artificial Sequence
<220> FEATURE:
<223> OTHER INFORMATION: pCRO28 Zika T18 peptide

<400> SEQUENCE: 94

Val Glu Ile Thr Pro Asn Ser Pro Arg
1               5

<210> SEQ ID NO 95
<211> LENGTH: 18
<212> TYPE: PRT
<213> ORGANISM: Artificial Sequence
<220> FEATURE:
<223> OTHER INFORMATION: pCRO28 Zika T19 peptide

<400> SEQUENCE: 95

Ala Glu Ala Thr Leu Gly Gly Phe Gly Ser Leu Gly Leu Asp Cys Glu
1               5                   10                  15

Pro Arg

<210> SEQ ID NO 96
<211> LENGTH: 16
<212> TYPE: PRT
<213> ORGANISM: Artificial Sequence
<220> FEATURE:
<223> OTHER INFORMATION: pCRO28 Zika T20 peptide

<400> SEQUENCE: 96

Thr Gly Leu Asp Phe Ser Asp Leu Tyr Tyr Leu Thr Met Asn Asn Lys
1               5                   10                  15

<210> SEQ ID NO 97
<211> LENGTH: 6
<212> TYPE: PRT
<213> ORGANISM: Artificial Sequence
<220> FEATURE:
<223> OTHER INFORMATION: pCRO28 Zika T21 peptide

<400> SEQUENCE: 97

His Trp Leu Val His Lys
1               5

<210> SEQ ID NO 98
<211> LENGTH: 24

```
<212> TYPE: PRT
<213> ORGANISM: Artificial Sequence
<220> FEATURE:
<223> OTHER INFORMATION: pCRO28 Zika T22 peptide

<400> SEQUENCE: 98

Glu Trp Phe His Asp Ile Pro Leu Pro Trp His Ala Gly Ala Asp Thr
1               5                   10                  15

Gly Thr Pro His Trp Asn Asn Lys
            20

<210> SEQ ID NO 99
<211> LENGTH: 7
<212> TYPE: PRT
<213> ORGANISM: Artificial Sequence
<220> FEATURE:
<223> OTHER INFORMATION: pCRO28 Zika T23 peptide

<400> SEQUENCE: 99

Glu Ala Leu Val Glu Phe Lys
1               5

<210> SEQ ID NO 100
<211> LENGTH: 5
<212> TYPE: PRT
<213> ORGANISM: Artificial Sequence
<220> FEATURE:
<223> OTHER INFORMATION: pCRO28 Zika T24 peptide

<400> SEQUENCE: 100

Asp Ala His Ala Lys
1               5

<210> SEQ ID NO 101
<211> LENGTH: 29
<212> TYPE: PRT
<213> ORGANISM: Artificial Sequence
<220> FEATURE:
<223> OTHER INFORMATION: pCRO28 Zika T26 peptide

<400> SEQUENCE: 101

Gln Thr Val Val Val Leu Gly Ser Gln Glu Gly Ala Val His Thr Ala
1               5                   10                  15

Leu Ala Gly Ala Leu Glu Ala Glu Met Asp Gly Ala Lys
            20                  25

<210> SEQ ID NO 102
<211> LENGTH: 7
<212> TYPE: PRT
<213> ORGANISM: Artificial Sequence
<220> FEATURE:
<223> OTHER INFORMATION: pCRO28 Zika T28 peptide

<400> SEQUENCE: 102

Leu Ser Ser Gly His Leu Lys
1               5

<210> SEQ ID NO 103
<211> LENGTH: 15
<212> TYPE: PRT
<213> ORGANISM: Artificial Sequence
<220> FEATURE:
<223> OTHER INFORMATION: pCRO28 Zika T34 peptide

<400> SEQUENCE: 103

Gly Val Ser Tyr Ser Leu Cys Thr Ala Ala Phe Thr Phe Thr Lys
1               5                   10                  15
```

<210> SEQ ID NO 104
<211> LENGTH: 24
<212> TYPE: PRT
<213> ORGANISM: Artificial Sequence
<220> FEATURE:
<223> OTHER INFORMATION: pCRO28 Zika T35 peptide

<400> SEQUENCE: 104

Ile Pro Ala Glu Thr Leu His Gly Thr Val Thr Val Glu Val Gln Tyr
1               5                   10                  15

Ala Gly Thr Asp Gly Pro Cys Lys
            20

<210> SEQ ID NO 105
<211> LENGTH: 17
<212> TYPE: PRT
<213> ORGANISM: Artificial Sequence
<220> FEATURE:
<223> OTHER INFORMATION: pCRO28 Zika T36 peptide

<400> SEQUENCE: 105

Val Pro Ala Gln Met Ala Val Asp Met Gln Thr Leu Thr Pro Val Gly
1               5                   10                  15

Arg

<210> SEQ ID NO 106
<211> LENGTH: 16
<212> TYPE: PRT
<213> ORGANISM: Artificial Sequence
<220> FEATURE:
<223> OTHER INFORMATION: pCRO28 Zika T37 peptide

<400> SEQUENCE: 106

Leu Ile Thr Ala Asn Pro Val Ile Thr Glu Ser Thr Glu Asn Ser Lys
1               5                   10                  15

<210> SEQ ID NO 107
<211> LENGTH: 21
<212> TYPE: PRT
<213> ORGANISM: Artificial Sequence
<220> FEATURE:
<223> OTHER INFORMATION: pCRO28 Zika T38 peptide

<400> SEQUENCE: 107

Met Met Leu Glu Leu Asp Pro Pro Phe Gly Asp Ser Tyr Ile Val Ile
1               5                   10                  15

Gly Val Gly Glu Lys
            20

<210> SEQ ID NO 108
<211> LENGTH: 7
<212> TYPE: PRT
<213> ORGANISM: Artificial Sequence
<220> FEATURE:
<223> OTHER INFORMATION: pCRO28 Zika T40 peptide

<400> SEQUENCE: 108

Ile Thr His His Trp His Arg
1               5

<210> SEQ ID NO 109
<211> LENGTH: 19
<212> TYPE: PRT

<213> ORGANISM: Artificial Sequence
<220> FEATURE:
<223> OTHER INFORMATION: pCRO28 Zika T41 peptide

<400> SEQUENCE: 109

```
Ser Gly Ser Thr Gly Gly Ser Gly Gly Ser Gly Gly Ser His His His
1               5                   10                  15

His His His
```

<210> SEQ ID NO 110
<211> LENGTH: 38
<212> TYPE: PRT
<213> ORGANISM: Artificial Sequence
<220> FEATURE:
<223> OTHER INFORMATION: pCRO28 Zika L1 peptide

<400> SEQUENCE: 110

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys
        35
```

<210> SEQ ID NO 111
<211> LENGTH: 46
<212> TYPE: PRT
<213> ORGANISM: Artificial Sequence
<220> FEATURE:
<223> OTHER INFORMATION: pCRO28 Zika L2 peptide

<400> SEQUENCE: 111

```
Pro Thr Val Asp Ile Glu Leu Val Thr Thr Thr Val Ser Asn Met Ala
1               5                   10                  15

Glu Val Arg Ser Tyr Cys Tyr Glu Ala Ser Ile Ser Asp Met Ala Ser
            20                  25                  30

Asp Ser Arg Cys Pro Thr Gln Gly Glu Ala Tyr Leu Asp Lys
        35                  40                  45
```

<210> SEQ ID NO 112
<211> LENGTH: 9
<212> TYPE: PRT
<213> ORGANISM: Artificial Sequence
<220> FEATURE:
<223> OTHER INFORMATION: pCRO28 Zika L3 peptide

<400> SEQUENCE: 112

```
Gln Ser Asp Thr Gln Tyr Val Cys Lys
1               5
```

<210> SEQ ID NO 113
<211> LENGTH: 17
<212> TYPE: PRT
<213> ORGANISM: Artificial Sequence
<220> FEATURE:
<223> OTHER INFORMATION: pCRO28 Zika L4 peptide

<400> SEQUENCE: 113

```
Arg Thr Leu Val Asp Arg Asn His Thr Asn Gly Cys Gly Leu Phe Gly
1               5                   10                  15

Lys
```

<210> SEQ ID NO 114

<211> LENGTH: 8
<212> TYPE: PRT
<213> ORGANISM: Artificial Sequence
<220> FEATURE:
<223> OTHER INFORMATION: pCRO28 Zika L5 peptide

<400> SEQUENCE: 114

Gly Ser Leu Val Thr Cys Ala Lys
1               5

<210> SEQ ID NO 115
<211> LENGTH: 5
<212> TYPE: PRT
<213> ORGANISM: Artificial Sequence
<220> FEATURE:
<223> OTHER INFORMATION: pCRO28 Zika L6 peptide

<400> SEQUENCE: 115

Phe Ala Cys Ser Lys
1               5

<210> SEQ ID NO 116
<211> LENGTH: 4
<212> TYPE: PRT
<213> ORGANISM: Artificial Sequence
<220> FEATURE:
<223> OTHER INFORMATION: pCRO28 Zika L8 peptide

<400> SEQUENCE: 116

Met Thr Gly Lys
1

<210> SEQ ID NO 117
<211> LENGTH: 38
<212> TYPE: PRT
<213> ORGANISM: Artificial Sequence
<220> FEATURE:
<223> OTHER INFORMATION: pCRO28 Zika L9 peptide

<400> SEQUENCE: 117

Ser Ile Gln Pro Glu Asn Leu Glu Tyr Arg Ile Met Leu Ser Val His
1               5                   10                  15

Gly Ser Gln His Ser Gly Met Ile Val Asn Asp Thr Gly His Glu Thr
            20                  25                  30

Asp Glu Asn Arg Ala Lys
        35

<210> SEQ ID NO 118
<211> LENGTH: 49
<212> TYPE: PRT
<213> ORGANISM: Artificial Sequence
<220> FEATURE:
<223> OTHER INFORMATION: pCRO28 Zika L10 peptide

<400> SEQUENCE: 118

Val Glu Ile Thr Pro Asn Ser Pro Arg Ala Glu Ala Thr Leu Gly Gly
1               5                   10                  15

Phe Gly Ser Leu Gly Leu Asp Cys Glu Pro Arg Thr Gly Leu Asp Phe
            20                  25                  30

Ser Asp Leu Tyr Tyr Leu Thr Met Asn Asn Lys His Trp Leu Val His
            35                  40                  45

Lys

<210> SEQ ID NO 119

<211> LENGTH: 24
<212> TYPE: PRT
<213> ORGANISM: Artificial Sequence
<220> FEATURE:
<223> OTHER INFORMATION: pCRO28 Zika L11 pepide

<400> SEQUENCE: 119

Glu Trp Phe His Asp Ile Pro Leu Pro Trp His Ala Gly Ala Asp Thr
1               5                   10                  15

Gly Thr Pro His Trp Asn Asn Lys
            20

<210> SEQ ID NO 120
<211> LENGTH: 7
<212> TYPE: PRT
<213> ORGANISM: Artificial Sequence
<220> FEATURE:
<223> OTHER INFORMATION: pCRO28 Zika L12 peptide

<400> SEQUENCE: 120

Glu Ala Leu Val Glu Phe Lys
1               5

<210> SEQ ID NO 121
<211> LENGTH: 5
<212> TYPE: PRT
<213> ORGANISM: Artificial Sequence
<220> FEATURE:
<223> OTHER INFORMATION: pCRO28 Zika L13 peptide

<400> SEQUENCE: 121

Asp Ala His Ala Lys
1               5

<210> SEQ ID NO 122
<211> LENGTH: 30
<212> TYPE: PRT
<213> ORGANISM: Artificial Sequence
<220> FEATURE:
<223> OTHER INFORMATION: pCRO28 Zika L14 peptide

<400> SEQUENCE: 122

Arg Gln Thr Val Val Val Leu Gly Ser Gln Glu Gly Ala Val His Thr
1               5                   10                  15

Ala Leu Ala Gly Ala Leu Glu Ala Glu Met Asp Gly Ala Lys
            20                  25                  30

<210> SEQ ID NO 123
<211> LENGTH: 9
<212> TYPE: PRT
<213> ORGANISM: Artificial Sequence
<220> FEATURE:
<223> OTHER INFORMATION: pCRO28 Zika L15 peptide

<400> SEQUENCE: 123

Gly Arg Leu Ser Ser Gly His Leu Lys
1               5

<210> SEQ ID NO 124
<211> LENGTH: 4
<212> TYPE: PRT
<213> ORGANISM: Artificial Sequence
<220> FEATURE:
<223> OTHER INFORMATION: pCRO28 Zika L16 peptide

<400> SEQUENCE: 124

```
Cys Arg Leu Lys
1

<210> SEQ ID NO 125
<211> LENGTH: 4
<212> TYPE: PRT
<213> ORGANISM: Artificial Sequence
<220> FEATURE:
<223> OTHER INFORMATION: pCRO28 Zika L18 peptide

<400> SEQUENCE: 125

Leu Arg Leu Lys
1

<210> SEQ ID NO 126
<211> LENGTH: 15
<212> TYPE: PRT
<213> ORGANISM: Artificial Sequence
<220> FEATURE:
<223> OTHER INFORMATION: pCRO28 Zika L19 peptide

<400> SEQUENCE: 126

Gly Val Ser Tyr Ser Leu Cys Thr Ala Ala Phe Thr Phe Thr Lys
1               5                   10                  15

<210> SEQ ID NO 127
<211> LENGTH: 24
<212> TYPE: PRT
<213> ORGANISM: Artificial Sequence
<220> FEATURE:
<223> OTHER INFORMATION: pCRO28 Zika L20 peptide

<400> SEQUENCE: 127

Ile Pro Ala Glu Thr Leu His Gly Thr Val Thr Val Glu Val Gln Tyr
1               5                   10                  15

Ala Gly Thr Asp Gly Pro Cys Lys
            20

<210> SEQ ID NO 128
<211> LENGTH: 33
<212> TYPE: PRT
<213> ORGANISM: Artificial Sequence
<220> FEATURE:
<223> OTHER INFORMATION: pCRO28 Zika L21 peptide

<400> SEQUENCE: 128

Val Pro Ala Gln Met Ala Val Asp Met Gln Thr Leu Thr Pro Val Gly
1               5                   10                  15

Arg Leu Ile Thr Ala Asn Pro Val Ile Thr Glu Ser Thr Glu Asn Ser
            20                  25                  30

Lys

<210> SEQ ID NO 129
<211> LENGTH: 21
<212> TYPE: PRT
<213> ORGANISM: Artificial Sequence
<220> FEATURE:
<223> OTHER INFORMATION: pCRO28 Zika L22 peptide

<400> SEQUENCE: 129

Met Met Leu Glu Leu Asp Pro Pro Phe Gly Asp Ser Tyr Ile Val Ile
1               5                   10                  15

Gly Val Gly Glu Lys
            20
```

```
<210> SEQ ID NO 130
<211> LENGTH: 26
<212> TYPE: PRT
<213> ORGANISM: Artificial Sequence
<220> FEATURE:
<223> OTHER INFORMATION: pCRO28 Zika L24 peptide

<400> SEQUENCE: 130

Ile Thr His His Trp His Arg Ser Gly Ser Thr Gly Gly Ser Gly Gly
1               5                   10                  15

Ser Gly Gly Ser His His His His His His
            20                  25
```

The invention claimed is:

1. An isolated recombinant glycosylation site modified flavivirus E-protein fusion loop epitope, wherein the epitope comprises at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon occupies any of positions 98-110 (DRGWGNGCGLFGK) SEQ ID NO: 1 of the natural flavivirus E-protein fusion loop amino acid sequence, wherein X is any amino acid residue except proline and Ser/Thr denotes a serine or threonine residue.

2. The isolated recombinant flavivirus E-protein fusion loop epitope according to claim 1 comprising two glycosylation sites that are not present in a natural flavivirus E-protein fusion loop sequence.

3. An isolated recombinant flavivirus E-protein comprising a glycosylation site modified flavivirus E-protein fusion loop epitope, wherein the epitope comprises at least one glycosylation site for an N-linked glycan that is not present in a natural flavivirus E-protein fusion loop sequence, wherein the at least one glycosylation site is an N-linked glycosylation sequon (Asn-X-Ser/Thr) and the Asn (N) residue of the sequon occupies any of positions 98-110 (DRGWGNGCGLFGK) SEQ ID NO: 1 of the natural flavivirus E-protein fusion loop amino acid sequence, wherein X is any amino acid residue except proline and Ser/Thr denotes a serine or threonine residue.

4. The isolated recombinant protein of claim 3, further comprising at least one additional N-linked glycan attached thereto.

5. The isolated recombinant protein of claim 3, which is the product of expression of a recombinant DNA or RNA sequence.

6. The isolated recombinant protein of claim 3, comprising an N-linked glycosylation sequon (Asn-X-Ser/Thr) such that an Asn (N) residue of the sequon occupies any of positions 98-101 and/or 106-110.

7. The isolated recombinant protein of claim 3, wherein X is selected from the following 13 amino acid residues of Gly, His, Asn, Gln, Tyr, Val, Ala, Met, Ile, Lys, Arg, Thr or Ser.

8. The isolated recombinant protein of claim 3, wherein the flavivirus E-protein is a dengue virus E-protein and the Asn (N) residue of the sequon occupies position 101, 108 or both 101 and 108 of the amino acid sequence of the flavivirus E-protein fusion loop or the flavivirus E-protein is a Zika E-protein and the Asn (N) residue of the sequon occupies position 100 of the amino acid sequence of the flavivirus E-protein fusion loop.

9. The isolated recombinant protein of claim 8, wherein the flavivirus is a dengue virus and the amino acid sequence of the analogue flavivirus E-protein fusion loop 98-110 is selected from: DRGNGSGCGLNGS (SEQ ID NO: 2), DRGNGSGCGLFGK (SEQ ID NO: 3) and DRGWGNGCGLNGS (SEQ ID NO: 4).

10. The isolated recombinant protein of claim 8, wherein the flavivirus is a Zika virus and the amino acid sequence of the analogue flavivirus E-protein fusion loop 98-110 is DRNHTNGCGLFGK (SEQ ID NO: 5).

11. A composition comprising the isolated recombinant glycosylation site modified flavivirus E-protein fusion loop epitope according to claim 1 or the isolated recombinant protein according to claim 3 and a diluent.

12. The composition of claim 11, further comprising a pharmaceutically acceptable diluent, adjuvant and/or carrier.

13. The composition of claim 12 comprising one or more flavivirus analogues selected from an analogue of DEN-1, an analogue of DEN-2, an analogue of DEN-3, an analogue of DEN-4 and an analogue of Zika.

14. The composition of claim 12 comprising four dengue analogues representing each of the four dengue virus serotypes DEN-1 DEN-2 DEN-3 and DEN-4.

15. The composition of claim 12 comprising a zika virus analogue.

16. The composition of claim 12 comprising four dengue analogues representing each of the four dengue serotypes DEN-1 DEN-2 DEN-3 and DEN-4 and a zika virus analogue.

17. The composition of claim 12, wherein the composition further comprises an adjuvant, and is prepared for administration to a subject in need thereof for prophylactic or therapeutic treatment of a flavivirus infection.

18. The composition of claim 12 combined with and further comprising sera from a subject to determine if the subject is seropositive or seronegative for the flavivirus.

* * * * *